US012486212B2

(12) United States Patent
Shim et al.

(10) Patent No.: US 12,486,212 B2
(45) Date of Patent: Dec. 2, 2025

(54) PRODUCTION AND SEPARATION OF 3-HYDROXYPROPIONIC ACID

(71) Applicant: Noroo IC Co., Ltd., Suwanee, GA (US)

(72) Inventors: Jeung Yeop Shim, Tampa, FL (US); Ki Soo Park, Yongin (KR); Ashok Somasundar, Suwon (KR); Sung Hoon Park, Ulsan (KR)

(73) Assignee: NOROO IC CO., LTD., Suwanee, GA (US)

( * ) Notice: Subject to any disclaimer, the term of this patent is extended or adjusted under 35 U.S.C. 154(b) by 65 days.

(21) Appl. No.: 18/752,282

(22) Filed: Jun. 24, 2024

(65) Prior Publication Data

US 2024/0368064 A1 Nov. 7, 2024

Related U.S. Application Data

(60) Division of application No. 18/080,163, filed on Dec. 13, 2022, now Pat. No. 12,091,381, which is a division of application No. 16/858,065, filed on Apr. 24, 2020, now Pat. No. 11,566,250, which is a continuation of application No. 16/758,815, filed as application No. PCT/IB2018/058351 on Oct. 25, 2018, now Pat. No. 11,059,769.

(60) Provisional application No. 62/594,318, filed on Dec. 4, 2017, provisional application No. 62/577,361, filed on Oct. 26, 2017.

(51) Int. Cl.

| | |
|---|---|
| ***C12N 15/52*** | (2006.01) |
| ***B01D 11/04*** | (2006.01) |
| ***C07C 51/377*** | (2006.01) |
| ***C07C 51/48*** | (2006.01) |
| ***C07C 59/01*** | (2006.01) |
| ***C12N 15/78*** | (2006.01) |
| *B01D 5/00* | (2006.01) |
| *B01D 17/02* | (2006.01) |
| *C07C 57/04* | (2006.01) |

(52) U.S. Cl.

CPC .............. *C07C 51/48* (2013.01); *B01D 11/04* (2013.01); *C07C 51/377* (2013.01); *C07C 59/01* (2013.01); *C12N 15/78* (2013.01); *B01D 5/0027* (2013.01); *B01D 17/0214* (2013.01); *C07C 57/04* (2013.01); *C12N 2830/002* (2013.01)

(58) Field of Classification Search

CPC ......... C12N 15/63; C12N 15/67; C12N 15/52

See application file for complete search history.

(56) References Cited

U.S. PATENT DOCUMENTS

| | | | |
|---|---|---|---|
| 2,469,701 | A | 5/1949 | Redmon |
| 6,852,517 | B1 | 2/2005 | Suthers et al. |
| 7,279,598 | B2 | 10/2007 | Meng et al. |
| 9,630,900 | B2 | 4/2017 | Blaschke et al. |
| 9,926,256 | B2 | 3/2018 | Lingoes et al. |
| 10,017,451 | B2 | 7/2018 | De Haan et al. |
| 11,059,769 | B2 | 7/2021 | Shim et al. |
| 11,566,250 | B2 | 1/2023 | Shim et al. |
| 11,584,706 | B2 | 2/2023 | Shim et al. |
| 12,091,381 | B2 | 9/2024 | Shim et al. |
| 2006/0149100 | A1 | 7/2006 | Meng et al. |
| 2007/0219391 | A1 | 9/2007 | Lilga et al. |
| 2009/0076297 | A1 | 3/2009 | Bogan, Jr. et al. |
| 2009/0298144 | A1 | 12/2009 | Tsobanakis et al. |
| 2011/0144377 | A1 | 6/2011 | Eliot et al. |
| 2013/0345470 | A1 | 12/2013 | Tengler et al. |
| 2015/0315115 | A1 | 11/2015 | Kuppinger et al. |
| 2016/0221916 | A1 | 8/2016 | Blaschke et al. |
| 2018/0312852 | A1 | 11/2018 | Park et al. |
| 2020/0354728 | A1 | 11/2020 | Shim et al. |
| 2021/0009496 | A1 | 1/2021 | Shim et al. |
| 2021/0292267 | A1 | 9/2021 | Shim et al. |
| 2023/0151375 | A1 | 5/2023 | Shim et al. |

FOREIGN PATENT DOCUMENTS

| | | |
|---|---|---|
| CN | 105647845 | 6/2016 |
| EP | 2660235 | 11/2013 |
| JP | S58-158189 | 9/1983 |
| JP | H5-001019 | 1/1993 |
| JP | 2013505727 | 2/2013 |
| JP | 2013071898 | 4/2013 |
| JP | 2014-530095 | 11/2014 |
| JP | 2015-500866 | 1/2015 |
| JP | 2016503071 | 2/2016 |
| JP | 2016-512688 | 5/2016 |
| KR | 101048151 | 7/2011 |
| KR | 101048485 | 7/2011 |
| KR | 101069016 | 9/2011 |
| KR | 101157376 | 6/2012 |
| KR | 101247881 | 3/2013 |
| KR | 20130095395 | 8/2013 |
| KR | 101312835 | 9/2013 |
| KR | 20140095608 | 8/2014 |
| KR | 101555867 | 10/2015 |

(Continued)

OTHER PUBLICATIONS

"Gene Engineering," 3rd ed. Qiu (ed.) Aug. 1993, 138-140, 12 pages (with machine translation).

Ainala et al., "Complete Genome Sequence of Pseudomonas denitrificans ATCC 13867", genomeA, 2013, 2 pages.

Ainala et al., "Heterologous gene expression in Pseudomonas denitrificans using Cm inducible promoter: Case study with KGSADH," Theories and Applications of Chem. Eng., 2016, 22(1):460.

Arasu et al., "Isolation of a Novel Pseudomonas Species SP2 Producing Vitamin B12 under Aerobic Condition", Biotechnology and Bioprocess Engineering, 2013, 18: 43-51.

(Continued)

*Primary Examiner* — Tekchand Saidha

(74) *Attorney, Agent, or Firm* — The PL Law Group, PLLC

(57) ABSTRACT

The disclosure provides methods and apparatus for producing 3-hydroxypropionic acid or a salt thereof, for removing 3-hydroxypropionic acid from aqueous solution (e.g., aqueous broth), and for using it to make various chemicals.

12 Claims, 67 Drawing Sheets

Specification includes a Sequence Listing.

(56) References Cited

FOREIGN PATENT DOCUMENTS

| | | |
|---|---|---|
| KR | 101609257 | 4/2016 |
| KR | 20160108324 | 9/2016 |
| KR | 20160146588 | 12/2016 |
| KR | 20160149440 | 12/2016 |
| KR | 20170001088 | 1/2017 |
| KR | 101877303 | 7/2018 |
| WO | WO 2004/005221 | 1/2004 |
| WO | WO 2005/003074 | 1/2005 |
| WO | WO 2004/024876 | 5/2006 |
| WO | WO 2007/106100 | 9/2007 |
| WO | WO 2011/038364 | 3/2011 |
| WO | WO 2012/027279 | 3/2012 |
| WO | WO 2013/192450 | 12/2013 |
| WO | WO 2013/192451 | 12/2013 |
| WO | WO 2014/062997 | 4/2014 |
| WO | WO 2012/091114 | 6/2014 |
| WO | WO 2014/144400 | 9/2014 |
| WO | WO 2015/057644 | 4/2015 |
| WO | WO 2016/007306 | 1/2016 |
| WO | WO 2016/200239 | 12/2016 |

OTHER PUBLICATIONS

Ashok et al., "Development of recombinant Klebsiella pneumoniae ΔdhaT stain fro the co-production of 3-hydroxypropionic acid and 1,3-propanediol from glycerol", Applied Microbiology and Biotechnology, 2011, 90:1253-1265.
Ashok et al., "Effect of puuC overexpression and nitrate addition on glycerol metabolism and anaerobic 3-hydroxypropionic acid production in recombinant Klebsiella pneumoniae ΔglpKΔdhaT", Metabolic Engineering, 2013, 15:10-24.
Ashok et al., "Production of 3-Hydroxypropionic Acid From Glycerol by Recombinant Klebsiella pneumoniae ΔdhaTΔyqhD Which Can Produce Vitamin B12 Naturally", Biotechnology and Bioengineering, Feb. 2013, 14 pages.
Chun et al., "Elucidation of Toxicity of Organic Acids Inhibiting Growth of *Escherichia coli* W", Biotechnology and Bioprocess Engineering, 2014, 19: 858-865.
Cie et al., "Renewable Acrylic Acid", University of Pennsylvania School of Engineering and Applied Science, Apr. 10, 2012, 263 pages.
Dishisha et al., "Bio-based 3-hydroxypropionic-and acrylic acid production from biodiesel glycerol via integrated microbial and chemical catalysis", Microbial Cell Factories, Dec. 21, 2015, 19 pages.
EP European Search Report in European Appln. No. 18871598.1, dated Apr. 29, 2021, 12 pages.
Eun-Hee et al., ""Development of microbial conversion process for production of 3-hydroxypropionic acid, "" May 1, 2015, 1-137.
Fowler et al., "Using a riboswitch sensor to examine coenzyme B12 metabolism and transport in E. coli," Chemistry & Biology, Jul. 30, 2010, 17(7):756-65.
GenBank Accession No. AB241137.1, "Azospirillum brasilense AraE gene for alfa-ketoglutaric semialdehyde dehydrogenase, complete cds," published Sep. 28, 2006 , 2 pages.
International Preliminary Report on Patentabiltiy in International Appln. No. PCT/IB2018/058351, dated Apr. 26, 2020.
International Search Report and Written Opinion in International Appln. No. PCT/IB2018/058351, dated Mar. 22, 2019, 30 pages.
Jo et al., "Cloning, expression, and characterization of an aldehyde dehydrogenase from *Escherichia coli* K-12 that utilizes 3-Hydroxypropionaldehyde as a substrate", Applied Microbiology and Biotechnology, 2008, 81:51-60.
Ko et al., "Aldehyde dehydrogenase activity is important to the production of 3-hydroxypropionic acid from glycerol by recombinant Klebsiella pneumoniae", Process Biochemistry, Apr. 2012, 47:1135-1143.
Ko et al., "Deletion of Putative Oxidoreductases from Klebsiella pneumoniae J2B Could Reduce 1,3-propanediol During the Production of 3-hydroxypropionic Acid from Glycerol", Biotechnology and Bioprocess Engineering, 2015, 20: 834-843.
Ko et al., "Evaluation of Newly Isolated Klebsiella pneumoniae Strains for the Co-Production of 3-hydroxypropionic acid and 1,3-propanediol from Glycerol", Korean Society of Biotechnology and Bioengineering Journal, 2016, 31(4): 246-255.
Kumar et al., "Co-production of 3-hydroxypropionic acid and 1,3-propanediol from glycerol using resting cells of recombinant Klebsiella pneumoniae J2B strain overexpressing aldehyde dehydrogenase", Applied Microbiology and Biotechnology, 2012, 96:373-383.
Kumar et al., "Microbial Production of 3-Hydroxypropionic Acid From Renewable Sources: A Green Approach as an Alternative to Conventional Chemistry", Bioprocessing of Renewable Resources to Commodity Bioproducts, 2014, pp. 381-407.
Kumar et al., "Recent advances in biological production of 3-hydroxypropionic acid", Biotechnology Advances, 2013, pp. 945-961.
Kumar et al., "Simultaneous production of 3-hydroxypropionic acid and 1,3-propanediol from glycerol using resting cells of the lactate dehydrogenase-deficient recombinant Klebsiella pneumoniae overexpressing an aldehyde dehydrogenase", Bioresource Technology, 2013, 135: 555-563.
Lee et al., "3-Hydroxyisobutyrate Dehydrogenase-I from Pseudomonas denitrificans ATCC 13867 Degrades 3-Hydroxypropionic Acid", The Korean Society of Biotechnology and Bioengineering, 2014, 19:1-7.
Lee et al., "Production of 3-Hydroxypropionic Acid from Acrylic Acid by Newly Isolated Rhodococcus erythropolis LG12", Journal of Microbiology and Biotechnology, Nov. 28, 2008, 8 pages.
Li et al., "Improvement of 1,3-propanediol Oxidoreductase (DhaT) Stability Against 3-hydroxypropionaldehyde by Substitution of Cysteine Residues", Biotechnology and Bioprocess Engineering, 2016, 21: 695-703.
Lim et al., ""Optimum rebalancing of the 3-hydroxypropionic acid production pathway from glycerol in *Escherichia coli*"", ACS Synthetic Biology, 2016, 39 pages.
Matsumoto et al., "Salting-out extraction of 3-hydroxypropionic acid with reactive extraction and aqueous two-phase systems," Solvent Extraction Research and Development, Japan, Feb. 24, 2017, 24(2):141-7.
Nhnam et al., "Heterologous gene expression in Pseudomonas denitrificans using Cm inducible promoter: Case study with KGSADH," Theories and Application of Chem. Eng., 2016, 22(1), 460.
No Author Listed, "Development of Microbial Conversion Process for Production of 3-Hydroxypropionic Acid," Institute for Research & Industry University Cooperation Pusan National University, Final Report hosted by the Ministry of Science, ICT and Future Planning, Aug. 2015, 146 pages (with English translation).
Office Action in Chinese Appln. No. 201880069310.5, dated Nov. 1, 2023, 16 pages (with English translation).
Office Action in Indonesian Appln. No. P00202003669, dated Aug. 29, 2022, 8 pages (with English translation).
Office Action in Indonesian Appln. No. P00202003669, dated Jan. 8, 2024, 6 pages (with English translation).
Office Action in Japanese Appln. No. 2020-543421, dated Jul. 16, 2021, 11 pages (with English translation).
Office Action in Japanese Appln. No. 2020-543421, dated Mar. 1, 2022, 9 pages (with English translation).
Office Action in Japanese Appln. No. 2020-543421, dated Sep. 27, 2022, 8 pages (with English translation).
Office Action in Japanese Appln. No. 2022-088728, dated May 23, 2023, 12 pages (with English translation).
Office Action in Japanese Appln. No. 2022-088728, dated Sep. 12, 2023, 6 pages (with English translation).
Office Action in Japanese Appln. No. 2023-043691, dated Mar. 5, 2024, 14 pages (with English translation).
Office Action in Korean Appln. No. 10-2020-7015109, dated Nov. 18, 2023, 12 pages (with English translation).
Office Action in Singaporean Appln. No. 11202003616P, dated Aug. 10, 2023, 8 pages.
Office Action in Singaporean Appln. No. 11202003616P, dated Jul. 24, 2022, 8 pages.

(56) References Cited

OTHER PUBLICATIONS

Office Action in Singaporean Appln. No. 11202003616P, dated Oct. 29, 2021, 13 pages.
Park et al., "Spectrophotometric assay for sensitive detection of glycerol dehydratase activity using aldehyde dehydrogenase", Journal of Bioscience and Bioengineering, 2016, 6 pages.
Partial Supplementary European Search Report in European Appln. No. 18871598.1, dated Jan. 28, 2021, 12 pages.
Raj et al., "A Novel NAD+-dependent Aldehyde Dehydrogenase Encoded by the puuC Gene of Klebsiella pneumoniae DSM 2026 that Utilizes 3-Hydroxypropionaldehyde as a Substrate", Biotechnology and Bioprocess Engineering, 2010, 15: 131-138.
Raj et al., "Effect of process parameters on 3-hydroxypropionic acid production from clycerol using a recombinant *Escherichia coli*", Applied Microbiology and Biotechnology, Apr. 8, 2009, 84:649-657.
Raj et al., "Production of 3-hydroxypropionic acid from glycerol by a novel recombinant Escherichia coli BL21 strain", Process Biochemistry, 2008, 43:1440-1446.
Rathnasingh et al., "Development and Evaluation of Efficient Recombinant Escherichia coli Strains for the Production of 3-Hydroxypropionic Acid From Glycerol", Wiley InterScience, Jun. 4, 2009, 11 pages.
Rathnasingh et al., "Production of 3-hydroxypropionic acid via malonyl-CoA pathway using recombinant *Escherichia coli* strains", Journal of Biotechnology, 2012, 157:633-640.
Read, "B-Hydroxypropionic Acid", Organic Syntheses, 7:54, 1927.
Rhee et al., "Activation of gene expression by a ligand-induced conformational change of a protein-DNA complex," Journal of Biological Chemistry, May 1, 1998, 273(18):11257-66.
Sankaranarayanan et al, "Measurement of crude-cell-extract glycerol dehydratase activity in recombinant *Escherichia coli* using coupled-enzyme reactions", Society for Industrial Microbiology and Biotechnology, 2017, 12 pages.
Sankaranarayanan et al., "Production of 3-hydroxypropionic acid by balancing the pathway enzymes using synthetic cassette architecture," Journal of Biotechnology, Oct. 10, 2017, 259:140-7.
Sankaranarayanan et al., "Production of 3-hydroxypropionic acid from glycerol by acid tolerant *Escherichia coli*", Society of Industrial Microbiology and Biotechnology, 2014, 12 pages.
Seo et al., "Predictive design of mRNA translation initiation region to control prokaryotic translation efficiency," Metabolic Engineering, Jan. 1, 2013, 15:67-74.
Son et al., "Structural insights into the production of 3-hydroxypropionic acid by aldehyde dehydrogenase from Azospirillum brasilense", Scientific Reports, 2017, 10 pages.
Tsuda, "9. Solvent Extraction: 9.1. Solvent extraction of organic compounds in the handling of natural products," Journal of The Japan Society for Analytical Chemistry, 1973, 22(7):934-942, 18 pages (with machine translation).
Watanabe et al., "A Novel α-Ketoglutaric Semialdehyde Dehydrogenase," The Journal of Biological Chemistry, Sep. 29, 2006, 281(39):28876-88.
Zhou et al., "Cloning, Expression and Characterization of 3-Hydroxyisobutyrate Dehydrogenase from Pseudomonas denitrificans ATCC 13867", PLOS One, 2013, vol. 8, Issue 5, 11 pages.
Zhou et al., "Development of a deletion mutant of Pseudomonas denitrificans that does not degrade 3-hydroxypropionic acid", Biotechnological Products and Process Engineering, 2014, 10 pages.
Zhou et al., "Inducible gene expression system by 3-hydroxypropionic acid", Biotechnology for Biofuels, 2015, 8: 169-176.
Zhou et al., "Production of 3-Hydroxypropionic Acid From Glycerol by Recombinant Pseudomonas denitrificans", Biotechnology and Bioengineering, 2013, 11 pages.
Office Action in Japanese Appln. No. 2022-088728, dated Dec. 27, 2024, 4 pages (with English translation).
Office Action in Korean Appln. No. 2024-7005487, dated Dec. 9, 2024, 9 pages (with English translation).

| $K_D$ (nM) | − 3-HP | + 3-HP |
|---|---|---|
| $F_{12}$ | 10.7 | 5.4 |
| $F_{12M}$ | 18.6 | 19.8 |
| $F_{1M2}$ | 79.8 | 316 |
| $F_{1M2M}$ | N/A | N/A |

KGSADH specific activity (U/mg)
(-) 3-HP
(+) 3-HP
$P_{mmsA}$
Hyb-5
Hyb-10
Hyb-15
Hyb-20

M
kDa
70
55
35

% mRNA
Time (min)
kgsA
mmsA(20)kgsA
mmsA
mmsR

Time (min)
kgsA
mmsA (20)kgsA
mmsA
mmsR

FIG. 19A
| Strain | Prediction (a.u.) | Fold |
|---|---|---|
| $P_{mmsA}$ | 26884 | 0.09 |
| UTR-0 | 302528 | 1.00 |
| UTR-1 | 66824 | 0.22 |
| UTR-2 | 319930 | 1.06 |
| UTR-3 | 625945 | 2.07 |
| UTR-4 | 1168900 | 3.90 |
| UTR-5 | 2025947 | 6.70 |
| UTR-6 | 3748169 | 12.39 |
FIG. 19B
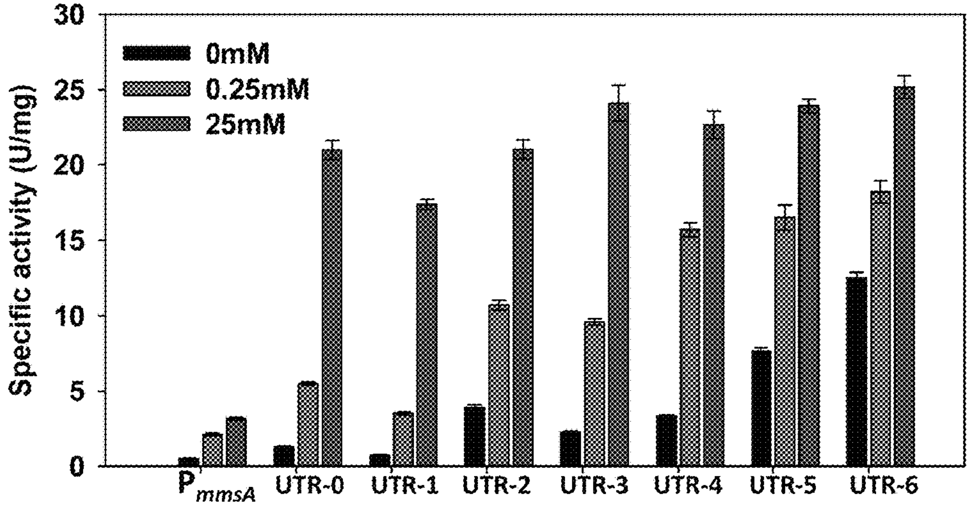
FIG. 19C
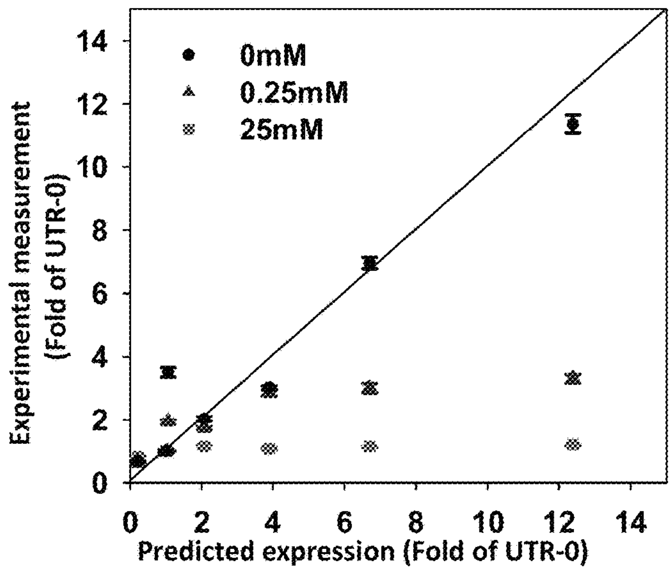

A. RS1 before *cobG*

Highly conserved regions:
P5-L5 (regulatory domain)
J6/3 (receptor domain)-
GAA of J11/10 (interact with regulatory domain)

B. RS2 in front of cobW

Highly conserved regions:
P5-L5 (regulatory domain)
J6/3 (receptor domain)-
GAA of J11/10 (interact with regulatory domain)

C. RS3 in front of cbtB

Highly conserved regions:
(regulatory domain)
J6/3 (receptor domain)-
GAA of J11/10 (interact with regulatory domain)

D. RS4 in front of *btuB*

Highly conserved regions:
P5-L5 (regulatiory domain)
J6/3 (receptor domain) -
GAA of J11/10 (interact with regulatory domain)

Medium components:
- M9 minimal
- 0 g/L YE
- 10 g/L gluconate
- W/ or W/O 20 μM B12

Conditions:
- 200 rpm, 30 °C
- 20 mL working volume in 25 mL flasks
- Sampling time: 12 hrs. after inoculation Medium components:
- M9 minimal
- 0 g/L YE
- 10 g/L gluconate
- 0.1 – 100 nM CoB12

Conditions:
- 200 rpm, 30 °C
- 1.2 mL working volume in 2 mL well (using 96 wells block)
- Sampling time: 12h after inoculation Medium components:
- M9 minimal
- 0 g/L YE
- 10 g/L gluconate
- 0 – 0.1 mg/L $CoCl_2$ Conditions:
- 200 rpm, 30 °C
- 1.2 mL working volume in 2 mL well (using 96 wells block)
- Sampling time: 24h after inoculation Control: *Pd.* ΔΔΔ without essential gene deletion Glycerol

3-HPA

3-HP

FIG. 55A
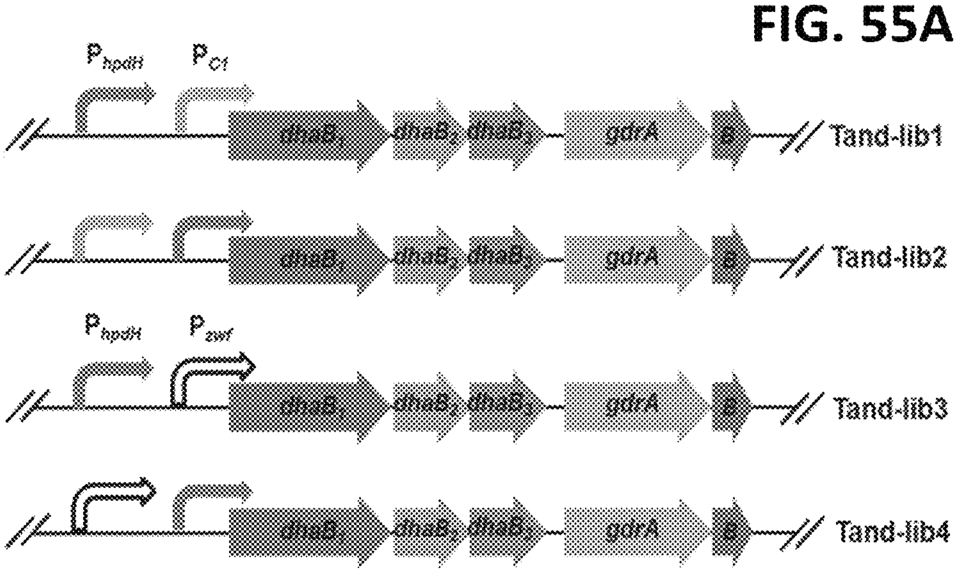
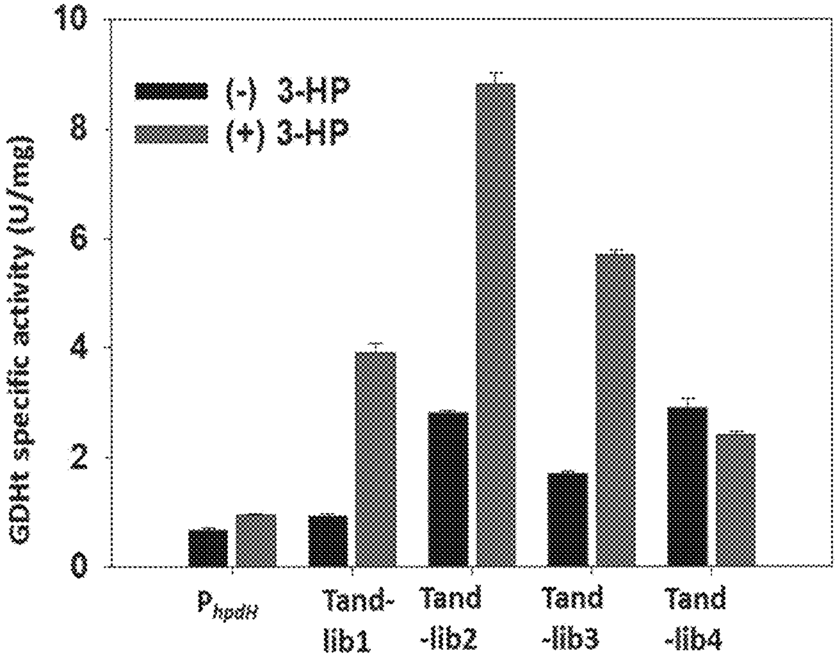
FIG. 55B

-35 -10 RBS *hpdH*

PC3 5' CGTATTTTTATCGCGAACGAACGACTAGGCTCCATCGTCATACCCAAAAGAACAAGAACGACGAGGGACTTTCC 3'

PC3-N1 5' CGTATTNNNNNNNNNNACGAACGACTAGGCTCCATCGTCATACCCAAAAGAACAAGAACGACGAGGGACTTTCC 3'

PC3-N2 5' CGTATTTTTATCGCGANNNNNNNNNNAGGCTCCATCGTCATACCCAAAAGAACAAGAACGACGAGGGACTTTCC 3'

PC3-N3 5' CGTATTTTTATCGCGAACGAACGACTNNNNNNNNNNGTCATACCCAAAAGAACAAGAACGACGAGGGACTTTCC 3'

PC3-N4 5' CGTATTTTTATCGCGAACGAACGACTAGGCTCCATCNNNNNNNNNNAAAGAACAAGAACGACGAGGGACTTTCC 3'

PC3-N5 5' CGTATTTTTATCGCGAACGAACNNNNNNNNNNCATCGTCATACCCAAAAGAACAAGAACGACGAGGGACTTTCC 3'

PC3-N6 5' CGTATTTTTATCGCGAACGAACGACTAGGCTCNNNNNNNNNNCCCAAAAGAACAAGAACGACGAGGGACTTTCC 3'

PC3-N7 5' CGTATTTTTATCGCGAACNNNNNNNNNNGCTCCATCGTCATACCCAAAAGAACAAGAACGACGAGGGACTTTCC 3'

FIG. 56

PRODUCTION AND SEPARATION OF 3-HYDROXYPROPIONIC ACID

CROSS REFERENCE TO RELATED APPLICATIONS

This application is a divisional of U.S. patent application Ser. No. 18/080,163, filed Dec. 13, 2022, which is a divisional of U.S. patent application Ser. No. 16/858,065, filed Apr. 24, 2020, now U.S. Pat. No. 11,566,250, issued Jan. 31, 2023, which is a continuation of U.S. patent application Ser. No. 16/758,815, filed Apr. 23, 2020, now U.S. Pat. No. 11,059,769, issued Jul. 13, 2021, which claims priority under 35 U.S.C. § 120 to International Patent Application No. PCT/IB2018/058351, filed Oct. 25, 2018, which claims the benefit of priority under 35 U.S.C. § 119 (e) of U.S. Provisional Application No. 62/577,361, filed on Oct. 26, 2017 and Provisional Application No. 62/594,318, filed on Dec. 4, 2017, the entire contents of each of which are incorporated herein by reference.

SEQUENCE LISTING

This application contains a Sequence Listing that has been submitted electronically as an XML file named "43961-0002005_SL_ST26.XML." The XML file, created on Jun. 20, 2024, is 115,006 bytes in size. The material in the XML file is hereby incorporated by reference in its entirety.

TECHNICAL FIELD

This disclosure relates to the production of 3-hydroxypropionic acid, including its production from glycerol by recombinant strains, as well as its removal from an aqueous solution (e.g., aqueous broth), and use thereof for producing various chemicals.

BACKGROUND

3-Hydroxypropionic acid (3-HP) and 3-hydroxypropanoate (a salt of 3-HP) are used in the industrial production of various chemicals, such as acrylic acid, which can be used as a cross-linking agent for polymer coatings, metal lubricants and antistatic agents for textiles.

SUMMARY

The disclosure provides methods and apparatus for producing 3-HP or a salt thereof, for removing 3-HP from aqueous solution (e.g., aqueous broth), and for using it to make various chemicals.

In some embodiments, this disclosure provides methods of producing 3-HP or a salt thereoff from glycerol using a genetically modified strain of *Pseudomonas denitrificans*.

In certain embodiments, this disclosure provides methods to create *Pseudomonas* strains that can produce 3-HP or a salt thereof at a high titer without external supplementation of coenzyme B12.

In some embodiments, this disclosure provides an expression system (e.g., an expression module or an expression construct) for use in *Pseudomonas* strains. Such an expression system can include, inter alia, a tandem promoter system which includes two or more promoters operably linked to control expression of a downstream gene. Such a promoter can be an inducible promoter or a constitutive promoter. Optionally, an expression system includes at least one inducible promoter. An expression system can be used to produce target proteins/enzymes or to enhance metabolic pathways to produce target products at high titer, such as 3-HP or a salt thereof, by minimizing toxic intermediates, and/or increase vitamin B12 production, a cofactor in the first reaction in the 3-HP synthetic pathway.

In some embodiments, this disclosure provides nucleic acids that encode these systems, the recombinant bacteria expressing these systems, and/or the methods of culturing the bacteria to produce 3-HP or a salt thereof. These bacteria have been modified to include one or more expression systems that respond to the target product levels, in this case 3-HP or a salt thereof in the media and express the genes used for the production of the target product, e.g., 3-HP or a salt thereof. In some cases, these bacteria have also been modified to include one or more expression systems to increase expression of the genes used for the production of B12. The conditions for culturing said bacterium, to increase 3-HP production (or a salt thereof), are also provided herein.

In one aspect, the disclosure provides for an expression system, comprising, consisting of, or consisting essentially of a first promoter that is inducible by a small molecule, a second promoter, a first gene encoding a protein involved in the synthesis of 3-HP (or a salt thereof) or B12, a modified UTR, and a native sequence encoding up to 20 amino acids from the N-terminus of a native *Pseudomonas denitrificans* protein, wherein the native sequence is operably linked to the 3'-terminus of the modified UTR and operably linked to the 5'-terminus of the first gene, and the first and second promoters are operably linked in tandem upstream of the modified UTR.

In some embodiments of all aspects, the expression system further comprises, consists of, or consists essentially of a third promoter; and a second gene encoding a transcriptional regulator configured to regulate expression of the first gene, wherein the third promoter is operably connected to the second gene. In some instances, the second promoter is inducible by the small molecule. In some cases, the native sequence is operably linked to the 5'-terminus of the first gene to define a fusion gene, the second promoter is a native promoter for the native *Pseudomonas denitrificans* protein, and the second promoter is operably linked to the 5'-terminus of the fusion gene. In some embodiments the first promoter is operably linked to the 5'-terminus of the second promoter, the second promoter is operably linked to the 5'-terminus of the modified UTR, and the modified UTR is operably linked to the 5'terminus of the fusion gene.

In one aspect, the disclosure provides for a nucleic acid, comprising, consisting of, or consisting essentially of a first and a second promoter, wherein the first promoter is an inducible promoter and is inducible by a small molecule; the first and second promoters are operably linked to a first gene; and the first gene encodes a protein involved in the synthesis of 3-hydroxypropionic acid (3-HP) (or a salt thereof) or coenzyme B12.

In some embodiments of all aspects, the first gene encodes a protein involved in the synthesis of 3-hydroxypropionic acid (3-HP) (or a salt thereof) and is selected from the group consisting of a glycerol dehydratase, a glycerol dehydratase reactivase, and an aldehyde dehydrogenase. In some cases, the first gene comprises at least one gene selected from the group consisting of dhaB1, dhaB2, dhaB3, gdrA, gdrB, and kgsA. In some instances, the first gene comprises a dhaB1 gene, a dhaB2 gene, a dhaB3 gene, a gdrA gene, and a gdrB gene.

In some embodiments, the first gene is dhaB1, and the sequence comprises, consists of, or consists essentially of a sequence that is at least 95% identical to SEQ ID NO: 1. In some cases, the first gene is dhaB2, and the sequence comprises, consists of, or consists essentially of a sequence that is at least 95% identical to SEQ ID NO: 2. In some instances, the first gene is dhaB3, and the sequence comprises, consists of, or consists essentially of a sequence that is at least 95% identical to SEQ ID NO: 3.

In some embodiments of all aspects, the first gene is gdrA, and the sequence comprises, consists of, or consists essentially of a sequence that is at least 95% identical to SEQ ID NO: 4. In some cases, the first gene is grdB and the sequence comprises, consists of, or consists essentially of a sequence that is at least 95% identical to SEQ ID NO: 5.

In some embodiments of all aspects, the first gene comprises, consists of, or consists essentially of an aldehyde dehydrogenase gene. In some instances, the aldehyde dehydrogenase is kgsA. In some cases, kgsA comprises, consists of, or consists essentially of a sequence that is at least 95% identical to SEQ ID NO: 6.

In some embodiments of all aspects, the small molecule is an acid or alcohol. In some cases, the small molecule acid or alcohol is selected from the group consisting of L-lactic acid (LAC), acetic acid (AcOH), propionic acid (PA), 3-hydroxypropionic acid (3-HP), 3-hydroxybutyrate (3-HB), 1,3-propanediol (1,3-PDO), 2,3-butanediol (2,3-BDO), L-valine (L-val), and 3-hydroxyisobutyrate (3-HIB), or salts thereof. In some instances, the small molecule acid or alcohol is selected from the group consisting of 3-hydroxypropionic acid (3-HP), 3-hydroxybutyrate (3-HB), L-valine (L-val), and 3-hydroxyisobutyrate (3-HIB). In some cases, the small molecule is 3-hydroxypropionic acid (3-HP) (or a salt thereof).

In some embodiments of all aspects, the nucleic acid comprises, consists of, or consists essentially of a sequence that is at least 85% identical to SEQ ID NO: 65. In some cases, the nucleic acid comprises, consists of, or consists essentially of SEQ ID NO: 65.

In some embodiments of all aspects, the second promoter is operably linked to the 3'-terminus of the first promoter and the first gene is operably downstream of the second promoter. In some embodiments of all aspects, the first promoter is operably linked to the 3'-terminus of the second promoter and the first gene is operably downstream of the second promoter.

In some embodiments of all aspects, the second promoter is a constitutive promoter. In some instances, the second promoter is a second inducible promoter. In some cases, the intergenic space between the first and the second promoter does not include a terminator sequence. In some instances, first promoter and the second promoter regulate expression of the first gene.

In some embodiments of all aspects, the first promoter is derived from a $P_{mmsA}$ promoter, a $P_{hbdH\text{-}1}$ promoter, a $P_{hbdH\text{-}4}$ promoter, or a $P_{hpdH}$ promoter. In some instances, the first promoter comprises, consists of, or consists essentially of a sequence that is at least 95% identical to SEQ ID NO: 14 ($P_{mmsA}$ promoter). In some cases, the first promoter comprises, consists of, or consists essentially of a sequence that is at least 95% identical to SEQ ID NO: 13 (PhbdH-1 promoter). In some instances, the first promoter comprises, consists of, or consists essentially of a sequence that is at least 95% identical to SEQ ID NO: 11 (PhbdH-4 promoter). In some cases, the first promoter comprises, consists of, or consists essentially of a sequence that is at least 95% identical to SEQ ID NO: 12 (PhpdH promoter). In some instances, the first promoter comprises, consists of, or consists essentially of a sequence that is selected from the group consisting of SEQ ID NO: 11; SEQ ID NO: 12; SEQ ID NO: 13; and SEQ ID NO: 14.

In some embodiments of all aspects, the first promoter comprises, consists of, or consists essentially of a $P_{mmsA}$ promoter and the nucleic acid further comprises an operator site operably linked to the 5'-terminus of the $P_{mmsA}$ promoter. In some cases, the nucleic acid described here in comprises, consists of, or consists essentially of a sequence that is 95% identical to SEQ ID NO: 15. In some instances, the nucleic acid described herein comprises, consists of, or consists essentially of a sequence that is 95% identical to SEQ ID NO: 16 (O1 of MmsA operator) and a sequence that is 95% identical to SEQ ID NO: 17 (O2 of MmsA operator). In some embodiments of all aspects, the nucleic acid described herein comprises, consists of, or consists essentially of a sequence that is 95% identical to SEQ ID NO: 18 (PmmsA and operator FIG. 3). In some cases, the nucleic acid described herein comprises, consists of, or consists essentially of a sequence selected from the group consisting of SEQ ID NO: 15, 18, 19 (PmmsA2a), 20 (PmmsA2b), and 21 (PmmsA2ab).

In some embodiments of all aspects, the second promoter is derived from a $P_{mmsA}$ promoter, a $P_{hbdH\text{-}1}$ promoter, a $P_{hbdH\text{-}4}$ promoter, a $P_{hpdH}$ promoter, or a $P_{zwf}$ promoter. In some cases, the second promoter comprises, consists of, or consists essentially of a sequence that is at least 95% identical to SEQ ID NO: 11 (PhbdH-4 promoter). In some instances, the second promoter comprises, consists of, or consists essentially of a sequence that is at least 95% identical to SEQ ID NO: 12 (PhpdH promoter). In some embodiments of all aspects, the second promoter comprises, consists of, or consists essentially of a sequence that is at least 95% identical to SEQ ID NO: 14 (PmmsA promoter). In some cases, the second promoter comprises, consists of, or consists essentially of a sequence that is at least 95% identical to SEQ ID NO: 13 (PhbdH-1 promoter). In some embodiments of all aspects, the second promoter comprises, consists of, or consists essentially of a sequence that is at least 95% identical to SEQ ID NO: 7 (Pzwf). In some cases, the second promoter comprises, consists of, or consists essentially of a sequence that is at least 95% identical to SEQ ID NO: 8 (Pzwf-1). In some instances, the second promoter comprises, consists of, or consists essentially of a sequence that is at least 95% identical to SEQ ID NO: 9 (Pzwf-7). In some embodiments of all aspects, the second promoter comprises, consists of, or consists essentially of a sequence that is at least 95% identical to SEQ ID NO: 62 (Pzwf-7 shorter). In some cases, the second promoter comprises, consists of, or consists essentially of a sequence that is at least 95% identical to SEQ ID NO: 10 (Pzwf-12). In some instances, the second promoter comprises, consists of, or consists essentially of a sequence selected from the group consisting of SEQ ID NO: 7, 8, 9, 10, 11, 12, 13, 14, 52-60, 61, 62, and 63 (e.g., Pzwf promoters).

In some embodiments of all aspects, the first promoter comprises, consists of, or consists essentially of the $P_{mmsA}$ promoter and the second promoter comprises, consists of, or consists essentially of the $P_{hbdH\text{-}4}$ promoter. In some cases, the first promoter comprises, consists of, or consists essentially of a sequence that is at least 95% identical to SEQ ID NO: 14 (PmmsA promoter sequence), and the second promoter comprises, consists of, or consists essentially of a sequence that is at least 95% identical to SEQ ID NO: 11 (PhbdH-4 promoter). In some instances, the first promoter comprises, consists of, or consists essentially of the PhbdH-1 promoter and the second promoter comprises, consists of, or consists essentially of the PhpdH promoter. In some cases, the first promoter comprises, consists of, or consists essentially of a sequence that is at least 95% identical to SEQ ID NO: 13 (PhbdH-1 promoter sequence), and the second promoter comprises, consists of, or consists essentially of a sequence that is at least 95% identical to SEQ ID NO: 12 (PhpdH promoter).

In some embodiments of all aspects, the second promoter comprises, consists of, or consists essentially of a PhbdH promoter and the nucleic acid further comprises, consists of, or consists essentially of an operator site operably linked to the N-terminus of the PhbdH promoter. In some cases, the operator site comprises, consists of, or consists essentially of one or more sequence that is at least 95% identical to SEQ ID NO: RBS-1, RBS-2, ABS-1, ABS-2, and ABS-3. In some instances, the operator site comprises, consists of, or consists essentially of a sequence that is at least 95% identical to SEQ ID NOs: RBS-1 site and ABS-2. In some cases, the operator site comprises, consists of, or consists essentially of SEQ ID NOs: RBS-1 site and ABS-2.

In some embodiments of all aspects, the nucleic acid further comprises, consists of, or consists essentially of a gene encoding a transcriptional regulator that regulates expression of the first gene. In some instances, the transcriptional regulator binds to the first or second promoter. In some cases, the transcriptional regulator is a LysR-type transcriptional regulator (LTTR). In some embodiments, the transcriptional regulator is MmsR or HpdR. In some cases, the transcriptional regulator is MmsR.

In some embodiments of all aspects, the transcriptional regulator binds to the first promoter. In some cases, the transcriptional regulator is derived from a mmsR protein and the first promoter is derived from a PmmsA promoter. In some cases, the transcriptional regulator comprises, consists of, or consists essentially of a mmsR protein and the first promoter comprises, consists of, or consists essentially of a PmmsA promoter.

In some embodiments of all aspects, the nucleic acid described herein further comprises, consists of, or consists essentially of an operator site, wherein the MmsR protein binds to the operator site. In some cases, the nucleic acid described herein comprises, consists of, or consists essentially of a sequence that is at least 95% identical to SEQ ID NO: 19 (PmmsA2a). In some instances, the nucleic acid described herein comprises, consists of, or consists essentially of a sequence that is selected from the group consisting of SEQ ID NO: 19-21 (PmmsA2a, A2b, A2ab). In some cases, the transcriptional regulator binds to the second promoter. In some embodiments of all aspects, the second promoter is a constitutive promoter. In some cases, the transcriptional regulator is a HpdR protein and the second promoter is derived from a hpdH promoter. In some instances, the second promoter comprises, consists of, or consists essentially of a sequence that is at least 95% identical to the sequence of $P_{hpdH}$ SEQ ID NO: 12.

In some embodiments of all aspects, the transcriptional regulator binds to the first promoter and has enhanced binding to the first promoter in the presence of the small molecule. In some cases, the transcriptional regulator binds to the second promoter and has enhanced binding to the second promoter in the presence of the small molecule. In some instances, the transcriptional regulator is self-regulating. In some cases, the nucleic acid described herein further comprises, consists of, or consists essentially of a third promoter that is operably linked to the gene encoding the first transcriptional regulator.

In some embodiments of all aspects, the third promoter comprises, consists of, or consists essentially of a sequence that is 95% identical to the sequence selected from the group consisting of SEQ ID NO: 7-10 and 52-63. In some cases, the second constitutive promoter is selected from the group consisting of SEQ ID NOs: 9, 10, 57-60, 62, and 63; the transcriptional regulator comprises, consists of, or consists essentially of a MmsR protein; and the first promoter comprises, consists of, or consists essentially of $P_{mmsA}$. In some instances, the second constitutive promoter is selected from the group consisting of SEQ ID NOs: 9, 10, 57-60, 62, and 63; the transcriptional regulator comprises, consists of, or consists essentially of a HpdR protein; and the first promoter comprises, consists of, or consists essentially of PhbdH. In some cases, the third promoter comprises, consists of, or consists essentially of SEQ ID NO: 10. In some cases, the third promoter comprises, consists of, or consists essentially of SEQ ID NO: 62.

In some embodiments of all aspects, the first gene comprises, consists of, or consists essentially of a modified 5' UTR of the gene. In some instances, the first gene comprises, consists of, or consists essentially of a sequence selected from the group consisting of SEQ ID NO: 22-28 and 64. (UTR 0-6). In some cases, the 5' UTR comprises, consists of, or consists essentially of SEQ ID NO: 28 (UTR-6). In some instances, the first gene comprises, consists of, or consists essentially of a gene encoding kgsA and the 5'UTR comprises, consists of, or consists essentially of SEQ ID NO: 28 (UTR-6).

In some embodiments of all aspects, at least the 10 codons at the 5'terminus of the first gene are optimized for translation in *Pseudomonas denitrificans*. In some cases, up to 10 codons at the 5'terminus of the first gene are optimized for translation in *Pseudomonas denitrificans*. In some instances, codon optimization comprises, consists of, or consists essentially of: measuring a codon frequency of each amino acid in a gene encoding a native *Pseudomonas denitrificans* protein; using the codon frequency of the native protein to replace the 10 codons at the 5'-terminus of the first gene with an optimized 10 codons, wherein the codon for each amino acid of the optimized 10 codons is present at the same frequency as the codon frequency of the native protein. In some cases, the codon frequency for each amino acid in the optimized second 10 codons is more than 0. In some instances, the codon frequency is measured of each amino acid in the 10 codons at the 5' terminus of the gene encoding the native *Pseudomonas denitrificans* protein.

In some embodiments of all aspects, the nucleic acid comprises, consists of, or consists essentially of a sequence that is 95% identical to a sequence selected from the group consisting of SEQ ID NOs: 29, 30, and 31. (Opt1-3). In some cases, the first gene comprises, consists of, or consists essentially of a gene encoding kgsA and comprises, consists of, or consists essentially of a sequence selected from the group consisting of SEQ ID NO: 29-31. In some instances, the first gene is fused at its 5'-terminus to a sequence encoding up to 20 amino acids that are derived from the 5'terminus of a second gene encoding a native *Pseudomonas denitrificans* protein, thereby creating a fusion gene. In some cases, the mRNA of the fusion gene has a higher stability than the mRNA of the first gene alone. In some instances, the fusion gene increases gene translation when compared to the first gene alone. In some embodiments of all aspects, the mRNA of the fusion gene is more resistant to ribonuclease degradation than the mRNA of the first gene alone. In some cases, the fusion gene increases gene translation in comparison to the first gene alone.

In some embodiments of all aspects, the first gene is fused at its 5'-terminus to a sequence encoding up to 20 (5, 10, 15, or 20) amino acids that are derived from the 5'terminus of a second gene encoding a native *Pseudomonas denitrificans* protein, thereby creating a fusion gene, and the second promoter is derived from the native promoter for the second gene. In some cases, the second promoter is derived from the $P_{mmsA}$ promoter and the fusion gene comprises, consists of, or consists essentially of a sequence encoding at least 5, 10, 15, or 20 amino acids in the N-terminus of a native MmsA protein. In some instances, the second promoter comprises, consists of, or consists essentially of the $P_{mmsA}$ promoter and the fusion gene comprises, consists of, or consists essentially of a sequence encoding five or more amino acids from the N-terminus of a native MmsA gene, and the fusion gene is operably linked to the 3' end of the $P_{mmsA}$ promoter. In some cases, the nucleic acid comprises, consists of, or consists essentially of a sequence selected from the group consisting of SEQ ID NOs: 32-35.

In some embodiments of all aspect, the first gene is fused at its 5'-terminus to a sequence encoding up to 20 (5, 10, 15, or 20) amino acids that are derived from a sequence encoding the N-terminus of a native *Pseudomonas denitrificans* MmsA protein. In some cases, the nucleic acid described herein comprises, consists of, or consists essentially of a sequence selected from the group consisting of SEQ ID NOs: 32-35 (Pcm-mmsA (5) (10) (15) (20)).

In some embodiments of all aspect, the first gene encodes a protein involved in the synthesis of vitamin B12. In some cases, the first gene comprises, consists of, or consists essentially of a gene selected from the group consisting of cobJ, cobI, cobH, cobG, cobL, cobF, cobK, gst, xre, chID, chlI, dahp, cobN, cobW, cbtBA, cobE, cobM, btuB, cobO, cob, cobR, cobD, cobC, cobQ, cobU, cobP, bgpM, and cobV. In some instances, the first gene comprises, consists of, or consists essentially of bgpM. In some cases, the first gene is derived from a *Pseudomonas* species selected from the group consisting of *P. denitrifcans; P. aeruginosa; P. entomophila; P. putida; P. syringae; P. fluorescens; P mendocina*; and *P. stutzeri.*

In another aspect, the disclosure provides for a nucleic acid comprising, consisting of, or consisting essentially of a first promoter operably linked to a first gene that encodes a protein involved in the synthesis of coenzyme B12. In some cases, the first promoter is a constitutive promoter. In some instances, the nucleic acid comprises, consists of, or consists essentially of a sequence selected from SEQ ID NOs: 7-10 and 52-63. In some embodiments of all aspects, the first gene comprises, consists of, or consists essentially of one or more genes selected from the group consisting of cobJ, cobI, cobH, cobG, cobL, cobF, cobK, gst, xre, chlD, chlI, dahp, cobN, cobW, cbtBA, cobE, cobM, btuB, cobO, cob, cobR, cobD, cobC, cobQ, cobU, cobP, bgpM, and cobV. In some cases, the first gene is from a *Pseudomonas* species selected from the group consisting of *P. denitrifcans; P. aeruginosa; P. entomophila; P. putida; P. syringae; P. fluorescens; P mendocina*; and *P. stutzeri.*

In some embodiments of all aspects, the nucleic acid described herein further comprises, consists of, or consists essentially of a second promoter operably linked to the first promoter. In some cases, the first and the second promoter regulate expression of the first gene. In some instances, the first promoter is not a native promoter for the first gene.

In another aspect, the disclosure provides for a nucleic acid comprising a cobG gene, a $P_{edd}$ promoter, a $P_{sucA}$ promoter, and a cobL gene; wherein the $P_{edd}$ promoter is operably linked to the cobG gene and the $P_{sucA}$ promoter, and the $P_{sucA}$ promoter is operably linked to the cobL gene. In some cases, the $P_{edd}$ promoter comprises, consists of, or consists essentially of the sequence SEQ ID NO: 36; and the $P_{sucA}$ promoter comprises, consists of, or consists essentially of the sequence SEQ ID NO: 37. In some embodiments, the nucleic acid described herein comprises, consists of, or consists essentially of the sequence SEQ ID NO: 38.

In one aspect, the disclosure provides for a nucleic acid comprising, consisting of, or consisting essentially of a cobG gene, a $P_{sp9}$ promoter, a $P_{zwf}$ promoter, and a cobL gene; wherein the $P_{sp9}$ promoter is operably linked to the cobG gene and the $P_{zwf}$ promoter, and the $P_{zwf}$ promoter is operably linked to the cobL gene. In some cases, the $P_{sp9}$ promoter comprises, consists of, or consists essentially of SEQ ID NO: 39; and the $P_{zwf}$ promoter comprises SEQ ID NO: 40. In some instances, the nucleic acid described herein comprises, consists of, or consists essentially of SEQ ID NO: 41.

In one aspect, the disclosure provides for a nucleic acid comprising, consisting of, or consisting essentially of a cobW gene, a $P_{zwf}$ promoter, a $P_{sp9}$ promoter, and a cbtB gene, wherein the $P_{zwf}$ promoter is operably linked to the cobW gene and the $P_{sp9}$ promoter, and the $P_{sp9}$ promoter is operably linked to the cbtB gene. In some cases, the Pzwf promoter comprises SEQ ID NO: 42; and the Psp9 promoter comprises SEQ ID NO: 43. In some instance, the nucleic acid described herein comprises, consists of, or consists essentially of SEQ ID NO: 44.

In one aspect, the disclosure provides for a nucleic acid comprising, consisting of, or consisting essentially of a cobW gene, a $P_{tkt}$ promoter, a $P_{sp2}$ promoter, and a cbtB gene, wherein the $P_{tkt}$ promoter is operably linked to the cobW gene and the $P_{sp2}$ promoter, and the $P_{sp2}$ promoter is operably linked to the cbtB gene. In some instances, the $P_{tkt}$ promoter comprises, consists of, or consists essentially of SEQ ID NO: 45; and the Psp2 promoter comprises, consists of, or consists essentially of SEQ ID NO: 46. In some cases, the nucleic acid described herein comprises, consists of, or consists essentially of SEQ ID NO: 47.

In one aspect, the disclosure provides for a nucleic acid comprising, consisting of, or consisting essentially of a $P_{zwf}$ promoter operably linked to a tonB gene (e.g., a butB gene). In some cases, the Pzwf promoter comprises, consists of, or consists essentially of SEQ ID NO: 48. In some instances, the nucleic acid described herein comprises, consists of, or consists essentially of SEQ ID NO: 49.

In one aspect, the disclosure provides for a nucleic acid comprising, consisting of, or consisting essentially of a $P_{sp9}$ promoter operably linked to a tonB gene (e.g., a butB gene). In some cases, the Psp9 promoter comprises, consists of, or consists essentially of SEQ ID NO: 50. In some instances, the nucleic acid described herein comprises, consists of, or consists essentially of SEQ ID NO: 51.

In some embodiments of all aspects, the nucleic acid comprises, consists of, or consists essentially of one or more sequences derived from *Pseudomonas denitrificans*. In some cases, the first or the second promoters are derived from *Pseudomonas denitrificans*. In some instances, the nucleic acid comprises, consists of, or consists essentially of one or more sequences derived from an *Enterobacter, Lactobacillus, Pseudomonas*, or Azospirillum bacterium. In some cases, the first gene is derived from an *Enterobacter, Lactobacillus, Pseudomonas*, or Azospirillum bacterium.

In one aspect, the disclosure provides for a nucleic acid comprising a DhaB expression module that comprises, consists of, or consists essentially of a sequence that is at least 85% identical to SEQ ID NO: 66 (DhaB expression module). In some cases, the sequence is at least 90% identical to SEQ ID NO: 66. In some instances, the nucleic acid described herein comprises, consists of, or consists essentially of SEQ ID NO: 66.

In one aspect, the disclosure provides for a nucleic acid comprising a DhaB expression module that comprises, consists of, or consists essentially of a sequence that is at least 85% identical to SEQ ID NO: 67 (kgsA expression module). In some cases, the sequence is at least 90% identical to SEQ ID NO: 67. In some instances, the sequence comprises, consists of, or consists essentially of SEQ ID NO: 67.

In one aspect, the disclosure provides for a nucleic acid comprising a DhaB expression module comprising, consisting of, or consisting essentially of a UTR of the gdrA gene comprising, consisting of, or consisting essentially of SEQ ID NO: 68 and a UTR of the gdrB gene comprising, consisting of, or consisting essentially of SEQ ID NO: 69. In some cases, the nucleic acid comprises, consists of, or consists essentially of a sequence that is at least 85% identical to a sequence selected from the group consisting of SEQ ID NO: 70-72. In some instances, the nucleic acid comprises, consists of, or consists essentially of a sequence selected from the group consisting of SEQ ID NO: 70-72.

In one aspect, the disclosure provides for a nucleic acid comprising a coenzyme B12 sensor comprising, consisting of, or consisting essentially of a sequence that is at least 85% identical to a sequence selected from the group consisting of SEQ ID NO: 73 and 74. In some cases, the nucleic acid described herein comprises, consists of, or consists essentially of a sequence selected from the group consisting of SEQ ID NO: 73 and 74.

In one aspect, the disclosure provides for a nucleic acid comprising, consisting of, or consisting essentially of a coenzyme B12 expression module that comprises, consists of, or consists essentially of a first gene involved in the synthesis of coenzyme B12, a first promoter that is induced by a small molecule, and a second promoter, wherein the first and second promoters are operably linked in tandem upstream of the first gene such that they regulate expression of the first gene. In some cases, the nucleic acid further comprises, consists of, or consists essentially of a second gene involved in the synthesis of coenzyme B12, a third promoter that is induced by a small molecule, and a fourth promoter, wherein the third and fourth promoters are operably linked in tandem upstream of the second gene such that they regulate expression of the second gene. In some embodiments of all aspects, the nucleic acid further comprises, consists of, or consists essentially of a third gene involved in the synthesis of coenzyme B12, a fifth promoter that is induced by a small molecule, and a sixth promoter, wherein the fifth and sixth promoters are operably linked in tandem upstream of the third gene such that they regulate expression of the third gene. In some cases, the nucleic acid further comprises, consists of, or consists essentially of a fourth gene involved in the synthesis of coenzyme B12, a seventh promoter that is induced by a small molecule, and a eighth promoter, wherein the seventh and eighth promoters are operably linked in tandem upstream of the fourth gene such that they regulate expression of the fourth gene. In some instances, the first, second, third, and fourth genes each comprise, consist of, or consist essentially of one or more genes selected from the group consisting of cobJ, cobI, cobH, cobG, cobL, cobF, cobK, gst, xre, chlD, chlI, dahp, cobN, cobW, cbtBA, cobE, cobM, btuB, cobO, cob, cobR, cobD, cobC, cobQ, cobU, cobP, bgpM, and cobV. In some cases, the first gene comprises, consists of, or consists essentially of bgpM.

In some embodiments of all aspects the nucleic acid does not include any native riboswitches that regulate genes involved in the production of coenzyme B12. In some cases, the nucleic acid does not include SEQ ID NOs: 75 or 76.

In another aspect, the disclosure provides for a recombinant bacterium comprising, consisting of, or consisting essentially of the nucleic acid described herein. In some cases, the bacterium is a *Pseudomonas* species. In some instances, the bacterium is *Pseudomonas denitrificans*.

In some embodiments of all aspects, the nucleic acid is on an expression plasmid. In some cases, the nucleic acid is integrated into the bacterium's chromosome. In some instances, the nucleic acid is on an episome.

In another aspect, the disclosure provides for a recombinant bacterium comprising, consisting of, or consisting essentially of a first nucleic acid comprising, consisting of, or consisting essentially of a DhaB expression module and a second nucleic acid comprising, consisting of, or consisting essentially of a ALDH expression module. In some cases, the DhaB expression module comprises, consists of, or consists essentially of any one of the nucleic acids described herein. In some instances, the ALDH expression module comprises, consists of, or consists essentially of any one of the nucleic acids described herein.

In some embodiments of all aspects, the first and the second nucleic acids are on expression plasmids. In some cases, the first and the second nucleic acids are on episomes. In some instances, the first and the second nucleic acids are integrated into the bacterium's chromosome. In some cases, the first nucleic acid is integrated into the bacterium's chromosome and the second nucleic acid is on an expression plasmid. In some instances, the first nucleic acid is on an expression plasmid and the second nucleic acid is integrated into the bacterium's chromosome. In some embodiments of all aspects, the first nucleic acid is integrated into the bacterium's chromosome and the second nucleic acid is on an episome. In some instances, the first nucleic acid is on an episome and the second nucleic acid is integrated into the bacterium's chromosome.

In some embodiments of all aspects, the first nucleic acid is integrated into the bacterium's chromosome at a first position and the second nucleic acid is integrated into the bacterium's chromosome at a second position; and the first and second positions are within 2500 kilo base pairs of each other. In some cases, the first and second positions are within 100 kilo base pairs of each other. In some instances, the first and second positions are within 50 kilo base pairs of each other. In some cases, the first and second positions are within 1000 base pairs of each other.

In some embodiments of all aspects, the first nucleic acid is integrated into the bacterium's chromosome at a first position that is within 4000 base pairs of the origin of replication. In some cases, the first position is within 1000 base pairs of the origin of replication.

In another aspect, the disclosure provides for a recombinant bacterium comprising, consisting of, or consisting essentially of a coenzyme B12 expression module that comprises, consists of, or consists essentially of a first gene involved in the synthesis of coenzyme B12, a first promoter that is induced by a small molecule, and a second promoter, wherein the first and second promoters are operably linked in tandem upstream of the first gene.

In some embodiments of all aspects, the bacterium is a *Pseudomonas denitrificans* bacterium. In some cases, the bacterium comprises, consists of, or consists essentially of a deletion at a first position of a first riboswitch which regulates expression of the first gene, and the first and second promoters are integrated into the bacterium's chromosome at the first position such that they regulate expression of the first gene. In some instances, the bacterium further comprises, consists of, or consists essentially of a second deletion at a second position of a second riboswitch which regulates expression of a second gene involved in the synthesis of coenzyme B12, a third deletion at a third position of a third riboswitch which regulates expression of a third gene involved in the synthesis of coenzyme B12, and a fourth deletion at a fourth position of a fourth riboswitch which regulates expression of a fourth gene involved in the synthesis of coenzyme B12. In some cases, the recombinant bacterium further comprises, consists of, or consists essentially of a third promoter and a fourth promoter which are operably linked in tandem and integrated into the chromosome at the second position such that they regulate expression of the second gene; a fifth promoter and a sixth promoter which are operably linked in tandem and integrated into the chromosome at the third position such that they regulate expression of the third gene; and a seventh and eighth promoter which are operably linked in tandem and integrated into the chromosome at the fourth position such that they regulate expression of the fourth gene. In some embodiments of all aspects, the bacterium produces more coenzyme B12 than native *Pseudomonas denitrificans*. In some embodiments of all aspects, the recombinant bacterium described herein further comprises, consists of, or consists essentially of a coenzyme B12 expression module.

In another aspect, the disclosure provides for a method of producing 3-HP or a salt thereof, comprising, consisting of, or consisting essentially of culturing a recombinant bacterium described herein under conditions sufficient to produce 3-HP or a salt thereof. In some cases, the conditions are sufficient to produce at least 85 g/L of 3-HP or a salt thereof. In some instances, the conditions are sufficient to produce at least 90 g/L of 3-HP or a salt thereof. In some embodiments of all aspects, the conditions are sufficient to produce at least 95 g/L of 3-HP or a salt thereof. In some cases, the conditions are sufficient to produce at least 100 g/L of 3-HP or a salt thereof.

In some embodiments of all aspects, culturing the bacterium does not include the addition of external coenzyme B12. In some cases, culturing the bacterium comprises addition external coenzyme B12 to the culture.

In some cases, culturing comprises, consists of, or consists essentially of growing the bacterium in a media comprising a carbon source selected from the group consisting of glycerol, glucose, gluconate, glutamate, and citric acid. In some instances culturing comprising, consisting of, or consisting essentially of inducing the bacterium to produce 3-HP or a salt thereof by adding glycerol. In some cases, the glyercol is add mid-log phase.

In some embodiments of all aspects, culturing comprises, consists of, or consists essentially of growing the bacterium in a media comprising a nitrogen source selected from the group consisting of yeast extract, corn steep liquor powder, and corn steep liquor paste.

In some embodiments of all aspects, culturing comprises, consists of, or consists essentially of growing the bacterium at a pH between 6.8 and 7.8. In some cases, culturing comprises, consists of, or consists essentially of adding one or more bases selected from the group consisting of NaOH, KOH, $NaHCO_3$, $NH_4HCO_3$, $NH_4OH$, $(NH_4)_2CO_3$, and $Na_2CO_3$. In some instances, culturing comprises, consists of, or consists essentially of adding at least one base selected from the group consisting of NaOH, KOH, $NaHCO_3$, $NH_4HCO_3$, $NH_4OH$, $(NH_4)_2CO_3$, and $Na_2CO_3$. In some cases, culturing comprises, consists of, or consists essentially of diluting the base concentration and increasing the acid concentration (see FIG. 46 and FIG. 49).

In some embodiments of all aspects, culturing comprises, consists of, or consists essentially of growing the bacterium at a temperature between 28 and 40 degrees Celsius. In some cases, culturing comprises, consists of, or consists essentially of growing the bacterium at 33 degrees Celsius.

In another aspect, the disclosure provides for a method of producing 3-HP or a salt thereof, the method comprising, consisting of, or consisting essentially of: providing the recombinant bacterium described herein in a culture media suitable for growth of the bacterium and production of 3-HP or a salt thereof. In some cases the method described herein comprises, consists of, or consists essentially of separating 3-HP or a salt thereof from the bacterium or culture media.

In some instances, the culture media comprises, consists of, or consists essentially of a dissolved oxygen concentration that is approximately 2-20% dissolved oxygen. In some embodiments of all aspects the dissolved oxygen concentration is no more than 20%. In some cases, the dissolved oxygen concentration is at least 2%.

Further, this disclosure relates to methods of providing and reacting 3-hydroxypropionic acid.

The disclosure provides methods for removing 3-hydroxypropionic acid (3-HP) from an aqueous solution. The methods can be relatively simple and inexpensive to perform. The methods can provide relatively high yields of 3-HP.

The disclosure also provides methods for making acrylic acid. The methods can be relatively simple and inexpensive to perform. The methods can be performed with little, or no, acrylic acid polymerization taking place. The methods can provide relatively high yields of acrylic acid.

In one aspect, the present disclosure provides a method removing 3-HP from an aqueous solution without using a counter-current liquid flow.

In another aspect, the present disclosure provides a method that includes evaporating a first solvent, condensing the evaporated first solvent, and directing a flow of the first solvent to remove 3-HP from the aqueous solution.

In another aspect, the present disclosure provides a method including using a water-immiscible solvent to remove 3-HP from an aqueous solution with a yield of at least 50%.

Inanother aspect, the present disclosure provides a method including using an organic liquid containing at least two solvents to remove 3-hydroxypropionic acid (3-HP) from an aqueous solution.

In another aspect, the present disclosure provides a method including using a liquid to remove 3-HP from an aqueous solution, wherein the liquid includes a two different solvents (e.g., a water-miscible solvent and a water-immiscible solvent).

In another aspect, the present disclosure provides a method including removing 3-HP from an aqueous solution, wherein pH of the aqueous solution is at least about 3.

In another aspect, the present disclosure provides a method that includes reacting 3-HP to form acrylic acid at a pressure of less than about one atmosphere.

In another aspect, the present disclosure provides a method that includes reacting 3-HP to form acrylic acid in a reaction mixture, and removing gaseous acrylic acid from the reaction mixture.

In another aspect, the present disclosure provides a method that includes reacting a liquid containing 3-HP to form acrylic acid.

In another aspect, the present disclosure provides a method that includes reacting 3-HP to form acrylic acid with a yield of at least about 70%.

Unless otherwise defined, all technical and scientific terms used herein have the same meaning as commonly understood by one of ordinary skill in the art to which this disclosure belongs. Methods and materials are described herein for use in the disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the disclosure, including definitions, will control.

Other features and advantages of the disclosure will be apparent from the following detailed description and figures, and from the claims.

DESCRIPTION OF DRAWINGS

(FIG. 1A) Hypothetical schematic representation of MmsR-based regulation. hpdH, 3-hydroxypropionate dehydrogenase; mmsA, methylmalonate semialdehyde dehydrogenase; hbdH-4, 3-hydroxyisobutyrate dehydrogenase IV. (FIG. 1B) Relative mRNA abundance of mmsA (gray bar) and hbdH-4 (black bar) in the presence of various inducer molecules.

(FIG. 2A) The mRNA levels in deletion mutant *P. denitrificans* ΔhpdHΔhbdH4ΔhbdH1 (designated as ΔΔΔ) that lack 3-HP degrading enzymes. (FIG. 2B) The mRNA levels upon deletion and complementation of transcriptional activator, MmsR. ΔmmsR, *P. denitrificans* mmsR deletion mutant; and mmsR-C, *P. denitrificans* ΔmmsR with mmsR-complementation from a plasmid.

(FIG. 3A) DNA sequence of mmsR-mmsA intergenic region and mutations in the promoter region for its characterization in vivo and in vitro. The 5'-end mapping of (FIG. 3A) $P_{mmsA}$ (FIG. 3B) MmsA binding sites (O1 and O2).

(FIG. 6A) SDS-PAGE, (FIG. 6B) Blue Native-PAGE and (FIG. 6C) relative mRNA levels by recombinant MmsR bearing his-tag to either N- or C-terminus. Lane 1, host *E. coli* BL21 (cell-free extract); lane 2, recombinant *E. coli* BL21 cultured without IPTG induction (cell-free extract); lanes 3, 4, 5, and 7 correspond to cell-free extract, soluble fraction, insoluble fraction and purified protein, respectively, from recombinant *E. coli* BL21; lanes 9, 11, and 13 correspond to purified MmsR protein at 65,220,550 nM, respectively.

(FIG. 10A) DNA sequence of hpdR-hpdH intergenic region showing putative promoter and operator regions. (FIG. 10B) Consensus of the operator palindromic sites.

(FIG. 12A) Transcription at chromosomal levels, (FIG. 12B) GFP fluorescence at plasmid level, (FIG. 12C) GFP fluorescence at various time intervals, and (FIG. 12D) sensitivity at various 3-HP concentrations.

(FIG. 14A) Comparison of mRNA (transcription) and (FIG. 14B) KgsA activity.

(FIG. 15A) Schematics of operator mutagenesis, (FIG. 15B) kgsA mRNA expression levels, (FIG. 15C) GFP fluorescence with the selected operator mutation, $PmmsA_{2a}$.

(FIG. 17A) Enzymatic activity of KgsA. (FIG. 17B) SDS-PAGE analysis of crude-cell extracts expressing fusion proteins. The stability of the transcripts were also measured (FIGS. 17C and 17D).

(FIG. 18A) Arrangement of tandem promoter and its transcripts; TSS, transcription start site; RBS, ribosome biding site; UTR, 5'-unstranslated region, (FIG. 18B) mRNA expression, and (FIG. 18C) KgsA activity.

FIGS. 19A-C are a table and graphs showing the effect of 5'UTR on expression of kgsA. (FIG. 19A) Prediction of 5'UTR strength for kgsA expression systems. (FIG. 19B) Specific KgsA activity of the UTR constructs with varying induction at 0, 0.25 and 25 mM 3-HP. (FIG. 19C) Comparison of the 5'UTR strength between the theoretical prediction and experimental measurement at different 3-HP concentration.

FIG. 25A shows the structure of RS1 before cobG. FIG. 25B shows the structure of RS2 in front of cobW. FIG. 25C shows the structure of RS3 in front of cbtB. FIG. 25D shows the structure of RS4 in front of btuB.

(FIG. 29B) The concentration of coenzyme B 12 was quantified using both the *Salmonella typhimurium* metE–cbiB– and $B_{12}$ riboswitch-based biosensor.

(FIG. 30A) Schematics of the expression cassette construction, (FIG. 30B) Integration of kgsA gene into the site of hbdH-4 gene in ΔmmsA mutant strain.

FIGS. 55A-B show a development of 3-HP inducible tandem promoter library for controlled expression of DhaB at various expression levels. (FIG. 55A) Schematics of tandem promoter construction, (FIG. 55B) Specific DhaB activity of various tandem promoter library constructs.

FIG. 56 is a schematic illustrating the sequences of PC3 promoter regions.

DETAILED DESCRIPTION

Figure 1A:
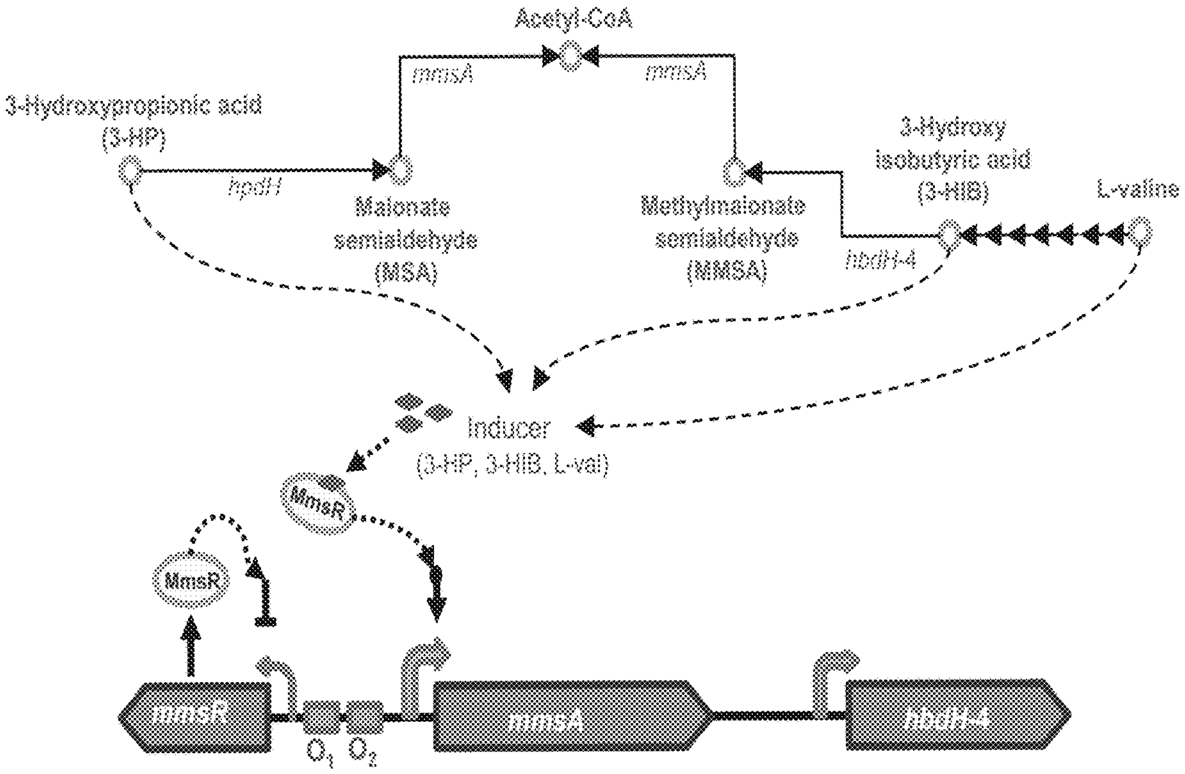
FIGS. 1A-B are a schematic and graph showing gene expression regulation by the LysR-type transcriptional activator protein, MmsR, in 3-hydroxypropionate degrading pathway of *Pseudomonas denitrificans*.

This disclosure provides an industrial microbial strain (including, e.g., *Pseudomonas* strains) with enhanced expression systems for producing 3-HP or a salt thereof from glycerol. Enzymes involved in the production of 3-HP or a salt thereof and regulatory regions thereof were integrated into the chromosomes of an industrial strain. 3-HP inducible promoters were identified, characterized, and operably linked to enzymes involved in the production of 3-HP or a salt thereof. The expression of the 3-HP enzymes can be increased by combining a 3-HP inducible promoter with a constitutive, inducible, and/or synthetic promoter, and thereby creating a tandem promotor system. The tandem promoter system can be fused with a UTR (either native or synthetic) and other regulatory domains that control or enhance expression to improve the expression of the system. The tandem promoter system (e.g., the tandem promoter system merged with an UTR) can also be fused to a sequence encoding the initial amino acids (e.g., a sequence encoding up to twenty amino acids) of a highly expressed native gene. These modifications can increase expression of the enzymes, downstream genes in this case genes, involved in 3-HP production (or production of a salt thereof). Further, the positioning of these expression systems in the chromosome of the industrial strain was investigated and the effect on 3-HP (or a salt thereof) production was evaluated. Designed positioning of the expression systems can avoid accumulation of toxic 3-HPA and can increase 3-HP production through channeling.

Additionally, the disclosure provides for an industrial strain that can produce 3-HP at high titer without external supplementation of coenzyme B12 (B12). Regulatory regions that control the expression of enzymes in the B12 production pathway were identified and characterized. The removal of many of these regulatory regions (including, e.g., secondary structures) improved expression of the B12 enzymes. The integration of either constitutive or 3-HP inducible expression systems described herein, can increase expression of the native B12 enzymes and increase B12 production. This allows for the production of 3-HP (or a salt thereof) without the external addition of B12.

The disclosure also provides methods for removing 3-HP from an aqueous solution. For example, 3-HP may be removed from an aqueous solution by solvent extraction. The disclosure also provides methods for purifying 3-HP (e.g., after its removal from an aqueous solution.) In addition, the disclosure also provides methods of making acrylic acid from 3-HP (e.g., after its removal from an aqueous solution and optionally after its purification). Further, the disclosure provides methods of purifying acrylic acid.

Production of 3-Hydroxypropionic Acid by Recombinant Bacteria

The compositions and methods described herein are useful in the production of 3-hydroxypropionic acid (3-HP) (or a salt thereof) from a carbon source using recombinant microorganisms. In some cases, the carbon source is glycerol. Glycerol is converted into 3-hydroxypropionaldehyde (3-HPA) by glycerol/diol dehydratase (e.g., DhaB), by a reaction that involves coenzyme B12. 3-HPA is in turn converted into 3-HP by aldehyde dehydrogenase (ALDH) (e.g., KgsA, EaldH, KaldH) in a reaction that needs NAD (P) (+). The conversion of glycerol to 3-HP involves several rate-limiting factors that can hinder the production of 3-HP (or a salt thereof) at high titers. Such factors include, for example, coenzyme B12, the complex nature of the enzymes in the pathway, NAD+ regeneration, and the toxicity of 3-hydroxypropanealdehyde (3-HPA) and 3-HP to cells. In this study, 3-HP (or a salt thereof) was produced at high titers, e.g., titer sufficient enough for 3-HP commercialization.

The loss of enzyme activities during 3-HP production (or production of a salt thereof) due to the accumulation of toxic intermediates is a challenging problem to the production of high titers of 3-HP (or a salt thereof). 3-HPA is a toxic intermediate that accumulates during 3-HP production. Studies have shown that when 3-HP pathway enzymes are incubated with 3-HPA, enzymatic activity declines in a dose-dependent manner. Aldehydes are known to react with amino acid residues such as lysine, cysteine and histidine by targeting the ε-amino group (NH3+), the sulfhydryl group (—SH) and the imidazole group, respectively. Accumulation of 3-HPA damages proteins including, for example, glycerol dehydratase or diol dehydratase, the enzyme responsible for 3-HPA synthesis in the glycerol to 3-HP synthetic pathway. The inactivation of glycerol or diol dehydratase by 3-HPA results in a reduction in 3-HP (or a salt thereof) production, and low titers. Potential approaches for overcoming enzyme inactivation by toxic intermediates include, inter alia, to develop enzymes which are highly resistance to 3-HPA toxicity or to continuously synthesize the new enzymes. The compositions and methods described herein can reduce the accumulation of toxic intermediates (e.g., 3-HPA) during 3-HP production from glycerol, thereby increasing the amounts of 3-HP or a salt thereof that can be produced by recombinant bacteria.

In some embodiments, a recombinant microorganism as described herein can express one or more genes encoding enzymes that catalyze the production of 3-HP or a salt thereof from a carbon source, e.g., one or more genes encoding glycerol dehydratase, diol dehydratase, and/or aldehyde dehydrogenase. In some embodiments, a protein involved in the synthesis of a compound can be one or more enzymes that catalyze the production of the compound from a carbon source. A protein involved in the synthesis of 3-HP or a salt thereof can be, e.g., one or more proteins that make up glycerol dehydratase, diol dehydratase, and/or aldehyde dehydrogenase. In some embodiments, the carbon source is glycerol, but other sources of carbon can be used, e.g., glucose, glutamate, gluconate, and citric acid. The recombinant organism can express a glycerol dehydratase enzyme (e.g., DhaB), or a diol dehydratase enzyme, which catalyzes glycerol into 3-hydroxypropanealdehyde (3-HPA). DhaB is a complex enzyme with three subunits, encoding for a complex glycerol/diol dehydratase (dhaBCD)). DhaB is complexed with coenzyme B12. During its catalytic activity (converting glycerol to 3-HPA) coenzyme B12 is damaged, this damaged coenzyme B12 will be replaced with new active coenzyme B12 by another enzyme glycerol dehydratase reactivation factor (GdrAB) or diol dehydratase reactivation factor. GdrAB is a complex enzyme with two subunits GdrA and GdrB The recombinant organism can also express a gene encoding aldehyde dehydrogenase (ALDH), which then catalyzes 3-HPA into 3-HP. This catalysis involves NAD (P) (+). Expression of aldehyde dehydrogenase (ALDH enzyme) can include expression of the kgsA gene. Thus, in some embodiments, the recombinant microorganism expresses the DhaB enzyme, which catalyzes glycerol into 3-HPA, and the ALDH enzyme, which then converts 3-HPA into 3-HP.

The recombinant microorganisms described herein can be bacteria or fungi. In some embodiments, the recombinant microorganism is a bacterium. The recombinant bacterium can be any genetically-engineered bacterium capable of producing 3-HP from a carbon source in culture conditions, such as in a bioprocessor or bioreactor. In some embodiments, the bacterium grows under aerobic conditions. In some embodiments, the bacterium grows under anaerobic conditions. In some embodiments, the genome of the bacterium naturally contains genes that are useful for producing 3-HP from a carbon source, such as glycerol, e.g., the genes that encode glycerol dehydratase or diol dehydratase (such as DhaB) and/or aldehyde dehydrogenase (such as ksgA). In some embodiments, the genome of the bacterium does not naturally contain genes that are useful for producing 3-HP from a carbon source, such as glycerol. In some embodiments, a bacterium that does not naturally contain or express genes used for the production of 3-HP from glycerol can be genetically modified to express at least one gene used for 3-HP production. For example, a bacterium that does not express glycerol dehydratase (DhaB), diol dehydratase, and/or aldehyde dehydrogenase (ALDH) can be genetically engineered to express DhaB and/or ALDH.

In some embodiments the recombinant bacterium is a *Pseudomonas* strain, a *Klebsiella* strain, or an *Escherichia* strain. In some embodiments, the recombinant bacterium is a strain of *Pseudomonas denitrificans, Klebsiella pneumonia*, or *Escherichia coli*. In some embodiments, the recombinant bacterium is a strain of *Pseudomonas denitrificans. Pseudomonas denitrificans* is an aerobic microorganism, which can naturally synthesize a cofactor, coenzyme B12. Coenzyme B12 is an important cofactor for 3-HP production from glycerol. Additionally, *P. denitrificans* can regenerate NAD+ efficiently. NAD+ regeneration is very important for uninterrupted production of 3-HP. Therefore, *Pseudomonas denitrificans* is assumed to be a suitable microorganism for 3-HP production (or production of a salt thereof).

In some embodiments, the recombinant bacterium expresses at least one glycerol dehydratase and/or diol dehydratase enzyme from an *Enterobacter* bacterium (e.g., *Klebsiella* or *Salmonella* or *Citrobacter*) or *Lactobacillus* bacterium or *Propionibacterium* or *Proteus* or *Serratia* species or *Clostridium*, e.g., at least one glycerol dehydratase enzyme (e.g., DhaB) from an *Enterobacter* (e.g., *Klebsiella*, or *Salmonella* or *Citrobacter*) or *Lactobacillus* or *Propionibacterium* or *Proteus* or *Serratia* or *Clostridium* species. In some embodiments, the recombinant bacterium expresses two or more glycerol dehydratase enzymes (e.g., DhaB), and/or diol dehydratase enzymes, wherein each of the dehydratase enzymes (e.g., DhaB) can be from a different *Enterobacter* (e.g., *Klebsiella*, or *Salmonella* or *Citrobacter*) or *Lactobacillus* or *Propionibacterium* or *Proteus* or *Serratia* or *Clostridium* species. In some embodiments, the recombinant bacterium expresses at least one aldehyde dehydrogenase enzyme (ALDH) from an *Enterobacter* bacterium (e.g., *Klebsiella*, or *Salmonella* or *Citrobacter*) or *Lactobacillus* or *Propionibacterium* or *Proteus* or *Serratia* or *Clostridium* species, e.g., at least one ALDH enzyme. In some embodiments, the recombinant bacterium expresses two or more ALDH enzymes, wherein each of the ALDH enzymes can be from a different *Enterobacter* or *Lactobacillus* strain. In some embodiments, the recombinant bacterium expresses at least one glycerol dehydratase (e.g., DhaB) and/or diol dehydratase from an *Enterobacter* bacterium (e.g., *Klebsiella* or *Salmonella*) or *Lactobacillus* bacterium and at least one aldehyde dehydrogenase (ALDH) enzyme from an *Enterobacter* bacterium (e.g., *Klebsiella* or *Salmonella*) or *Lactobacillus* bacterium.

In some embodiments, the recombinant bacterium expresses at least one gene encoding at least one glycerol dehydratase and/or diol dehydratase from bacteria in this case *Klebsiella pneumoniae*, e.g., dhaB1, dhaB2, dhaB3, gdrA, and/or gdrB from *Klebsiella pneumoniae*. In some embodiments, the recombinant bacterium expresses at least one gene encoding at least one aldehyde dehydrogenase from *Azospirullum brasilense*, e.g., kgsA from *Azospirullum brasilense*. In some embodiments, the recombinant bacterium expresses at least one gene encoding at least one glycerol dehydratase from *Klebsiella pneumoniae*, e.g., dhaB1, dhaß2, dhaB3, gdrA, and/or gdrB from *Klebsiella pneumoniae*, or at least one gene encoding at least one diol dehydratase, and at least one gene encoding at least one aldehyde dehydrogenase from *Azospirullum brasilense*, e.g., kgsA from *Azospirullum brasilense*. In some embodiments, the recombinant bacterium is a *Pseudomonas denitrificans* strain that expresses at least one gene encoding at least one glycerol dehydratase and/or diol dehydratase from *Klebsiella pneumoniae*, e.g., dhaB1, dhaB2, dhaB3, gdrA, and/or gdrB from *Klebsiella pneumoniae*, and at least one gene encoding at least one aldehyde dehydrogenase from *Azospirullum brasilense*, e.g., kgsA from *Azospirullum brasilense.*

In some embodiments, the recombinant bacterium has at least one nucleic acid with at least one glycerol dehydratase gene and/or diol dehydratase gene (e.g., dhal, dhaB2, dhaß3, gdrA, and/or gdrB gene) from an *Enterobacter* bacterium (e.g., *Klebsiella* or *Salmonella*) or *Lactobacillus* bacterium, e.g., at least one glycerol/diol dehydratase gene (e.g., dhaB1, dhaB2, dhaB3, gdrA, and/or gdrB gene) from *Klebsiella pneumoniae*. In some embodiments, the recombinant bacterium has at least one nucleic acid with at least two glycerol dehydratase genes and/or diol dehydratase genes (e.g., two or more of dhaB1, dhaB2, dhaB3, gdrA, and/or gdrB genes) from a *Enterobacter* bacterium (e.g., *Klebsiella* or *Salmonella*) or *Lactobacillus* bacterium, e.g., at least two glycerol dehydratase genes (e.g., two or more of dhaß1, dhaß2, dhaß3, gdrA, and/or gdrB genes) or diol dehydratase genes from *Klebsiella pneumoniae*. In some embodiments, the recombinant bacterium has at least one nucleic acid with at least one aldehyde dehydrogenase gene (kgsA gene) from an *Azospirullum* bacterium, e.g., at least one aldehyde dehydrogenase gene (kgsA gene) from an *Azospirullum brasilense* strain. In some embodiments, the recombinant bacterium has at least one nucleic acid with at least two aldehyde dehydrogenase genes (e.g., kgsA genes) from an *Azospirullum* bacterium, e.g., at least two aldehyde dehydrogenase genes (e.g., kgsA genes) from an *Azospirullum brasilense* strain. In some embodiments, the recombinant bacterium has at least one nucleic acid with at least one glycerol dehydratase gene and/or diol dehydratase gene (e.g., dhaB1, dhaB2, dhaB3, gdrA, and/or gdrB gene) from a *Enterobacter* bacterium (e.g., *Klebsiella* or *Salmonella*) or *Lactobacillus* bacterium, e.g., at least one glycerol dehydratase gene (e.g., dhaB dhaB1, dhaB2, dhaB3, gdrA, and/or gdrB gene) from *Klebsiella pneumonia*, and at least one nucleic acid with at least one aldehyde dehydrogenase gene (kgsA gene) from an *Azospirullum* bacterium, e.g., at least one aldehyde dehydrogenase gene (kgsA gene) from an *Azospirullum brasilense* strain.

dhaB1w

SEQ ID NO: 1

ATGAAAAGATCAAAACGATTTGCAGTACTGGCCCA

GCGCCCCGTCAATCAGGACGGGCTGATTGGCGAGT

GGCCTGAAGAGGGGCTGATCGCCATGGACAGCCCC

TTTGACCCGGTCTCTTCAGTAAAAGTGGACAACGG

TCTGATCGTCGAGCTGGACGGCAAACGCCGGGACC

AGTTTGACATGATCGACCGATTTATCGCCGATTAC

GCGATCAACGTTGAGCGCACAGAGCAGGCAATGCG

CCTGGAGGCGGTGGAAATAGCCCGCATGCTGGTGG

ATATTCACGTCAGTCGGGAGGAGATCATTGCCATC

ACTACCGCCATCACGCCGGCCAAAGCGGTCGAGGT

GATGGCGCAGATGAACGTGGTGGAGATGATGATGG

CGCTGCAGAAGATGCGTGCCCGCCGGACCCCCTCC

AACCAGTGCCACGTCACCAATCTCAAAGATAATCC

GGTGCAGATTGCTGCTGACGCCGCCGAGGCCGGGA

TCCGCGGCTTCTCAGAACAGGAGACCACGGTCGGT

ATCGCGCGCTATGCGCCGTTTAACGCCCTGGCGCT

GTTGGTCGGTTCGCAGTGCGGCCGCCCCGGCGTTT

TGACGCAGTGCTCGGTGGAAGAGGCCACCGAGCTG

GAGCTGGGCATGCGTGGCTTAACCAGCTACGCCGA

GACGGTGTCGGTCTACGGCACCGAAGCGGTATTTA

-continued

CCGACGGCGATGATACTCCGTGGTCAAAGGCGTTC

CTCGCCTCGGCCTACGCCTCCCGCGGGTTGAAAAT

GCGCTACACCTCCGGCACCGGATCCGAAGCGCTGA

TGGGCTATTCGGAGAGCAAGTCGATGCTCTACCTC

GAATCGCGCTGCATCTTCATTACCAAAGGCGCCGG

GGTTCAGGGGCTGCAAAACGGCGCGGTGAGCTGTA

TCGGCATGACCGGCGCTGTGCCGTCGGGCATTCGG

GCGGTGCTGGCGGAAAACCTGATCGCCTCTATGCT

CGACCTCGAAGTGGCGTCCGCCAACGACCAGACTT

TCTCCCACTCGGATATTCGCCGCACCGCGCGCACC

CTGATGCAGATGCTGCCGGGCACCGACTTTATTTT

CTCCGGCTACAGCGCGGTGCCGAACTACGACAACA

TGTTCGCCGGCTCGAACTTCGATGCGGAAGATTTT

GATGATTACAACATCCTGCAGCGTGACCTGATGGT

TGACGGCGGCCTGCGTCCGGTGACCGAGGCGGAAA

CCATTGCCATTCGCCAGAAAGCGGCGCGGGCGATC

CAGGCGGTTTTCCGCGAGCTGGGGCTGCCGCCAAT

CGCCGACGAGGAGGTGGAGGCCGCCACCTACGCGC

ACGGTAGCAACGAGATGCCGCCGCGTAACGTGGTG

GAGGATCTGAGTGCGGTGGAAGAGATGATGAAGCG

CAACATCACCGGCCTCGATATTGTCGGCGCGCTGA

GCCGCAGCGGCTTTGAGGATATCGCCAGCAATATT

CTCAATATGCTGCGCCAGCGGGTCACCGGCGATTA

CCTGCAGACCTCGGCCATTCTCGATCGGCAGTTCG

AGGTGGTGAGTGCGGTCAACGACATCAATGACTAT

CAGGGGCCGGGCACCGGCTATCGCATCTCTGCCGA

ACGCTGGGCGGAGATCAAAAATATTCCGGGCGTGG

TTCAGCCCGACACCATTGAATAA

DhaB1

SEQ ID NO: 77

MKRSKRFAVLAQRPVNQDGLIGEWPEEGLIAMDSP

FDPVSSVKVDNGLIVELDGKRRDQFDMIDRFIADY

AINVERTEQAMRLEAVEIARMLVDIHVSREEIIAI

TTAITPAKAVEVMAQMNVVEMMMALQKMRARRTPS

NQCHVTNLKDNPVQIAADAAEAGIRGFSEQETTVG

IARYAPFNALALLVGSQCGRPGVLTQCSVEEATEL

ELGMRGLTSYAETVSVYGTEAVFTDGDDTPWSKAF

LASAYASRGLKMRYTSGTGSEALMGYSESKSMLYL

ESRCIFITKGAGVQGLQNGAVSCIGMTGAVPSGIR

AVLAENLIASMLDLEVASANDQTFSHSDIRRTA

RTLMQMLPGTDFIFSGYSAVPNYDNMFAGSNFDAE

-continued

DFDDYNILQRDLMVDGGLRPVTEAETIAIRQKAAR

AIQAVFRELGLPPIADEEVEAATYAHGSNEMPPRN

VVEDLSAVEEMMKRNITGLDIVGALSRSGFEDIAS

NILNMLRQRVTGDYLQTSAILDRQFEVVSAVNDIN

DYQGPGTGYRISAERWAEIKNIPGVVQPDTIE dhaB2

SEQ ID NO: 2

ATGCAACAGACAACCCAAATTCAGCCCTCTTTTAC

CCTGAAAACCCGCGAGGGCGGGGTAGCTTCTGCCG

ATGAACGCGCCGATGAAGTGGTGATCGGCGTCGGC

CCTGCCTTCGATAAACACCAGCATCACACTCTGAT

CGATATGCCCCATGGCGCGATCCTCAAAGAGCTGA

TTGCCGGGGTGGAAGAAGAGGGGCTTCACGCCCGG

GTGGTGCGCATTCTGCGCACGTCCGACGTCTCCTT

TATGGCCTGGGATGCGGCCAACCTGAGCGGCTCGG

GGATCGGCATCGGTATCCAGTCGAAGGGGACCACG

GTCATCCATCAGCGCGATCTGCTGCCGCTCAGCAA

CCTGGAGCTGTTCTCCCAGGCGCCGCTGCTGACGC

TGGAAACCTACCGGCAGATTGGCAAAAACGCCGCG

CGCTATGCGCGCAAAGAGTCACCTTCGCCGGTGCC

GGTGGTGAACGATCAGATGGTGCGGCCGAAATTTA

TGGCCAAAGCCGCGCTATTTCATATCAAAGAGACC

AAACATGTGGTGCAGGACGCCGAGCCCGTCACCCT

GCACGTCGACTTAGTTAGGGAGTAA

DhaB2

SEQ ID NO: 78

MQQTTQIQPSFTLKTREGGVASADERADEVVIGVG

PAFDKHQHHTLIDMPHGAILKELIAGVEEEGLHAR

VVRILRTSDVSFMAWDAANLSGSGIGIGIQSKGTT

VIHQRDLLPLSNLELFSQAPLLTLETYRQIGKNAA

RYARKESPSPVPVVNDQMVRPKFMAKAALFHIKET

KHVVQDAEPVTLHVDLVRE dhaB3

SEQ ID NO: 3

ATGAGCGAGAAAACCATGCGCGTGCAGGATTATCC

GTTAGCCACCCGCTGCCCGGAGCATATCCTGACGC

CTACCGGCAAACCATTGACCGATATTACCCTCGAG

AAGGTGCTCTCTGGCGAGGTGGGCCCGCAGGATGT

GCGGATCTCCTGCCAGACCCTTGAGTACCAGGCGC

AGATTGCCGAGCAGATGCAGCGCCATGCGGTGGCG

CGCAATTTCCGCCGCGCGGCGGAGCTTATCGCCAT

TCCTGACGAGCGCATTCTGGCTATCTATAACGCGC

TGCGCCCGTTCCGCTCCTCGCAGGCGGAGCTGCTG

GCGATCGCCGACGAGCTGGAGCACACCTGGCATGC

-continued

GACAGTGAATGCCGCCTTTGTCCGGGAGTCGGCGG

AAGTGTATCAGCAGCGGCATAAGCTGCGTAAAGGA

AGCTAA

DhaB3

SEQ ID NO: 79

MSEKTMRVQDYPLATRCPEHILTPTGKPLTDITLE

KVLSGEVGPQDVRISCQTLEYQAQIAEQMQRHAVA

RNFRRAAELIAIPDERILAIYNALRPFRSSQAELL

AIADELEHTWHATVNAAFVRESAEVYQQRHKLRK

GS gdrA

SEQ ID NO: 4

ATGCCGTTAATAGCCGGGATTGATATCGGCAACGC

CACCACCGAGGTGGCGCTGGCGTCCGACGACCCGC

AGGCGAGGGCGTTTGTTGCCAGCGGGATCGTCGCG

ACGACGGGCATGAAAGGGACGCGGGACAATATCGC

CGGGACCCTCGCCGCGCTGGAGCAGGCCCTGGCGA

AAACACCGTGGTCGATGAGCGATGTCTCTCGCATC

TATCTTAACGAAGCCGCGCCGGTGATTGGCGATGT

GGCGATGGAGACCATCACCGAGACCATTATCACCG

AATCGACCATGATCGGTCATAACCCGCAGACGCCG

GGCGGGGTGGGCGTTGGCGTGGGGACGACTATCGC

CCTCGGGCGGCTGGCGACGCTGCCGGCGGCGCAGT

ATGCCGAGGGGTGGATCGTACTGATTGACGACGCC

GTCGATTTCCTTGACGCCGTGTGGTGGCTCAATGA

GGCGCTCGACCGGGGGATCAACGTGGTGGCGGCGA

TCCTCAAAAAGGACGACGGCGTGCTGGTGAACAAC

CGCCTGCGTAAAACCCTGCCGGTGGTAGATGAAGT

GACGCTGCTGGAGCAGGTCCCCGAGGGGGTAATGG

CGGCGGTGGAAGTGGCCGCGCCGGGCCAGGTGGTG

CGGATCCTGTCGAATCCCTACGGGATCGCCACCTT

CTTCGGGCTAAGCCCGGAAGAGACCCAGGCCATCG

TCCCCATCGCCCGCGCCCTGATTGGCAACCGTTCA

GCGGTGGTGCTCAAGACCCCGCAGGGGGATGTGCA

GTCGCGGGTGATCCCGGCGGGCAACCTCTACATTA

GCGGCGAAAAGCGCCGCGGAGAGGCCGATGTCGCC

GAGGGCGCGGAAGCCATCATGCAGGCGATGAGCGC

CTGCGCTCCGGTACGCGACATCCGCGGCGAACCGG

GCACTCACGCCGGCGGCATGCTTGAGCGGGTGCGC

AAGGTAATGGCGTCCCTGACCGACCATGAGATGAG

CGCGATATACATCCAGGATCTGCTGGCGGTGGATA

CGTTTATTCCGCGCAAGGTGCAGGGCGGGATGGCC

-continued

GGCGAGTGCGCCATGGAAAATGCCGTCGGGATGGC
GGCGATGGTGAAAGCGGATCGTCTGCAAATGCAGG
TTATCGCCCGCGAACTGAGCGCCCGACTGCAGACC
GAGGTGGTGGTGGGCGGCGTGGAGGCCAACATGGC
CATCGCCGGGGCGTTAACCACTCCCGGCTGTGCGG
CGCCGCTGGCGATCCTCGACCTCGGCGCCGGCTCG
ACGGATGCGGCGATCGTCAACGCGGAGGGGCAGAT
AACGGCGGTCCATCTCGCCGGGGCGGGGAATATGG
TCAGCCTGTTGATTAAAACCGAGCTGGGCCTCGAG
GATCTTTCGCTGGCGGAAGCGATAAAAAAATACCC
GCTGGCCAAAGTGGAAAGCCTGTTCAGTATTCGTC
ACGAGAATGGCGCGGTGGAGTTCTTTCGGGAAGCC
CTCAGCCCGGCGGTGTTCGCCAAAGTGGTGTACAT
CAAGGAGGGCGAACTGGTGCCGATCGATAACGCCA
GCCCGCTGGAAAAAATTCGTCTCGTGCGCCGGCAG
GCGAAAGAGAAAGTGTTTGTCACCAACTGCCTGCG
CGCGCTGCGCCAGGTCTCACCCGGCGGTTCCATTC
GCGATATCGCCTTTGTGGTGCTGGTGGGCGGCTCA
TCGCTGGACTTTGAGATCCCGCAGCTTATCACGGA
AGCCTTGTCGCACTATGGCGTGGTCGCCGGGCAGG
GCAATATTCGGGGAACAGAAGGGCCGCGCAATGCG
GTCGCCACCGGGCTGCTACTGGCCGGTCAGGCGAA
TTAA

GdrA

SEQ ID NO: 80

MPLIAGIDIGNATTEVALASDDPQARAFVASGIVA
TTGMKGTRDNIAGTLAALEQALAKTPWSMSDVSRI
YLNEAAPVIGDVAMETITETIITESTMIGHNPQTP
GGVGVGVGTTIALGRLATLPAAQYAEGWIVLIDDA
VDFLDAVWWLNEALDRGINVVAAILKKDDGVLVNN
RLRKTLPVVDEVTLLEQVPEGVMAAVEVAAPGQVV
RILSNPYGlATFFGLSPEETQAIVPIARALIGNRS
AVVLKTPQGDVQSRVIPAGNLYISGEKRRGEADVA
EGAEAIMQAMSACAPVRDIRGEPGTHAGGMLERVR
KVMASLTDHEMSAIYIQDLLAVDTFIPRKVQGGMA
GECAMENAVGMAAMVKADRLQMQVIARELSARLQT
EVVVGGVEANMAIAGALTTPGCAAPLAILDLGAGS
TDAAIVNAEGQITAVHLAGAGNMVSLLIKTELGLE
DLSLAEAIKKYPLAKVESLFSIRHENGAVEFFREA
LSPAVFAKVVYIKEGELVPIDNASPLEKIRLVRRQ
AKEKVFVTNCLRALRQVSPGGSIRDIAFVVLVGGS

-continued

SLDFEIPQLITEALSHYGVVAGQGNIRGTEGPRNA
VATGLLLAGQAN gdrB

SEQ ID NO: 5

ATGTCGCTTTCACCGCCAGGCGTACGCCTGTTTTA
CGATCCGCGCGGGCACCATGCCGGCGCCATCAATG
AGCTGTGCTGGGGGCTGGAGGAGCAGGGGGTCCCC
TGCCAGACCATAACCTATGACGGAGGCGGTGACGC
CGCTGCGCTGGGCGCCCTGGCGGCCAGAAGCTCGC
CCCTGCGGGTGGGTATTGGGCTCAGCGCGTCCGGC
GAGATAGCCCTCACTCATGCCCAGCTGCCGGCGGA
CGCGCCGCTGGCTACCGGACACGTCACCGATAGCG
ACGATCATCTGCGTACGCTCGGCGCCAACGCCGGG
CAGCTGGTTAAAGTCCTGCCGTTAAGTGAGAGAAA
CTGA

GdrB

SEQ ID NO: 81

MSLSPPGVRLFYDPRGHHAGAINELCWGLEEQGVP
CQTITYDGGGDAAALGALAARSSPLRVGIGLSASG
EIALTHAQLPADAPLATGHVTDSDDHLRTLGANAG
QLVKVLPLSERN kgsA

SEQ ID NO: 6

ATGAGAGGATCGGGATCCGCTAACGTGACTTATAC
GGATACGCAACTGCTGATCGACGGTGAGTGGGTCG
ACGCCGCGAGCGGCAAGACGATCGACGTCGTGAAC
CCGGCGACCGGCAAGCCGATCGGCAGGGTGGCCCA
TGCGGGCATCGCCGATCTCGACCGTGCGCTCGCCG
CCGCGCAAAGCGGCTTCGAGGCATGGCGCAAGGTG
CCCGCGCACGAGCGCGCGGCGACGATGCGCAAGGC
GGCCGCGCTGGTGCGTGAACGCGCCGACGCGATCG
CGCAGCTGATGACGCAGGAGCAGGGCAAGCCGCTC
ACCGAAGCGCGCGTCGAAGTGCTGTCGTCCGCGGA
CATCATCGAATGGTTCGCGGACGAAGGCCGCCGCG
TGTACGGCCGGATCGTGCCGCCGCGCAACCTCGGC
GCACAGCAGACGGTCGTGAAGGAGCCGGTCGGCCC
GGTCGCCGCGTTCACGCCGTGGAATTTCCCGGTCA
ACCAGGTCGTGCGCAAGCTGAGCGCCGCGCTGGCA
ACCGGCTGTTCGTTCCTCGTGAAAGCGCCGGAAGA
AACCCCCGCGTCGCCGGCCGCGCTGCTGCGCGCCT
TCGTCGACGCAGGCGTGCCGGCCGGCGTGATCGGC
CTCGTGTACGGCGATCCGGCCGAAATCTCGTCGTA
CCTGATCCCGCACCCGGTGATCCGCAAGGTCACGT

-continued

TCACGGGTTCGACGCCGGTCGGCAAGCAGCTCGCC

TCGCTGGCGGGCCTGCACATGAAGCGCGCGACGAT

GGAGCTGGGCGGGCACGCACCGGTGATCGTGGCCG

AAGACGCCGACGTTGCGCTCGCGGTGGCAGCGGCC

GGCGGCGCGAAGTTCCGCAACGCGGGGCAGGTCTG

CATCTCGCCGACGCGCTTCCTCGTGCACAACAGCA

TCCGCGACGAATTCACGCGCGCGCTGGTCAAGCAT

GCCGAAGGGCTGAAGGTCGGCAACGGCCTCGAGGA

AGGCACGACGCTCGGCGCGCTCGCGAACCCGCGCC

GGCTGACCGCGATGGCGTCGGTCATCGACAACGCG

CGCAAGGTCGGTGCGAGCATCGAAACCGGCGGCGA

GCGGATCGGCTCGGAAGGCAACTTCTTCGCGCCGA

CCGTGATCGCGAACGTGCCGCTCGATGCGGACGTG

TTCAACAACGAGCCGTTCGGCCCGGTCGCGGCGAT

TCGCGGTTTCGACAAGCTCGAAGAGGCGATCGCGG

AAGCGAACCGTTTGCCGTTCGGTCTTGCCGGCTAC

GCGTTCACGCGTTCGTTCGCGAACGTGCACCTGCT

CACGCAGCGCCTCGAAGTCGGGATGCTGTGGATCA

ACCAGCCGCCGACTACATGGCCGGAAATGCCGTTC

GGCGGCGTGAAGGACTCGGGCTACGGTTCGGAAGG

CGGCCCGGAAGCGCTCGAGCCGTACCTCGTCACGA

AGTCGGTGACGGTAATGGCCGTCTGA

KgsA

SEQ ID NO: 82

MANVTYTDTQLLIDGEWVDAASGKTIDVVNPATG

KPIGRVAHAGIADLDRALAAAQSGFEAWRKVPAH

ERAATMRKAAALVRERADAIAQLMTQEQGKPLTE

ARVEVLSAADIIEWFADEGRRVYGRIVPPRNLGA

QQTVVKEPVGPVAAFTPWNFPVNQVVRKLSAALA

TGCSFLVKAPEETPASPAALLRAFVDAGVPAGVI

GLVYGDPAEISSYLIPHPVIRKVTFTGSTPVGKQ

LASLAGLHMKRATMELGGHAPVIVAEDADVALAV

KAAGGAKFRNAGQVCISPTRFLVHNSIRDEFTRA

LVKHAEGLKVGNGLEEGTTLGALANPRRLTAMAS

VIDNARKVGASIETGGERIGSEGNFFAPTVIANV

PLDADVFNNEPFGPVAAIRGFDKLEEAIAEANRL

PFGLAGYAFTRSFANVHLLTQRLEVGMLWINQPA

TPWPEMPFGGVKDSGYGSEGGPEALEPYLVTKSV

TVMAV

In some embodiments, the diol dehydratase gene is from a *Klebsiella* bacterium, e.g., *Klebsiella pneumoniae*. In some embodiments, the diol dehydratase is from *Klebsiella pneumoniae* sub-species *pneumoniae* MGH78478. In some embodiments, the diol dehydratase gene can be one or more of pduC, pduD, pduE, pduG, and/or pduH. In some embodiments, the recombinant bacterium expresses at least one diol dehydrogenase enzyme, including, e.g., PduC, PduD, PduE, PduG, and/or PduH.

In some embodiments, the recombinant bacterium has at least one nucleic acid with at least one sequence selected from SEQ ID NOs: 1-6 or SEQ ID NOs: 83-87. In some embodiments, the recombinant bacterium has at least one nucleic acid with at least one sequences selected from SEQ ID NOs: 1-5. In some embodiments, the recombinant bacterium has at least one nucleic acid with at least one sequences selected from SEQ ID NOs: 83-87. In some embodiments, the recombinant bacterium has at least one nucleic acid with SEQ ID NO: 6. In some embodiments, the recombinant bacterium has at least one nucleic acid with at least one sequences selected from SEQ ID NOs: 1-5 and/or SEQ ID NOs: 83-87, and another nucleic acid with SEQ ID NO: 6.

In some embodiments, the recombinant bacterium has at least one nucleic acid with at least one sequence that is at least 80% identical to any of SEQ ID NOs: 1-6 and SEQ ID NOs: 83-87. In some embodiments, the recombinant bacterium has at least one nucleic acid with at least one sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any of SEQ ID NOs: 1-6 and SEQ ID NO: 83-87. In some embodiments, the recombinant bacterium has at least one nucleic acid with at least one sequence that varies from the nucleic acid sequence of any of SEQ ID NOs: 1-6 and SEQ ID NOs: 83-87 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

In some embodiments, the recombinant bacterium expresses at least one protein with an amino acid sequence selected from SEQ ID NOs: 77-82 and 88-92. In some embodiments, the recombinant bacterium expresses at least one protein with an amino acid sequence that is at least 80% identical to any of SEQ ID NOs: 77-82 and 88-92. In some embodiments, the recombinant bacterium expresses at least one protein with an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any of SEQ ID NOs: 77-82 and 88-92. In some embodiments, the recombinant bacterium expresses at least one protein with an amino acid sequence that varies from the amino acid sequence of any of SEQ ID NOs: 77-82 and 88-92 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more amino acids.

Promoters

As used herein, the term "promoter" refers to a DNA sequence that contains the regulatory nucleic acid sequences used for expression of an operably linked gene. A core promoter contains the essential nucleotide sequences for promoter function, including the TATA box and the transcription start site. By this definition, a core promoter may or may not have detectible activity in the absence of specific sequences that may, e.g., enhance the activity or confer tissue specific activity. Promoters can be either constitutive or inducible. A constitutive promoter controls transcription of a gene at a constant rate during the life of a cell. An inducible promoter's activity fluctuates as determined by the presence (or absence) of a specific inducer, e.g., the presence (or absence) of an extracellular or environmental factor. A "3-HP inducible promoter" is a promoter that increases expression of an operably linked gene or genes upon the exposure of a cell carrying such a promoter to 3-HP, e.g., exposure of a cell carrying a 3-HP promoter to 3-HP that is present in cell culture media or in a bioreactor. In some cases, the promoter includes one or more operator sites.

The recombinant microorganisms described herein express at least one gene used to produce 3-HP (or a salt thereof) from glycerol under the control of at least one promoter. In some embodiments, the expression system includes at least one inducible promoter that increases expression of the gene in response to a stimulus (i.e., an inducer, e.g., 3-HP). Once the stimulus contacts the inducible promoter, the promoter turns on or upregulates the expression of the gene. In some embodiments, the inducible promoter is induced by 3-HP. The stimulus or inducer that causes upregulation of gene expression by at least one inducible promoter in the expression system is 3-HP. In some embodiments, the stimulus or inducer that causes upregulation of gene expression by at least one inducible promoter in the expression system is chemically and/or structurally similar to 3-HP. In some embodiments, the stimulus or inducer that causes upregulation of gene expression by at least one inducible promoter in the expression system is a small molecule, for example, a small organic molecule such as an acid or alcohol. In some embodiments, the small molecule is structurally similar to 3-hydroxypropionic acid (3-HP) or 3-hydroxypropanealdehyde (3-HPA). 3-HP is a carboxylic acid having the chemical structure C3H603, with a molecule weight of 90.08. In some embodiments, the small various acids structurally similar to 3-HP or the intermediates appearing in the L-valine degradation pathway and central carbon metabolism. In some embodiments, the small molecule acid or alcohol can be any of, but not limited to, L-lactic acid (LAC), acetic acid (AcOH), propionic acid (PA), 3-hydroxybutyrate (3-HB), 1,3-propanediol (1,3-PDO), 2,3-butanediol (2,3-BDO), L-valine (L-val), and 3-hydroxyisobutyrate (3-HIB). In some embodiments, the inducible promoter can be induced by two or more inducers.

Presented herein are novel promoters which can be induced by the C3 platform chemical, 3-HP. This disclosure reports the mechanism of 3-HP activating/initiating the gene expression by these novel promoters. In our experiments we observed that when *Pseudomonas* strains were provided with 3-HP as the sole carbon source, the strains actively consumed 3-HP and showed growth. We identified that several enzymes, namely putative 3-hydroxyisobutyrate dehydrogenase IV (HbdH-4), 3-hydroxypropionate dehydrogenase (HpdH) and/or methylmalonatesemialdehyde dehydrogenase (MmsA) were involved in 3-HP degradation. Interestingly, we found that the transcription of the genes encoding these enzymes were substantially up-regulated at a high level, but only in the presence of 3-HP or similar small acids. Analysis of gene arrangement near these 3-HP-degrading genes revealed the presence of putative transcriptional regulator proteins, corresponding mmsA, hbdH-4 or hpdH. These transcriptional regulator proteins, when complexed by 3-HP, activate the transcription of mmsA, hpdH, and others.

The inducible nature of the promoters described herein and their high induction efficiency, makes them useful for expression of pathway enzymes for 3-HP synthesis, development of 3-HP-responsive biosensors, and/or for expression of pathway enzymes for coenzyme B12 production. Here we elucidate different 3-HP-inducible gene regulation systems. At the cellular level, the specificity and/or spectrum of the small-molecule inducer(s) was studied using various acids structurally similar to 3-HP or the intermediates appearing in the L-valine degradation pathway and central carbon metabolism.

Using these promoters, a library of promoters was generated wherein the promoters were inducible by small acids and displayed different expression levels. This library was used in combinations with other native or synthetic promoters to develop tandem promoter system. Here we tried to simulate a tandem promoter system by combining small acid inducible system and native/synthetic promoter libraries to express target genes such as 3-HP synthetic pathway genes.

In some embodiments, the inducible promoter is induced by 3-HP. In some embodiments, the inducible promoter is a naturally-occurring promoter, e.g., a promoter that drives expression of a gene in a bacterium, such as a *Pseudomonas* bacterium. In some embodiments, the inducible promoter is a naturally-occurring 3-HP inducible promoter that is present in a bacterium, e.g., a *Pseudomonas* bacterium, such as *Pseudomonas denitrificans*. In *Pseudomonas* bacteria, e.g., *P. denitrificans*, some native promoters that drive expression of proteins involved in 3-HP degradation are in turn upregulated by 3-HP, including the promoters that drive expression of 3-hydroxyisobutyrate dehydrogenase I (HbdH-1), 3-hydroxyisobutyrate dehydrogenase IV (HbdH-4), 3-hydroxypropionate dehydrogenase (HpdH), and methylmalonatesemialdehyde dehydrogenase (MmsA). In some embodiments, a recombinant bacterium described herein expresses at least one gene that is used to produce 3-HP from glycerol under the control of at least one native promoter of the mmsA gene (the PmmsA promoter), hpdH gene (the PhpdH promoter), or the hbdH-4 gene (the PhbdH-1 promoter) of *P. denitrificans*. In some embodiments, the inducible promoter is a synthetic promoter.

$P_{hbdH}$-4 promoter (SEQ ID NO: 11)

GCCCCCGCCTACCCGCCCCAGCCACCCCGGACTCA

GCAAGGATGCTGGCCCGGGCCTGGGCGGAGACGTC

TTTCGCGCCCGACCATCAGAACAAGAGGACAACCC

C $P_{hpdH}$ promoter (SEQ ID NO: 12)

TGTGGGAGCGGGCGTGCCCGCGAAGAGGCCAGCAC

AGACTTACCACTGTGCTAAAACGCACAGCGGCTGC

GCGAAATCTCGTGTTTCCTCCACGAAATTACTCAC

TAAGATGGATCGGGACAAGAATAATAATCAGGCCC

GAGGTTGCAC $P_{hpdH}$-1 promoter (SEQ ID NO: 13)

TGCGTAATGCCCCACCGTTCTGCCAGGCAACGCGA

AACCTGTAGGAGCGGCCTTGTGTCGCGATGGGCTG

CGCAGCAGCCCCGGCATTTTTTGCATCGATGCGGA

GATCTGGGGCTGCTGCGCAGCCCATCGCGACACAA

GGCCGCTCCTACAGGTTCCTGGCCCGCATGGGTAA

AGTTCGAACCAGTCAGGAGTCATTG

-continued $P_{mmsA}$ promoter (SEQ ID NO: 14)

CCTCGAATGTGCAAAAACGCAGACCATACTTGCAC

ATCACCGCATTGAGTACATCAAAAATGCACTGTTA

GGATCGATCCAGACAACAAAAAAGCCACAGGCTGG

GAGAATCCCG

In some embodiments, the recombinant bacterium expresses at least one gene that is used to produce 3-HP (or a salt thereof) from glycerol under the control of at least one promoter represented by any of SEQ ID NOs: 11-14. In some embodiments, the recombinant bacterium expresses at least one gene from any of dhaB1, dhaB2, dhaB3, gdrA, gdrB, and/or kgsA under the control of at least one promoter represented by SEQ ID NOs: 11-14.

In some embodiments, the recombinant bacterium expresses at least one gene that is used to produce 3-HP (or a salt thereof) from glycerol under the control of at least one promoter that has a sequence that is at least 80% identical to any of SEQ ID NOs: 11-14. In some embodiments, the recombinant bacterium expresses at least one gene that is used to produce 3-HP or a salt thereof from glycerol under the control of at least one promoter that has a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any of SEQ ID NOs: 11-14. In some embodiments, the recombinant bacterium expresses at least one gene that is used to produce 3-HP or a salt thereof from glycerol under the control of at least one promoter that has a sequence that differs from any of SEQ ID NOs: 11-14 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

In some embodiments, the expression systems described herein include at least two promoters in tandem that control at least one gene involved in the production of 3-HP or a salt thereof from a carbon source, such as glycerol. Tandem promoter systems are observed in microorganisms to control the expression of downstream genes under various physiological or environmental conditions. Such systems aid in the controlled regulation of target gene expression at different stages of cell growth. The tandem promoters can be native or endogenous to a microorganism, such as a promoter naturally found in a bacteria strain, or can be synthetic. In some embodiments, one or more of the promoters can be a native promoter. In some embodiments, one or more of the promoters can be a synthetic promoter.

The tandem promoters of the expression systems described herein can include one or more inducible promoter, and/or one or more constitutive promoter. In some cases, the tandem promoters include two or more inducible promoters. Tandem promoters that include two or more inducible promoters can either have two of the same inducible promoters, i.e., the inducible promoters are induced by the same inducer or stimulus, or two different inducible promoters, i.e., the inducible promoters are induced by different inducers or stimuli. In some embodiments, the tandem promoters include at least one inducible promoter and at least one constitutive promoter. For example, the tandem promoters can combine a 3-HP inducible promoter and a constitutive promoter to regulate expression of a gene involved in 3-HP synthesis.

In some embodiments, there is no terminator sequence between the tandem promoters, e.g., between any of the two or more promoters in the expression system, such that each of the promoters can regulate the expression of a gene that is located downstream of the tandem promoters.

In some embodiments, the tandem promoters include at least two 3-HP inducible promoters. In some embodiments, the tandem promoters include a first promoter that is a 3-HP inducible promoter, and a second promoter that is a 3-HP inducible promoter. In some embodiments, the first 3-HP inducible promoter and the second 3-HP inducible promoters can each be a $P_{mms.A}$ promoter (SEQ ID NO: 14), a $P_{hbaH\text{-}1}$ promoter (SEQ ID NO: 13), a PhbdH-4 promoter (SEQ ID NO: 11), or a $P_{hpdH}$ promoter (SEQ ID NO: 12).

In some embodiments, the tandem promoters include a first promoter that is a 3-HP inducible promoter and a second promoter that is a constitutive promoter, wherein the first 3-HP inducible promoter is located 5' or upstream of the second constitutive promoter. In some embodiments, the first 3-HP inducible is a $P_{mmsA}$ promoter (SEQ ID NO: 14), a $P_{hbdH\text{-}1}$ promoter (SEQ ID NO: 13), a $P_{hbdH\text{-}4}$ promoter (SEQ ID NO: 11), or a $P_{hpdH}$ promoter (SEQ ID NO: 12). In some embodiments, the second constitutive promoter is a $P_{zwf}$ (SEQ ID NO: 7) promoter. In some embodiments, the sequence of the second constitutive promoter is at least 80% identical to SEQ ID NO: 7. In some embodiments, the sequence of the second constitutive promoter is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7. In some embodiments, the sequence of the second constitutive promoter differs from SEQ ID NO: 7 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides. In some embodiments, the sequence of the second constitutive promoter is SEQ ID NO: 8 (Pzwf-1), SEQ ID NO: 9 (Pzwf-7), SEQ ID NO: 10 (Pzwf-12), SEQ ID NO: 52 (Pzwf-2), SEQ ID NO: 53 (Pzwf-3), SEQ ID NO: 54 (Pzwf-4), SEQ ID NO: 55 (Pzwf-5), SEQ ID NO: 56 (Pzwf-6), SEQ ID NO: 57 (Pzwf-7), SEQ ID NO: 58 (Pzwf-8), SEQ ID NO: 59 (Pzwf-10), SEQ ID NO: 60 (Pzwf-11), SEQ ID NO: 61, SEQ ID NO: 62, or SEQ ID NO: 63.

Pzwf constitutive promoter (SEQ ID NO: 7)

GGCGACCAACAACGGCGCGAGGTGGCAAAAATATC

TTGTTTAATTACTACATATTTGTCTTAATGCCGGC

GTGTAAGGCTAACTATCGTTCAAAATTTAGTTGGT

AACAACAA

Pzwf-1 constitutive promoter (SEQ ID NO: 8)

GGCGACCAACAACGGCGCGAGGTGGCAAAAACGGT

TTGACACAGTAATTAAAAAGACGTATAATTGCGTT

GTGTAAGGCTAACTATCGTTCAAAATTTAGTTGGT

AACAACAA

Pzwf-1 shorter constitutive promoter (SEQ ID NO: 61)

ACGGTTTGACACAGTAATTAAAAAGACGTATAATTGCGTT

Pzwf-7 constitutive promoter (SEQ ID NO: 9)

GGCGACCAACAACGGCGCGAGGTGGCAAAAGTATA

TTGACATTCCATGCGAAGGTCGTTATAATACAGTA

-continued

GTGTAAGGCTAACTATCGTTCAAAATTTAGTTGGT
AACAACAA

Pzwf-7 shorter
(SEQ ID NO: 62)
GTATATTGACATTCCATGCGAAGGTCGTTATAATACAGTA

Pzwf-12 constitutive promoter
(SEQ ID NO: 10)
GGCGCGAGGTGGCAAAATAATCTTGACAACTGGAG
AGAATTGTGGTATAATGGGAGCGTGTAAGGCTAAC
TATCGTTCAAAATTTAGTTGGTAACAACAA Pzwf-12 shorter constitutive promoter
(SEQ ID NO: 63)
TAATCTTGACAACTGGAGAGAATTGTGGTATAATGGGAGC Pzwf #2 constitutive promoter
(SEQ ID NO: 52)
TCCACTTGACATACCCTAACATCGGGATTATAATGTCTGC Pzwf #3 constitutive promoter
(SEQ ID NO: 53)
GTTGGTTGACATGGCGCTGTCGATCGGATATAATGTTTGT Pzwf #4 constitutive promoter
(SEQ ID NO: 54)
GCGTCTTGACATCTTACTAGATTGTGCGTATAATAGTCGC Pzwf #5 constitutive promoter
(SEQ ID NO: 55)
GGCGTTTGACATGTGGATGTAATCCTGTTATAATTTTTTA Pzwf #6 constitutive promoter
(SEQ ID NO: 56)
GATCCTTGACAGCGAGGTATGAGTGAGGTATAATGTAACC Pzwf #7 constitutive promoter
(SEQ ID NO: 57)
TGCGTTTGACAATTTGTTACGTTAGTGCTATAATCTAGTT Pzwf #8 constitutive promoter
(SEQ ID NO: 58)
TACCCTTGACATAACGGCATTCTGGTGGTATAATCATGCC Pzwf #10 constitutive promoter
(SEQ ID NO: 59)
GGGGGTTGACAACTGCGTGTTTGTCTGTTATAATATCCCG Pzwf #11 constitutive promoter
(SEQ ID NO: 60)
GAGAATTGACAGATGACTTATTTCGTTGAATTCCTGC In some embodiments, the sequence of the tandem promoters in an expression cassette can be SEQ ID NO: 65, SEQ ID NO: 70, SEQ ID NO: 71, or SEQ ID NO: 72. In some embodiments, the sequence of the tandem promoters in an expression cassette can be at least 80% identical to SEQ ID NO: 65, SEQ ID NO: 70, SEQ ID NO: 71, or SEQ ID NO: 72. In some embodiments, the sequence of the tandem promoters in an expression cassette can be at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 65, SEQ ID NO: 70, SEQ ID NO: 71, or SEQ ID NO: 72. In some embodiments, the sequence of the tandem promoters in an expression cassette can vary from the sequence of any of SEQ ID NOs: 70-72 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

Pcm-Pc4 tandem promoter
(SEQ ID NO: 65)
CCTCGAATGTGCAAAAACGCAGACCATACTTGCAC
ATCACCGCATTGAGTACATCAAAAATGCACTGTTA
GGATCGATCCAGACAACAAAAAAGCCACAGGCTGG
GAGAATCCCGGCCCCCGCCTACCCGCCCCAGCCAC
CCCGGACTCAGCAAGGATGCTGGCCCGGGCCTGGG
CGGAGACGTCTTTCGCGCCCGACCATCAGAACAAG
AGGACAACCCC Pc3-Pc1 tandem promoter
(SEQ ID NO: 70)
CGTGGCGACTCTCATTGTTAGAAAACGCACAGCAG
GTGACTTTAAACGTTCGTATTTTTATCGCGAACGA
ACGACTAGGCTCCATCGTCATACCCAAAAGAACAA
GAACGACGAGGGACTTTCCGGCGTTTGACATGTGG
ATGTAATCCTGTTATAATTTTTTAGTGTAAGGCTA
ACTATCGTTCAAAATTTAGGTGGTAACAACAAATG Pc1-Pc3 tandem promoter
(SEQ ID NO: 71)
GGCGTTTGACATGTGGATGTAATCCTGTTATAATT
TTTTAGTGTAAGGCTAACTATCGTTCAAAATTTAG
GTGGTAACAACAACGTGGCGACTCTCATTGTTAGA
AAACGCACAGCAGGTGACTTTAAACGTTCGTATTT
TTATCGCGAACGAACGACTAGGCTCCATCGTCATA
CCCAAAAGAACAAGAACGACGAGGGACTTTCCATG Pc3-Pzwf tandem promoter
(SEQ ID NO: 72)
CGTGGCGACTCTCATTGTTAGAAAACGCACAGCAG
GTGACTTTAAACGTTCGTATTTTTATCGCGAACGA
ACGACTAGGCTCCATCGTCATACCCAAAAGAACAA
GAACGACGAGGGACTTTCCGGCGACCAACAACGGC
GCGAGGTGGCAAAAATATCTTGTTTAATTACTACA
TATTTGTCTTAATGCCGGCGTGTAAGGCTAACTAT
CGTTCAAAATTTAGTTGGTAACAACAAATG Transcriptional Regulator The regulatory regions of 3-HP-degrading genes are located near sequences encoding native LysR-family transcriptional regulator (LTTR) proteins. When complexed by 3-HP, the LysR-family transcriptional regulator proteins activate transcription. In bacteria, LTTR proteins upregulate downstream genes by interacting with RNA polymerase. As a consequence, the amount of LTTR protein influences the transcriptional levels of downstream target genes.

In some embodiments, at least one transcriptional regulator protein is expressed in combination with at least one 3-HP production gene described herein in a recombinant microorganism, such as a bacterium. In some cases, at least one transcriptional regulator protein is an LTTR protein under the control of at least one constitutive or inducible promoter. In some cases, the transcriptional regulator protein binds to a site upstream of the at least one 3-HP production gene and regulates the expression of the at least one gene involved in 3-HP synthesis.

In some embodiments, a recombinant bacterium as described herein expresses at least one LTTR protein and at least one gene used for the production of 3-HP or a salt thereof, e.g., at least one glycerol dehydratase, diol dehydratase, and/or aldehyde dehydrogenase. In some embodiments, the LTTR protein is MmsR. In some embodiments, the MmsR promoter is expressed under the control of a constitutive promoter in the recombinant bacterium. In some embodiments, the constitutive promoter is the $P_{zwf}$ promoter (SEQ ID NO: 7). In some embodiments, the constitutive promoter has been mutated to increase or to reduce expression of MmsR relative to the Pzwf promoter. In some embodiments, the constitutive promoter is a Pzwf (SEQ ID NO: 7) promoter. In some embodiments, the sequence of the constitutive promoter is at least 80% identical to SEQ ID NO: 7. In some embodiments, the sequence of the constitutive promoter is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7. In some embodiments, the sequence of the constitutive promoter differs from SEQ ID NO: 7 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides. In some embodiments, the constitutive promoter is SEQ ID NO: 8 (Pzwf-1), SEQ ID NO: 9 (Pzwf-7), SEQ ID NO: 10 (Pzwf-12), SEQ ID NO: 52 (Pzwf-2), SEQ ID NO: 53 (Pzwf-3), SEQ ID NO: 54 (Pzwf-4), SEQ ID NO: 55 (Pzwf-5), SEQ ID NO: 56 (Pzwf-6), SEQ ID NO: 57 (Pzwf-7), SEQ ID NO: 58 (Pzwf-8), SEQ ID NO: 59 (Pzwf-10), SEQ ID NO: 60 (Pzwf-11), SEQ ID NO: 61, SEQ ID NO: 62, or SEQ ID NO: 63. In some embodiments, the mmsR gene is chromosomally located, e.g., at the mmsR gene under the control of a constitutive promoter is expressed from a chromosome in the recombinant bacterium.

5'UTR

In some embodiments, an expression system as described herein can have a 5'UTR operably linked to a gene of interest (e.g., a gene involved in 3-HP synthesis), wherein the 5'UTR is from a native gene regulated by a 3-HP inducible promoter in a bacterium that naturally produced 3-HP, e.g., *P. denitrificans*. In some embodiments, an expression as described herein has the 5'UTR of the mmsA gene (SEQ ID NO: 64) of *P. denitrificans*.

In some cases, mutation of the 5'UTR can improve the rate of translation initiation for the mRNA transcript and/or improve the stability of the mRNA transcript produced by the expression system. In some embodiments, an expression system as described herein can have a 5'UTR having a sequence that is at least 80% identical to SEQ ID NO: 64. In some embodiments, an expression system described herein can have a 5'UTR having a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 64. In some embodiments, an expression system described herein can have a 5'UTR having a sequence that varies from SEQ ID NO: 64 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 3 or more nucleotides. In some embodiments, an expression system described herein can have a 5'UTR having any sequence selected from SEQ ID NOs: 22-28.

In a non-limiting example, an expression system having the PmAdH-4 tandem promoter, Opt-3, Hyb-20 and chromosomal MmsR has the 5'UTR of the mmsA gene. In some embodiments, the mmsA 5'UTR can be mutated.

```
mmsA 5'UTR
                                        (SEQ ID NO: 64)
CGACGGCAAGCCCGTCGAGTCCACCATGGCTAACG

TGACTTACACCGATACCCAACTGCT

mmsA 5'UTR mutant UTR-0
                                        (SEQ ID NO: 22)
CGACGGCAAGCCCAAGCAGGACACCATGGCTAACG

TGACTTACACCGATACCCAACTGCT

mmsA 5'UTR mutant UTR-1
                                        (SEQ ID NO: 23)
CGACGGCAAGCCAACTGAACCCACCATGGCTAACG

TGACTTACACCGATACCCAACTGCT

mmsA 5'UTR mutant UTR-2
                                        (SEQ ID NO: 24)
CGACGGCAAGCCCTAACTGGACACCATGGCTAACG

TGACTTACACCGATACCCAACTGCT

mmsA 5'UTR mutant UTR-3
                                        (SEQ ID NO: 25)
CGACGGCAAGCCCTAACAGGACACCATGGCTAACG

TGACTTACACCGATACCCAACTGCT

mmsA 5'UTR mutant UTR-4
                                        (SEQ ID NO: 26)
CGACGGCAAGCCCAAGCTGGACACCATGGCTAACG

TGACTTACACCGATACCCAACTGCT

mmsA 5'UTR mutant UTR-5
                                        (SEQ ID NO: 27)
CGACGGCAAGCCCTAGCAGGACACCATGGCTAACG

TGACTTACACCGATACCCAACTGCT

mmsA 5'UTR mutant UTR-6
                                        (SEQ ID NO: 28)
CGACGGCAAGCCCAAGCAGGACACCATGGCTAACG

TGACTTACACCGATACCCAACTGCT
```

Figures 17A, 17B, 17C, 17D:
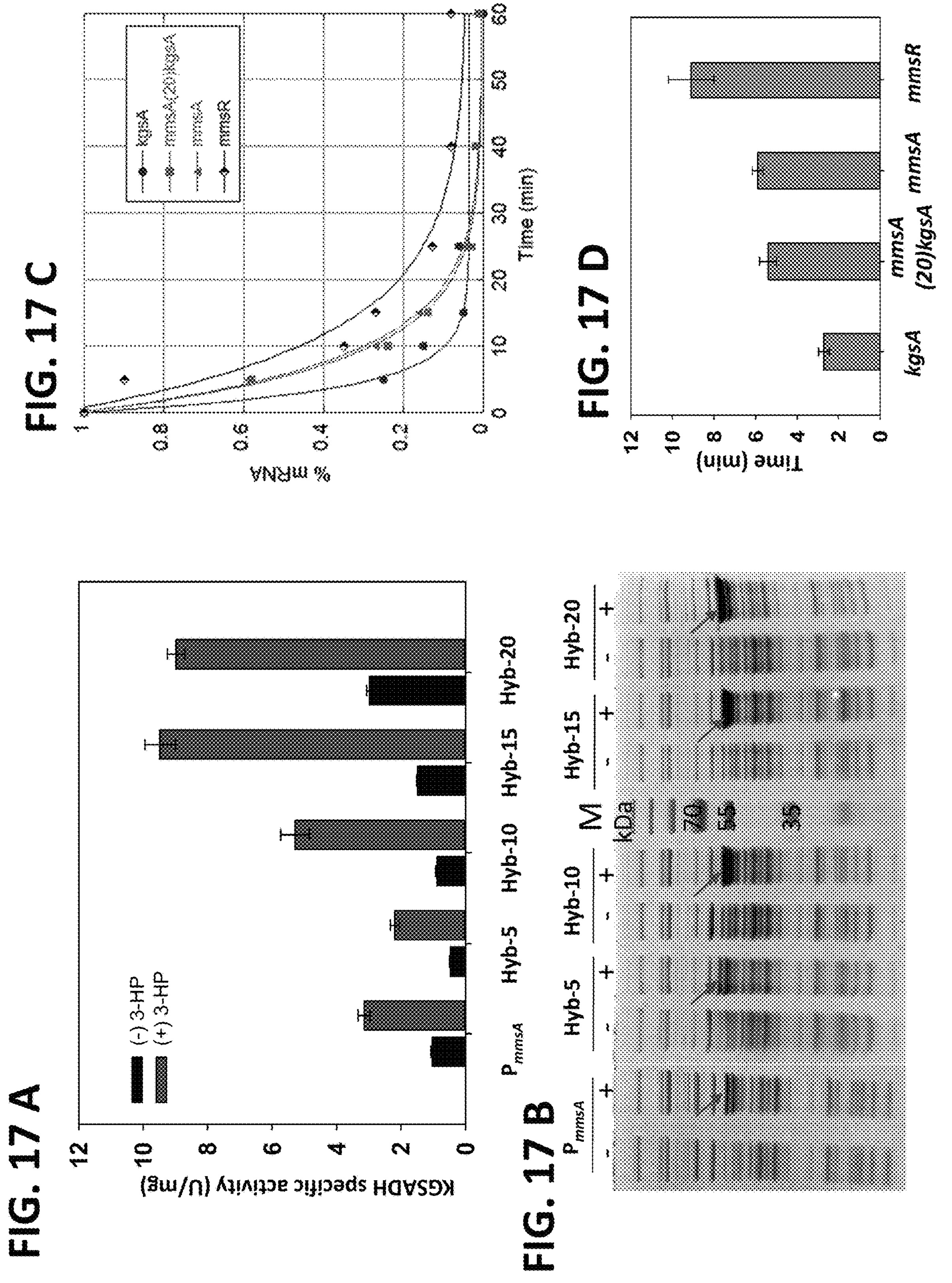
FIGS. 17A-D is a set of graphs showing the effect of fusion of the native MmsA protein on the expression and enzymatic activity of KgsA. Various lengths of the mmsA N-terminal sequences corresponding to 5, 10, 15 and 20 amino acid-long (designated asHyb-5, Hyb-10, Hyb-15 and Hyb-20, respectively) were linked to the kgsA 5'-terminal DNA sequence.

Optimization of Gene Expression in *P. denitrificans* by Fusing Initial Few Amino Acids of Native Protein For optimizing the expression of heterologous proteins in *P. denitrificans*, a novel approach was adopted. The heterologous proteins were fused with a few of the initial amino acids (5-20 AA) of highly expressing native enzymes at N-terminal of a target protein (e.g., 5-20 amino acids at the N-terminal of the native protein were fused to the N-terminal of the heterologous protein). For example, varying lengths (e.g., 5, 6, 7, 8, 9, 10, 11, 12, 13, 14, 15, 16, 17, 18, 19, or 20 amino acids-long; designated Hyb-5, Hyb-6, Hyb-7, Hyb-8, Hyb-9, Hyb-10, Hyb-11, Hyb-12, Hyb-13, Hyb-14, Hyb-15, Hyb-16, Hyb-17, Hyb-18, Hyb-19, and Hyb-20, respectively) of the N-terminal end of mmsA was joined to the full-length heterologous kgsA gene and expressed from the multi-copy plasmid (FIG. 17). The highest activity was obtained with Hyb-20 (+3-HP, 9.3 U/mg protein; −3-HP, 3.0 U/mg protein). On the other hand, Hyb-5 did not show any change either in its expression or its enzyme activities (FIG. 17A). SDS-PAGE analysis indicated that protein production increased when kgsA was fused with N-terminal mmsA fragments (more than five amino acids were added) (FIG. 17B). To understand the mechanism for the improved expression and mRNA stability in wild type and Hyb-20 kgsA recombinant strains, the transcripts were measured and compared. Stability of the mmsA and mmsR transcripts was also determined (FIGS. 17C and 17D). The half-life of the wild type kgsA transcript (2.7 min) was 2.3-fold shorter than that of mmsA (6.1 min); however, by fusing initial 20 aa of mmsA (20), the half-life of mRNA of fusion protein was substantially improved to 5.7 minutes which was comparable to the half-life of mRNA of native mmsA. This suggests that the fusion protein (mRNA transcript) becomes less susceptible to endogenous nuclease attack. Transcription level of the hybrid mmsA(20)kgsA gene, determined by RT-PCR, was also two-times higher than that of the wild type kgsA gene (data not shown). We believe that higher mRNA stability along with the improved transcription should have contributed to the improved KgsA activity of the hybrid enzymes. Among the several genes examined, mmsA showed the highest mRNA stability with the half-life of 9.5 min (Data not shown).

Production of Coenzyme B12 by Recombinant Bacteria

The production of 3-HP from glycerol by 3-HP or salt thereof producing microorganisms is limited without the external addition of coenzyme B12. Coenzyme B12 is an essential cofactor for glycerol/diol dehydratase enzyme activity, which is used for the first reaction in the 3-HP synthetic pathway, wherein glycerol is catalytically converted into 3-hydroxypropanealdehyde. Therefore, a continuous supply of coenzyme B12 is essential for the uninterrupted production of 3-HP or a salt thereof from glycerol by microorganisms, such as bacteria. Coenzyme B12 can be synthesized naturally under either aerobic or anaerobic conditions by a limited number of microorganisms (Anaerobic producers of coenzyme B12 include, e.g., *Klebsiella, Streptococcus, Salmonella* species. Aerobic producers of coenzyme B12 include, e.g., *Pseudomonas, Rhizobium, Rhodobacter* species). However, the microorganisms that have been evaluated as potential hosts for producing 3-HP or salts thereof from glycerol appear to not produce sufficient amounts of coenzyme B12 to produce 3-HP at high titers. Further analysis has shown that coenzyme B12 production is transcriptionally and translationally regulated. These processes can be genetically modified in recombinant microorganisms, e.g., bacteria, to increase coenzyme B12 production, thereby increasing 3-HP (or salt thereof) titers without the supplementation of bacteria with external coenzyme B12.

Figure 23:
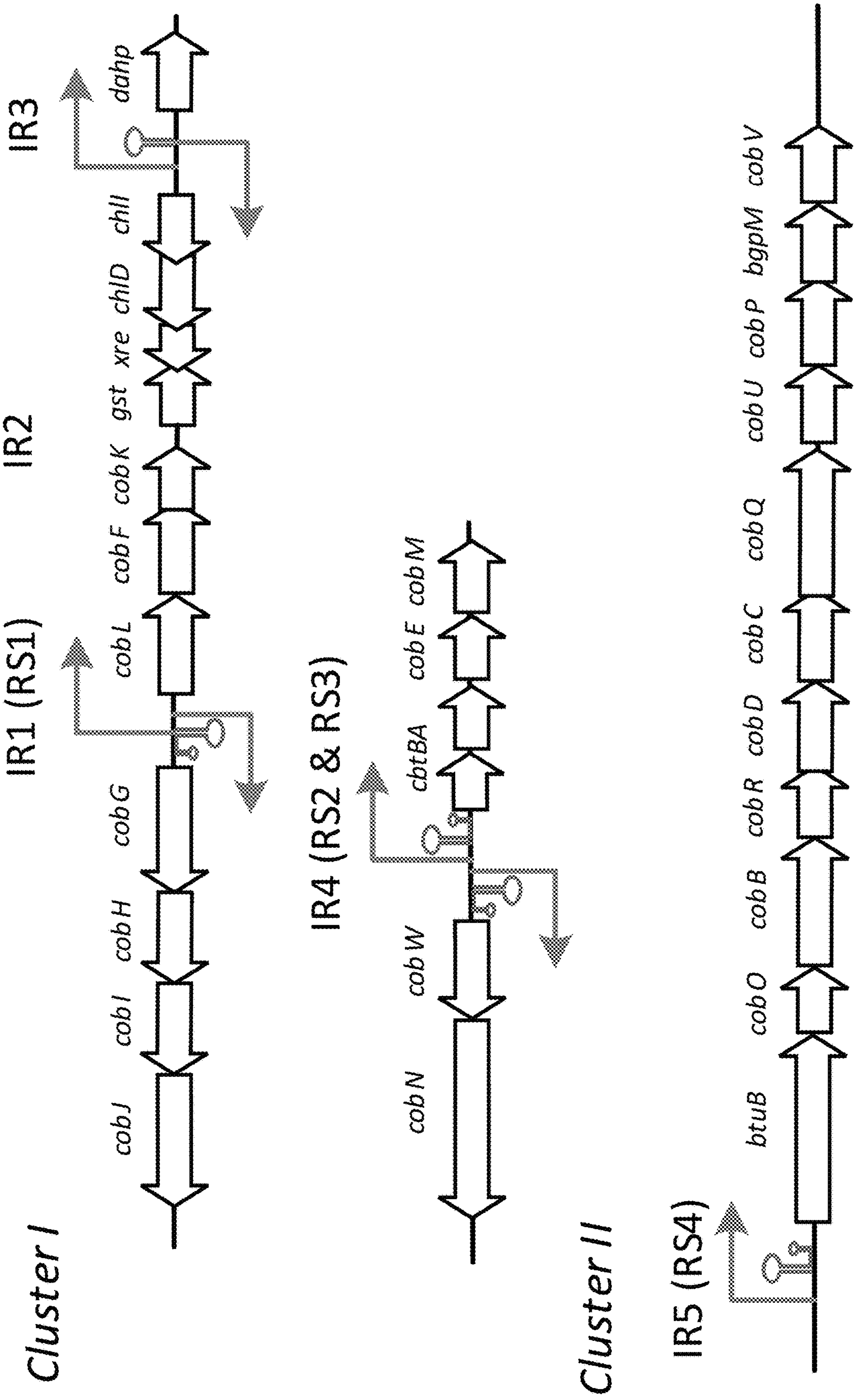
FIG. 23 is a schematic of the Vitamin B12 (Coenzyme B12) gene clusters and riboswitches in *P. denitrificans*.

As shown in FIG. 23, two gene clusters (cluster I and cluster II) are responsible for producing the proteins used for the production of coenzyme B12 in *P. denitrificans*. Riboswitches and other secondary structures have been identified in the promoter regions of the operons present in clusters I and II (see FIG. 23). These riboswitches appear to regulate the expression of the B12 biosynthetic operons, and may repress gene expression. In some embodiments described herein, one or more riboswitches or other secondary structures may be removed from one or more operon promoter regions of cluster I and/or cluster II in the genome of *P. denitrificans*. In some embodiments, one or more of riboswitch 1, 2, 3, and/or 4, as depicted in FIG. 23 and FIGS. 25A-D, or portion thereof, is deleted in the genome of *P. denitrificans*. In some embodiments, all or part of the DNA sequence of riboswitch 1 (SEQ ID NO: 75) or riboswitch 2 (SEQ ID NO: 76) is removed from the genome of *P. denitrificans*. In some embodiments, all or part of the DNA sequence of riboswitch 1 (SEQ ID NO: 75) and riboswitch 2 (SEQ ID NO: 76) is removed from the genome of *P. denitrificans*.

Any of the expression systems described herein can be used to increase expression of the genes involved in the production of coenzyme B12 and/or to increase production of coenzyme B12. The 3-HP inducible promoter systems described herein can be used to replace the regulatory regions of the B12 production genes (e.g., the translational and/or transcriptional regulators). This disclosure provides for methods of increasing production of coenzyme B12 such that the supplementation of coenzyme B12 is not used for the production of 3-HP by an organism. Provided herein are recombinant organisms that can include an expression system for the control and/or upregulation of a gene(s) for the production of 3-HP and an expression system for the control and/or upregulation of a gene(s) for the production of coenzyme B12.

```
Riboswitch 1 (RS1)
                                      (SEQ ID NO: 75)
Ccagatgccgacgatggtcagccagggcgtcatgg

ggattcctctgaagggatgcgatgatcgatccgac

gggcaggcttgttccgccctcgggcaaagcaggca

taatacccgcatcgtcggtgctcgtaggacgcttc

gctgtttgaaggcgatgcatccgagagccgaagag

ggaacacggaaaaaccgtggctgcccccgcaactg

taagcagcgagtccgcgcacttcgaccacagcgtc

tgttgtcgtcgatctggccactgggcaaccgggaa

ggccgtgccggatgaggacctgccagccaggagac

ctgccgacgaaaccagtcgcgcgtgcagacatcga

gcggggtgtatcggtgtcgtgaagtcccctgtggg

gattcgcaggtcaccgcgacccagccctggtgacc

tca

Riboswitch 2 (RS2)
                                      (SEQ ID NO: 76)
ggcggatgaagggcgcgcgcgcgggttcgccgcgc

aacgaaggtcgccaccggatcaccccgcccggttg

tctgttgataacgaaccggttccggatctcgcgag

ctagagccaggcaaggcggaggatcgtcggggacg

cggagttgactgtagtcaatgagcagtccacgacg

atccgccaacgcagcatggccgacgcgcagcagat

cgaaaaccagtcacgaggcaggtctcctggctcac

agcccttgatcgtcctttcgccttcccgccgtagt

cggcagtggcgtgtgaaagaacaggctgttcacag

ttgcgggggcagccgtggcgcatccgaagatttcc

acgttccctcttagctccggccagtgccggagaac

ctcgaagggaggaaggctacgcagcgtggccgggg

cggtcaatcgccggggatcgggcgacgcgcagttg

acgctgcgggactgccgtggtcagctagcgcggtt

tcaggtgtctcgcgccgacgcgcgcgaggtgaaac

gggaagccggtgcgtccgcaaggaccagtccggcg

ctgcccccgcaacggtaagcgcatcgagggtcgtc

agtagccactgtgccaaggcatgggaaggctggcc
```

-continued

```
catccggcgagagtctctcgctggcgtcgcaagcc

cggagaccggcctggaatcctcacattttggcaaa

cccgcggtgggcgggcgcaggccgtggcgcgaccg

atccggcgcgttcgaatgcgttcaacctctgcgtt

ctcactcttttcagagggaacgttcatgtccagca

gcatcctgacgcaacaggcg
```

Expression System Placement for Channeling

The expression systems described herein can be genetically introduced into a host microorganism, e.g., a bacterium, using any methods well known in the art. In some cases, the expression system can be introduced into a microorganism using a plasmid, artificial chromosome, or other vector. In some embodiments, the expression system can be integrated into the genome of a microorganism, e.g., integrated into a chromosome.

Multiple copies of the expression system can be introduced into a microorganism, e.g., a bacterium. Multiple copies of the expression system can be introduced into a microorganism, e.g., a bacterium, on at least one plasmid, artificial chromosome, or other vector. For example, multiple copies of an expression system can be introduced into a bacterium on a single plasmid, or on two or more different plasmids (i.e., plasmids with different sequences, selection markers, etc.). Multiple copies of an expression system can be integrated into the genome of a microorganism. In some embodiments, multiple copies of an expression system can be integrated at the same location in the genome, e.g., at the same chromosomal location. In some embodiments, multiple copies of an expression system can be integrated at different locations, e.g., at different chromosomal locations. In some embodiments, multiple copies of an expression system are integrated at different locations in a *Pseudomonas* bacterium, such as *P. denitrificans*. In some embodiments, two or more expression systems that regulate different genes involved in 3-HP production from a carbon source, e.g., one or more glycerol dehydratase or diol dehydratase gene, and an aldehyde dehydrogenase gene, are integrated into the genome of a *Pseudomonas* bacterium. In some embodiments, the two or more expression systems are integrated at the same location of the genome. In some embodiments, the two or more expression systems are integrated at different chromosomal locations.

In some embodiments, one or more expression systems described herein are introduced into a bacterium, such as *Pseudomonas denitrificans* bacterium. In some embodiments, an expression system that regulates one or more genes encoding a glycerol dehydratase gene and/or diol dehydratase gene (e.g., at least one of the dhaB1, dhaB2, dhaB3, gdrA, and/or gdrB genes) and an expression system that regulates one or more genes encoding an aldehyde dehydrogenase (e.g., at least one ksgA gene) are introduced into a *P. denitrificans* bacterium, and, optionally, at integrated into the genome of the bacterium. In some embodiments, the expression systems that regulate the glycerol dehydratase (and/or diol dehydratase) and aldehyde dehydrogenase genes are integrated at different chromosomal locations.

In some embodiments, expression systems that regulate glycerol dehydratase (and/or diol dehydratase) and aldehyde dehydrogenase genes are integrated at different chromosomal locations. The particular chromosomal integration site can significantly influence the levels of expression of an expression system or module, such that the level of gene expression at one integration site will be different than the level of gene expression at a different integration site. In addition, the positioning of the insertion of particular genes in a pathway into the chromosome can balance the activity of synthetic pathway enzymes and avoid the accumulation of toxic intermediates, such as 3-hydroxypropanealdehyde. For example, in many prokaryotes, the genes encoding enzymes of one pathway are clustered together. This clustered arrangement is observed in bacteria which is believed to avoid the accumulation of intermediates produced by the pathway in the cell. In prokaryotes, transcription and translations occurs simultaneously, and in many cases, the product of a first enzyme encoded by a first gene will be the substrate of a second enzyme encoded by a second gene in the pathway. If the genes are located close to each other, the substrate for the second enzyme encoded by the second gene in a pathway, which was produced by an enzyme encoded by a first gene, will be localized near the second enzyme. This kind of mechanism increases the efficiency of the pathway and avoids the accumulation of potentially toxic intermediates, by allowing intermediates to be immediately consumed it the next enzyme in the pathway. This kind of clustering of genes very close to each other is known as channeling.

Thus, it is possible to regulate the levels of 3-HPA and 3-HP in a recombinant bacterium by regulating the levels of the glycerol dehydratase (and/or diol dehydratase) and aldehyde dehydrogenase by integrating expression systems regulating these enzymes at different chromosomal positions, such that the positioning of the glycerol dehydratase and the aldehyde dehydrogenase in the chromosome will produce a channeling effect, e.g., by leading to the rapid conversion of 3-HPA to 3-HP. Producing a channeling effect via the positioning of separate expression systems regulating glycerol dehydratase (and/or diol dehydratase) and aldehyde dehydrogenase can prevent the accumulation of 3-HPA in bacterial cells, which is toxic to the cells, thereby allowing the cells to survive and grow longer, and produce higher titers of 3-HP or a salt thereof.

In some cases, a first location of integration of a first expression system in relation to a second location of integration of a second expression system affects the production levels of 3-HP or a salt thereof. In some cases, the first expression system can be an expression system expressing a glycerol dehydratase or diol dehydratase enzyme (e.g., one or more dhaB and/or gdrAB gene(s)). In some cases, the second expression system can be an expression system expressing aldehyde dehydrogenase enzyme (e.g., one or more ALDH genes, e.g., kgsA, ealdH, and/or kaldH gene(s)). In some cases this system of integrating the two expression systems in close in relation to one another can reduce the buildup of toxic intermediates (e.g., 3-HPA) and reduce exposure of other enzymes to these toxic intermediates, thereby increasing production of 3-HP or a salt thereof.

In some embodiments, an expression system or module encoding at least one glycerol dehydratase (and/or one or more diol dehydratase gene), as described herein, is positioned within about 500-2,500,000 nucleotide base pairs (e.g., between about 500 base pairs to 2,500 kilo base pairs) (e.g., nucleotides or basepairs) or less of an expression system or module encoding at least one aldehyde dehydrogenase, as described herein in, in the chromosome of a recombinant bacterium, e.g., *P. denitrificans* (e.g., within about 500-2,500,000 base pairs of each other). In some embodiments, expression systems, as described herein, encoding at least one glycerol dehydratase (or diol dehydratase) enzyme and at least one aldehyde dehydrogenase enzyme are located within about 2,500 kilo nucleotides, 1,500 kilo nucleotides, 500 kilo nucleotides, 250 kilo nucleotides, 150 kilo nucleotides, 50,000 nucleotides, 25,000 nucleotides, 15,000 nucleotides, 10,000 nucleotides, 8,000 nucleotides, 6,000 nucleotides, 4,000 nucleotides, 3,800 nucleotides, 3,600 nucleotides, 3,400 nucleotides, 3,200 nucleotides, 3,000 nucleotides, 2,800 nucleotides, 2,600 nucleotides, 2,400 nucleotides, 2,200 nucleotides, 2,000 nucleotides, 1,800 nucleotides, 1,600 nucleotides, 1,400 nucleotides, 1,200 nucleotides, 1,000 nucleotides, 900 nucleotides, 800 nucleotides, 700 nucleotides, 600 nucleotides, 500 nucleotides, 400 nucleotides, 300 nucleotides, 200 nucleotides, 100 nucleotides, 50 nucleotides, or fewer nucleotides of each other. In some embodiments, the distance between the sites of integration of the genes or expression systems is approximately 4000 basepairs. In some embodiments the sites of integration were at least approximately 1500 basepairs apart (e.g., approximately 1500 basepairs; 2000 basepairs; 2500 basepairs; 3000 basepairs; 3500 basepairs; 4000 basepairs; 4500 basepairs; 5000 basepairs; 5500 basepairs; 6000 basepairs; 6500 basepairs; 7000 basepairs; 7500 basepairs; 8000 basepairs; 8500 basepairs; 9000 basepairs; 9500 basepairs; 10,000 basepairs; 20,000 basepairs; 50,000 basepairs; 100,000 basepairs; 200,000 basepairs; or 500,000 basepairs). In some embodiments, an expression system, as described herein, encoding at least one glycerol dehydratase enzyme or a diol dehydratase, and an expression system, as described within, encoding at least one aldehyde dehydrogenase enzyme are positioned within about 500 nucleotides of each other in the bacterial chromosome (e.g., the distance between the sites of integration of the genes or expression systems is approximately 500 basepairs).

In some embodiments, the location of integration into the bacterial chromosome of an expression system affects the expression level of the expression system. In some cases, the closer to the origin of replication, the higher the expression levels of the expression system. In some embodiments, the expression system was integrated at between about 500-4000 nucleotides (e.g., nucleotides or basepairs) away from the origin of replication. In some embodiments, the expression system was integrated at ~4000 nucleotides away, ~3000 nucleotides away, ~2000 nucleotides away, ~1000 nucleotides away, ~750 nucleotides away, or ~500 nucleotides away from the replication origin. In some embodiments, the integration site closest to the origin of replication is approximately 500 nucleotides away from the origin of replication. In some embodiments, the integration site closest to the origin of replication is at least 500 nucleotides (e.g., approximately 500 nucleotides; 600 nucleotides; 700 base nucleotides pairs; 800 nucleotides; 900 nucleotides; 1000 nucleotides; 1100 nucleotides; 1200 nucleotides; 1300 nucleotides; 1400 nucleotides; 1500 nucleotides; 2000 nucleotides; 2500 nucleotides; 4000 nucleotides; or 5000 nucleotides) away from the origin of replication. In some embodiments, the expression system was integrated at about 500 nucleotides away from the origin of replication.

As described above, a system was created to channel 3-HPA through the DhaB and ALDH enzymes to improve 3-HP production and cell viability. This system reduces the exposure of other enzymes and cellular components to toxic 3-HPA and increases production of 3-HP or a salt thereof. In one embodiment, the dhaB, gdrAB genes, and kgsA were located next to each other. In another case, the location of kgsA was more than 2000 bp away from the DhaB and GdrAB encoding genes. The position of integration of the genes in relation to one another and in relation to the origin of replication influences expression and activity.

Figure 51:
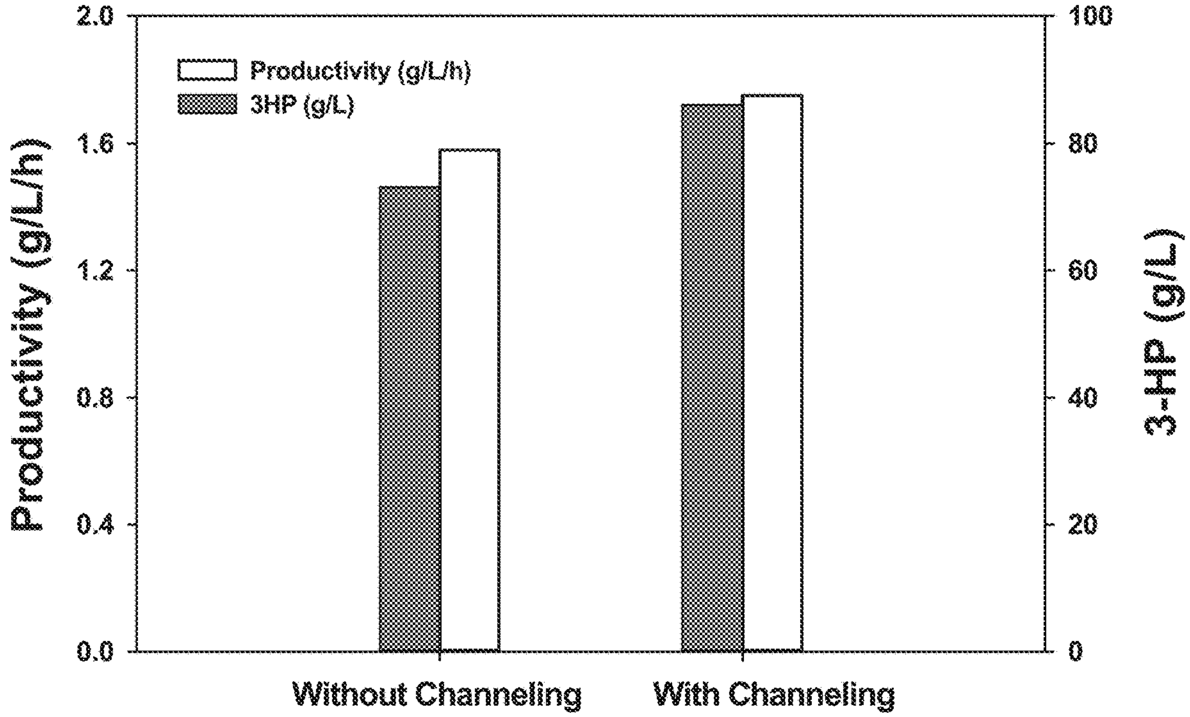
FIG. 51 is a graph showing the effect of substrate channeling on 3-HP production.

When the kgsA was placed at different locations (close to DhaB, GdrAB (strain P4-20), and 2000 bp away from DhaB, GdrAB (strain P4-10)) we notice a difference in enzyme activities. In strains P4-10 and P4-20 the enzymatic activities were synchronized (by altering gene regulation modules such as promoters, UTR) in order to study the channeling effect. With these modifications, both the strains (with (P4-20) and without (P4-10) channeling effect) showed similar KgsA and DhaB activities. The only difference between these two strains (with and without channeling strains) was the location of the kgsA gene in relation to the dhaB and gdrAB genes (FIG. 51).

In these same strains (P4-10 and P4-20), the production of 3-HP was compared. The P4-20 strain, in which the genes (the kgsA gene, and the dhaB and gdrAB genes) were channeled (e.g., located close to each other), showed a higher 3-HP production rate and improved 3-HP titer when compared to the P4-10 strain, in which the genes (the kgsA gene, and the dhaB and gdrAB genes) were not channeled (e.g., located 2000 bp apart on the chromosome). In strain P4-20 the level of 3-HPA accumulation was lower than in P4-10. In some cases this is due to the consumption of 3-HPA by the closely located KgsA enzyme. In the P4-20 strain, the DhaB enzyme (which produces the 3-HPA) is closely located to the KgsA enzyme, and thus the 3-HPA is rapidly consumed by the KgsA enzyme before it can accumulate, and/or affect the enzymes.

Bioproduction

Optimum physiological parameters such as media, aeration, temperature, pH, and induction time of target product, individually or in combination has substantially effect on the cell growth and target molecule production.

Media is an important parameter in bioprocess which plays a very vital role in maintaining the cell viability and to improve the titer of the target product, therefore it has to be formulated appropriately for efficient 3-HP production. The bioprocess to produce 3-HP or a salt thereof using analytical grade chemicals is commercially not viable. Therefore careful selection and formulation of media components was very important. Among the components, coenzyme B12 for DhaB enzyme activity, carbon source and nitrogen source are the expensive components supplemented in medium for 3-HP production, hence, it is highly important to identify and examine less expensive media components and also formulate a suitable medium for 3-HP production and commercialization.

Apart from industrial medium formulation, the bioprocess conditions such as, temperature, pH, aeration, etc. was studied and optimized in bioreactor conditions. Cellular metabolism and NAD+ regeneration, which are extremely critical to 3-HP production, were analytically studied by varying physiological parameters under controlled conditions. The effect of pH, which plays a vital role in improving the acid tolerance of recombinant strains and enzyme efficiencies of 3-HP production pathway, was examined. Aeration and temperature and induction time optimization was studied carefully as each physiological parameter significantly influence 3-HP production. An improvement in performance of recombinant strains to produce 3-HP from glycerol by bioprocess optimization was achieved.

As described in the examples, various carbon sources that could support recombinant strains to grow to higher cell densities and also product 3-HP at high titer were investigated, including, e.g., glucose, glutamate, gluconate, and citric acid. The pH of the growth conditions was also investigated, and in some cases neutralizing base was used in the bioreactor to maintain pH. Also provided herein are bacterial strains that can grow at higher acidic concentrations and/or with higher 3-HP concentrations. In some cases, the level of bicarbonate in the growth culture is controlled.

Nitrogen is another important component in the media. As shown in the examples that follow, the production of 3-HP using various nitrogen sources was also investigated, including, e.g., corn steep liquor, yeast extract, etc.

Aeration is an important property for cell growth. Aeration of the culture conditions is used for cell growth, however too much aeration can reduce levels of 3-HP production. The examples that follow demonstrate proper aeration for the bioproduction of 3-HP.

This disclosure also provides for identifying the optimal temperature for cell growth and target molecule production by recombinant microorganisms. This involves a balance of the optimal temperature for cell growth and the optimal temperature for target molecule production.

The induction timing for the production of 3-HP can also be adjusted based on the culture conditions and the recombinant bacteria. For example, induction by the addition of glycerol (as a source for 3-HP) at mid log phase produced high levels of 3-HP by the recombinant strains. Other culture conditions and/or recombinant strains can produce high levels of 3-HP by inducing at early or late log phase.

Removing 3-HP from an Aqueous Solution

In some embodiments, a method of extracting 3-HP from an aqueous solution includes: evaporating a water-immiscible solvent; condensing the vaporized water-immiscible solvent to a liquid state; using the liquid water-immiscible solvent to extract 3-HP from an aqueous phase containing the 3-HP to provide a solution of 3-HP in the water-immiscible solvent; separating the solution of 3-HP in the water-immiscible solvent from the aqueous phase. Generally, before being contacted with the liquid water-immiscible solvent, the aqueous phase containing 3-HP further contains a water-miscible solvent.

Generally, any appropriate water-miscible or water-immiscible solvents, or any combination thereof, may be used for removing 3-HP from an aqueous solution. Exemplary embodiments of these solvents and combinations thereof are described in the corresponding "Water-immiscible solvents", "Water-miscible solvents", "Combinations of solvents" sections of the disclosure.

In general, any appropriate process conditions may be used in a method of removing 3-HP from an aqueous solution. Illustrative exemplary process parameters are disclosed below in the section entitled "Process parameters."

In general, 3-HP is a polar organic acid that is relatively highly soluble in water and is relatively poorly soluble in organic solvents. 3-HP is a commercially available product. For example, 3-HP may be purchased from Sigma-Aldrich as a 30 wt. % solution in water (Catalog No. 792659), while 5-6 wt. % solution of 3-HP in ethyl acetate is difficult to obtain. Without wishing to be bound by theory, it is believed that adding a water-miscible solvent (e.g., methanol) to an aqueous solution of 3-HP decreases the solubility of 3-HP in the resultant aqueous solution and thereby facilitates the removal of 3-HP from the aqueous solution by a water-immiscible solvent (e.g., ethyl acetate).

Aqueous Solution

As used herein, the term "aqueous solution" refers to a solution of at least one solute in liquid that includes one or more solvents (e.g., a mixture of solvents), wherein at least one solvent is water and the weight percentage of water in the solvent or mixture of solvents is at least about 50% (e.g., at least about 60%, at least about 70%, at least about 80%, at least 90%). In some embodiments, aqueous solution is a solution in which water is the only solvent.

In some embodiments, the amount of 3-HP in an aqueous solution is from about 10 g/L to about 150 g/L (e.g., about 20 g/L to about 140 g/L, about 30 g/L to about 130 g/L, about 40 g/L to about 120 g/L, about 50 g/L to about 110 g/L, about 50 g/L to about 100 g/L, about 60 g/L to about 100 g/L, about 60 g/L to about 80 g/L, or about 80 g/L to about 120 g/L). The concentration of 3-HP in a solution may be expressed as a mass of 3-HP in a specified volume of the solution containing 3-HP (titer), an amount of 3-HP in a specified mass of the solvent (molality), or an amount of 3-HP in a specified volume of the solution (molarity). Any other way to express concentration of a solute in a solution may additionally or alternatively be used to describe concentration of 3-HP in the aqueous solution. As an example, in some embodiments, the titer of 3-HP in an aqueous solution is at least about 40 g/L (e.g., about 50 g/L, about 60 g/L, about 70 g/L, about 80 g/L, about 90 g/L, about 100 g/L, or about 120 g/L).

In some embodiments, an aqueous solution is a fermentation broth obtained after decellularization. Any method to remove whole cells from a broth may be employed for decellularization. As an example, a fermentation broth may be decellularized using a centrifuge. In some embodiments, an aqueous solution is a fermentation broth (e.g., a culture media) obtained after culturing or growing a microorganism. In some cases, the aqueous solution is decellularized. In some embodiments, the broth containing 3-HP may be obtained by culturing a microorganism that produces 3-HP. Illustrative examples of such microorganisms include a Gram-negative bacteria, such as *E. coli, Oligotropha carboxidovorans, Klebsiella pneumoniae* or *Pseudomononas* sp.; and Gram-positive bacteria such as *Bacillus subtilis, Lactobaccilus* sp. or *Lactococcus* sp. Microorganisms that may produce 3-HP by fermentation include any member of genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula* or *Saccharomyces*. In some embodiments, the microorganism that produces 3-HP is a recombinant bacterium described herein. Some examples of recombinant bacterium that produce 3-HP are a *Pseudomonas* strain, a *Klebsiella* strain, or an *Escherichia* strain. Some examples of the microorganisms that may produce 3-HP by fermentation include *Alcaligenes eutrophus* (*Cupriavidus necator*), *Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae.*

A fermentation media in the broth may include a variety of nutrients and ingredients that are generally useful in a bacterial or fungal growth media (e.g., carbon and/or nitrogen sources). Illustrative and non-limiting examples of such nutrients and ingredients are described herein. An example of a carbon source is sugar, such as, for example, glucose, glutamate, gluconate, fructose, arabinose, or galactose, citric acid, or a citric acid cycle intermediate such as a pyruvate or succinate, or a combination thereof. Another example of a carbon source is glycerol. Exemplary nitrogen sources include ammonium salts, corn steep liquor, yeast extract, and nitrates. Illustrative examples of additional ingredients useful in the fermentation media also include serum proteins, vitamins, nucleic acids and amino acids.

In some embodiments, a decellularized broth containing 3-HP after fermentation contains from about 0.5 wt. % to about 5 wt. % (e.g., from about 1 wt. % to about 3 wt. %) of a carbon source, such as, for example, glycerol.

In some embodiments, a decellularized fermentation broth contains from about 0.5 wt. % to about 20 wt. % (e.g., from about 1 wt. % to about 10 wt. %) of a combined amount of additional ingredients (e.g., such as those described herein) used by a microorganism to produce 3-HP.

In some embodiments, a broth after fermentation and decellularization has a pH of from about 7 to about 8 (e.g., from about 7 to about 7.5). Such a broth may contain a salt of 3-HP, such as, for example, a sodium salt or a potassium salt. In some embodiments, an acid may be added to the decellularized fermentation broth to decrease the pH and obtain a free acid form of 3-HP in the broth. Any appropriate inorganic or organic acid maybe used to adjust the pH of the fermentation broth. Exemplary inorganic acids include HCl, $H_2SO_4$, $HNO_3$, and $H_3PO_4$. Exemplary organic acids include formic acid, oxalic acid, acetic acid, tartaric acid, malonic acid, glutaric acid, succinic acid, and trifluoroacetic acid. In some embodiments, a saturated aqueous solution of oxalic acid is used to adjust the pH of the aqueous solution. The concentration of a saturated solution of oxalic acid at about room temperature is, for example, from about 40 g/L to about 50 g/L (e.g., about 45 g/L).

In some embodiments, the pH of the aqueous solution containing 3-HP is from about 3 to about 7 (e.g., from about 4 to about 7, from about 4 to about 5, from about 4 to about 6, from about 4.1 to about 4.9, from about 4.2 to about from 4.7, about from 4.2 to about 4.8, from about 4.3 to about 4.6, or from about 4.3 to about 4.5). In some embodiments, the pH of the aqueous solution is at least about 3 (e.g., at least about 3.5, at least about 4, or at least about 4.1), and/or at most about 7 (e.g., at most about 6.5, at most about 6, at most about 5.5, or at most about 5.0). In some embodiments, the pH of the aqueous solution is about 4, about 4.1, about 4.2, about 4.3, about 4.4, about 4.5, about 4.6, or about 4.7.

In some embodiments, the pH of the aqueous solution gradually increases as 3-HP is removed from the aqueous solution. In such embodiments, the pH of the aqueous solution may be adjusted (continuously or discontinuously) during the removal process by continuously or discontinuously adding one or more acids to the aqueous solution to address as desired any gradual increase in pH due to 3-HP removal.

In some embodiments, 3-HP may be removed from the aqueous solution with a yield of at least about 20% (e.g., at least about 30%, at least about 40%, at least about 50%, at least about 60%, at least about 70%, at least about 80%, at least about 90%, at least about 95%, or at least about 99%). In some embodiments, 3-HP may be removed from the aqueous solution such that only trace amount of 3-HP may be detected in the aqueous solution (e.g., by HPLC or LCMS). In some embodiments, 3-HP may be completely removed from the aqueous solution (i.e., the yield of the removal process is 100%).

As used herein the term "yield" refers to a ratio (expressed as a percentage) of a total amount of obtained product to a theoretical amount of product that could be obtained by the process used to obtain the product, based on the amount of starting materials used in the process.

In some embodiments, 3-HP may be removed from the aqueous solution without using a counter-current fluid flow. As used herein, the term "counter-current fluid flow" refers to a bidirectional flow of two immiscible liquids after contact and phase separation. In some embodiments, the flow rates of the liquids are equal. In other embodiments, the flow rate of one liquid is greater than the flow rate of the other liquid. Counter-current extraction of a solute from an aqueous solvent by a water-immiscible solvent is but one example of a counter-current fluid flow. In embodiments in which 3-HP is removed from an aqueous solution without using a counter-current flow, the 3-HP may be, for example, extracted from the aqueous solution with an organic solvent, without using any of the techniques and apparatuses for counter-current flow of the aqueous solution and the organic solvent. Counter-current flow techniques and apparatuses are described, for example, in PCT publication Nos. WO 2005/003074, WO 2013/192450 and WO 2013/192451.

In some embodiments, 3-HP may be removed from the aqueous solution by using an organic solvent, or a combination of two or more organic solvents. In some embodiments, the organic solvent for the removal of 3-HP from the aqueous solution may be used after (1) evaporating the solvent; and (2) condensing the evaporated solvent. In some embodiments, a flow of the condensed solvent may be directed to remove 3-HP from the aqueous solution, for example, by directing the flow of the solvent to the aqueous solution, to achieve effective mixing of the solvent and the aqueous phase such that 3-HP is extracted from the aqueous phase by the solvent.

As used herein, the term "evaporating" refers to conversion of a liquid to a gaseous phase (vapor). When the vapor pressure is equal to the pressure exerted on the liquid by surrounding atmosphere, evaporating of the liquid is referred to as "boiling". In some embodiments, evaporating occurs when the liquid is heated. Typically, boiling of a liquid occurs when the liquid is heated at or above its boiling point. When the liquid containing more than one solvent is heated, it is understood that the solvent having a lower boiling point evaporates first, followed by evaporation of the solvent having a higher boiling point, unless the two solvents form an azeotropic mixture and evaporate at the same time.

As used herein, the term "condensing" refers to a process of conversion of a vapor to a liquid. Typically, condensation of a vapor occurs when the vapor is cooled below the boiling point of the liquid.

Water-Immiscible Solvents

In some embodiments, a water-immiscible solvent (e.g., a water-immiscible organic solvent) may be used in the process of removing 3-HP from aqueous solution. That is, the water-immiscible solvent and the aqueous solution may be combined such that a solution of 3-HP is formed in the water-immiscible solvent. The solution of 3-HP in the water-immiscible solvent may then be separated from the aqueous phase.

As used herein, the term "water-immiscible solvent" refers to a solvent that is incapable of being mixed with water to form a homogeneous liquid. For example, solubility of the water-immiscible solvent in water is less than about 3 wt. % (e.g., less than about 2 wt. %, or less than about 1 wt. %). For example, less than about 3 g (e.g., less than about 2 g, or less than about 1 g) of water-immiscible solvent is soluble in 100 mL of water.

In some embodiments, the water-immiscible solvent has density of less than about 1 g/mL. In such embodiments, the water-immiscible solvent is less dense than water, and when combined with water, the solvent forms an organic phase above the aqueous phase. In some embodiments, the water-immiscible solvent has density from about 0.5 g/mL to about 1 g/mL (e.g., about 0.5 g/mL, about 0.6 g/mL, about 0.75 g/mL, about 0.85 g/mL, about 0.9 g/mL, or about 0.95 g/mL).

Illustrative examples of a water-immiscible solvent that is less dense than water include a C5-10 alkane, a C5-8 cycloalkane, an aromatic hydrocarbon solvent, a C1-6 alkyl acetate, a C4-6 alcohol, and a C16 alkyl ether. Combinations of such water-immiscible solvents may be used.

Illustrative C5-10 alkanes include n-pentane, n-hexane, n-heptane, n-octane and isooctane.

Illustrative C5-8 cycloalkanes include cylcopentane and cyclohexane.

Illustrative aromatic hydrocarbon solvents include benzene, toluene, o-xylene, m-xylene, p-xylene, and cumene.

Illustrative C1-6 alkyl acetates include methyl acetate, ethyl acetate, n-propyl acetate, isopropyl acetate, n-butyl acetate, isobutyl acetate, sec-butyl acetate, tert-butyl acetate, n-pentyl acetate, and n-hexyl acetate.

Illustrative C46 alcohols include n-butyl alcohol, isobutyl alcohol, tert-butyl alcohol, n-pentyl alcohol and n-hexyl alcohol.

Illustrative C1-6 alkyl ethers include diethyl ether, dipropyl ether, ethyl propyl ether, methyl tert-butyl ether (MTBE), and methyl hexyl ether.

In some embodiments, the water-immiscible solvent has density of greater than about 1 g/mL. In such embodiments, the water-immiscible solvent is denser than water, and when combined with water, the solvent forms an organic phase below the aqueous phase. In some embodiments, a water-immiscible solvent has density from about 1 g/mL to about 1.5 g/mL (e.g., about 1.1 g/mL, about 1.15 g/mL, about 1.2 g/mL, about 1.25 g/mL, about 1.3 g/mL, or about 1.4 g/mL).

In some embodiments, a water-immiscible solvent that is denser than water is a $C_{1-4}$ alkane, a $C_{1-4}$ alkene, a $C_{4-6}$ cycloalkane, a $C_{4-6}$ cycloalkene, an aromatic hydrocarbon solvent, a $C_{1-6}$ alkyl acetate, a $C_{2-6}$ alcohol, or a $C_{1-6}$ alkyl ether. Optionally, such a solvent is substituted with one or more (e.g., 1, 2, 3, 4, or 5) independently selected halogen atoms, such as, for example one or more Cl atoms, one or more Br atoms, one or more F atoms, or a combination thereof. Illustrative embodiments of such water-immiscible solvents include $C_{1-4}$ haloalkanes, $C_{1-4}$ haloalkenes, $C_{2-6}$ haloalcohols, and halogenated aromatic hydrocarbon solvents. Combinations of the water-immiscible solvents noted in this paragraph may be used.

Illustrative examples of a $C_{1-6}$ haloalkane include chloroform, bromoform, a chlorofluorocarbon, methylene chloride, carbon tetrachloride, 1,1-dichloro-1-fluoroethane, 1,1,1-trichloroethane, and perfluorodecalin.

Illustrative examples of a $C_{1-4}$ haloalkene include 1,2-dichloroethene, 1,1-dichloroethene, and trichloroethylene.

Illustrative examples of a halogenated aromatic hydrocarbon solvent include chlorobenzene, 1,2-difluorobenzene, 1,2,4-trichlorobenzene, and trifluorotoluene.

Illustrative examples of a $C_{2-6}$ haloalcohol include hexafluoro-2-propanol, 2,2,2-trifluoroethanol, and trichloro-2-methyl-2-propanol.

When a water-immiscible solvent is used of removing 3-HP from aqueous solution, the conditions may be selected such that the concentration of 3-HP in the water-immiscible solvent may be from about 1 g/L to about 300 g/L (e.g., from about 5 g/L to about 250 g/L, from about 10 g/L to about 200 g/L, from about 20 g/L to about 150 g/L, from about 30 g/L to about 100 g/L, from about 40 g/L to about 90 g/L, or from about 50 g/L to about 80 g/L).

In general, the amount of water-immiscible solvent relative to the amount of aqueous solution can be selected as appropriate. In some embodiments, an amount of water-immiscible solvent is from about 50 v/v % to about 150 v/v % (e.g., from about 80 v/v % to about 120 v/v %, or from about 90 v/v % to about 110 v/v %) based on the amount of the aqueous solution. For example, an amount of water-immiscible solvent may be about 50 v/v %, about 60 v/v %, about 70 v/v %, about 80 v/v %, about 90 v/v %, about 100 v/v %, about 105 v/v %, about 110 v/v %, about 120 v/v %, about 125 v/v %, about 130 v/v %, or about 140 v/v %, based on an amount of the aqueous solution.

Water-Miscible Solvents

In some embodiments, a water-miscible solvent (e.g., a water-miscible organic solvent) may be used in the process of removing 3-HP from the aqueous solution. As used herein, the term "water-miscible" refers to a solvent that may be combined with water in any proportion to form a homogenous liquid.

In general, in embodiments in which a water-miscible solvent is used in the process of removing 3-HP from the aqueous solution, the water-miscible solvent is combined with the aqueous solution to form a homogenous aqueous solution. As an example, a water-miscible solvent may be poured into an aqueous solution to form a homogeneous liquid. As another example, a water-miscible solvent may be added to the aqueous solution to form a homogenous liquid after: (1) evaporating the water-miscible solvent; (2) condensing the evaporated water-miscible solvent; and (3) directing the flow of the condensed water-miscible solvent to the aqueous solution.

In embodiments in which a water-miscible solvent is used in the process of removing 3-HP from the aqueous solution, a single water-miscible solvent can be used or a combination of water-miscible solvents can be used.

In some embodiments, a water-miscible solvent is a $C_{1-3}$ alcohol. Illustrative examples of $C_{1-3}$ alcohols include methanol, ethanol, n-propanol, and isopropanol.

In some embodiments, a water-miscible solvent is a polar aprotic solvent. Illustrative examples of polar aprotic solvents include tetrahydrofuran (THF), dimethyl sulfoxide (DMSO), hexamethylphosphoric triamide (HMPT), dimethylformamide (DMF), acetonitrile, dioxane, and acetone.

Generally, the amount of water-miscible solvent relative to the amount of aqueous solution can be selected as appropriate. In some embodiments, an amount of water-miscible solvent is from about 1 v/v % to about 50 v/v % (e.g., from about 1 v/v % to about 40 v/v %, from about 1 v/v % to about 30 v/v %, from about 5 v/v % to about 50 v/v %, from about 10 v/v % to about 40 v/v %, from about 15 v/v % to about 35 v/v %, or from about 20 v/v % to about 30 v/v %) based on the amount of the aqueous solution. For example, an amount of water-miscible solvent may be about 5 v/v %, about 10 v/v %, about 15 v/v %, about 20 v/v %, about 25 v/v %, about 30 v/v %, or about 40 v/v %, based on an amount of the aqueous solution.

Combinations of Water-Immiscible Solvent and Water-Miscible Solvent

In some embodiments, both a water-miscible solvent and a water-immiscible solvent are used in the process of removing 3-HP from the aqueous solution. In such embodiments, in general, the volume ratio of the water-immiscible solvent to the water-miscible solvent may be selected as appropriate. In some embodiments, the volume ratio of the water-immiscible solvent to the water-miscible solvent is from about 10:1 to about 1:1 (e.g., from about 9:1 to about 2:1, from about 8:1 to about 2:1, from about 7:1 to about 2:1, from about 6:1 to about 2:1, or from about 5:1 to about 3:1). For example, the volume ratio of water-immiscible solvent to water-miscible solvent is about 2:1, about 3:1, about 4:1, about 4.5:1, about 5:1, about 8:1, or about 10:1.

In general, the ratio of 1) a combined volume of the water-miscible solvent and the water-immiscible solvent to 2) a volume of the aqueous solution can be selected as appropriate. In some embodiments, the ratio of 1) a combined volume of the water-miscible solvent and the water-immiscible solvent to 2) a volume of the aqueous solution can be from about 1:1 to about 2:1 (e.g., from about 1:1 to about 1.5:1), such as, for example, about 1:1, about 1.2:1, about 1.3:1, about 1.4:1, or about 1.5:1.

Generally, the relative boiling point of the water-miscible solvent and the water-immiscible solvent can be selected as appropriate. In some embodiments, the boiling point of the water-miscible solvent is lower than the boiling point of the water-immiscible solvent. In some embodiments, the boiling point of the water-miscible solvent is higher than the boiling point of the water-immiscible solvent.

In general, the water-immiscible solvent and the water-miscible solvent, as well as their respective amounts, can be selected as appropriate.

In some embodiments, the water-miscible solvent is selected from methanol, ethanol, acetone, acetonitrile, THF, dimethyl sulfoxide (DMSO), hexamethylphosphoric triamide (HMPT), and dimethylformamide (DMF), and the water-immiscible solvent is selected from methyl acetate, ethyl acetate, n-propyl acetate, isopropyl acetate, n-butyl acetate, isobutyl acetate, sec-butyl acetate, tert-butyl acetate, benzene, chlorobenzene, toluene, o-xylene, m-xylene, and p-xylene, n-butyl alcohol, isobutyl alcohol, tert-butyl alcohol, diethyl ether, methyl tert-butyl ether (MTBE), methyl hexyl ether, chloroform, methylene chloride, and carbon tetrachloride. In such embodiments, the amount of water-miscible solvent and water-immiscible solvent can be selected as appropriate. As an example, in such embodiments, the amount of the water-miscible solvent can be from about 5 v/v % to about 50 v/v % based on the amount of the aqueous solution, the volume ratio of water-miscible solvent to water-immiscible solvent can be from about 1:10 to about 1:2, and/or the ratio of 1) a combined volume of the water-miscible solvent and the water-immiscible solvent to 2) a volume of the aqueous solution can be from about 1:1 to about 2:1.

In some embodiments, the water-miscible solvent is a $C_{1-3}$ alcohol (e.g., methanol, ethanol or isopropanol), and the water-immiscible solvent is an aromatic hydrocarbon solvent (e.g., benzene, toluene, o-xylene, m-xylene, p-xylene or chlorobenzene). In such embodiments, the amount of water-miscible solvent and water-immiscible solvent can be selected as appropriate. As an example, in such embodiments, the amount of the water-miscible solvent can be from about 5 v/v % to about 50 v/v % based on the amount of the aqueous solution, the volume ratio of water-miscible solvent to water-immiscible solvent can be from about 1:10 to about 1:2, and/or the ratio of 1) a combined volume of the water-miscible solvent and the water-immiscible solvent to 2) a volume of the aqueous solution can be from about 1:1 to about 2:1.

In some embodiments, the water-miscible solvent is a $C_{1-3}$ alcohol (e.g., methanol, ethanol or isopropanol), and the water-immiscible solvent is a $C_{1-6}$ alkyl acetate (e.g., methyl acetate, ethyl acetate, n-propyl acetate, isopropyl acetate, n-butyl acetate, isobutyl acetate, sec-butyl acetate or tert-butyl acetate). In such embodiments, the amount of water-miscible solvent and water-immiscible solvent can be selected as appropriate. As an example, in such embodiments, the amount of the water-miscible solvent can be from about 5 v/v % to about 50 v/v % based on the amount of the aqueous solution, the volume ratio of water-miscible solvent to water-immiscible solvent can be from about 1:10 to about 1:2, and/or the ratio of 1) a combined volume of the water-miscible solvent and the water-immiscible solvent to 2) a volume of the aqueous solution can be from about 1:1 to about 2:1.

In some embodiments, the water-miscible solvent is a $C_{1-3}$ alcohol (e.g., methanol, ethanol or isopropanol), and the water-immiscible solvent is a $C_{1-6}$ alkyl ether (e.g., diethyl ether, methyl tert-butyl ether (MTBE) or methyl hexyl ether). In such embodiments, the amount of water-miscible solvent and water-immiscible solvent can be selected as appropriate. As an example, in such embodiments, the amount of the water-miscible solvent can be from about 5 v/v % to about 50 v/v % based on the amount of the aqueous solution, the volume ratio of water-miscible solvent to water-immiscible solvent can be from about 1:10 to about 1:2, and/or the ratio of 1) a combined volume of the water-miscible solvent and the water-immiscible solvent to 2) a volume of the aqueous solution can be from about 1:1 to about 2:1.

In some embodiments, the water-miscible solvent is a $C_{1-3}$ alcohol (e.g., methanol, ethanol or isopropanol), and the water-immiscible solvent is a $C_{1-6}$ haloalkane (e.g., chloroform, methylene chloride or carbon tetrachloride). In such embodiments, the amount of water-miscible solvent and water-immiscible solvent can be selected as appropriate. As an example, in such embodiments, the amount of the water-miscible solvent can be from about 5 v/v % to about 50 v/v % based on the amount of the aqueous solution, the volume ratio of water-miscible solvent to water-immiscible solvent can be from about 1:10 to about 1:2, and/or the ratio of 1) a combined volume of the water-miscible solvent and the water-immiscible solvent to 2) a volume of the aqueous solution can be from about 1:1 to about 2:1.

In some embodiments, the water-miscible solvent is methanol, and the water-immiscible solvent is butyl acetate. In such embodiments, the amount of methanol and butyl acetate can be selected as appropriate. As an example, in such embodiments, the amount of methanol is from about 5 v/v % to about 50 v/v % of the aqueous solution, the volume ratio of methanol to butyl acetate can be from about 1:10 to about 1:2, and/or the ratio of 1) a combined volume of methanol and butyl acetate to 2) a volume of the aqueous solution can be from about 1:1 to about 2:1.

In some embodiments, the water-miscible solvent is methanol, and the water-immiscible solvent is MTBE. In such embodiments, the amount of methanol and MTBE can be selected as appropriate. As an example, in such embodiments, the amount of methanol can be from about 5 v/v % to about 50 v/v % of the aqueous solution, the volume ratio of methanol to MTBE is can be from about 1:10 to about 1:2, and/or the ratio of 1) a combined volume of methanol and MTBE to 2) a volume of the aqueous solution can be from about 1:1 to about 2:1.

In some embodiments, the water-miscible solvent is methanol, and the water-immiscible solvent can be isobutyl alcohol. In such embodiments, the amount of methanol and isobutyl alcohol can be selected as appropriate. As an example, in such embodiments, the amount of methanol can be from about 5 v/v % to about 50 v/v % of the aqueous solution, the volume ratio of methanol to isobutyl alcohol can be from about 1:10 to about 1:2, and/or the ratio of 1) a combined volume of methanol and isobutyl alcohol to 2) a volume of the aqueous solution can be from about 1:1 to about 2:1.

In some embodiments, the water-miscible solvent is methanol, and the water-immiscible solvent is tert-butyl alcohol. In such embodiments, the amount of methanol and tert-butyl alcohol can be selected as appropriate. As an example, in such embodiments, the amount of methanol can be from about 5 v/v % to about 50 v/v % of the aqueous solution, the volume ratio of methanol to tert-butyl alcohol can be from about 1:10 to about 1:2, and/or the ratio of 1) a combined volume of methanol and tert-butyl alcohol to 2) a volume of the aqueous solution can be from about 1:1 to about 2:1.

In some embodiments, the water-miscible solvent is methanol, and the water-immiscible solvent is benzene. In such embodiments, the amount of methanol and benzene can be selected as appropriate. As an example, in such embodiments, the amount of methanol can be from about 5 v/v % to about 50 v/v % of the aqueous solution, the volume ratio of methanol to benzene can be from about 1:10 to about 1:2, and/or the ratio of 1) a combined volume of methanol and benzene to 2) a volume of the aqueous solution can be from about 1:1 to about 2:1.

In some embodiments, the water-miscible solvent is methanol, and the water-immiscible solvent is toluene. In such embodiments, the amount of methanol and toluene can be selected as appropriate. As an example, in such embodiments, the amount of methanol can be from about 5 v/v % to about 50 v/v % of the aqueous solution, the volume ratio of methanol to toluene can be from about 1:10 to about 1:2, and/or the ratio of 1) a combined volume of methanol and toluene to 2) a volume of the aqueous solution can be from about 1:1 to about 2:1.

In some embodiments, the water-miscible solvent is methanol, and the water-immiscible solvent is chloroform. In such embodiments, the amount of methanol and chloroform can be selected as appropriate. As an example, in such embodiments, the amount of methanol can be from about 5 v/v % to about 50 v/v % of the aqueous solution, and volume ratio of methanol to chloroform can be from about 1:10 to about 1:2, and/or the ratio of 1) a combined volume of methanol and chloroform to 2) a volume of the aqueous solution can be from about 1:1 to about 2:1.

In particular exemplary embodiments, the water-miscible solvent is methanol and the water-immiscible solvent is ethyl acetate. In such embodiments, the amount of methanol and ethyl acetate can be selected as appropriate. As an example, in such embodiments, the amount of methanol can be from about 15 v/v % to about 35 v/v % of the aqueous solution, and the volume ratio of methanol to ethyl acetate is from about 1:9 to about 3:7, and/or the ratio of 1) a combined volume of methanol and ethyl acetate to 2) a volume of the aqueous solution can be from about 1:1 to about 2:1. Also, in such embodiments, the concentration of 3-HP in the aqueous solution can be from about 50 g/L to about 80 g/L, the 3 pH of the aqueous solution can be from about 4 to about 5, and the temperature of the aqueous solution during the process of removing 3-HP from the aqueous solution is from about 15° C. to about 40° C.

In some embodiments, a method of extracting 3-HP from an aqueous solution includes: (1) providing an extraction vessel containing a decellularized fermentation broth containing 3-HP, a solvent vessel containing ethyl acetate in an amount of about 90 v/v % to about 110 v/v % based on the amount of the broth in the extraction vessel, and a condenser; (2) evaporating ethyl acetate from the solvent vessel; (3) condensing the vaporized ethyl acetate to a liquid state in the condenser; (4) directing a flow of ethyl acetate from the condenser to the extraction vessel such that a solution of 3-HP in ethyl acetate is formed in the extraction vessel; (5) separating the broth and the solution of 3-HP in ethyl acetate in the extraction vessel; and (6) directing a flow of the solution of 3-HP in ethyl acetate from the extraction vessel to the solvent vessel. In some embodiments, the extraction vessel also contains a methanol in an amount from about 20 v/v % to about 30 v/v %, based on the amount of the broth. In such embodiments, methanol is completely miscible with the broth and remains in the solvent vessel during the extraction process. The ratio of the amount of ethyl acetate to the amount of methanol in such system is from about 5:1 to about 3:1.

Process Parameters

In general, any appropriate flow rate can be used for a solvent (e.g., an organic solvent) during the process of removing 3-HP from the aqueous solution. For example, in some embodiments, a flow of a solvent during the process of removing 3-HP from the aqueous solution is from about 0.1 L/h to about 10 L/h (e.g., from about 0.5 L/h to about 8 L/h, from about 1 L/h to about 5 L/h, or from about 1 L/h to about 3 L/h).

Generally, any appropriate temperature can be used during the process of removing 3-HP from the aqueous solution. For example, in some embodiments, removing 3-HP from an aqueous solution is performed at a temperature of the aqueous solution from about 15° C. to about 50° C. (e.g., from about 15° C. to about 40° C., or from about 20° C. to about 30° C.). In some embodiments, removing 3-HP from an aqueous solution is performed at a temperature of the aqueous solution of at most about 50° C. (e.g., at about 40° C., or at about 30° C.). Optionally, removing 3-HP from an aqueous solution is performed at room temperature.

In some embodiments, heating 3-HP in a polar protic solvent, such as water or lower alcohol, results in decomposition of 3-HP as shown in Scheme 1:

Scheme 1

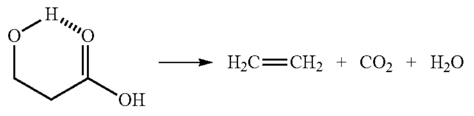

Referring to scheme 1, the hydrogen atom of the hydroxyl group in the 3 position may form a hydrogen bond with the carbonyl group of 3-HP, thereby forming a 6-membered ring. A polar protic solvent may facilitate the formation of the 6-membered ring and the decomposition of 3-HP to form ethylene, carbon dioxide and water. In one example, the decomposition may occur when the solution of 3-HP in the polar protic solvent (e.g., water) is heated at a temperature above 50° C. Hence, without wishing to be bound by theory, in some embodiments, keeping the temperature at or below 50° C. when removing 3-HP from the aqueous solution may reduce the undesired formation of ethylene and/or carbon dioxide.

In certain embodiments, the temperature of the solution of 3-HP in a water-immiscible solvent is at or near the boiling point of the water-immiscible solvent. As an example, when ethyl acetate is used in the process, the temperature of solution of 3-HP in ethyl acetate may be from about 78° C. to about 80° C. As another example, when isobutanol is used in the process, the temperature of solution of 3-HP in isobutanol may be from about 105° C. to about 110° C. Advantageously, the temperature is selected such that there is little or no 3-HP decomposition to undesired products when its solution in water-immiscible solvent is heated during removal of the compound from an aqueous solution.

In some embodiments, a process of removing 3-HP from an aqueous solution results in a yield of recovered 3-HP that is relatively high such as, for example, at least about 70% (e.g., at least about 80%, at least about 90%, at least about 95%, or at least about 99%).

Exemplary Systems and Methods for Removing 3-HP from an Aqueous Solution

Figure 58:
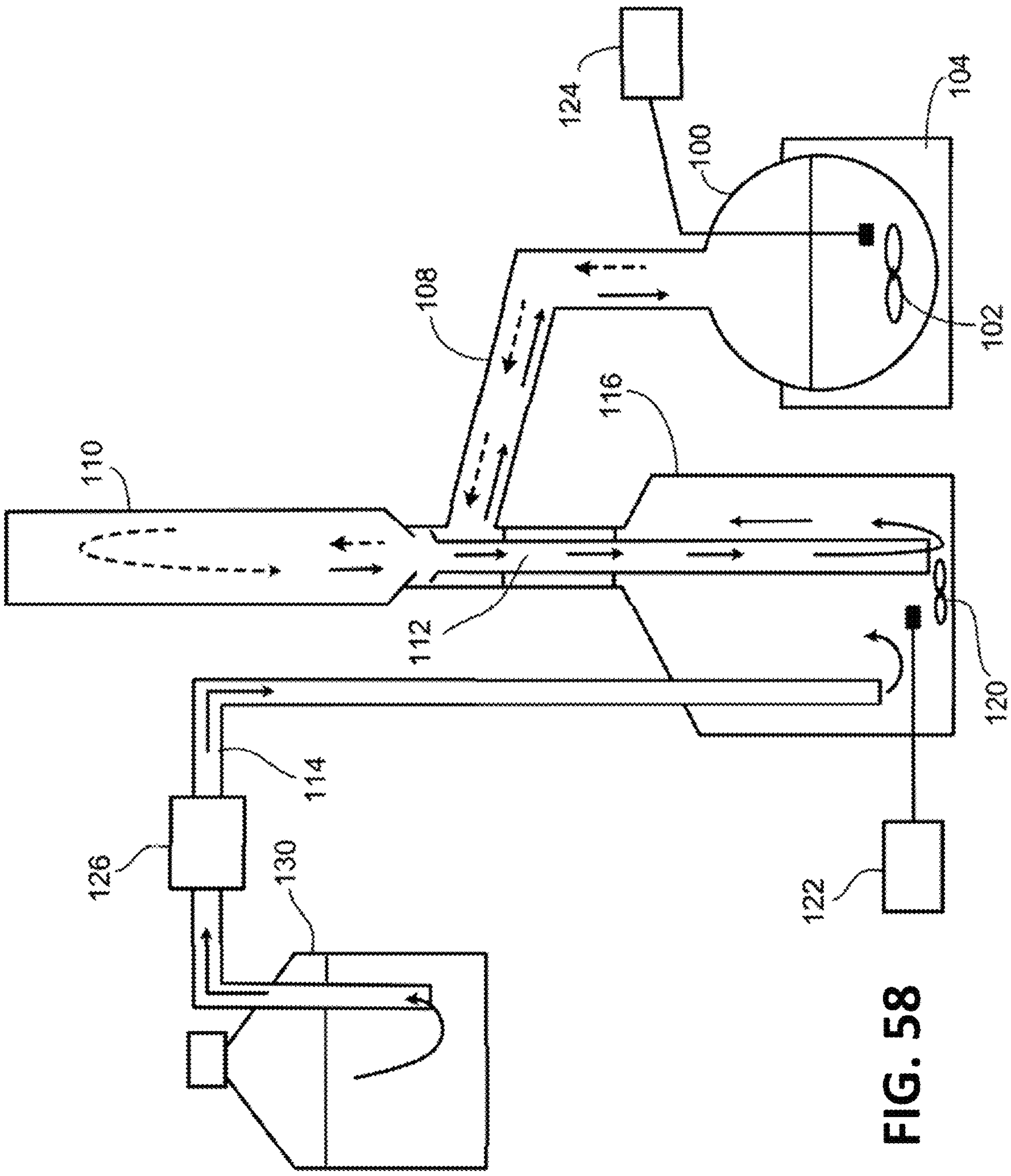
FIG. 58 illustrates an exemplary system for extracting 3-HP from an aqueous solution using a water-immiscible solvent that is less dense than water.

FIG. 58 illustrates an exemplary system for removing 3-HP from an aqueous solution using a water-immiscible solvent that is less dense than water. Referring to FIG. 58, the system includes a solvent vessel 100 and a condenser 110 hydronically connected to solvent vessel 100 via a side tube 108. Condenser 110 is also hydronically connected to an extraction vessel 116 via a syphon tube 112. Solvent vessel 100 includes a stirrer 102, a thermometer 124, and a heating element 104. Extraction vessel 116 includes a stirrer 120, a pH meter 122, and an inlet tube 114. Inlet tube 114 is connected to a peristaltic pump 126, which is configured to add an acid from an acid storage vessel 130 to extraction vessel 116 through inlet tube 114.

In some embodiments, both the water-miscible solvent and the water-immiscible solvent are disposed in solvent vessel 100. Generally, an aqueous solution of 3-HP (e.g., a decellularized fermentation broth containing 3-HP) is disposed in extraction vessel 116 after the water-miscible solvent and the water-immiscible solvent are disposed in solvent vessel 100, although optionally the aqueous solution of 3-HP can be disposed in extraction vessel 116 prior to, or simultaneously with, the water-miscible solvent being disposed in solvent vessel 100 and/or the water-immiscible solvent being disposed in solvent vessel 100. The amount of the aqueous solution of 3-HP initially disposed in extraction vessel 116 is selected so that it does not extend up to side arm 108 so that the aqueous solution of 3-HP does not transfer over into solvent vessel 100. Solvent vessel 100 is heated using heating element 104 until the temperature of the liquid contained in solvent vessel 100 reaches the boiling point of the solvent with the lower boiling point contained in solvent vessel 100 (either the water-immiscible solvent or the water-miscible solvent), e.g., as determined by thermometer 124. In general, the water-miscible solvent has a lower boiling than the water-immiscible solvent. The water-miscible solvent in solvent vessel 100 evaporates (without evaporation of the water-immiscible solvent in solvent vessel 100), and the water-miscible solvent vapor flows from solvent vessel 100 through side tube 108 to condenser 110. Condenser 110 uses a coolant at a temperature that is below the boiling point of the water-miscible solvent (e.g., from about 5° C. to about 25° C., about 5° C., about 10° C., or about 15° C.). Thus, the vaporized water-miscible solvent condenses to a liquid state in condenser 110, and the liquid water-miscible solvent (e.g., at about room temperature) flows to the bottom of extraction vessel 116 via siphon tube 112. The condensed water-miscible solvent combines with the aqueous solution of 3-HP to form an aqueous phase in extraction vessel 116. The amount of water-miscible solvent initially disposed in solvent vessel 100 and subsequently transferred to extraction vessel 116 is selected so that the aqueous phase in vessel 116 does not extend up to sidearm 108 so that the aqueous phase does not transfer over to solvent vessel 100. Solvent vessel 100 is subsequently heated to a higher temperature using heating element 104 until the temperature of the liquid contained in solvent vessel 100 reaches the boiling point of the water-immiscible solvent, causing the water-immiscible solvent in solvent vessel 100 to evaporate. The water-immiscible solvent vapor flows from solvent vessel 100 through side tube 108 to condenser 110. Condenser 110 uses a coolant at a temperature that is below the boiling point of the water-immiscible solvent (e.g., from about 5° C. to about 25° C., about 5° C., about 10° C., or about 15° C.). Thus, the vaporized water-immiscible solvent condenses to a liquid state in condenser 110, and the liquid water-immiscible solvent (e.g., at about room temperature) flows to the bottom of extraction vessel 116 via siphon tube 112. The condensed water-immiscible solvent mixes with the aqueous phase in extraction vessel 116, such that the water-immiscible solvent extracts 3-HP from the aqueous phase, thereby forming a solution of 3-HP in the water-immiscible solvent (organic phase). The result is that extraction vessel 116 contains an aqueous phase and an organic phase. Because the water-immiscible solvent is less dense than water, the organic phase is above the aqueous phase. The combined amount of the aqueous solution of 3-HP, the water-miscible solvent and the water-immiscible solvent initially disposed in the system is selected so that the organic phase in extraction vessel 116 reaches the side arm 108. Hence, the organic phase flows from extraction vessel 116 through side arm 108 to solvent vessel 100. In this manner, 3-HP is transferred from extraction vessel 116 to solvent vessel 100. As the amount of 3-HP in extraction vessel 116 decreases, the pH of the aqueous phase in extraction vessel 116 tends to increase, e.g., as detected by pH meter 122. In response to this increase in the pH, peristaltic pump 126 may pump an acid from acid storage vessel 130 to extraction vessel 116 via inlet tube 114, thereby adjusting the pH of the aqueous phase in extraction vessel 116. The aqueous phase in extraction vessel 116 may be stirred (e.g., continuously stirred) with stirrer 120 to enhance pH homogeneity of the aqueous phase. The temperature of the aqueous phase in extraction vessel 116 and of the organic phase in extraction vessel 116 may be about the same, and is typically from about 15° C. to about 40° C. (e.g., about room temperature). Typically, the pH of the aqueous phase in extraction vessel 116 is adjusted to be within ranges discussed above. For example, in some embodiments, the pH of the aqueous phase is from about 4 to about 7 (e.g., from about 4 to about 5, from about 4.2 to about 4.7, from about 4.3 to about 4.4, about 4.3, or about 4.4).

In certain embodiments, the water-miscible solvent is initially disposed in extraction vessel 116, and the water-immiscible solvent is initially disposed in solvent vessel 100. Generally, an aqueous solution of 3-HP (e.g., a decellularized fermentation broth containing 3-HP) is disposed in extraction vessel 116 after the water-miscible solvent is disposed in extraction vessel 116 and the water-immiscible solvent is disposed solvent vessel 100, although optionally the aqueous solution of 3-HP can be disposed in extraction vessel 116 prior to, or simultaneously with, the water-miscible solvent being disposed in extraction vessel 116 and/or the water-immiscible solvent being disposed in solvent vessel 100. The aqueous solution of 3-HP and the water miscible solvent in extraction vessel 116 combine to form an aqueous phase in extraction vessel 116. The combined amount of the aqueous solution of 3-HP and the water-miscible solvent are selected so that the aqueous phase does not extend up to side arm 108 so that the aqueous phase does not transfer over into solvent vessel 100. Solvent vessel 100 is heated using heating element 104 until the temperature of the water-immiscible solvent contained in solvent vessel 100 reaches its boiling point, e.g., as determined by thermometer 124. The water-immiscible solvent in solvent vessel 100 evaporates, and the water-immiscible solvent vapor flows from solvent vessel 100 through side tube 108 to condenser 110. Condenser 110 uses a coolant at a temperature that is below the boiling point of the water-immiscible solvent (e.g., from about 5° C. to about 25° C., about 5° C., about 10° C., or about 15° C.). Therefore, the vaporized water-immiscible solvent condenses to a liquid state in condenser 110, and the liquid water-immiscible solvent (e.g., at about room temperature) flows to the bottom of extraction vessel 116 via siphon tube 112. The condensed water-immiscible solvent mixes with the aqueous phase in extraction vessel 116, such that the water-immiscible solvent extracts 3-HP from the aqueous phase, thereby forming a solution of 3-HP in the water-immiscible solvent (organic phase). The result is that extraction vessel 116 contains an aqueous phase and an organic phase. Because the water-immiscible solvent is less dense than water, the organic phase is above the aqueous phase. The combined amount of the aqueous solution of 3-HP, the water-miscible solvent and the water-immiscible solvent initially disposed in the system is selected so that the organic phase in extraction vessel 116 reaches the side arm 108.

Hence, the organic phase flows from extraction vessel 116 through side arm 108 to solvent vessel 100. In this manner, 3-HP is transferred from extraction vessel 116 to solvent vessel 100. As the amount of 3-HP in extraction vessel 116 decreases, the pH of the aqueous phase in extraction vessel 116 tends to increase, e.g., as detected by pH meter 122. In response to this increase in the pH, peristaltic pump 126 may pump an acid from acid storage vessel 130 to extraction vessel 116 via inlet tube 114, thereby adjusting the pH of the aqueous phase in extraction vessel 116. The aqueous phase in extraction vessel 116 may be stirred (e.g., continuously stirred) with stirrer 120 to enhance pH homogeneity of the aqueous phase. The temperature of the aqueous phase in extraction vessel 116 and of the organic phase in extraction vessel 116 may be about the same, and is typically from about 15° C. to about 40° C. (e.g., about room temperature). Typically, the pH of the aqueous phase in extraction vessel 116 is adjusted to be within ranges discussed above. For example, in some embodiments, the pH of the aqueous phase is from about 4 to about 7 (e.g., from about 4 to about 5, from about 4.2 to about 4.7, from about 4.3 to about 4.4, about 4.3, or about 4.4).

Figure 59:
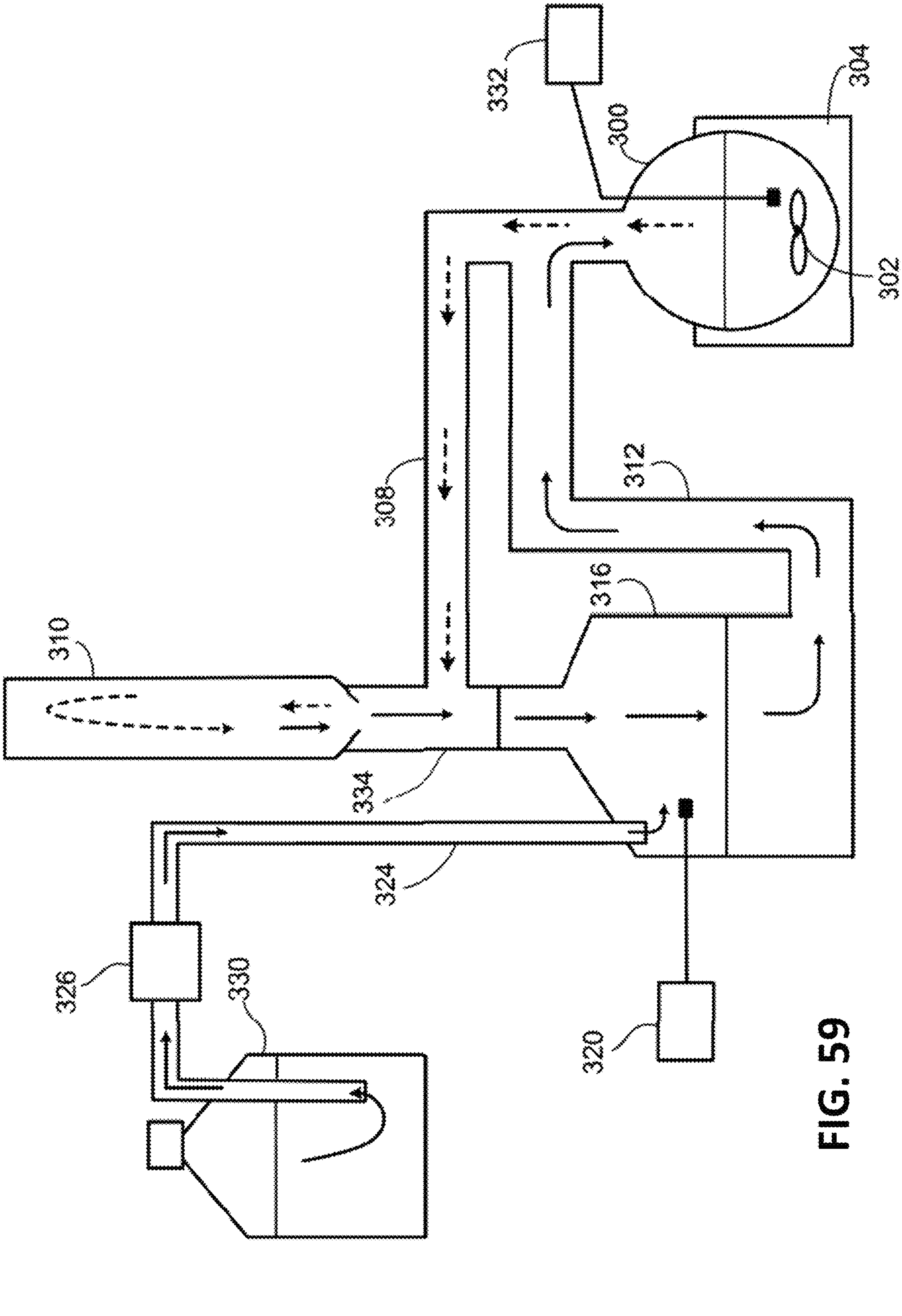
FIG. 59 illustrates an exemplary system for extracting 3-HP from an aqueous solution using a water-immiscible solvent that is denser than water.

FIG. 59 illustrates an exemplary system for removing 3-HP from an aqueous solution using a water-immiscible solvent that is denser than water. The system includes a solvent vessel 300, a condenser 310 and an extraction vessel 316. Solvent vessel 300 is hydronically connected to condenser 310 through a side tube 308. Solvent vessel 300 is also hydronically connected to extraction vessel 316 through a side tube 312. Condenser 310 is hydronically connected to extraction vessel 316 through a connection tube 334. Solvent vessel 300 includes a stirrer 302, a heating element 304, and a thermometer 332. Extraction vessel 316 includes a pH meter 320 and an inlet tube 324. Inlet tube 324 is connected to a peristaltic pump 326, which is configured to add an acid from an acid storage vessel 330 to extraction vessel 316 via inlet tube 324.

In some embodiments, both the water-miscible solvent and the water-immiscible solvent are disposed in extraction vessel 300. Generally, before the water-miscible solvent and water-immiscible solvent are disposed in solvent vessel 300, an aqueous solution of 3-HP (e.g., a decellularized fermentation broth containing 3-HP) is disposed in extraction vessel 316. Optionally, however, the aqueous solution of 3-HP can be disposed in extraction vessel 316 after, or simultaneously with, the water-miscible solvent being disposed in solvent vessel 300 and/or the water-immiscible solvent being disposed in solvent vessel 300. The volume of the aqueous solution of 3-HP disposed in extraction vessel 316 is selected so that the solution does not extend high enough to flow into solution vessel 300 via side tube 312. Solvent vessel 300 is heated using heating element 304 until the temperature of the liquid contained in solvent vessel 300 reaches the boiling point of the solvent with the lower boiling point contained in solvent vessel 300 (either the water-immiscible solvent or the water-miscible solvent), e.g., as determined by thermometer 332. In general, the water-miscible solvent has a lower boiling than the water-immiscible solvent. The water-miscible solvent in solvent vessel 300 evaporates (without evaporation of the water-immiscible solvent in solvent vessel 300), and the water-miscible solvent vapor flows from solvent vessel 300 through side tube 308 to condenser 310. Condenser 310 uses a coolant at a temperature that is below the boiling point of the water-miscible solvent (e.g., from about 5° C. to about 25° C., about 5° C., about 10° C., or about 15° C.). Thus, the vaporized water-miscible solvent condenses to a liquid state in condenser 310, and the liquid water-miscible solvent (e.g., at about room temperature) flows to the extraction vessel 316 via connection tube 334. The condensed water-miscible solvent combines with the aqueous solution of 3-HP to form an aqueous phase in extraction vessel 316. The amount of water-miscible solvent initially disposed in solvent vessel 300 and subsequently transferred to extraction vessel 316 is selected so that the aqueous phase in vessel 316 does not extend high enough to flow into solution vessel 300 via side tube 312. Solvent vessel 300 is subsequently heated to a higher temperature using heating element 304 until the temperature of the liquid contained in solvent vessel 300 reaches the boiling point of the water-immiscible solvent, causing the water-immiscible solvent in solvent vessel 300 to evaporate. The water-immiscible solvent vapor flows from solvent vessel 300 through side tube 308 to condenser 310. Condenser 310 uses a coolant at a temperature that is below the boiling point of the water-immiscible solvent (e.g., from about 5° C. to about 25° C., about 5° C., about 10° C., or about 15° C.). Thus, the vaporized water-immiscible solvent condenses to a liquid state in condenser 310, and the liquid water-immiscible solvent (e.g., at about room temperature) flows to extraction vessel 316 via connection tube 334. The condensed water-immiscible solvent mixes with the aqueous phase in extraction vessel 316, such that the water-immiscible solvent extracts 3-HP from the aqueous phase, thereby forming a solution of 3-HP in the water-immiscible solvent (organic phase). The result is that extraction vessel 316 contains an aqueous phase and an organic phase. Because the water-immiscible solvent is denser than water, the organic phase is beneath the aqueous phase. The combined amount of the aqueous solution of 3-HP, the water-miscible solvent and the water-immiscible solvent initially disposed in the system is selected so that the organic phase in extraction vessel 316 is sufficiently large that organic phase can transfer from extraction vessel 316 to solvent vessel 300 via side tube 312. In this manner, 3-HP is transferred from extraction vessel 316 to solvent vessel 300. As the amount of 3-HP in extraction vessel 316 decreases, the pH of the aqueous phase in extraction vessel 316 tends to increase, e.g., as detected by pH meter 320. In response to this increase in the pH, peristaltic pump 326 may pump an acid from acid storage vessel 330 to extraction vessel 316 via inlet tube 324, thereby adjusting the pH of the aqueous phase in extraction vessel 316. The temperature of the aqueous phase in extraction vessel 316 and of the organic phase in extraction vessel 316 may be about the same, and is typically from about 15° C. to about 40° C. (e.g., about room temperature). Typically, the pH of the aqueous phase in extraction vessel 316 is adjusted to be within ranges discussed above. For example, in some embodiments, the pH of the aqueous phase is from about 4 to about 7 (e.g., from about 4 to about 5, from about 4.2 to about 4.7, from about 4.3 to about 4.4, about 4.3, or about 4.4).

In certain embodiments, the water-miscible solvent is disposed in extraction vessel 316, and the water-immiscible solvent is disposed in extraction vessel 300. Generally, before this, an aqueous solution of 3-HP (e.g., a decellularized fermentation broth containing 3-HP) is disposed in extraction vessel 316. Optionally, however, the aqueous solution of 3-HP can be disposed in extraction vessel 316 after, or simultaneously with, the water-miscible solvent being disposed in extraction vessel 316 and/or the water-immiscible solvent being disposed in solvent vessel 300. The aqueous solution of 3-HP and the water miscible solvent in extraction vessel 316 combine to form an aqueous phase in extraction vessel 316. The combined amount of the aqueous solution of 3-HP and the water-miscible solvent in extraction vessel 316 is selected so that the aqueous phase in extraction vessel 316 does not extend high enough to flow into solution vessel 300 via side tube 312. Solvent vessel 300 is heated to a temperature using heating element 304 until the temperature of the liquid contained in solvent vessel 300 reaches the boiling point of the water-immiscible solvent, causing the water-immiscible solvent in solvent vessel 300 to evaporate. The water-immiscible solvent vapor flows from solvent vessel 300 through side tube 308 to condenser 310. Condenser 310 uses a coolant at a temperature that is below the boiling point of the water-immiscible solvent (e.g., from about 5° C. to about 25° C., about 5° C., about 10° C., or about 15° C.). Thus, the vaporized water-immiscible solvent condenses to a liquid state in condenser 310, and the liquid water-immiscible solvent (e.g., at about room temperature) flows to extraction vessel 316 via connection tube 334. The condensed water-immiscible solvent mixes with the aqueous phase in extraction vessel 316, such that the water-immiscible solvent extracts 3-HP from the aqueous phase, thereby forming a solution of 3-HP in the water-immiscible solvent (organic phase). The result is that extraction vessel 316 contains an aqueous phase and an organic phase. Because the water-immiscible solvent is denser than water, the organic phase is beneath the aqueous phase. The combined amount of the aqueous solution of 3-HP, the water-miscible solvent and the water-immiscible solvent initially disposed in the system is selected so that the organic phase in extraction vessel 316 is sufficiently large that organic phase can transfer from extraction vessel 316 to solvent vessel 300 via side tube 312. In this manner, 3-HP is transferred from extraction vessel 316 to solvent vessel 300. As the amount of 3-HP in extraction vessel 316 decreases, the pH of the aqueous phase in extraction vessel 316 tends to increase, e.g., as detected by pH meter 320. In response to this increase in the pH, peristaltic pump 326 may pump an acid from acid storage vessel 330 to extraction vessel 316 via inlet tube 324, thereby adjusting the pH of the aqueous phase in extraction vessel 316. The temperature of the aqueous phase in extraction vessel 316 and of the organic phase in extraction vessel 316 may be about the same, and is typically from about 15° C. to about 40° C. (e.g., about room temperature). Typically, the pH of the aqueous phase in extraction vessel 316 is adjusted to be within ranges discussed above. For example, in some embodiments, the pH of the aqueous phase is from about 4 to about 7 (e.g., from about 4 to about 5, from about 4.2 to about 4.7, from about 4.3 to about 4.4, about 4.3, or about 4.4).

Purification of 3-HP

In some embodiments, 3-HP may be purified after removal form the aqueous solution. As an example, crude 3-HP (3-HP after removal from the aqueous solution but before purification) may be converted to a salt, such as an alkali metal salt, followed by washing the salt with an organic solvent to provide a pure alkali metal salt of 3-HP. The pure alkali metal salt of 3-HP may be converted to a pure 3-HP free acid. In such embodiments, the alkali metal salt of 3-HP may be formed by treating the crude 3-HP with an alkali hydroxide, such as a sodium hydroxide or a potassium hydroxide. To perform the reaction, a solution of crude 3-HP in an organic solvent may be formed, and the resultant solution may be treated with an alkali metal hydroxide. In some embodiments, the organic solvent is at least one of acetone, methanol, or isopropanol. In some embodiments, pH of the solution of crude 3-HP in the organic solvent is from about 4 to about 5 (for example, about 4.3 or about 4.4). In some embodiments, alkali metal hydroxide is added to the reaction mixture until the pH of the reaction mixture is about 7. An alkali metal salt of 3-HP that has precipitated from the reaction mixture may be collected by filtration, and further washed with the organic solvent as described above.

To obtain pure 3-HP free acid, a salt of 3-HP, such as a sodium salt, may be dissolved in water and the resultant aqueous solution may be treated with any one of the acids described herein. For example, the aqueous solution of 3-HP salt may be treated with hydrochloric acid or an oxalic acid until pH of about 4 to about 5, and the pure 3-HP free acid may be removed from the resultant aqueous solution by any of the methods described herein.

Making Acrylic Acid

In some embodiments, a method of making acrylic acid from 3-HP includes reacting 3-HP to form acrylic acid. The method can provide a yield of acrylic acid of at least about 50% (e.g., at least about 60%, at least about 70%, at least about 80%, at least about 90%, at least about 95%, or at least about 99%). In certain embodiments, the method provides a quantitative yield of acrylic acid (i.e., 100% yield).

In some embodiments, the method includes reacting 3-HP in a liquid state. In such embodiments, 3-HP may be neat or may be in a solution in water or in one or more organic solvents. Exemplary organic solvents include DMSO, DMF and water.

Generally, the method of making acrylic acid can be performed at any appropriate temperature. In some embodiments, the method of making acrylic acid includes heating 3-HP at a temperature of at least about 50° C. (e.g., about 60° C., about 70° C., or about 80° C.). In some embodiments, reacting 3-HP occurs at a temperature of at most about 200° C. (e.g., about 190° C., or about 180° C.). In some embodiments, reacting 3-HP to produce acrylic acid is performed at a temperature from about 50° C. to about 200° C. (e.g., about 60° C. to about 190° C., or about 80° C. to about 180° C.).

In general, reacting 3-HP to form acrylic acid can be performed at any appropriate pressure. In some embodiments, when the pressure adjacent reaction mixture containing 3-HP is lower than atmospheric pressure, the acrylic acid evaporates from the reaction mixture at the reaction temperature. That is, acrylic acid may be removed from the reaction mixture in a gaseous form. In some embodiments, reacting 3-HP to form acrylic acid occurs at reduced pressure, such as, for example, at a pressure of less than one atmosphere adjacent the reaction mixture containing 3-HP. In certain embodiments, the pressure adjacent the reaction mixture containing 3-HP is less than about 700 mbar (e.g., less than about 500 mbar, less than about 400 mbar, less than about 300 mbar, less than about 200 mbar, less than about 150 mbar, less than about 120 mbar, or less than about 100 mbar). In some embodiments, the pressure adjacent the reaction mixture containing 3-HP is from about 50 mbar to about 200 mbar (e.g., from about 60 mbar to about 150 mbar, from about 70 mbar to about 130 mbar, or from about 70 mbar to about 100 mbar). In some embodiments, the pressure adjacent the reaction mixture containing 3-HP is about 70 mbar, about 74 mbar, about 75 mbar, about 80 mbar, about 90 mbar, about 100 mbar, or about 120 mbar.

In some embodiments, the reaction mixture contains a catalyst to catalyze the conversion of 3-HP to acrylic acid. Typically, an acid catalyst may be used to catalyze the conversion of 3-HP to acrylic acid.

Scheme 2

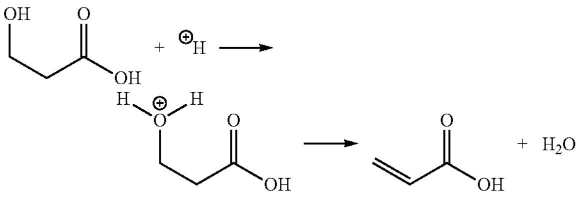

Referring to Scheme 2, when 3-HP is contacted with an acid, the hydroxyl group at position 3 is protonated, followed by elimination reaction yielding acrylic acid and water. Suitable examples of the reaction catalysts include any one of the organic and inorganic acids described herein. For example, a hydrochloric acid, a sulfuric acid, a polyphosphoric acid, an oxalic acid or an acetic acid may be used to catalyze the reaction of 3-HP to form acrylic acid. In some embodiments, a zeolite, a silica, or a sea sand may be used as a catalyst for the reaction. Suitable examples of a zeolite include molecular sieves, such as 3 A molecular sieves, 4 A molecular or 5 A molecular sieves.

In general, the amount of catalyst used may be selected as appropriate. In some embodiments, the reaction mixture may contain from about 1 wt. % to about 25 wt. % (e.g., from about 1 wt. % to about 20 wt. %, from about 2 wt. % to about 20 wt. %, from about 1 wt. % to about 10 wt. %, from about 1 wt. % to about 5 wt. %, or from about 2 wt. % to about 4 wt. %) of the catalyst, based on the amount of 3-HP the reaction mixture. In some embodiments, an amount of catalyst in the reaction mixture is about 1 wt. %, about 2 wt. %, about 3 wt. %, about 4 wt. %, about 5 wt. %, about 10 wt. %, about 20 wt. %, or about 25 wt. %, based on the amount of 3-HP the reaction mixture.

Acrylic acid that is being formed from 3-HP in the reaction mixture is prone to polymerization, to form a polyacrylic acid. The methods of making acrylic acid described herein advantageously avoid formation of polyacrylic acid and provide the desired product in high yield, such as, for example, a yield of at least 50%, (e.g., at least about 60%, at least about 70%, at least about 80%, at least about 90%, at least about 95%, or at least about 99%).

To reduce undesired polymerization, in some embodiments, 3-HP is reacted to form acrylic acid in the presence of a polymerization inhibitor. Illustrative examples of polymerization inhibitors include phenothiazine, hydroquinone, 4-tert-butylpyrocatechol, tert-butylhydroquinone, 1,4-benzoquinone, 6-tert-butyl-2,4-xylenol, 2,6-di-tert-butyl-p-cresol, 2,6-di-tert-butylphenol, or 4-methoxyphenol.

In general, the amount of polymerization inhibitor used may be selected as appropriate. In some embodiments, the polymerization inhibitor is present in the reaction mixture in an amount of about 1 wt. % to about 20 wt. % (e.g., from about 1 wt. % to about 10 wt. %, from about 1 wt. % to about 5 wt. %, from about 5 wt. % to about 15 wt. %) based on an amount of 3-HP in the reaction mixture. In some embodiments, the amount of the polymerization inhibitor is about 1 wt. %, about 2 wt. %, about 3 wt. %, about 5 wt. %, about 10 wt. %, or about 15 wt. %, based on the amount of 3-HP in the reaction mixture.

In some embodiments, the acrylic acid that is being formed from 3-HP is removed from the reaction mixture. Removing of acrylic acid may be performed continuously throughout the course of the reaction, optionally until all of the 3-HP has reacted to form acrylic acid, or removing of acrylic acid may be performed discontinuously during the reaction, optionally until all of the 3-HP has reacted to form acrylic acid.

As noted above, acrylic acid may be removed from the reaction mixture as gaseous acrylic acid. In such embodiments, the gaseous acrylic acid that has been removed from the reaction mixture may be condensed to a liquid state, collected and used for the intended purpose. In some embodiments, a coolant is used to condense the gaseous acrylic acid. For example, a temperature of the coolant used to condense the acrylic acid at a pressure lower than the atmospheric pressure is from about −5° C. to about 10° C. (e.g., from about 0° C. to about 5° C.).

Exemplary System and Method of Making Acrylic Acid

Figure 60:
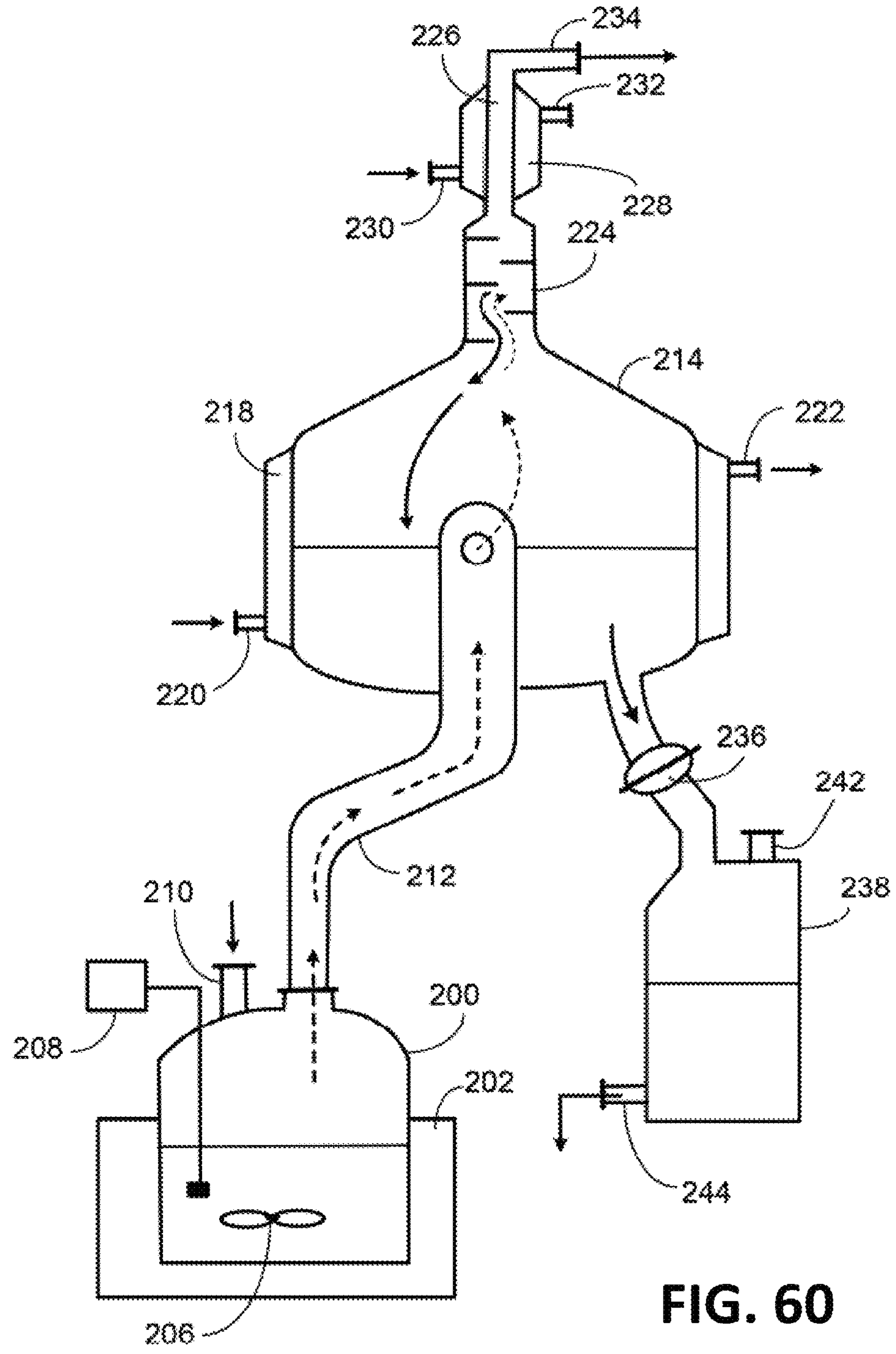
FIG. 60 illustrates an exemplary system for producing acrylic acid from 3-HP by reactive distillation.

An exemplary system for reacting 3-HP to form acrylic acid and distilling the acrylic acid from the reaction mixture is shown in FIG. 60. The system includes a reaction vessel 200, a still head 214 connected to reaction vessel 200 via a solvent line 212, a solvent trap 224, a condenser 226 above still head 214, and a collection vessel 238 connected to still head 214 via a valve 236 for collection of the distilled acrylic acid. Reaction vessel 200 includes a stirrer 206, a heating element 202, a thermometer 208 to control the temperature inside reaction vessel 200, and an inlet tube 210, through which a reaction mixture containing 3-HP (and optionally a solvent and a catalyst) may be added to reaction vessel 200. Still head 214 includes a cooling jacket 218 having a coolant inlet tube 220 and coolant outlet tube 222. Collection vessel 238 includes an inlet tube 242, through which additional ingredients, such as a polymerization inhibitor, may be added to the collection vessel 238. Collection vessel 238 also includes an outlet tube 244 for removing acrylic acid from the system. Inlet tube 242 may also be used for connecting collection vessel 238 to an additional vacuum line. Condenser 226 includes a cooling jacket 228 having a coolant inlet tube 230 and a coolant outlet tube 232. Condenser 226 also includes a junction 234, through which the system may be connected to a main vacuum line.

Prior to the removal process, reaction vessel 200 is charged with 3-HP and optionally a catalyst such as, for example, 4 A molecular sieves. A vacuum is then applied to the system to create a pressure inside the system at about 70-100 mbar. The reaction mixture is then heated using heating mantle 202 to a temperature of about 80° C. as determined using thermometer 208. At this temperature, 3-HP starts reacting to form the reaction products, acrylic acid and water. At the pressure of about 70-100 mbar, acrylic acid and water that formed in the course of the reaction evaporate and the vapor flows through solvent line 212 to still head 214. Some of the vapor containing acrylic acid and water condenses in still head 214 to form a liquid product contained in still head 214. The remaining vapor travels through trap 224 to condenser 226, where the remaining gaseous acrylic acid and water condense and flow through trap 224 down to still head 214. When a sufficient amount of liquid product mixture is collected in still head 214, the liquid flows to collection vessel 238 via open valve 236. Valve 236 may be closed to prevent undesired flow of the liquid contained in still head 214 to collection vessel 238.

In some embodiments, the present disclosure provides a method of reacting 3-HP to form acrylic acid, including (1) providing a reaction vessel containing 3-HP, a collection vessel, and a condenser; (2) reacting 3-HP to form acrylic acid in the reaction vessel; (3) evaporating the acrylic acid from the reaction vessel (3) condensing the vaporized acrylic acid to a liquid state in the condenser; and (4) directing a flow of acrylic acid from the condenser to the collection vessel. In some embodiments, the reaction vessel also contains a catalyst. In some embodiments, the reaction vessel also contains a polymerization inhibitor. Exemplary embodiments of the catalysts, polymerization inhibitors, amounts of the catalysts and polymerization inhibitors, as well as the reaction conditions are described in the "Making acrylic acid" section of the present application.

Purification of Acrylic Acid

In some embodiments, acrylic acid prepared by any of the methods described in the "Making acrylic acid" section of the present disclosure may be further purified to obtain acrylic acid that is free of any polymerization products and unreacted 3-HP. Conventional methods to purify acrylic acid include distillation of acrylic acid at atmospheric pressure (boiling point of acrylic acid is about 141° C. at about 760 mmHg) in the presence of a polymerization inhibitor, such as 4-methoxyphenol (MEHQ). When heated at or near its boiling point, acrylic acid rapidly polymerizes even in the presence of a polymerization inhibitor. Hence, the yield of a conventional process is merely satisfactory (e.g., 40-60%). The methods of the present disclosure advantageously allow to avoid polymerization and purify acrylic acid with a yield of at least about 50% (e.g., from about 75% to about 95%) based on the amount of crude acrylic acid before purification. In some embodiments, the pure acrylic acid is obtained in a form of an aqueous mixture. The concentration of acrylic acid in such mixture is from about 70 wt. % to about 90 wt. % (e.g., about 70 wt. %, about 75 wt. %, about 80 wt. %, about 85 wt. %, or about 90 wt. %).

In some embodiments, the present disclosure provides a method of purifying acrylic acid by distilling the acrylic acid at a reduced pressure. In such embodiments, the pressure exerted by the atmosphere surrounding the acrylic acid during distillation is typically from about 70 mbar to about 100 mbar (e.g., from about 75 mbar to about 105 mbar, or from about 80 mbar to about 100 mbar), and the temperature is typically from about 80° C. to about 120° C. (e.g., from about 90° C. to about 110° C., or from about 80° C. to about 100° C.). For example, in some embodiments, the pressure exerted by the atmosphere surrounding the acrylic acid during distillation is about 70 mbar, about 75 mbar, about 80 mbar, about 85 mbar, about 90 mbar, about 95 mbar, or about 100 mbar, and/or the temperature is about 80° C., about 85° C., about 90° C., about 95° C., or about 100° C.). In some embodiments, the distillation is carried out in the presence of a polymerization inhibitor, the amount of which can be selected as appropriate (e.g., from about 1 wt. % to about 20 wt. %). The polymerization inhibitor can be any one of the polymerization inhibitors described herein, or a combination thereof.

In some embodiments, the present disclosure provides a method of purifying acrylic acid by purging a vessel containing crude acrylic acid with a gas. In some embodiments, the gas is air, nitrogen or argon. In some embodiments, temperature of the gas is below the boiling point of acrylic acid. In such embodiments, the temperature is from about 40° C. to about 80° C. (e.g., about 50° C., about 60° C., or about 70° C.). In some embodiments, the purging is conducted at about atmospheric pressure. In this process, acrylic acid slowly evaporates (without boiling) at a temperature of the warm gas, and the flow of the warm gas carries the vapor of pure acrylic acid from the vessel. In some embodiments, a system for purging of acrylic acid with a gas contains a condenser with the temperature of the coolant in the condenser from about 5° C. to about 25° C. When the warm gas containing vapor of acrylic acid passes through the condenser, the acrylic acid condenses to a liquid state, while the carrier gas is not retained in the condenser and leaves the system. Pure acrylic acid maybe collected from the condenser and used for the intended purpose.

EXAMPLES

The disclosure is further described in the following examples, which do not limit the scope of the disclosure described in the claims.

Example 1. Specificity of Small-Molecule Inducers for MmsR Transcriptional Activator Protein 3-HP or similar small acid inducible gene expression systems are novel expression system identified in *P. denitrificans*. This expression systems regulate the expression of 3-HP degrading enzymes. Analysis of gene arrangement near 3-HP-degrading genes in *P. denitrificans* genome revealed the presence of a putative LysR-family transcriptional regulator, MmsR. It was speculated that the transcriptional regulator proteins, when complexed by 3-HP, activate the transcription of mmsA, hpdH, and others. The putative transcription activator protein MmsR is composed of an N-terminal helix-turn-helix domain for DNA binding, a C-terminal domain for inducer binding that responds to 3-HP, and a linker connecting the two domains. A study was conducted to determine the spectrum of molecules than can induce MmsR. Various acids and alcohols were tested for their ability to induce MmsR, including L-lactic acid (LAC), acetic acid (AcOH), propionic acid (PA), 3-hydroxybutyrate (3-HB), 1,3-propanediol (1,3-PDO) and 2,3-butanediol (2,3-BDO), as well as L-valine (L-val) and its degradation intermediate 3-hydroxyisobutyrate (3-HIB). Most of the acids and alcohols tested were chosen mainly due to their similarity to 3-HP in size and/or structure. However, L-val and 3-HIB were chosen based on their similarity to methylmalonylsemialdehyde dehydrogenase and 3-hydroxyisobutyldehydrogenase, because mmsA and hbdH-4, whose transcription is regulated by MmsR, encode methylmalonylsemialdehyde dehydrogenase and 3-hydroxyisobutyldehydrogenase, respectively, the enzymes involved in L-val degradation.

Figure 2A:
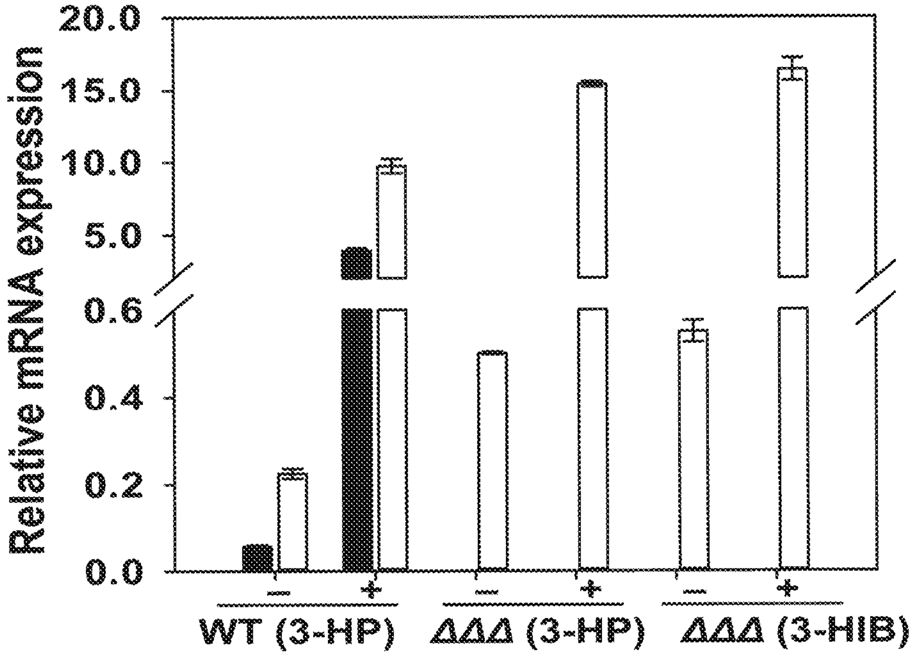
FIGS. 2A-B are graphs showing transcriptional analysis of mmsA (white bar) and hbdH-4 (black bar) genes by real-time PCR in wild-type (WT) and mutant *P. denitrificans* strains.

*P. denitrificans* was cultured on minimal medium with and without each compound to be tested, and transcription of mmsA and hbdH-4 was measured by quantitative RT-PCR (FIG. 2A). The housekeeping gene rpoD, encoding sigma factor 70, was used as a reference. Transcription of the two genes (mmsA and hbdH-4) was enhanced markedly upon exposure of *P. denitrificans* to 3-HIB (mmsA, 154-fold; hbdH-4, 146-fold), 3-HB (mmsA, 38-fold; hbdH-4, 32-fold) and L-val (mmsA, 72-fold; hbdH-4, 68-fold), and 3-HP (mmsA, 134-fold; hbdH-4, 128-fold). By contrast, limited or no induction was observed on exposure to LAC, AcOH, PA, 1,3-PDO and 2,3-BDO. 3-HP, 3-HB and 3-HIB are structurally similar, as they are all β-hydroxy acids. Both the carboxyl group and β-hydroxy appear to be integral to the ability of 3-HP, 3-HB and 3-HIB to bind to MmsR. L-val is much different from these three compounds structurally, and is converted to 3-HIB. The induction by L-val is attributable to L-val-derived 3-HIB rather than to L-val itself.

Figure 2B:
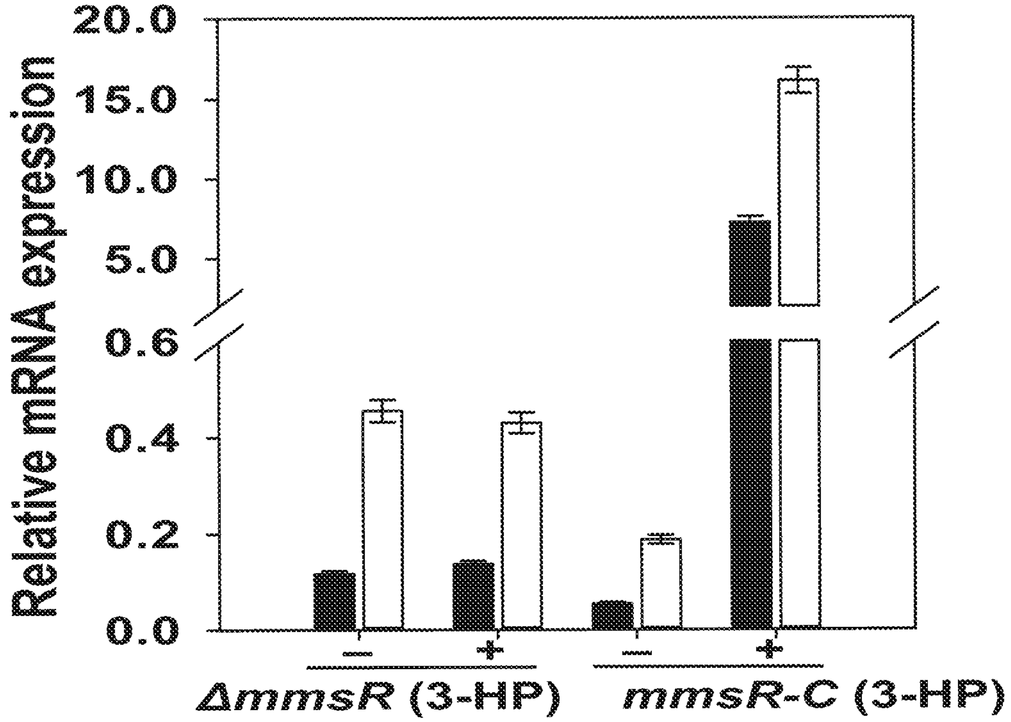

The possibility that malonate semialdhyde (MSA), which is derived from 3-HP, and methylmalonatesemialdhyde (MMSA), which is derived from L-val and 3-HIB, are the physiological inducers, rather than 3-HP and/or 3-HIB was also examined (see FIGS. 2A and 2B). In general, aldehydes are toxic, and aldehyde-degrading genes are often up-regulated when aldehydes accumulate in a cell. 3-HP is degraded by the enzymes encoded by hpdH, hbdH-4 and hbdH-1, and the deletion mutant *P. denitrificans* ΔhpdHΔhbdH-4ΔhbdH-1 does not degrade 3-HP at an appreciable rate. In this triple mutant, which does not produce MSA from 3-HP, transcription of mmsA was nonetheless up-regulated by 3-HP (FIG. 3). This indicated that 3-HP, without being converted to MSA, can activate MmsR protein. Similarly, transcription of mmsA was up-regulated by 3-HIB in the triple mutant, suggesting that 3-HIB is also a real inducer of MmsR. Interestingly, the transcription of mmsA in the triple deletion mutant *P. denitrificans*, either in the absence or presence of 3-HP, was higher than in the wild-type strain.

To confirm that MmsR is a transcriptional activator, deletion and subsequent complementation experiments were conducted (FIG. 2B). In the deletion mutant (ΔmmsR), transcription of both mmsA and hbdH-4 were low, and the level was not affected by 3-HP. However, when mmsR was re-introduced to the ΔmmsR mutant by a plasmid, up-regulation of both mmsA and hbdH-4 by 3-HP was fully restored. These results confirm that MmsR is the transcriptional activator protein for the expression of mmsA and hbdH-4. Interestingly, the basal-level transcriptions of mmsA and hbdH-4 in the ΔmmsR mutant were ~2-fold higher than those in the wild-type or mmsR-complemented recombinant (mmR-C). This suggests that the inducer-free MmsR protein might repress, to a certain extent, the transcription of mmsA and hbdH-4.

Although the expression of hbdH-4 was regulated by 3-HP, the promoter sequence was much different from that of mmsA, as the promoter lacked operator sites for binding of transcriptional activator proteins. In order to confirm that the hbdH-4 promoter is inducible, the mmsA hbdH-4 intergenic region was cloned on a plasmid with green fluorescence protein (GFP) as a reporter. In addition, electromobility shift assays (EMSA) were performed with the purified MmsR protein and the DNA fragment of the hbdH-4 promoter region. Both experiments showed that the hbdH-4 promoter is constitutive, and not inducible by 3-HP. GFP under the control of $P_{hbdH\text{-}4}$ was constitutively expressed, and binding between the MmsR proteins and the hbdH-4 promoter region was not present (data not shown). Furthermore, in qRT-PCR experiments for the cells grown in the presence of 3-HP, a large amount of polycistronic mRNA transcript of mmsA and hbdH-4 was detected. These results suggest that the transcription of hbdH-4 is controlled by two independent promoters, 3-HP inducible $P_{mmsA}$ and constitutive $P_{hbdH\text{-}4}$, and the significant up-regulation of hbdH-4 upon 3-HP addition (see FIGS. 1B and 2B) is attributed to the transcriptional read-through from $P_{mmsA}$. We also noticed that no terminator sequence was present in the mmsA and hbdH-4 intergenic region. $P_{mmsA}$ was studied in detail, since $P_{hbdH\text{-}4}$ is not inducible.

Figure 3A:
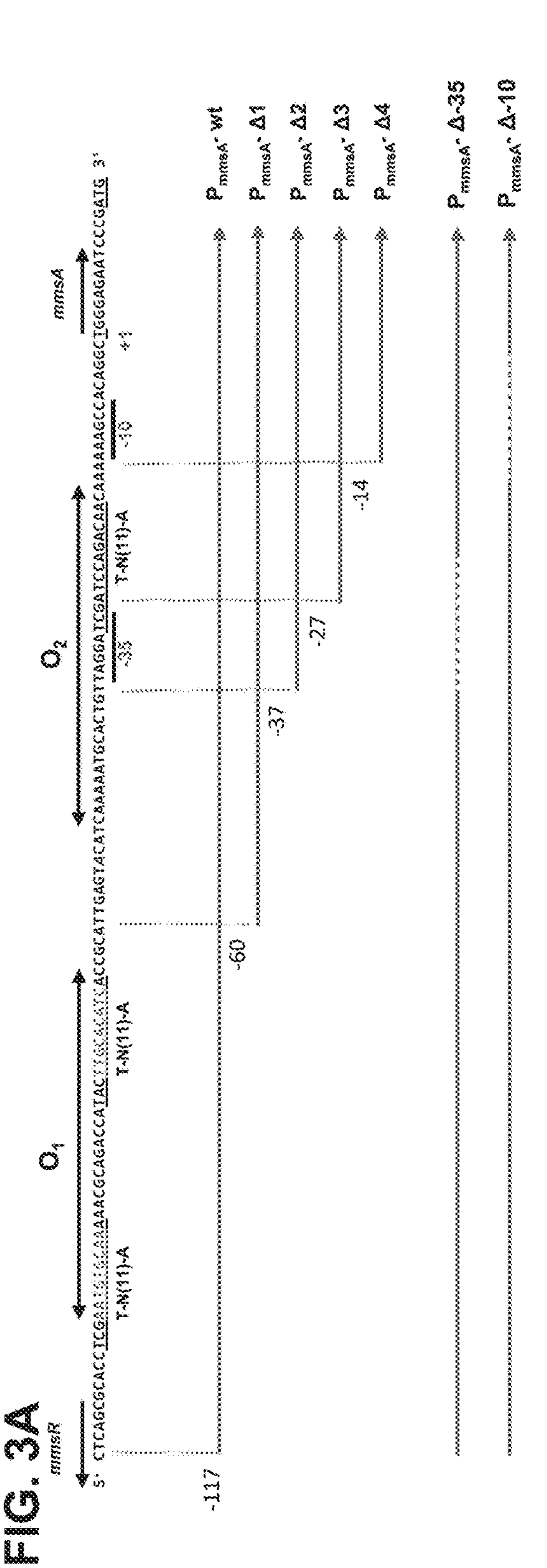
FIGS. 3A-B are a schematic analysis of the mmsR-mmsA intergenic region with promoter region and identification of regulatory protein, MmsA binding site.
Figure 3B:
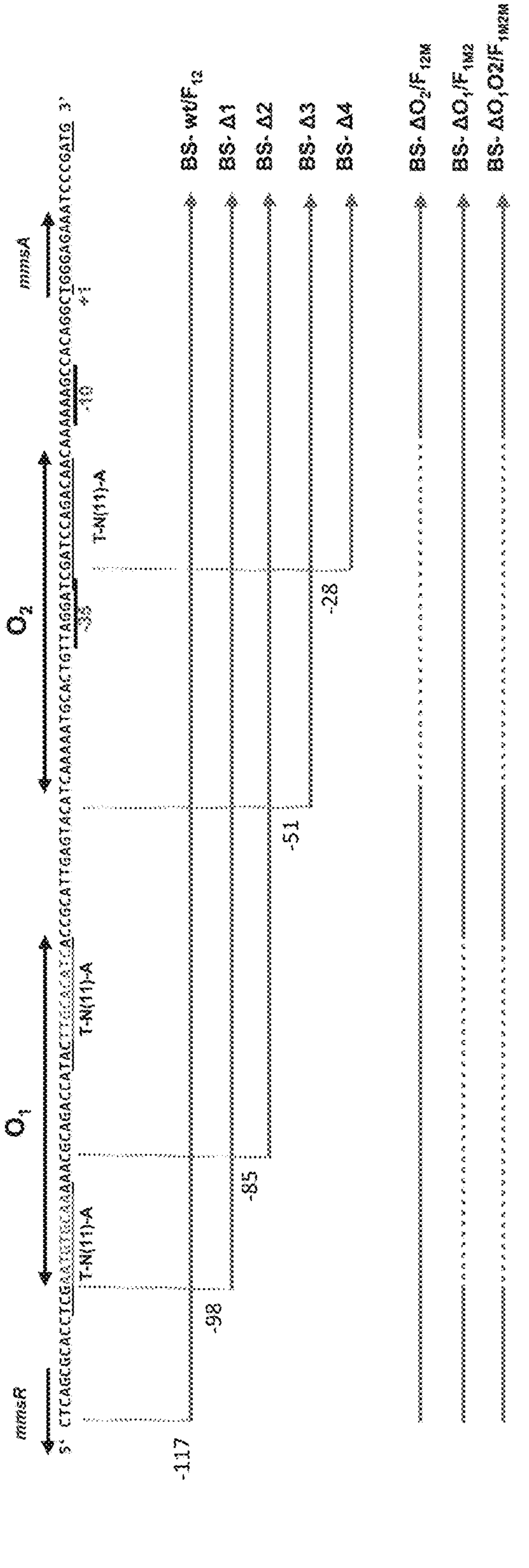

Example 2. In Silico Analysis of the mmsR-mmsA Intergenic Operator-Promoter Region In silico analysis of the intergenic region between the two divergently transcribed genes of mmsR and mmsA was conducted. This study characterized the cis-acting elements, including: (i) putative promoter upstream of the mmsA transcription start site (TSS), (ii) two putative, tandem operator sites, $O_1$ and $O_2$, and (iii) three T-$N_{11}$-A motifs, two embracing two half-sites of $O_1$ and the last one a half-site of $O_2$ (FIG. 3A). Each operator contained the DNA sequence of dyad symmetry centered at positions −81 and −33, respectively, upstream of the putative TSS of the mmsA gene. Inverted repeats are common in many prokaryotic operators recognized by regulatory proteins. The distance between the centers of the two palindromic regions was ~50 bp, corresponding to five turns of helical DNA. The nucleotide sequence in the dyad at the $O_1$ site, composed of two 9 bp fragments, 15 bp apart, was highly symmetrical, with only a single mismatch. The inverted repeat in the $O_2$ site, separated by 11 bp, was less symmetrical, 6 bases among 9 being mismatched. Alignment of the four palindromic fragments of the $O_1$ and $O_2$ operators showed the existence of the consensus sequence AACGTGTAA (FIG. 3B). Three bases A, G and T at positions 2, 4 and 5 (FIG. 3B, bold), respectively, were fully conserved in all of the fragments, and the three bases C, T, A at positions 3, 7 and 8 (underlined), respectively, were highly conserved in three fragments. It should be noted that the identity of the putative O2 region is somewhat questionable; one of its half site showed very poor conservation (3/9) and the size of spacer was 4 bp shorter than that in the O1. Additional evidence to confirm the identity of the O2 site should be obtained from in vivo and in vitro experiments (see Examples below).

The LysR-type transcriptional regulators (LTTR) is the largest family of transcription factors in prokaryotes. LTTR binding DNA sequences have two symmetrical operator regions termed RBS (Regulatory Binding Site) and ABS (Activator Binding Site), where RBS shows a greater degree of symmetry relative to ABS. In addition, the symmetrical half sites of RBS and ABS are known to be often embraced by T-(N11)-A motifs. These sequence characteristics, along with the structural characteristics of MmsR, indicate that MmsR belongs to LTTR family of transcriptional regulators. Our analysis of the sequence of the intergenic region (see FIG. 3A) also suggested that the transcription of mmsR is suppressed by its own product, MmsR. The $O_1$ site is located at the putative-10 region upstream of mmsR, and the $O_2$ site was completely overlapped with the putative-35 promoter regions upstream of mmsR, respectively. Binding of MmsR protein at the $O_1$ and $O_2$ sites can interfere with binding of RNA polymerase at the mmsR promoter and/or its travel along the DNA strand during transcription. We also noted that transcription of mmsA can possibly be interfered with by binding of MmsR protein, because the −35 region of mmsA is located in the 11 bp-long spacer region of the two half sites of the $O_2$ site. This might explain why the basal-level transcription of mmsA and hbdH-4 in the ΔmmsR mutant were 2-fold higher than those in the wild-type counterpart (see FIG. 2A and FIG. 2B). Extensive studies both in vivo and in vitro on the intergenic region were performed to verify the in silico predictions (see Examples below).

Example 3. In Vivo Characterization of the mmsR-mmsA Intergenic Operator-Promoter Region Characteristics of the promoter region controlling expression of the mmsA gene were studied by 5' end mapping and random mutagenesis in vivo. In order to identify the −10 and −35 region, various mutations were made in the $P_{mmsA}$ promoter region, including serial deletions in the upstream regions, or randomization of the putative-10 and −35 regions, and the mutant promoters were fused with the gfp reporter gene (FIG. 4). *P. denitrificans* lacking the mmsR gene was used as host for testing the mutant promoters, because MmsR can bind to the promoter and affects expression of the gfp reporter gene. When the promoter region between −117 and −60 ($P_{mmsA}$_Δ1) or −117 and −37 ($P_{mmsA}$_Δ2) was deleted, gfp expression decreased by about 16% compared to the control ($P_{mmsA}$_wt) which contains the whole-length promoter (Table 1). In comparison, when a longer upstream sequence before −27 ($P_{mmsA}$_Δ3) or −14 ($P_{mmsA}$_Δ4) was deleted, the promoter strength decreased significantly by 39 or 58%. These results suggest that the sequences deleted in $P_{mmsA}$_Δ3 and $P_{mmsA}$_Δ4 contain important elements for transcription, most probably the −10 and −35 regions as predicted by in silico analysis. Within addition, randomization in the putative-10 ($P_{mmsA}$_Δ−10) and −35 ($P_{mmsA}$_Δ−35) regions reduced the promoter strength by 52% in comparison to that of $P_{mmsA}$_wt. The 5' end mapping and random mutagenesis support the in silico prediction of −10 and −35 regions of $P_{mmsA}$.

TABLE 1

In vivo mmsR-mmsA intergenic region analysis based on expression of GFP (AU/OD; AU, arbitrary unit) after controlled serial mutagenesis of promoter and operator regions.

GFP (AU/OD)[b] × $10^3$

| Promoter identification | | Operator identification | | |
|---|---|---|---|---|
| | ΔmmsR | | mmsR-C[a] | |
| Plasmid | −3-HP | Plasmid | −3-HP | +3-HP[c] |
| 5' mapping | | | | |
| $P_{mmsA}$-wt | 9.0 ± 0.36 | BS_wt | 2.6 ± 0.08 | 90.2 ± 2.00 |
| $P_{mmsA}$-Δ1 | 7.4 ± 0.44 | BS_Δ1 | 2.5 ± 0.09 | 81.0 ± 2.10 |
| $P_{mmsA}$-Δ2 | 7.7 ± 0.33 | BS_Δ2 | 2.1 ± 0.05 | 2.2 ± 0.07 |
| $P_{mmsA}$-Δ3 | 5.5 ± 0.21 | BS_Δ3 | 2.4 ± 0.01 | 2.1 ± 0.09 |
| $P_{mmsA}$-Δ4 | 3.8 ± 0.22 | BS_Δ4 | 6.0 ± 0.09 | 5.0 ± 0.06 |
| Randomization | | | | |
| BS_Δ$O_1O_2$* | 4.1 ± 0.16 | BS_Δ$O_1O_2$ | 4.2 ± 0.06 | 4.3 ± 0.02 |
| $P_{mmsA}$-Δ-10 | 4.3 ± 0.18 | BS_Δ$O_2$ | 25.3 ± 0.63 | 56.7 ± 1.47 |
| $P_{mmsA}$-Δ-35 | 5.2 ± 0.20 | BS_Δ$O_1$ | 1.9 ± 0.09 | 1.4 ± 0.05 |

[a]Denoting the complementary expression of MmsR on plasmid
[b]Fluorescence was measured three times (n = 3) at 4 h after induction and averaged
[c]25 mM 3-HP was added to growth medium for induction 5' end mapping and random mutagenesis were also performed to study the location and identity of the operator regions ($O_1$ and $O_2$) in vivo. Because mmsR is possibly auto-regulated (see Examples below), mmsR was constitutively expressed from a plasmid under the control of the weak $P_{cI}$ promoter (hbdH-I promoter). As shown in Table 1, BS_wt and BS_Δ1, which contain both operators ($O_1$ and $O_2$), exhibited high 3-HP induction (up to ~34.6 fold). In comparison, when the first half site of the putative O1 site (BS_Δ2) was deleted, alone or along with the other half site of O1 or O2 (BS_Δ3 or BS_Δ4), the inducibility was completely lost.

Promoters with mutation in the O1 and/or O2 region were also investigated. Here, the operator sequences were randomized to destroy the dyad symmetry, but the −35 regions were not changed. As expected, randomization of O1, or both O1 and O2, completely abolished the inducibility by 3-HP. These results confirm the location and identity of the $O_1$ operator region, which was thought to be present downstream of −98. However, these results did not clearly define or identify the role of the O2 region. When the putative O2 region alone was randomized (BS_ΔO2), promoter strength in the absence of 3-HP greatly increased (~10 fold) compared to that of wild type BS_wt. When 3-HP is present, the strength was reduced by 37% (compared to that of wild type BS_wt) but still remained at a high level. In addition, when both the O1 and O2 were simultaneously mutated (BS_ΔO1O2), the promoter strength was markedly reduced, and the promoter was not inducible. This suggests that the O2 site functions in close cooperation with the O1 site, and has an important role in regulating $P_{mmsA}$ function and strength.

Collectively, the in vivo studies on the operator regions can be summarized as follows: (i) $O_1$ alone can activate transcription (with the 3-HP-MmsR complex), although less efficiently than when both $O_1$ and $O_2$ are present, (ii) binding of 3-HP-free MmsR to the $O_2$ operator can suppress transcription from the $P_{mmsA}$ promoter, and (iii) the high strength of the promoter of the ΔO2 mutant still involves the presence of the $O_1$ site. It is most probable that the $P_{mmsA}$ promoter is regulated positively (in the presence of 3-HP) as well as negatively (in the absence of 3-HP).

Figure 4A:
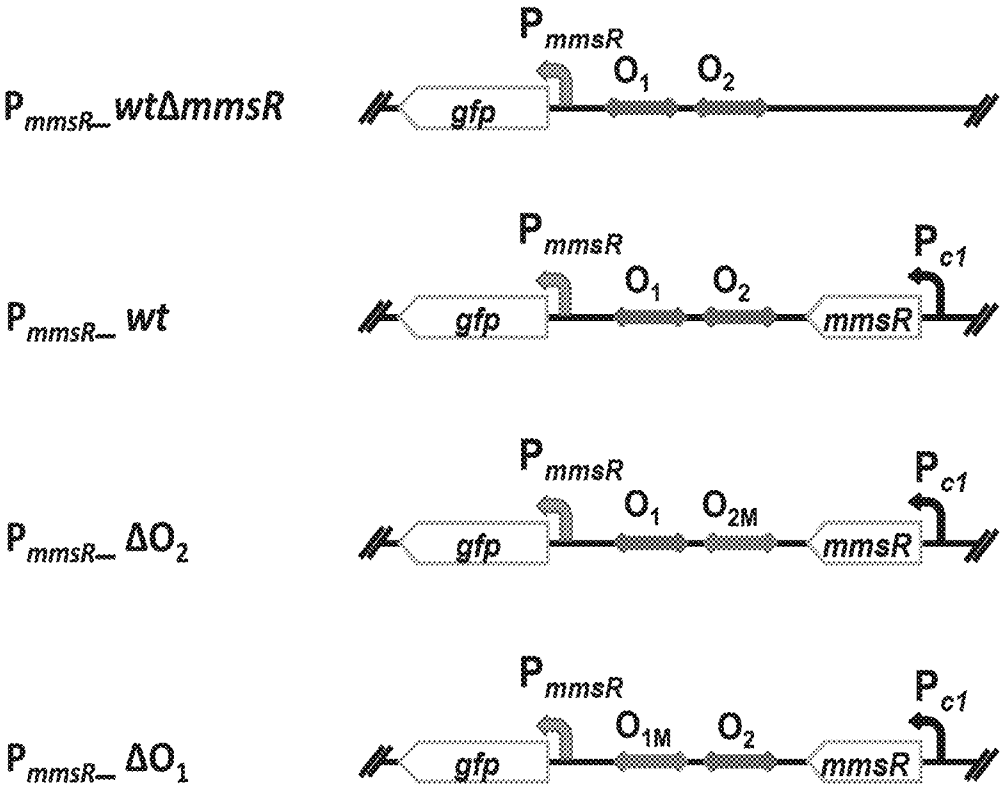
FIGS. 4A-B are a schematic and a graph showing an in vivo study to reveal the importance of $O_1$ and $O_2$ sites for transcription activation in mmsR promoter ($P_{mmsR}$) (FIG. 4A) and mmsA promoter ($P_{mmsA}$) (FIG. 4B). The $O_1$ or/and $O_2$ sites were randomized and promoter strength with mutations in $O_1$ or/and $O_2$ sites was examined using GFP as reporter protein. These mutations were introduced into *P. denitrificans* ΔhpdHΔhbdH1ΔhbdH4ΔmmsR and used as expression host.
Figure 4B:
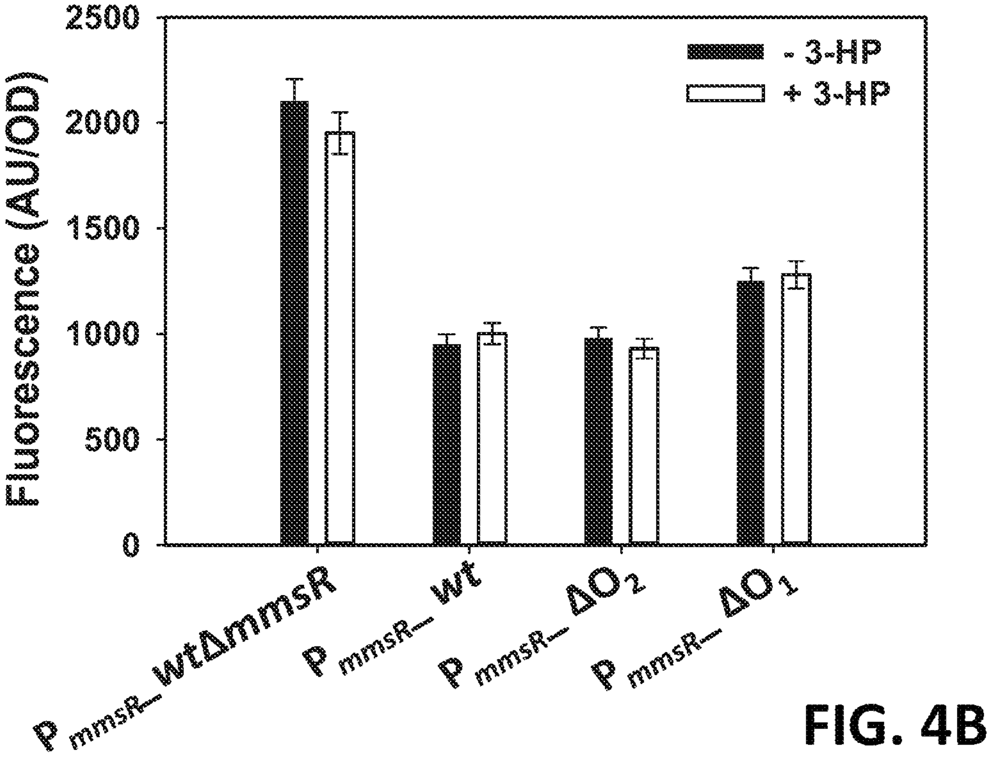
Figures 5A, 5B, 5C, 5D, 5E:
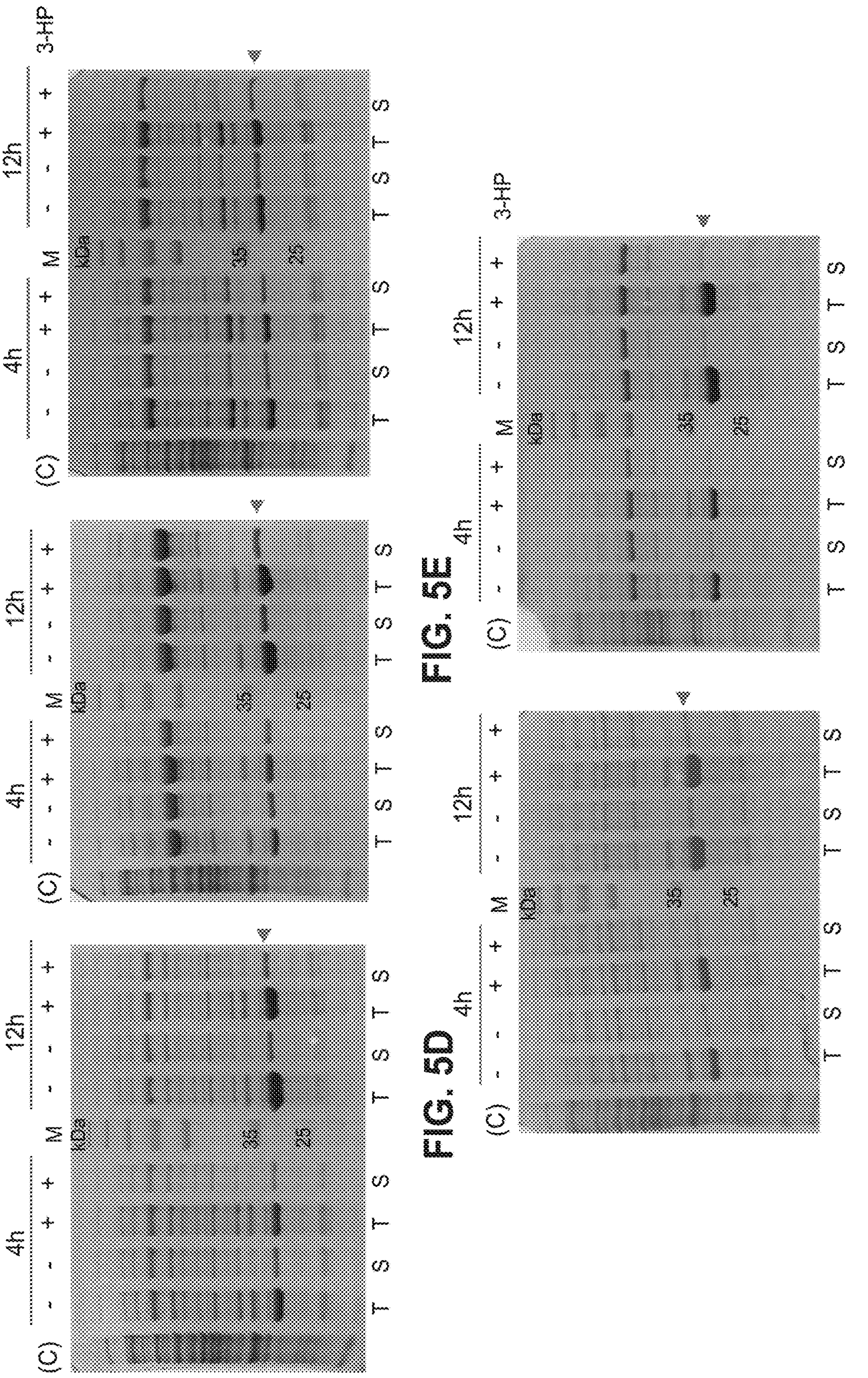
FIGS. 5A-E are pictures of SDS-PAGE analyses to study the solubility of recombinant C-His-tagged MmsR protein with the help of various chaperon plasmids such as pG-KJE8 (FIG. 5A), pGro7 (FIG. 5B), pKJE7 (FIG. 5C), pG-Tf2 (FIG. 5D), and pTf16 (FIG. 5E) in recombinant *E. coli* BL21. Cell lysate (T) and cell free extracts(S) recombinant strains with MmsR and chaperon were analyzed.

The effect on mmsR expression by MmsR binding in the operator region was also studied with a GFP reporter. The $P_{mmsR}$ promoter was negatively regulated by its own protein product, MmsR protein (FIG. 4B); GFP expression increased by ~2-fold when mmsR was deleted ($P_{mmsR}$_wtΔmmsR). Mutation in $O_2$ ($P_{mmsR}$_Δ$O_2$) did not affect the expression of GFP, whereas $O_1$ mutation ($P_{mmsR}$_Δ$O_1$) slightly increased it, by ~20%. These results suggest that occupation of the $O_1$ region alone by MmsR can repress the transcription from the $P_{mmsR}$ promoter. Furthermore, the presence of 3-HP did not affect the repression by MmsR protein, indicating that the repression is not 3-HP-dependent. Identification of −10 and −35 regions of $P_{mmsR}$ was also attempted by 5' end mapping of the putative promoter regions (FIG. 5A), but failed. The strength of the $P_{mmsR}$ promoter was too weak and the difference in the mutant promoters was not realizable (p>0.05).

The LTTR proteins and their cis-acting elements have been studied in several microorganisms. In *E. coli* and *Salmonella typhimurium* LT2, the IlvY protein (a LysR-type transcription regulatory protein) controlling the expression of the ilvC gene (encoding acetohydroxy acid isomerase; EC 1.1.1.86) has been investigated In these studies, transcription of the ilvC gene was induced by the substrates of acetohydroxy acid isomerase, acetohydroxybutyrate or acetolactate, and the induction was mediated by the IlvY protein. Similar to the $P_{mmsA}$ promoter, the promoter region of the ilvY and ilvC genes has two operators, $O_1$ and $O_2$, and each operator was composed of 9 bp-long inverted repeats. The repeats shared homologous sequences, AACGTTAC (T) A in *E. coli* and NG (A) CGTTG (A) TA in *S. typhimurium* LT2, respectively. Moreover, similar to the $P_{mmsA}$ promoter in *P. denitrificans*, symmetry between the two dyads in these strains was more stringent in $O_1$ (a single mismatch) than in $O_2$ (six mismatches). Another LysR-type activator AtzR, present in *Pseudomonas* sp., has been reported to show the dissimilarity in the ABS operator region. AtzR activates the expression of divergently transcribed cyanuric acid degradative operon atzDEF. However, ABS contains three motifs, designated ABS-1, ABS-2 and ABS-3, in which individual subsites have distinct roles in the activation process. In vivo mutational analysis showed that ABS-1 and ABS-2 subsites were involved for full activation of the PusDEF promoter. In contrast, ABS-3 functions as a 'subunit trap' leading to inactivation of PuzDEF when AtzR locates at the ABS-2 and ABS-3 subsites. For the $P_{mmsA}$ promoter, the $O_2$ region was assumed to completely overlap the −35 region as in many other LTTR-mediated systems. Transcription activators, IlvY, ClcR and AtuR from *E. coli, P. putida* and *P. aeruginosa*, respectively, also possess the same arrangement where −35 promoter element is situated within the O2 subsites. This region of overlap controls the up-regulation of a downstream gene by binding to a dimer of LTTRs. However, the function repressing the downstream gene in the absence of inducer molecules has not been reported.

Figure 6B:
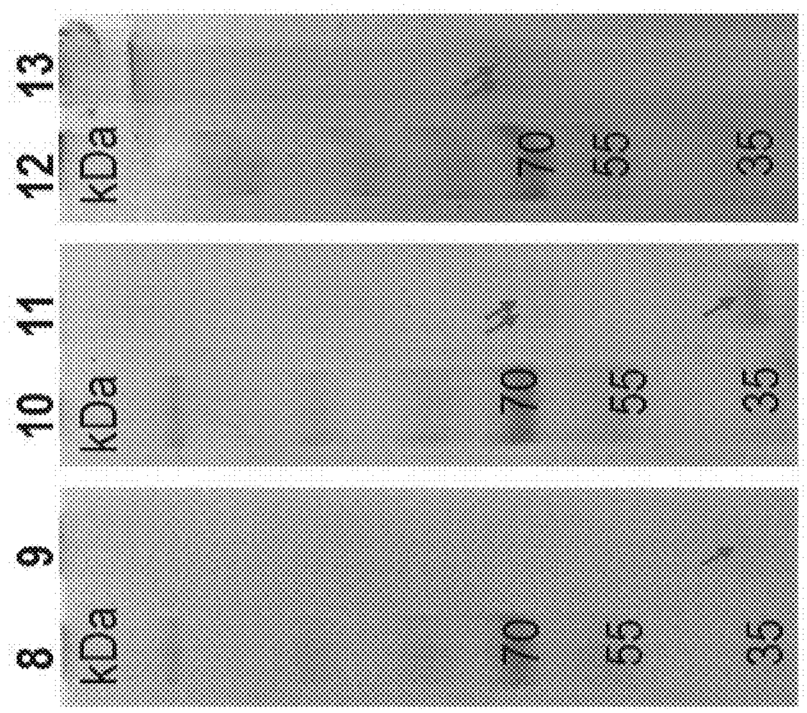
FIGS. 6A-C are pictures of gels showing expression, purification and oligomeric forms of recombinant MmsR protein.
Figure 6A:
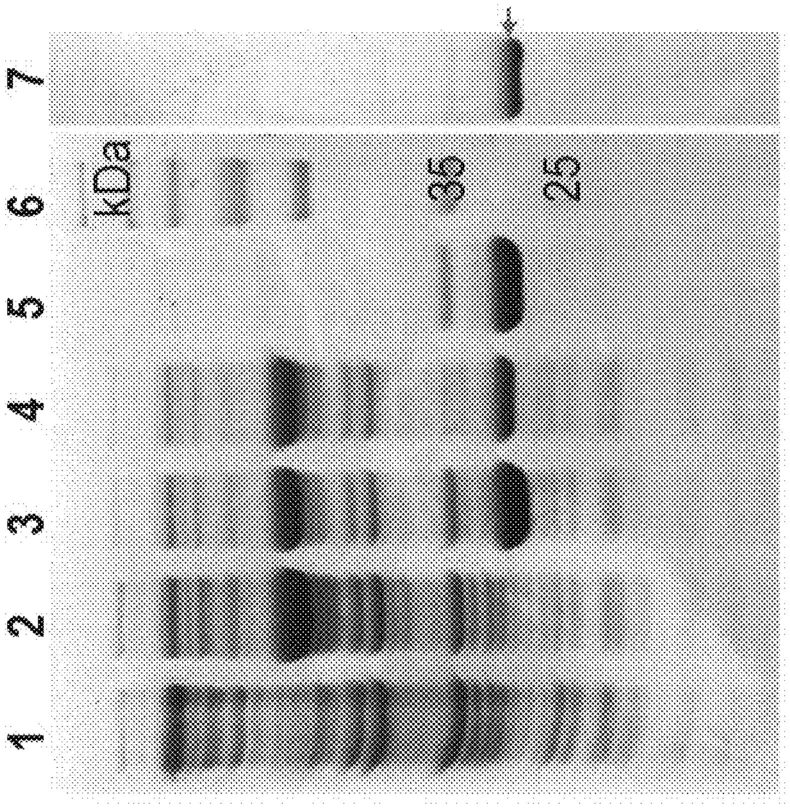
Figure 6C:
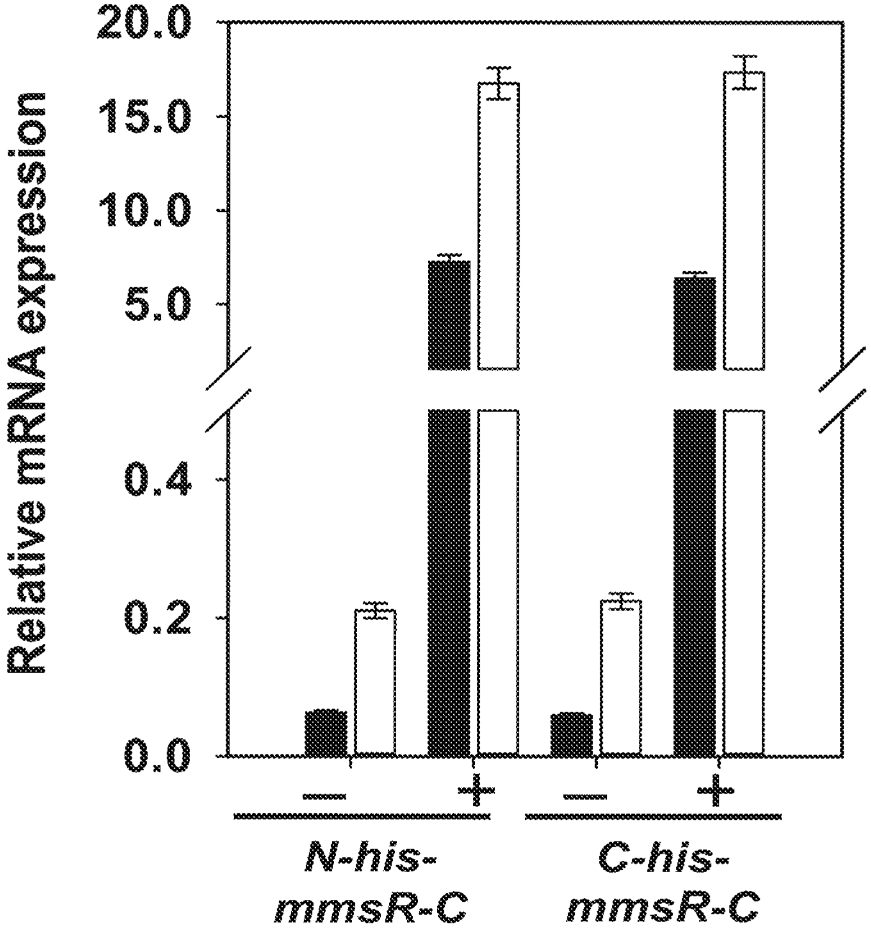

Example 4. Production of MmsR Protein and its Binding Operator Sites In Vitro For biochemical characterization in vitro, recombinant MmsR protein tagged with six histidine residues at the C terminus of the protein was produced and purified from recombinant *E. coli*. His-tagged MmsR protein appeared to function as well as the native MmsR protein in complementation experiments, conducted as described in Example 1 (see FIG. 6C), whether the His was present at the C-terminus or N-terminus of MmsR. As a result, only recombinant C-terminal His-tag MmsR was further studied in vitro. After optimization of the culture conditions (e.g., temperature, culture medium, IPTG concentration, harvest time and 3-HP concentration, as well as co-expression with various chaperons, such as GroEL-ES, DnaKJ-GrpE and trigger factors), the recombinant MmsR was expressed in soluble form at a high level in *E. coli* and purified by affinity chromatography (FIG. 5A-E). The size of the His-tag-fused MmsR protein was estimated to be 34.4 kDa, which is in good agreement with the size estimate based on a 6× his-mmsR gene sequence. According to native PAGE and/or gel filtration analyses, the MmsR protein was monomeric at the low concentration of 65 nM, while dimeric at the high concentration of 550 nM (FIG. 6B).

The binding of MmsR to the mmsR-mmsA intergenic region was studied in vitro by EMSA (FIG. 7A). 40 nM of the complete 130 bp DNA fragment was used as probe (designated the $F_{12}$ fragment; see the FIG. 3B) and 0-72.7 nM of the purified MmsR protein was incubated with the DNA probe in both the presence and absence of 3-HP as inducer. A DNA fragment randomized in both $O_1$ and $O_2$ ($F_{1M2M}$) was used as a control (see FIG. 3B and Table 2). In electrophoresis, a band shift appeared for the intact 130 bp DNA fragment when MmsR was added and the ratio of the shifted DNA to un-shifted DNA increased upon increasing the concentration of the protein during incubation. By contrast, no such mobility retardation was observed with the control DNA fragment up to 72.7 nM MmsR protein (data not shown). This indicated that MmsR has a strong binding affinity to the native $P_{mmsA}$, forming a binding complex in vitro. At high concentrations of the MmsR protein, multiple bands traveling shorter distances appeared. This was attributed to the formation of diverse oligomeric complexes among the DNA fragments and protein molecules. The DNA probe has two binding sites (O1 and O2) for MmsR and MmsR binds to the DNA as dimer, thus it is highly probable that DNA and protein form diverse oligomeric complexes when their concentrations are high. FIG. 7A also shows the effect of 3-HP on binding affinity between MmsR and the $P_{mmsA}$ promoter. The band shift appeared at lower MmsR concentration when 3-HP was added. Also, oligomeric complexes traveling shorter distance appeared earlier at lower MmsR concentrations when 3-HP was present. This suggested that 3-HP promotes the binding affinity between MmsR and the $P_{mmsA}$ promoter.

TABLE 2

Fragments for EMSA used in this study.

| Fragments | Sequence(5'-3') | Source |
|---|---|---|
| $F_{12}$ | GTCAGCCTCAGCGCACCTCG**AATGTGCAA**AAACGCAGACCAC**TTGCACATC**ACCGCATTGAGTACATC*AAAAATCAC*TGTTAGGATCGAT*CCAGACAACAAA*AAAGCCACAGGCTGGGAGAATCCCG | This study |
| $F_{12M}$ | GTCAGCCTCAGCGCACCTCG**AATGTGCAA**AAACGCAGACCATAC**TTGCACATC**ACCGCATTGAGTACATCA*ATCCTTGCT*TGTTAGGAT*CGCGCCCAGGCACAA*AAAAAGCCACAGGCTGGGAGAATCCCG | This study |
| $F_{1M2}$ | GTCAGCCTCAGCGCACCTCG**ATCCTTGCT**AAACGCAGACCATAC**CGCCCAGGC**ACCGCATTGAGTACATCA*AAAATGCAC*TGTTAGGATCGATCC*AGACAACAA*AAAAAGCCACAGGCTGGGAGAATCCCG | This study |
| $F_{1M2M}$ | GTCAGCCTCAGCGCACCTCG**ATCCTTGCT**AAACGCAGACCATAC**CGCCCAGGC**ACCGCATTGAGTACATCA*ATCCTTGCT*TGTTAGGATCGCGCC*CAGGCACAA*AAAAAGCCACAGGCTGGGAGAATCCCG | This study |
| DNaseI footprinting fragment | CCGCAGGTTGTCCCAGTCCATGTCAGCCTCAGCGCACCTCG**AATGTGCAA**AAACGCAGACCATAC**TTGCACATC**ACCGCATTGAGTACATCA*AAAATGCAC*TGTTAGGATCGATCC*AGACAACA*AAAAAGCCACAGGCTGGGAGAATCCCGATGACCGCAACTGCCCCG | This study |

[a]Bold letter indicated the half sites of O1 operator; italic letter indicated the half sites of O2 operator; underlined letter indicated site-directed mutagenesis region.

Figure 7B:
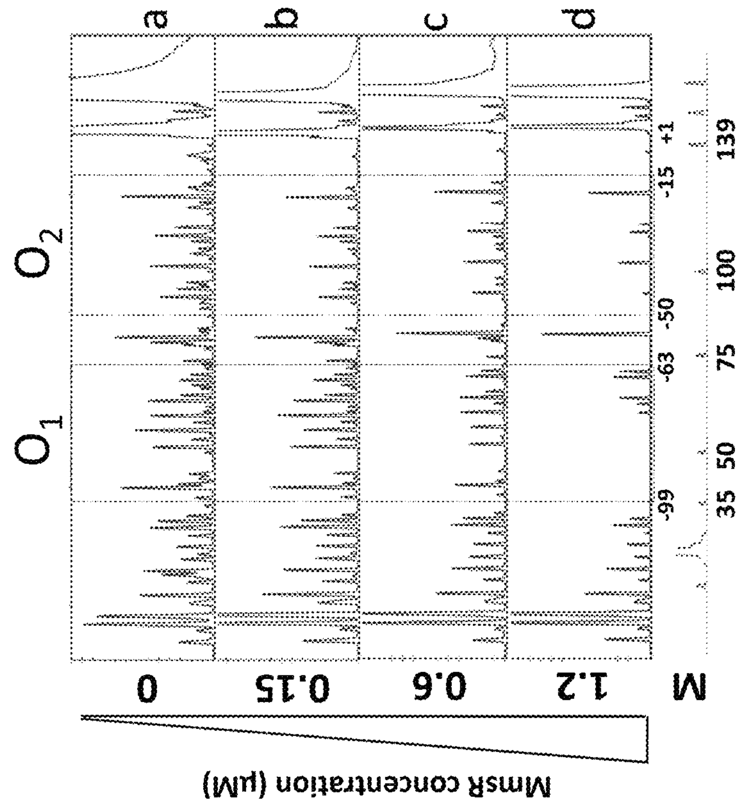
FIGS. 7A-B are pictures of in vitro electromobility shift assays (EMSA) to study binding of MmsR protein to operator site. DNA fragments containing mmsA promoter ($P_{mmsA}$) were intact ($F_{12}$), or mutated in either $O_2$ site ($F_{12M}$) or $O_1$ site ($F_{1M2}$). The experiments were conducted in the absence (upper panel) and presence (lower panel) of 3-HP (at 25 mM). Lane 1-10, increasing amounts of MmsR protein at 0, 0.36, 0.73, 1.45, 2.9, 5.8, 11.6, 14.5, and 24.2 nM; and the DNA fragments was fixed at 0.4 nM (FIG. 7A), Electropherograms from reactions with increasing amounts of MmsR (FIG. 7B). Operator regions protected from DNase I digestion by MmsR. At the bottom is a scale that gives nucleotide position relative to the MmsR transcription start site.
Figure 7A:
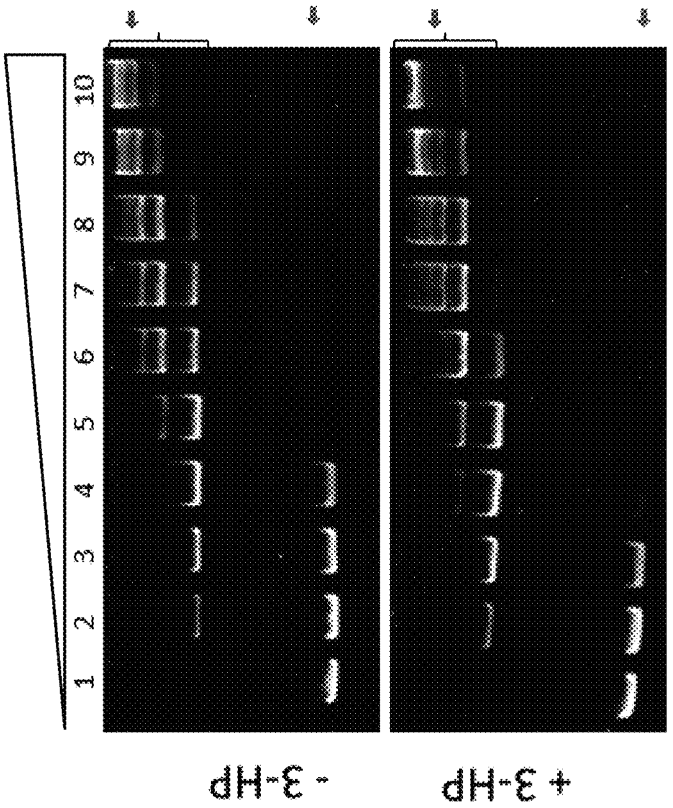

To analyze the MmsR binding regions in vitro, DNase I foot-printing analysis was performed by capillary electrophoresis (FIG. 7B). A longer 169 bp DNA fragment that includes the complete 130 bp intergenic region (used in the EMSA experiments described above), was used as probe (Table 2). The concentration of DNA was fixed at a specific concentration, while MmsR concentration varied at 0-1.2 μM. The foot-printing results clearly exhibit the presence of two protected regions by MmsR, which should correspond to operator $O_1$ (centered at position-81) and $O_2$ (centered at position-33), respectively. Protection became more evident as MmsR concentration increased. However, it was difficult to pinpoint the exact regions of protection at the base-pair level of the DNA sequence.

Figure 8:
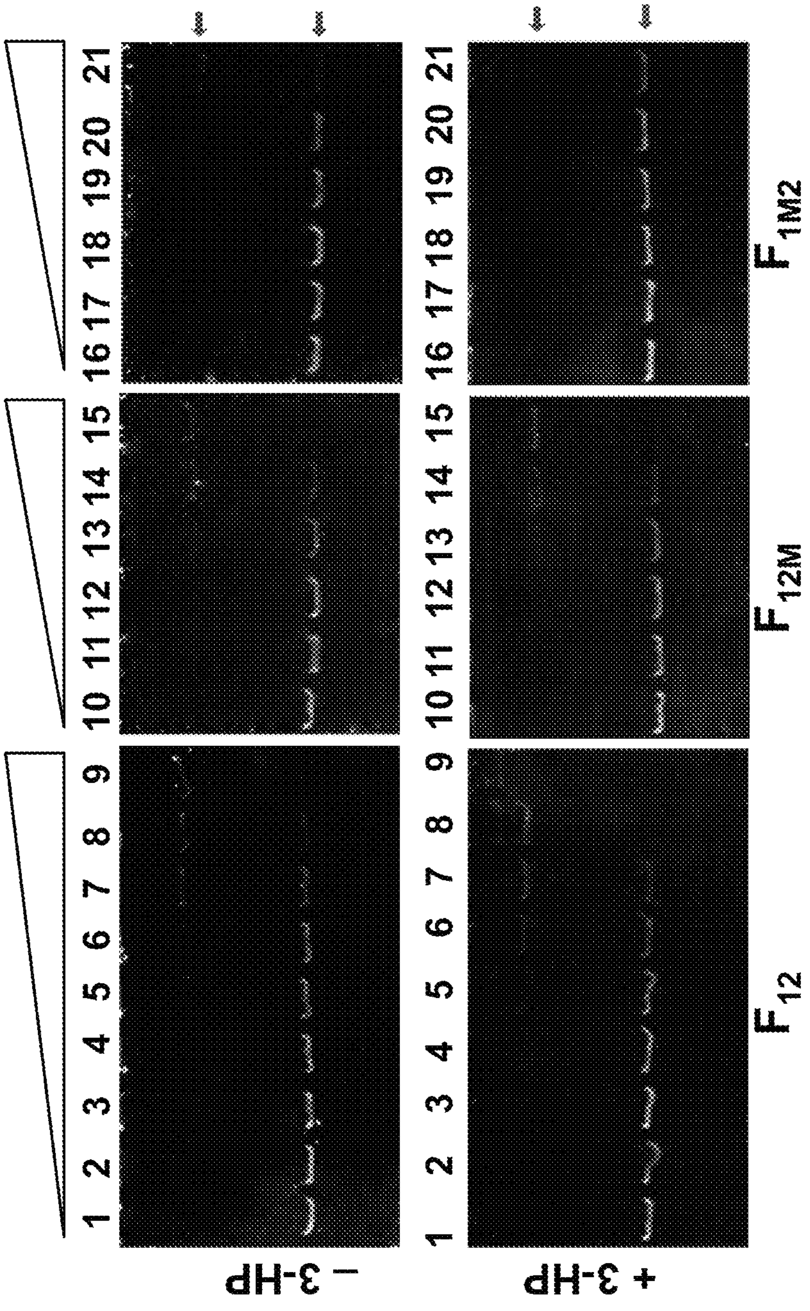
FIG. 8 is a picture of an electrophoretic mobility shift assay at low DNA concentration to estimate the dissociation constant between MmsR and the $P_{mmsA}$ promoter. ($F_{12}$) DNA fragment with both the operator O1 and O2 intact, ($F_{12M}$) with mutated O2 operator and ($F_{1M2}$) with mutated O1.
Figure 9:
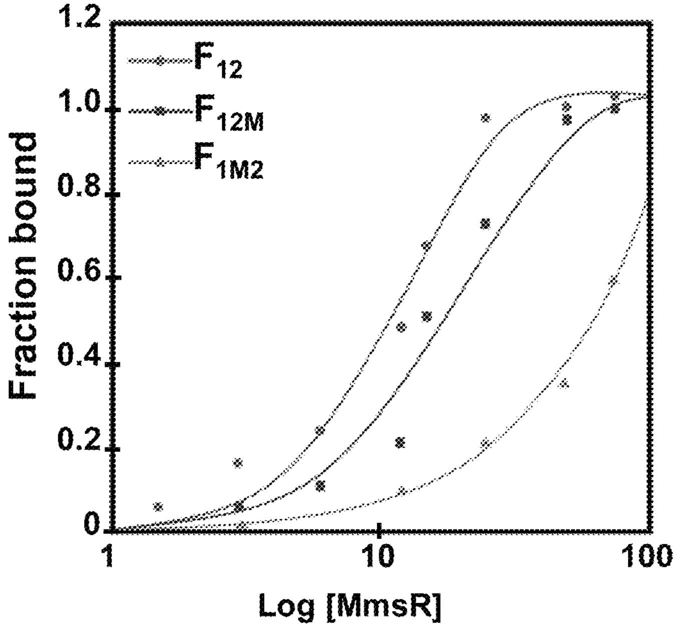
FIG. 9 is a graph and a table showing MmsR protein-DNA binding isotherm curves and dissociation constants for the binding. DNA fragments containing either intact promoter sequence ($F_{12}$) or mutated sequences were used.

The EMSA experiments were repeated at a low DNA concentration (0.4 nM) to estimate the dissociation constant, $K_D$, between MmsR and the $P_{mmsA}$ promoter (FIG. 8). Three DNA fragments, one containing both the $O_1$ and $O_2$ operator sites ($F_{12}$) and the other two having the same length as $F_{12}$ but mutated (randomized) in the palindromic regions of the $O_1$ ($F_{1M2}$) or $O_2$ ($F_{12M}$) operator site, were employed. Among the three DNA fragments, $F_{12}$ showed the highest affinity to MmsR, followed by $F_{12M}$ and then $F_{1M2}$. The dissociation constants for MmsR binding ($K_D$) to the three DNA fragments were determined from MmsR protein-DNA isotherm curves where the MmsR-bound DNA fraction was plotted against the free MmsR concentration in the reaction buffer (FIG. 9). The $K_D$ was 10.7 nM for $F_{12}$, 18.6 nM for $F_{12}$M, and 79.8 nM for $F_{1M2}$, when estimated for monomeric MmsR protein, in the absence of 3-HP (FIG. 9). 3-HP altered the binding affinity differently for the DNA fragments. In the presence of 3-HP, the $K_D$ values (for the monomeric MmsR concentration) were estimated to be 5.4 nM for $F_{12}$, 19.8 nM for $F_{12M}$, and 316 nM for $F_{1M2}$ (FIG. 9). The higher affinity of $F_{12}$ than $F_{12M}$ or $F_{1M2}$ suggested that there is some cooperativity in operator binding, such that MmsR binding to one operator (likely $O_1$) stimulates binding to the other operator (probably $O_2$). The presence of only one DNA-MmsR complex band for $F_{12}$ in the absence of 3-HP also supported the concept that there is cooperativity in binding between the two operators: if the binding of MmsR to $O_1$ does not stimulate the binding to $O_2$, two DNA-MmsR complex bands (one for $O_1$ binding and the other for $O_1$ and $O_2$ bindings) should have appeared.

Rhee et al. also studied the binding affinity of *E. coli* IlvY protein for DNA fragments containing either the tandem operators (0102) or the $O_1$ or $O_2$ operator alone. The binding affinity was highest for the fragment containing the tandem 0102 operator and lowest for the fragment having the $O_2$ operator alone, and the Kapp for monomeric IlvY was determined to be 4.4 nM for the tandem operator, 35.2 nM for $O_1$, and ~900 nM for $O_2$. However, Rhee et al. also reported that the inducer did not affect the binding of the IlvY protein to the operators. Here, in the presence of 3-HP, two retarded bands were distinguished at the highest protein concentrations. The change in properties of DNA binding protein in the presence of inducer could have an effect on the formation of complex. More probably, as explained in the above Examples, when concentrations of DNA and MmsR increased above certain levels, they can form multiple complex oligomeric structures having different mobilities.

Figure 10A:
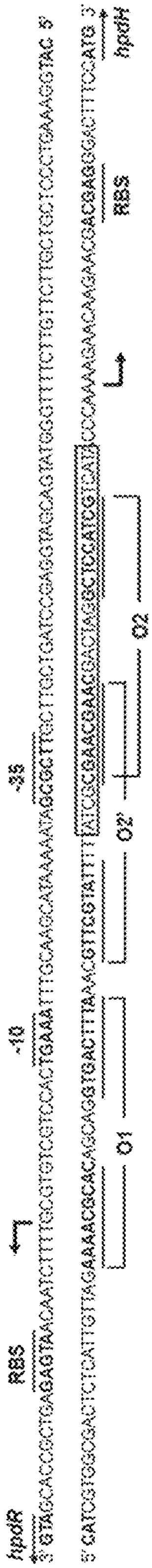
FIGS. 10A-B are a schematics of an analysis of hpdR-hpdH intergenic region.
Figure 10B:
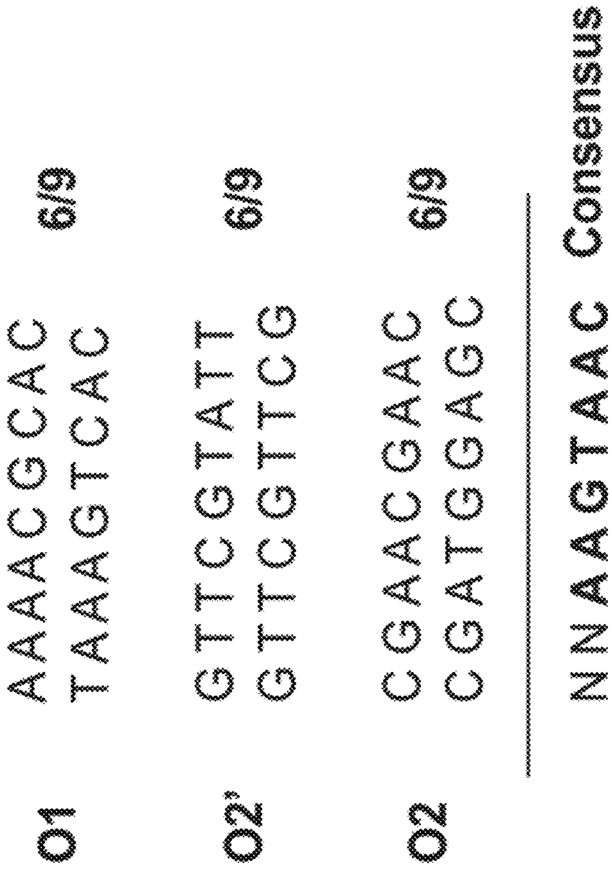

Example 5. Specificity of Small-Molecule Inducers for HpdR Transcriptional Activator Protein HpdR is a transcriptional activator protein, similar to MmsR, which can recognize 3-HP, or similar small acids, and stimulate the expression of specific genes in *P. denitrificans*. FIG. 10A shows the arrangement of genes and the intergenic region in the HpdR regulated operon in *P. denitrificans*. The hpdR and hpdH genes are conserved in all sequenced *Pseudomonas* genomes available in the *Pseudomonas* Genome Database, and the organization of this genomic region is the same. The hpdH gene encodes 3-hydroxypropionic acid dehydrogenase (EC no. 1.1.1.59), an enzyme involved in 3-HP catabolism. The hpdR gene encodes a LTTR protein, composed of 304 amino acid residues and divergently transcribed as compared to its structural gene, hpdH. Sequence analysis revealed that the intergenic region between hpdR and hpdH is 124 nucleotide bp long and contains two promoters for the expression of hpdR and hpdH, HpdR dimer binding sites (Regulator Binding Site and Activation Binding site, RBS and ABS respectively) and ribosome binding sites. The DNA binding site for HpdR was probably have three putative tandem operator sites, ABS-1, -2 and -3 and RBS-1 and -2, and only two T-N11-A motifs were located within this intergenic region, one at RBS-1 and the other overlaps with RBS-2 and ABS-1. The presence of T-N11-A motifs is one of typical features of the LTTR mediated expression system (see FIG. 10A). The three operators contained regions of dyad symmetry centered at position −52, −36 and −21, respectively, upstream relative to the hpdH transcription start site (TSS; predicted using NNPP tool). For the expression of the hpdR gene, the pseudo-palindromic repeats such as RBS-2 and ABS-2 masks the region between the transcription start site and −35 region, indicating that HpdR binding at these operator regions can completely eliminate binding of RNA polymerase and thus autorepress the transcription of its own gene, hpdR. On the other hand, the two 9-bp fragments in the RBS and ABS sites were 5, 7 and 6 nucleotides apart, respectively. The nucleotide sequences of the three inverted dyads were not completely symmetrical, as there were three mismatches in each subsite.

Example 6. Transcriptional Activation of hpdH by HpdR

Figure 11A:
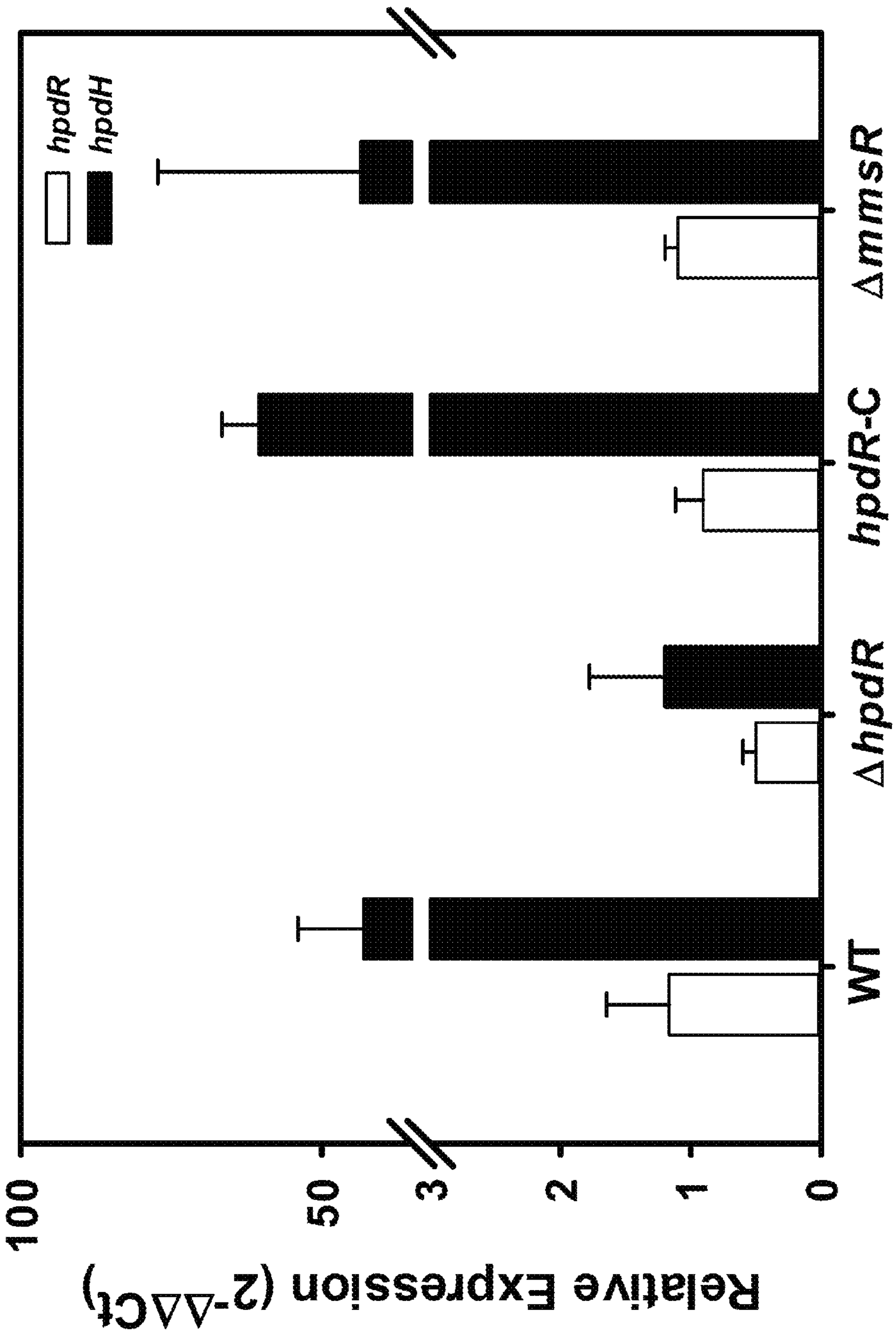
FIGS. 11A-B are graphs showing relative transcription of hpdR and hpdH (FIG. 11A) HpdR is the transcription factor that controls the expression of hpdH, (FIG. 11B) No cross talk between the two 3-HP inducible systems, HpdR and MmsR.
Figure 11B:
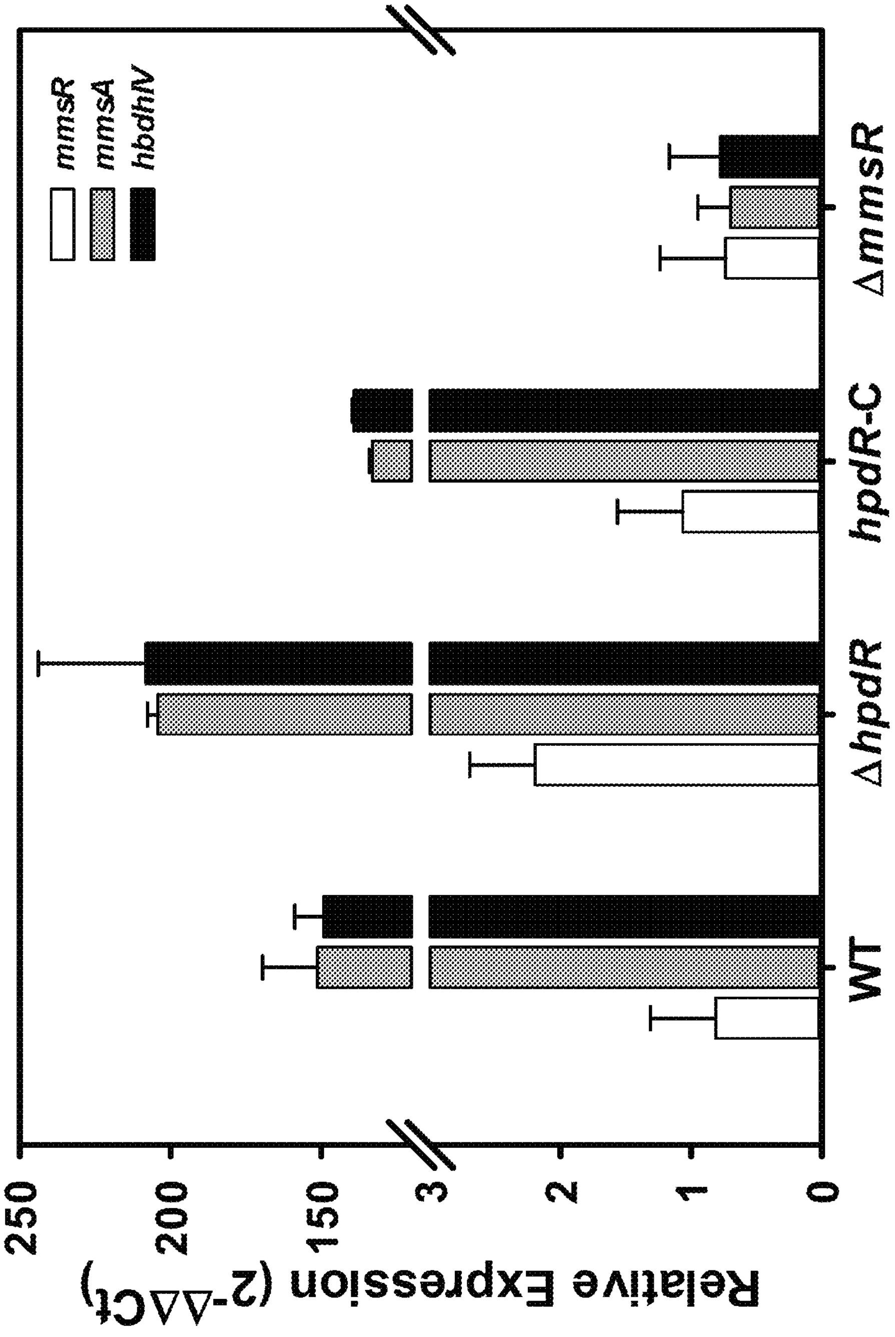

It has been suggested that HpdR is the transcriptional activator protein for the hpdH gene in *Pseudomonas denitrificans*. In order to test this in vivo, several *P. denitirificans* strains, including deletion mutant strains, i.e., PdAhpdR and PdΔmmsR, and a recombinant strain PdAhpdR harboring pUCPK'/Pc1-hpdR (for complementation study) were created and analyzed for hpdH transcription, along with a WT strain (ATCC13867). A PdΔmmsR strain having a deletion of the putative C4 transcriptional activator protein, was tested to see if there is cross-talk between the C3 and C4 transcriptional activator proteins, HpdR and MmsR. The mRNA expression levels were determined and compared in the presence and absence of 3-HP as inducer. The increase by 3-HP in hpdH expression from the *P. denitrificans* chromosome (WT) was 43.0±10.9 fold, while its transcriptional activator, HpdR, showed no change by 3-HP (FIG. 11A). In the C4 operon, the expression of mmsA and hpdH-IV was also activated by 3-HP by 151.3±18.2- and 149.3±9.6-folds, respectively, while that of mmsR was not at all (FIG. 11B). In *P. denitrificans* WT, the genes for regulatory proteins (i.e., hpdR and mmsR) were expressed at the low level, but the genes regulated by those proteins (hpdH, mmsA and hpdH-IV) were highly expressed in the presence of 3-HP. In particular, mmsA and hpdH-IV of the C4 operon showed high expression, indicating the existence of high-strength promoter(s). Once hpdR was deleted (ΔhpdR), the transcription of hpdH was not activated (1.20±0.58); when hpdR was complemented by a recombinant plasmid where HpdR was expressed (hpdR-C), its transcriptional activation was recovered to the wild type level (60.5±6.1). Thus, it could be concluded that hpdH, one of the catabolic genes in the C3 operon for 3-HP, is positively regulated by its transcriptional regulator HpdR when 3-HP is present as inducer. In order to study the crosstalk between the C3 and C4 operons, expression of C4 operon genes (mmsA and hbdH-IV) in the PdAhpdR, as well as hdpR-complemented recombinant *P. denitrificans* strains, was observed. Expression of mmsA and hbdH-IV was not affected by the presence and/or deletion of hpdR, indicating that the C3 transcriptional activator is specific to the C3 operon, and does regulate the C4 operon (FIG. 11B). Similarly, the C4 transcriptional activator (MmsR) did not affect the expression of C3 operon gene (data not shown). Taken together, these results indicate that, although HpdR and MmsR are activated by the same inducer molecule (3-HP), and belong to the same LTTR family, they are highly specific in their binding to operator sites and their subsequent transcriptional activation of the gene(s) under the control.

Example 7. Autoregulation of HpdR

LTTR regulatory proteins are known to autoregulate their own promoters by repressing transcription initiation in an inducer-independent manner. The regulatory binding site (operator) of HpdR upstream of hpdH has been implicated as a possible auto-regulatory site. To understand the autoregulation of HpdR in the C3 operon, we constructed several plasmids including (i) GFP expressed under the control of Phpar, with HpdR constitutively expressed using a PC1 or Pzwf promoter, and (ii) GFP constitutively expressed using $P_{eda}$ and $P_{fbp}$ promoters, respectively. The GFP fluorescence was expressed using the PhpaR promoter, where HpdR is expressed at two different levels with either the $P_{zwf}$ for PC1 (weaker than $P_{zwf}$) promoters. The autoregulation of GFP was monitored over 24-h culture period. When HpdR was expressed using Pzwf or PC1, the GFP reached a saturated level at 10 hr, and there was no more expression in spite of the constitutive expression of HpdR. However, the GFP fluorescence kept being expressed gradually when it was regulated by the constitutive promoters such as $P_{eda}$ and $P_{fbp}$. The expression level of GFP fluorescence was shown to be affected by its promoter strength, i.e., $P_{hpdR}$, $P_{eda}$, and $P_{fbp}$. This result was in accordance with the fact that LTTR protein autoregulates its own promoter (FIG. 12).

Example 8. Specificity of Inducers of HpdR in the C3 Operon

Figure 12A:
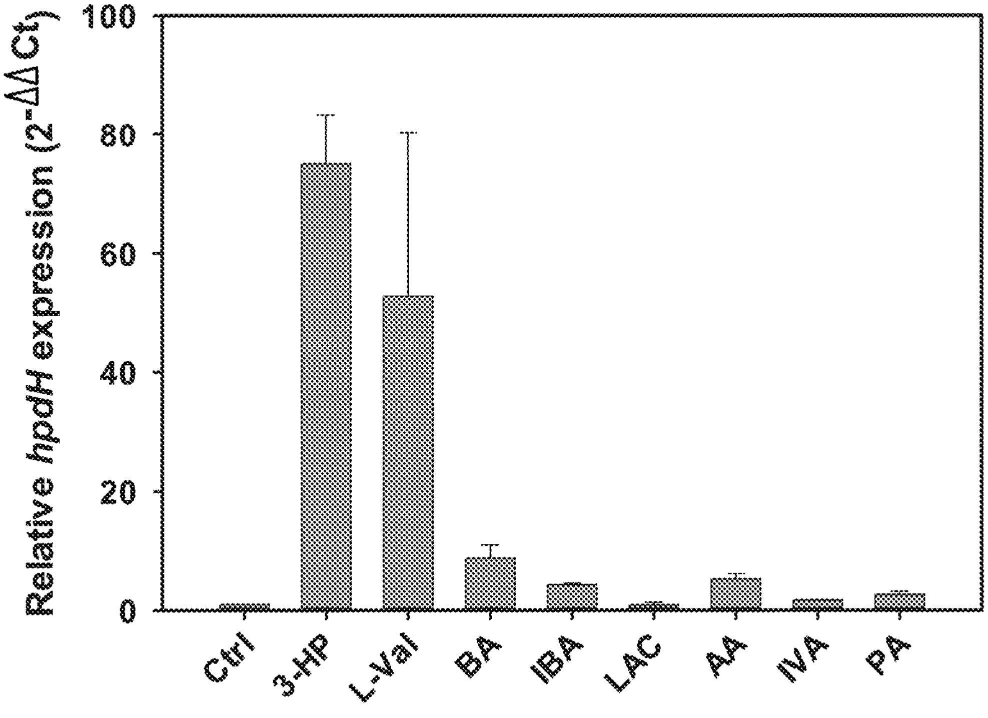
FIGS. 12A-D are graphs showing relative inducibility of hpdH transcription and GFP fluorescence in the presence of various acids.

Inducer specificity for HpdR was examined using several acids and aldehydes selected according to their similarity to 3-HP in carbon number (C3 or 4), molecular mass, and chemical structure, including 3-HP, L-val, BA, IBA, LAC, AA, IVA, and PA. Relative inducibility was examined based on the transcription of hpdH and gfp genes, as well as fluorescence from GFP. 3-HP was determined to be the best inducer for HpdR, based on transcription levels of HpdH and gfp, and GFP fluorescence. 3-HP increased the transcription of hpdH by 75±8.3-fold compared to a control (Ctrl) without the inducer. This was a statistically significant difference, as compared with the results from other chemicals (FIG. 12A). Transcription of hpdH also increased by 52.8±27.4-fold upon exposure to L-valine, making L-valine the second most potent inducer in these experiments. However, other acids and propionaldehyde were found to be less effective, or fail to induce the HpdR-mediated regulatory C3 gene expression system. These findings of 3-HP and L-valine inducibility using the C3 (hpdH and hpdR) regulon were similar to results described in the Examples above for the C4 regulon (mmsA and MmsR).

Figure 12B:
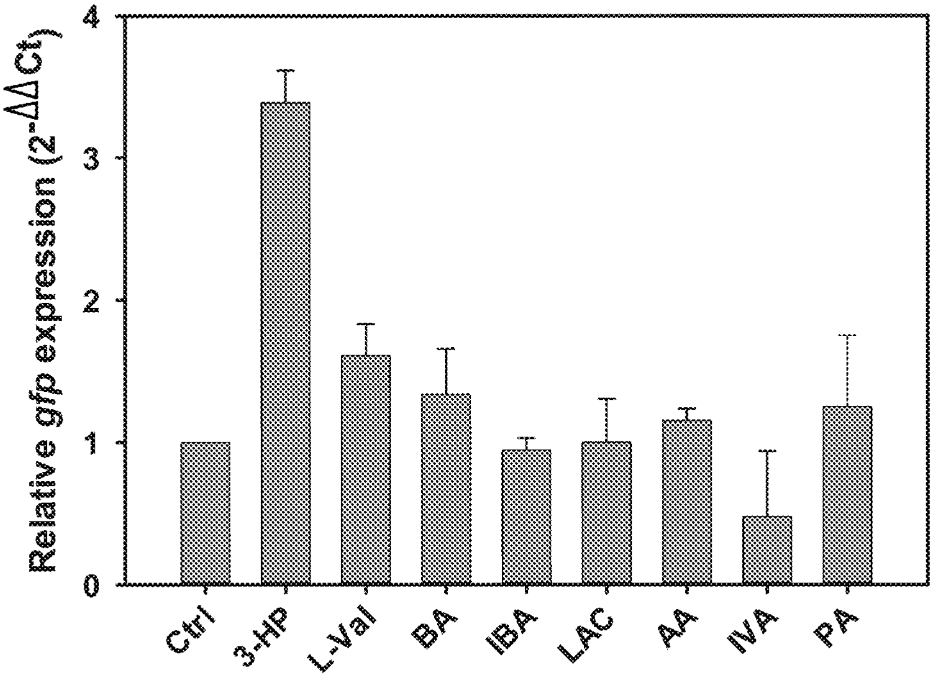
Figure 12C:
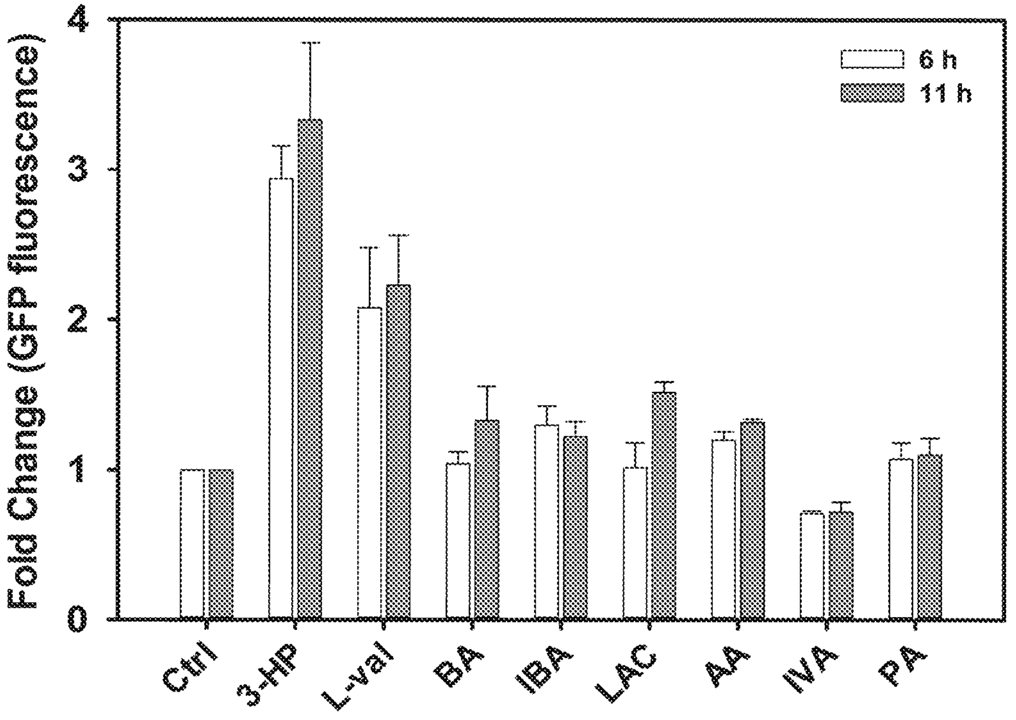

Structurally, 3-HP has both carboxyl and β-hydroxy groups that play an important role in binding ability of the ligand to HpdR. The L-valine was also tested because hpdH encoding 3-HP dehydrogenase is also involved in L-valine degradation and its metabolite can show the induction capability. L-valine, even though structurally different from 3-HP, can be easily converted to 3-hydroxyisobutryic acid (3-HIB), which can induce the Cm operon (manuscript in process), and induction by L-val is attributed to its conversion to 3-HIB. Together, the transcription of gfp as the reporter gene was examined. The hpdH gene was replaced with gfp in plasmid pUCPK'/Pzwf-hpdR-PC3-gfp, and gfp was heterogeneously expressed. The gfp-carrying reporter strain Pd ΔhpdR ΔhpdH was treated with several chemicals at 25 mM (pH 7.0~7.4), as described above, including including 3-HP, L-val, BA, IBA, LAC, AA, IVA, and PA. gfp mRNA expression was induced to the greatest extent with 3-HP, which led to a 3.4-fold increase in expression over control, This was statistically significant relevant to the control. The other chemicals that were tested did not induce mRNA expression (FIG. 12B). Similarly, GFP fluorescence was most induced by 3-HP (3- and 3.3-folds) at 6 and 11 hr post induction, respectively (FIG. 12C), which accorded with the gfp gene expression results which showed a 3-fold induction ratio. Thus, 3-HP is the best inducer for activating transcription of the target gene when complexed with HpdR in the C3 operon.

Figure 12D:
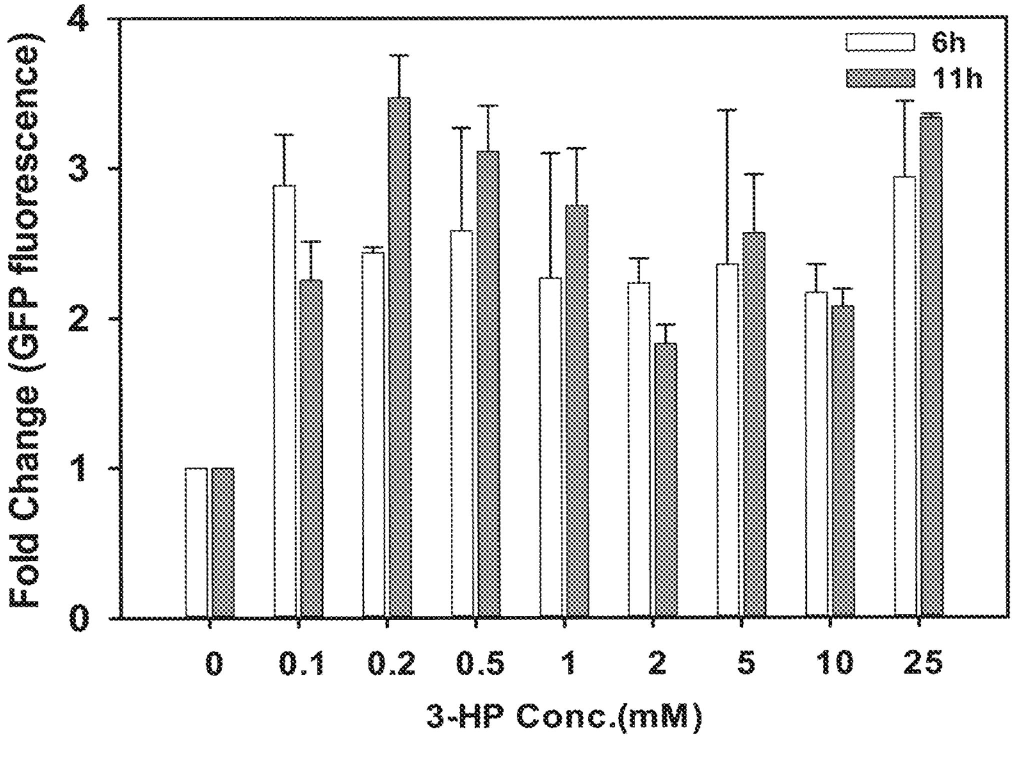

The dose effect of 3-HP on the inducible promoter system of hpdH was also studied by varying the concentrations of 3-HP ranged from 0.1 mM to 25 mM. The fold increases of GFP fluorescence in induction ratio was shown to be linear with 0~0.5 mM at 6 and 11 hr post induction. However, concentrations higher than 0.5 mM to 25 mM showed similar increases in the inducibility (FIG. 12D). The C3 operon in which the transcription of hdpH is regulated by HpdR in vivo and in vitro via 3-HP-mediated inducible process was characterized through examination of inducer specificity at the transcriptional and translational levels. The inducer specificity and the strength of the hpdH promoter system were studied. The resulting findings indicated that 3-HP showed the highest specificity when complexed with HpdR for induction of this gene expression system, and an overall 3-fold induction ratio of the hpdH promoter was observed in vivo for GFP expression.

Example 9. In Vivo Analysis of the HpdR Binding Site

In silico sequence analysis of the 5' region of $P_{hpdH}$ revealed the presence of five putative operators (RBS-1, RBS-2, ABS-1, ABS-2, and ABS-3). In order to elucidate the importance of these operators in the transcriptional activation of hpdH, studies were conducted, wherein the repeated sequence of each of the putative operators was mutated. Several recombinant plasmids, based on the pUCPK'/Pzwf-hpdR-PC3-gfp plasmid, where constructed such that one of the five operator repeats was replaced with a 9 bp random DNA sequence (ACAGGCGTA, generated by a Random DNA Sequence Generator tool, that does not show either conserved T-N11-A motif or sequence conservation with the actual subsites), and the inducibility of gene expression was then assessed by measuring GFP levels (reporter) (data not shown. Mutation of the either the RBS-1 or ABS-2 site strikingly decreased the 3-HP inducibility (data not shown. In comparison, the effect of the mutation on the ABS-1 or ABS-3 sites was less significant, and mutation of the RBS-2 site did affected the inducibility of the PC3 promoter only marginally. These results suggest that the RBS-1 and ABS-2 sites are key binding sites for HpdR to activate the transcription of hpdH (or gfp), while the other operator sites are less important for HpdR binding.

According to LTTR studies, a LysR protein dimer binds to two operator sites in a cooperative manner. In general, once RBS is first occupied, it helps ABS recruit the second LTTR dimer. If this is the case, the RBS site is more important than the ABS due to the functional role of the RBS in the efficient recruitment of the LTTR dimer for transcriptional activation of a target gene(s). Among the two repeats in one operator (i.e., RBS-1 and RBS-2), it is unclear which repeat is more essential in binding of LTTR protein. Both repeats accept helix-turn-helix motif of LysR protein and thus, both are equally important. However, considering the low promoter strength of PC3, the affinity of HpdR to the operator(s) can be weak and it can be attributed to the less contribution of RBS-2 in the recruitment of HpdR protein. This study showed no change in inducibility even though mutation of RBS-2 was examined, suggesting that the contribution of this repeat is not high enough. A more detailed study on the role of RBS-2 in aspects of LTTR binding could be implemented, by varying RBS-2 to have more consensus sequence for higher affinity to LysR. The less significant decrease in expression after mutation of the ABS site (both repeats of ABS) can be attributed to the fact that this ABS closely match the putative promoter site for hpdH and these mutations caused the alteration of hpdH promoter leading to the fluctuations of inducibility. The mutation on ABS-2 seemed to render the PC3 constitutive, resulting in no inducibility in HpdR-mediated activation of transcription in the presence of 3-HP. Taken together, mutations of each of the operators, except for RBS-2, caused the loss of inducibility in the case of HpdR complexed with 3-HP, and this alteration led to a functional modification of the promoter from being inducible to having constitutive characteristics. This change ingene expression resulting from operator mutations can be attributed to several hypothesized reasons: (i) weakened affinity of HpdR for the DNA binding site for activation of hpdH (or gfp) transcription; (ii) the inappropriate of a conformational change in the HpdR protein-operator DNA complex in terms of DNA bending leading to low transcription of target gene; (iii) significant change in hpdH promoter strength, causing decreased expression. Therefore, operator mutations can lead to the alteration of intrinsic promoter characteristics.

Figure 15A:
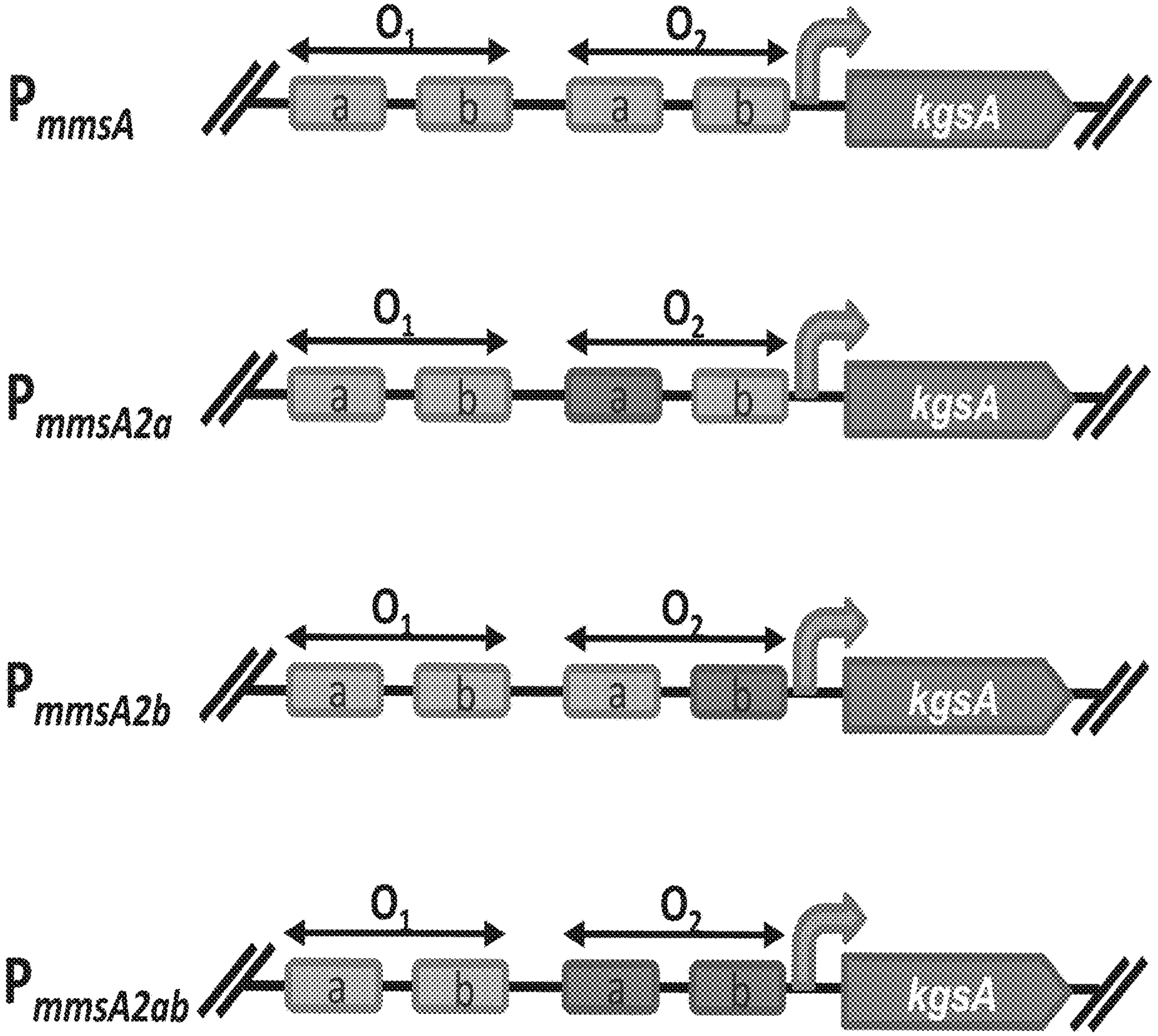
FIGS. 15A-C is a set of schematics showing how MmsR operator site randomization was applied for KgsA overexpression.
Figure 15B:
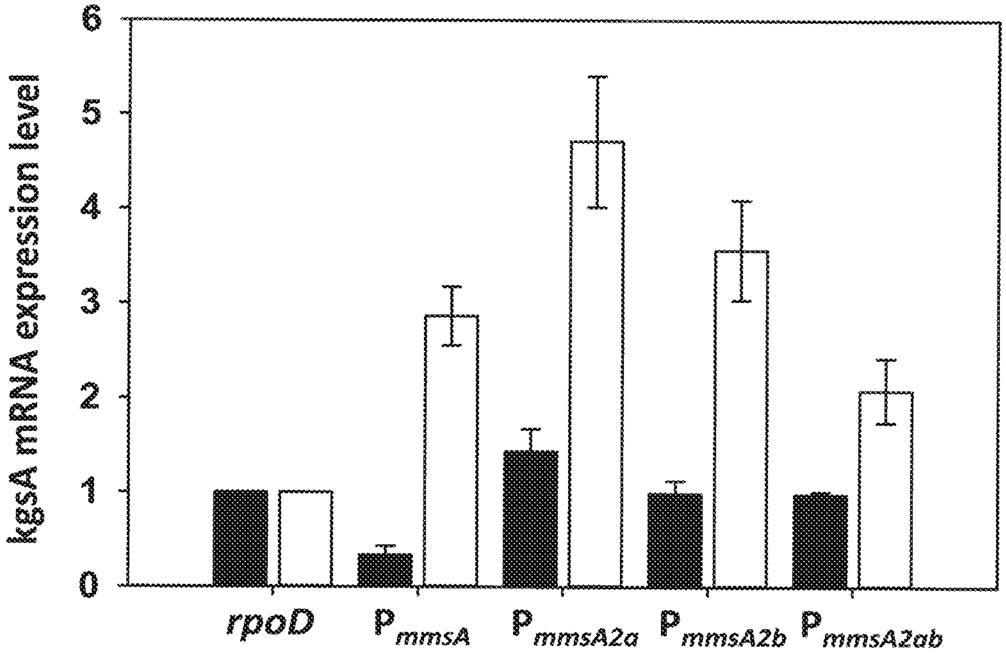

Example 10. Binding Site Randomization and Modification of Activator Expression Level Gene expression can be modified at the transcriptional and/or translational level. Initially, we modified the operator sites ($O_1$ and $O_2$) to try to improve transcription from the $P_{mmsA}$ promoter. The operator sites present in the intergenic region of mmsR-mmsA, to which the activator protein MmsR binds, play an important role in determining the affinity of promoter region to RNA polymerase. The kgsA gene was cloned downstream of the intergenic region of mmsR-mmsA in the multi-copy pUCPK plasmid, and two different portions of the $O_2$ operator sequence, each making up a half-site of the operator, were randomized independently ($P_{mmsA2a}$ and $P_{mmsA2b}$) or in combination ($P_{mmsA2ab}$) (FIG. 15A). Transcriptional activator MmsR was expressed from the bacterial chromosome under the native promoter ($P_{mmsR}$). The intact intergenic sequence, without mutation, was used as the control. The mutation in $O_{2a}$ or $O_{2b}$ significantly increased the transcription level, 7.3-10.6 folds without 3-HP and 1.3-1.7 folds with 3-HP. Mutation in the first half of the O2 region ($O_{2a}$) more significantly improved transcription efficiency than mutation in the second half ($O_{2b}$). When both half-sites of the $O_2$ operator were randomized, the basal level of transcription (without 3-HP) was comparable to the basal transcription level resulting from mutation of either $O_{2a}$ or $O_{2b}$ (FIG. 15B). However, the maximal transcription level in the presence of 3-HP decreased and the level was even lower than that of wild type promoter. The $O_2$ region completely overlaps the −35 region, where σ-factor of RNA polymerase binds. It is possible that the changes in the sequence surrounding the −35 region could directly affect the affinity/function of MmsR to the $P_{mmsA}$ promoter in term of up-regulation when responding to 3-HP. In this case, the decreased binding interaction by randomizing the half of $O_2$ region greatly increased the transcriptional level in inducible manner.

Figure 15C:
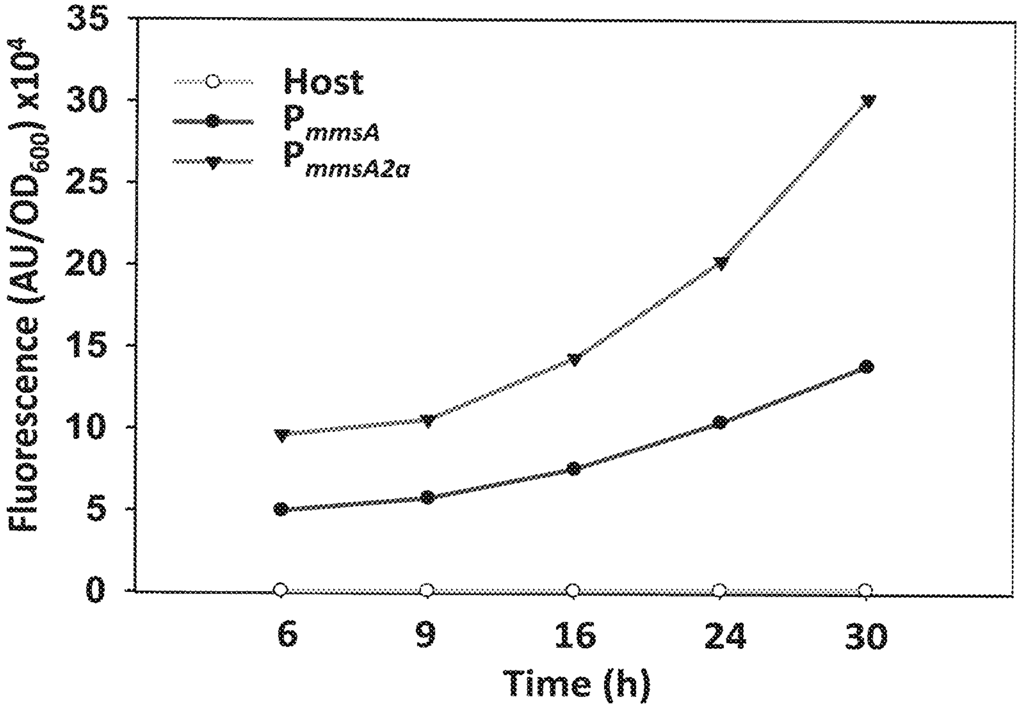

By using GFP as a reporter, the strengths of wild-type and mutant promoters were clearly compared (FIG. 15C). The result showed that a promoter having mutations in the first half of the O2 region ($P_{mmsA2a}$) performed ~2-fold higher in expressing GFP during an induction period with 25 mM 3-HP. This result was consistent with the transcription levels results shown in FIG. 15B. This study indicated that transcriptional levels can be modified by altering the operator binding sites region. We could increase both basal level expression of the promoter (greatly), and the induced level of expression of the promoter (by ~2 fold).

Figure 16B:
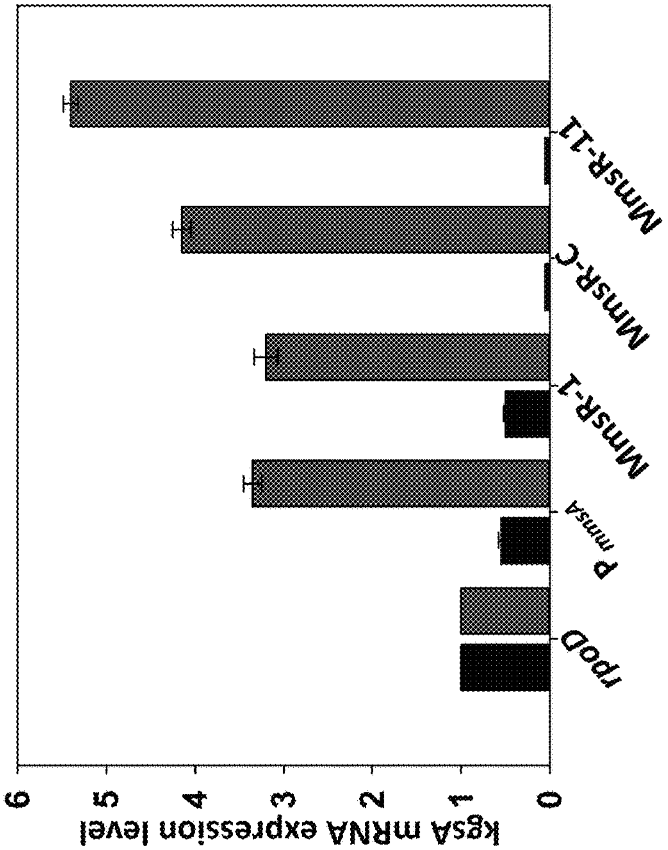
FIGS. 16A-B is a set of graphs showing the influence of MmsR overexpression on KgsA transcription with various constitutive synthetic promoters (FIG. 16A) Pzwf promoter library, (FIG. 16B) KgsA transcription.

In bacteria, the LysR-type transcriptional regulator (LTTR) protein effectively upregulates downstream genes by interacting with RNA polymerase. As a consequence, the amount of LTTR protein influences the transcriptional levels of target genes. To study the effect of MmsR expression on $P_{mmsA}$ promoter strength, we developed a library of constitutive $P_{zwf}$ promoters (FIG. 16A), and expressed MmsR under selected promoters from the $P_{zwf}$ library (FIG. 16B). In constructing this synthetic promoter library, the −35 and −10 consensus sequences of the Perf promoter were kept constant, and the space surrounding these sequences was randomized and the length was varied.

Figure 16A:
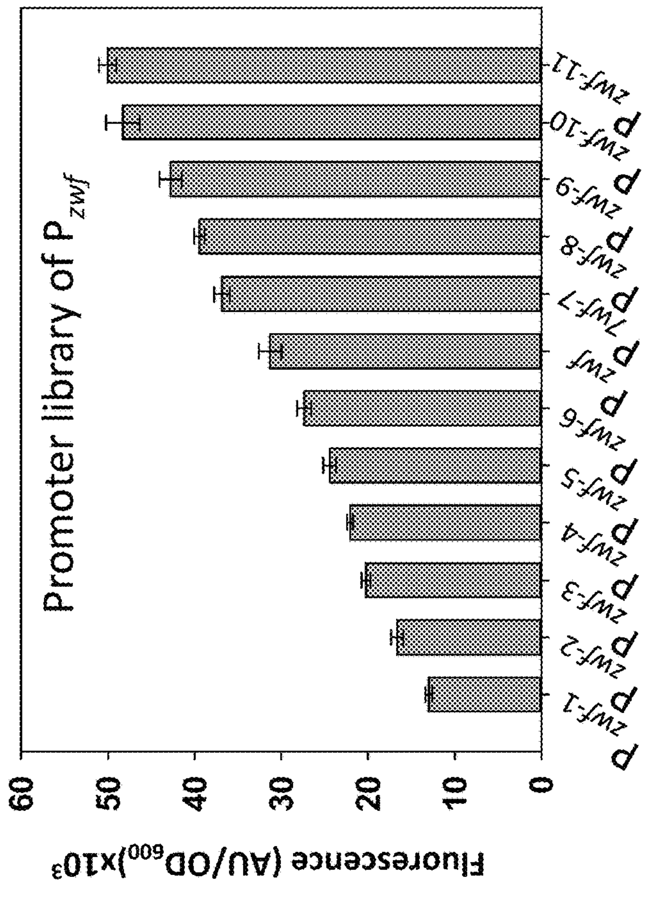

Several synthetic promoters in the library were evaluated, and these showed a distribution of promoter strengths as depicted in FIG. 16A. As a positive control, the constitutive promoter $P_{zwf}$ ($P_{zwf\text{-}7}$) was used. After the background signal was normalized, the library promoters generated GFP florescence levels that ranged from 11,500 ($P_{zwf\text{-}1}$) to 51,000 ($P_{zwf\text{-}12}$) relative florescence units ($AU/OD_{600}$). Thus, levels of promoter expression ranged by approximately 5 orders of magnitude with reference to wild type $P_{zwf\text{-}7}$ (32,200). Three promoters from this library were chosen: $P_{zwf\text{-}1}$ and $P_{zwf\text{-}11}$, corresponding to 0.4, 1, and 1.7-fold differences compared to the wild-type $P_{zwf}$, respectively. Transcriptional activator MmsR placed under the control of each of these derivative $P_{zwf}$ promoters was produced at varied levels, and transcription of the gene (kgsA) downstream of the $P_{mmsA}$ promoter was affected. The strain ($P_{mmsA}$) chromosomally expressing MmsR under native promoter, $P_{mmsR}$, was used as control. At low MmsR levels (MmsR-1 strain), when MmsR was under the control of the $P_{zwf\text{-}1}$ promoter, the mRNA expression of kgsA was comparable to that of control, whether 3-HP was absent or present. When the amount of MmsR was increased by placing it under the control of either of the two stronger $P_{zwf\text{-}1}$ and $P_{zwf\text{-}11}$ promoters (the MmsR−1 and MmsR-11 strains, respectively), the transcription of kgsA was improved in the presence of 3-HP. However, the basal expression level of kgsA was significantly reduced when 3-HP was absent. This result was understandable because of the repression regulation of apo-MmsR, as described previously. For inducibility, a higher MmsR expression level could greatly increase the difference between non-induced and induced situations by minimizing the basal level. This indicated that enhancing activator is a good strategy for hampering the leakage of target gene before inducing that commonly occurred in cases of strong inducible promoter.

Example 11. Comparison of Expression of Native mmsA Vs. Heterologous kgsA Gene Under the $P_{mmsA}$ Promoter

*P. denitrificans* can actively degrade 3-HP produced from glycerol. The enzymes 3-hydroxyisobutyrate dehydrogenase IV (HbdH-4) and methylmalonatesemialdehyde dehydrogenase (MmsA) encoded by hbdH-4 and mmsA, respectively, were partially responsible for the degradation of 3-HP (The mmsA promoter ($P_{mmsA}$) was highly induced (>140-fold) by 3-HP with the help of the activator protein, MmsR (This promoter was employed to develop a 3-HP sensor that can sensitively detect 3-HP at about 25 mM, when added externally.

Although $P_{mmsA}$ was highly inducible by 3-HP, the expression levels of heterologous genes, such as gfp or kgsA, put under the control of $P_{mmsA}$ was much lower than that of mmsA, which is inherently controlled by $P_{mmsA}$ in *P. denitrificans*. Before engineering of $P_{mmsA}$, the expression of a homologous (mmsA) and heterologous (kgsA) genes cloned under $P_{mmsA}$ was quantitatively compared by RT-PCR. Transcription of the heterologous gene kgsA was significantly lower than that of the native gene (mmsA), ~100-fold when expressed chromosomally and ~40-fold when expressed episomally using the multi-copy (~20 copies) pUCPK' plasmid. Crude-cell KgsA activities clearly showed the effects of 3-HP induction and gene dosage. When expressed from chromosome (Int-1), the activity was 0.08 U/mg protein without 3-HP and 0.15 U/mg protein with 3-HP, respectively. When expressed from the multi-copy plasmid, the activity was 1.02 U/mg protein without 3-HP and 3.15 U/mg protein with 3-HP, respectively. We notice that the KgsA activities, determined either with or without 3-HP, faithfully reflect the gene dosage effect and were almost proportional to the gene copy number. When KgsA was expressed from the multi-copy plasmid along with glycerol dehydratease (DhaB), and its crude-cell activity was 2.5 U/mg protein, good 3-HP production resulted. This suggests that when kgsA is integrated into the chromosome, the $P_{mmsA}$ promoter should be engineered to express the gene by ~20 fold higher. Fortunately, under the control of the $P_{mmsA}$ promoter, the homologous mmsA gene could be transcribed by ~100 fold higher than that of kgsA. The expression of kgsA can be improved by increasing the efficiency of its transcription and/or translation by altering the properties of the mmsA regulatory structure, even when the kgsA gene copy number is very low, such as 1 or 2 copies.

Example 12. Development of Tandem Promoter System

Attempts at optimizing gene expression levels in bacterial hosts have used rational and combinatorial approaches in altering transcription and translation levels. When a strong promoter and/or ribosome binding site (RBS) is used, gene expression increases. Synthetic promoter libraries providing a range of expression levels have been developed. In bacteria like *E. coli* and *B. subtilis*, vegetative and stationary phase promoters have also been identified, which have better response to one sigma factor of RNA polymerase than the other. Though the aforementioned regulatory modules can help express genes with better control at wide range of levels, they cannot express genes at levels under dynamic growth conditions. To address this problem, we developed new gene expression regulation modules by creating tandem promoters that incorporate the 3-HP inducible promoter expression module described previously in the Examples above. In nature, microorganisms use tandem promoters to maintain the concentration of certain molecules, and to regulate proteins during dynamic cell growth under different physiological conditions. We combined 3-HP or small acid inducible promoters, with range of constitutive or inducible promoters. The promoters were either natural or synthetic. Here, we developed a library of 3-HP inducible promoters fused with another promoter, which is either native/synthetic, and/or can activate genes in exponential/stationary growth phase. In some cases, the tandem promoter system had at least one inducible promoter and at least one constitutive promoter.

Figure 13A:
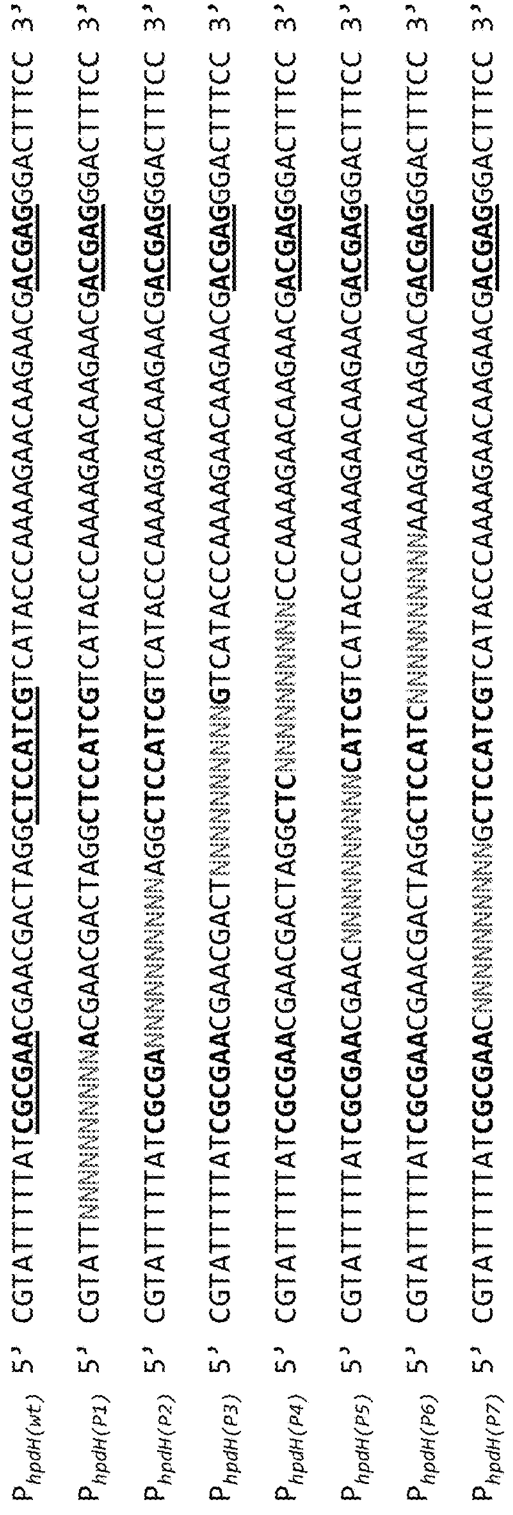
FIGS. 13A-B is a schematic showing locations of mutational randomization of the PC3 3-HP inducible promoter and a graph showing normalized GFP levels of the various promoters.
Figure 13B:
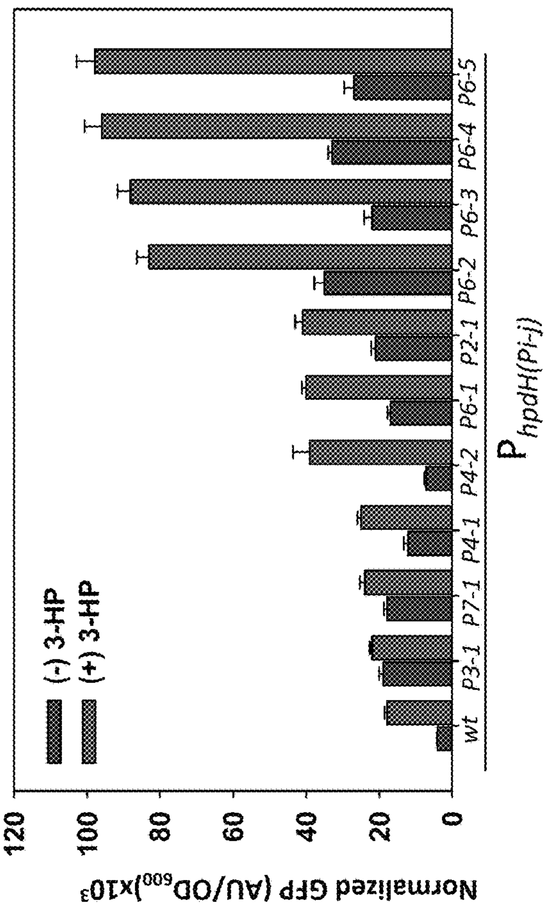
Figure 14A:
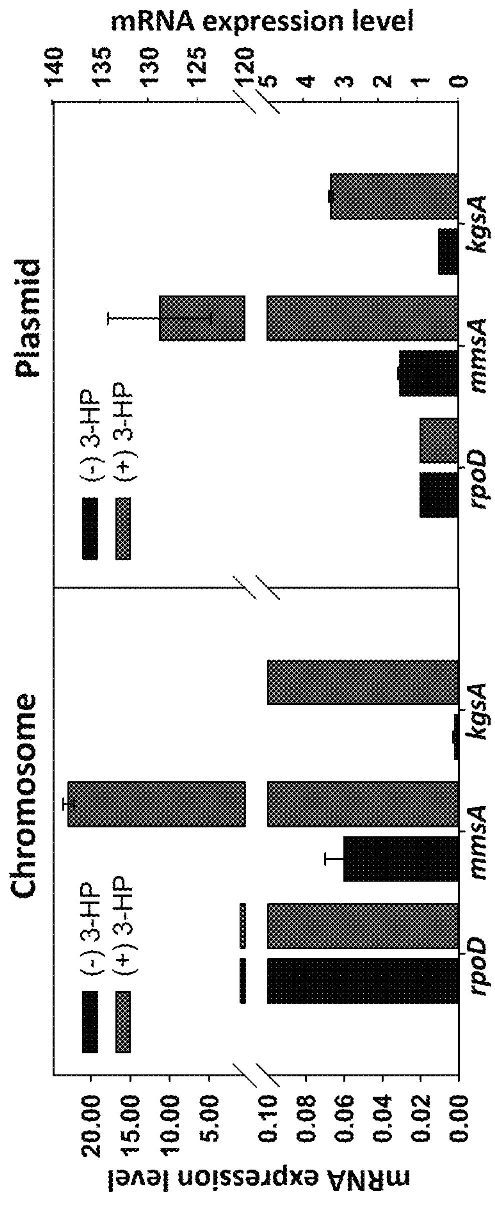
FIGS. 14A-B is a set of graphs showing a comparison of mmsA and kgsA transcription and enzyme activity at plasmid and genome level.
Figure 14B:
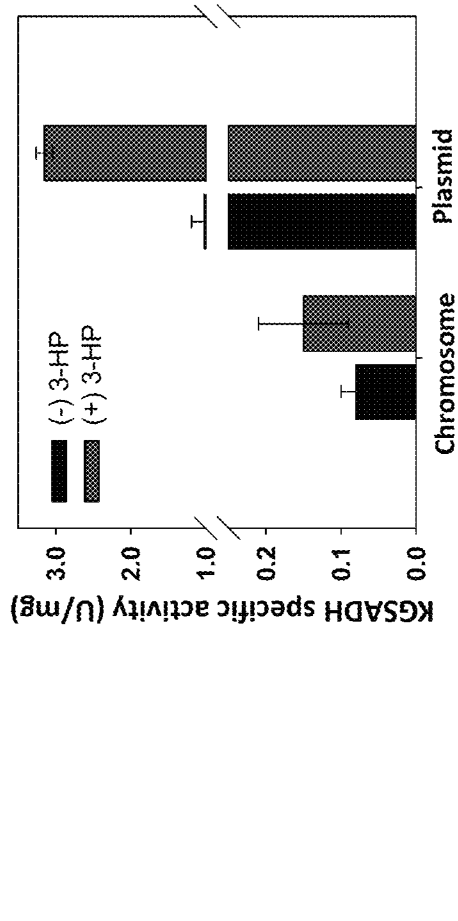

The small acid inducible promoters are activated by 3-HP once they are bound by an activator protein (similar to LysR). After characterizing the activator proteins that regulate 3-HP (or similar small acid) inducible promoter systems, it was determined that these promoters are not practical for use in recombinant protein expression by themselves because they express target proteins at low strength. Therefore, a library of small acid inducible promoters exhibiting a range of expression strengths was developed by creating random promoter mutations. The strength of each mutated promoter was analyzed by cloning mutant promoters upstream of a reporter gene (green florescence protein (GFP)). An in vivo analysis was performed by taking florescence measurements of strains carrying 3-HP inducible derived mutant plasmids. Briefly, four blocks of sequence, 10 bp in length, were randomized starting from the −51 position (start of the first repeat) up to −9 region from the predicted TSS. Although, mutation of the first 30 bp, i.e from −51 to −21, did not lead to any differences in florescence, mutation between −21 to −12 enhanced florescence levels significantly (up to ~6-fold). Therefore, mutational randomization near the −10 region significantly enhanced the promoter strength (FIG. 13). This result along with in silico predictions strongly supports our predicted locations for the promoter elements of 3-HP inducible promoters.

An auto-inducible promoter system, as described herein, is valuable for enzyme expression and regulation in biochemical and biofuel producing strains because a metabolic pathway can be enhanced by intermediates or final products of the pathway, without it being necessary to add any extra inducers. However, the types of auto-inducible promoters are quite limited in cells, and these promoters usually produce weak expression levels. Modification of an inducible system (e.g., by modifying promoter elements or operator regions) can be conducted to achieve better performance, but must be carefully conducted to so as to maintain the inducible properties of the promoter. We sought to increase the strength of transcription by an inducible promoter while maintaining the inducible properties of the promoter by employing an expression cassette that includes tandem promoters.

We designed a tandem promoter expression cassette that combines an inducible promoter and a constitutive promoter.

A tandem promoter expression cassette containing the $P_{mmsA}$ and $P_{hbdH\text{-}4}$ promoters controlling the kgsA gene was cloned into the pUCPK' plasmid, while the MmsR activator was produced from its native promoter in the chromosome. FIG. 17A schematically depicts the tandem promoter expression cassette, and the two mRNA transcripts produced by the promoters. By combining two promoters in tandem, two kinds of mRNA transcripts, one from the PmmsA promoter and the other from the PhbdH-4 promoter, were transcribed as shown in FIG. 17A, thereby increasing the number of kgsA mRNA transcripts. FIG. 17B shows that the tandem promoter system increased the mRNA expression level of kgsA by 1.75 fold compared to the native $P_{mmsA}$ promoter alone. FIG. 17C shows that use of the tandem promoter system led to an increase in KgsA enzyme activity of 3 fold relative to the enzyme activity resulting from use of the native $P_{mmsA}$ promoter alone.

When considering the translation efficiency of each of the promoters in the tandem construct, we found that one unit of transcript from the $P_{hbdH\text{-}4}$ promoter produced two units of protein/activity (the ratio was 1:2); whereas one unit of transcript form the $P_{mmsA}$ promoter produced one unit of protein/activity (the ratio was 1:1) (see FIG. 17). This result indicated that the 5' untranslated region (5' UTR) of the $P_{hbdH\text{-}4}$ promoter could result in higher translation levels compared to the 5' UTR region of the $P_{mmsA}$ promoter. Each transcript produced by the tandem promoter expression cassette inherited the UTR region of $P_{hbdH\text{-}4}$, which can significantly increase translation, leading to higher activity of KgsA compared to that of each promoter ($P_{mmsA}$ or $P_{hbdH\text{-}4}$) alone. Thus, relative to either single promoter alone, the inducibility of the $P_{hbdH\text{-}4}$ promoter was maintained (if slightly reduced) due to the contribution of the $P_{mmsA}$ promoter, the basal expression level without inducer was increased because of the constitutive promoter, which is useful for the expression of pathway enzymes at early time points.

FIG. 55A illustrates four different expression constructs that were constructed with tandem promoters that included at least one 3-HP inducible promoter. These combined phpdH with either Pc1 or Pzwf promoters. FIG. 55B shows that the tandem promoters had different strengths based on DhaB activity.

Example 13. UTR Engineering

The 5'-untranslated region (5'-UTR) and 5'-proximal coding sequence play an important role in controlling the translation initiation rate and mRNA stability, based on the accessibility of the ribosome to these elements. We created a library of mutations in the 5' UTR and 5'proximal coding sequence of the PmAdH-4 tandem promoter expression cassette in order to increase the translation of transcripts produced by genes put under the control of this system. Several factors made mutagenesis of these regions challenging, including the overall length of these regions and the case in which translation efficiency can be lost. RBS engineering is an easy-to-manipulate method for randomizing an RBS to modulate the affinity of a ribosome for its binding site. However, only 6-9 nucleotides in RBS were modified by this method, and the other important components (5'-UTR or 5'-coding sequence) for translation should be considered.

UTR Designer, an insilico tool, has been developed for the precise prediction of translation initiation levels. This tool considers the folding structure of the 5' untranslated region (5 'UTR) of mRNA (35 bp), the 5'-proximal coding sequence of the structural gene (25 bp) and the affinity between ribosome and the Shine-Dargarno region, to understand the translational controls of a target gene, so that modifications can be designed to alter translation levels. We used this tool to evaluate combinations of features for improving the transcription and translation of the $P_{hbdH\text{-}4}$ tandem promoter expression cassette, including the construct we generated having Opt-3 and Hyb-20 with the chromosomal expression of MmsR (which we refer to as UTR-0). As shown in FIG. 19C, the UTR Designer tool predicted a 12-fold increase which was higher than the 1.5 to 2 fold improvement we observed when this system was fully expressed under normal conditions (200 rpm, 37° C., 25 mM 3-HP) (data not shown). To clarify the effect of UTR modifications on translation initiation the expression levels of associated gene (in this case KgsA) was measured. The expression levels of proteins were measured on SDS-PAGE gel, we intentionally avoided addition of inducer to keep the expression at low levels so that the difference between various UTRs could be easily distinguished. This experiment considers only translation initiation effect. Therefore, the basal expression without inducer should give us better and sufficient evidence for evaluation; also, the growth condition was restricted by using low rate of shaker (150 rpm) to minimize the protein expression limitation.

As shown in FIGS. 19 A-C, UTR engineering successfully increased the levels of target protein. FIG. 19A shows that a wide range of translation levels were achieved in the library of mutations made to the 5' UTR and 5'proximal coding sequence of the $P_{hbdH\text{-}4}$ tandem promoter expression cassette, and observed when bacteria were grown under normal induced conditions (200 rpm, 37° C., 25 mM 3-HP). We found that the efficacy could be enhanced significantly (~30-fold), compared to the native $P_{mmsA}$ promoter.

Figure 18A:
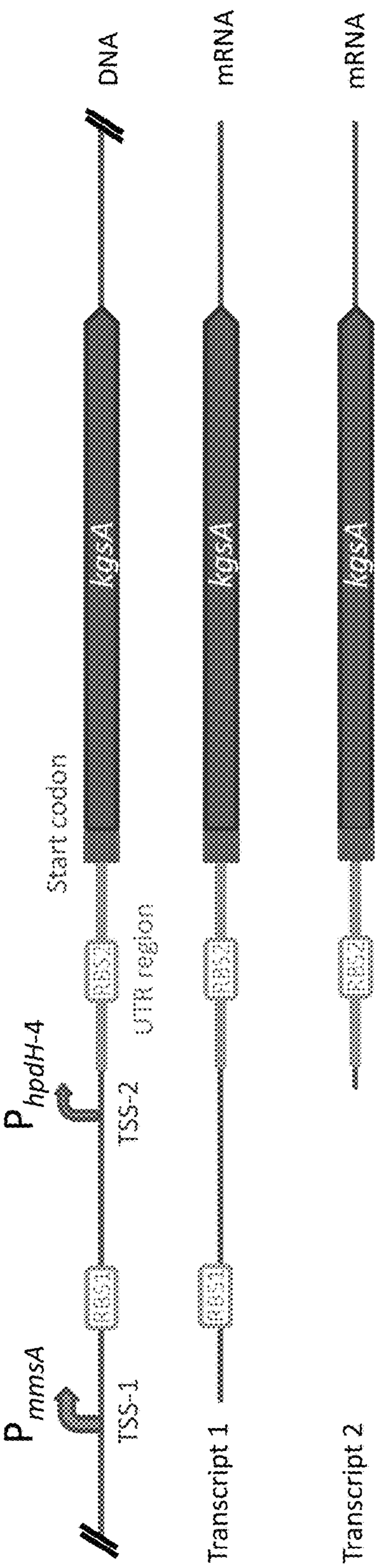
FIGS. 18A-C is a set of a schematic and graphs showing the effect of tandem promoters on expression of kgsA at mRNA and enzyme activities.
Figure 18B:
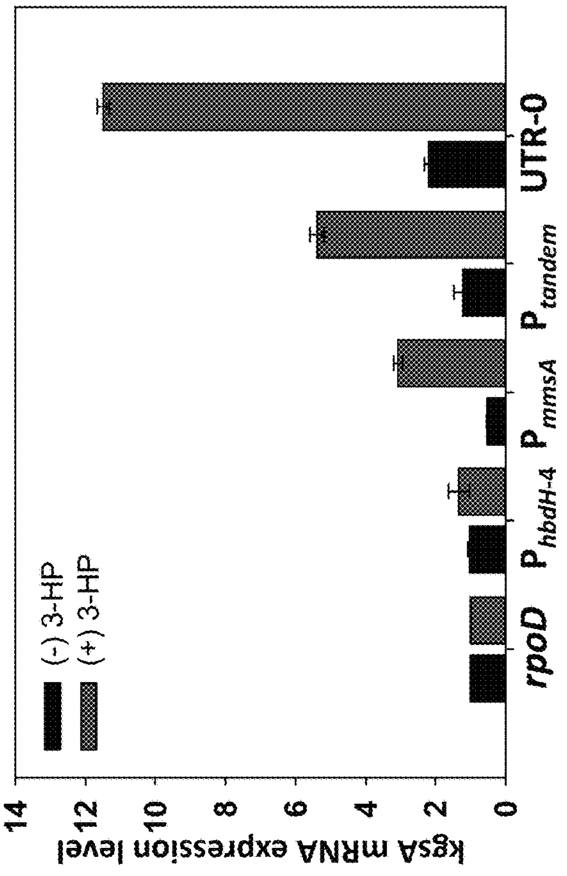
Figure 18C:
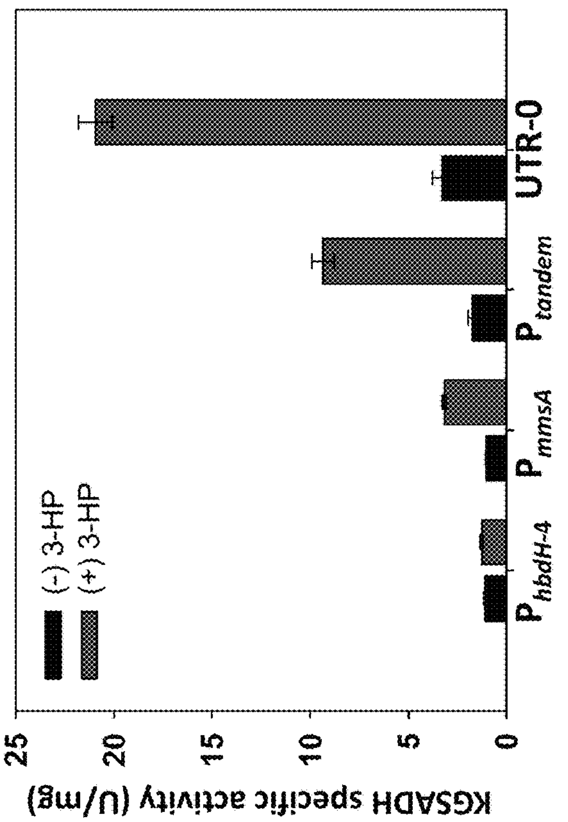
Figure 20A:
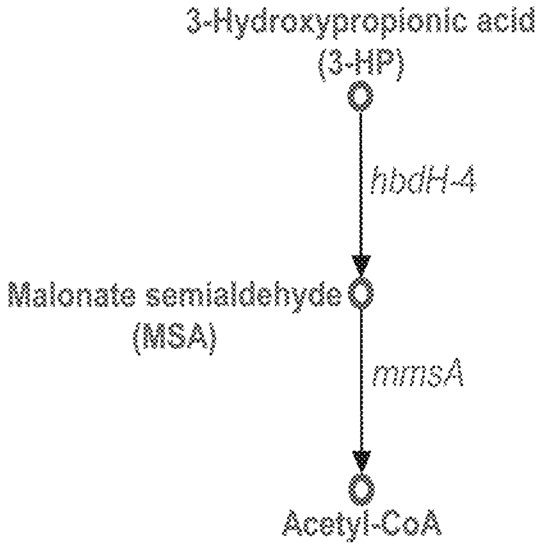
FIGS. 20A-B are schematics of the degradation of 3-HP into malonate semialdehyde by hbdH-4 and further to acetyl-CoA by mmsA (FIG. 20A) and a schematic of the genetic structure of the mmsR-mmsA intergenic region and its regulation (FIG. 20B).
Figure 20B:
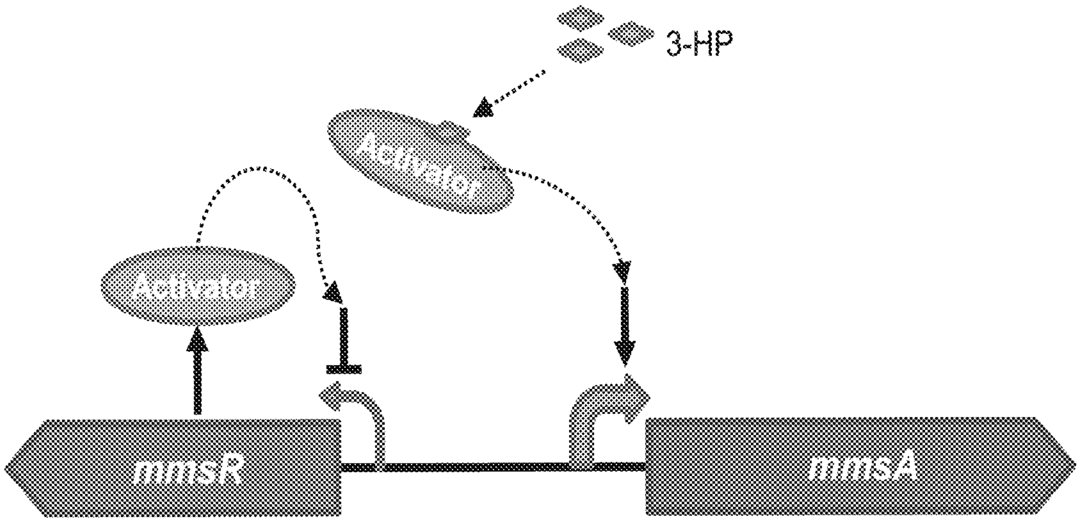

The UTR-6 construct exhibited the highest fold change, increasing levels by 12.5-fold and 30.8-fold compared to UTR-0 and $P_{mmsA}$, respectively, as determined bySDS-PAGE analysis (analyzed using BioRad Image Lab 2.2 software). UTR-6 was chosen for integration at the mmsA chromosomal location (the mmsR activator gene system was kept intact) of a recombinant *P. denitrificans* strain. Finally, the expression of target protein from chromosome was successfully observed over the expected levels, 2 and 1.7-fold, at transcriptional (mRNA) and translational (enzyme activity) levels, respectively as shown in FIG. 18B and FIG. 18C. This result indicated that UTR designer is a promising tool to facilitate the expression in wide range even achieve the desirable level of target gene with a small number of variants.

Example 14. Codon Optimization and Protein Hybridization

Even with an effective transcription system, the protein may not be produced efficiently if the translation system doesn't work well. Therefore, optimizing transcriptional and translational controls is often used to produce sufficient protein levels.

Codon preference is related to tRNA composition and controls translation propagation rate. Codon preference often influences the folding of proteins. It is usually recommended to use preferred codons when heterologous genes are cloned, but this often results in the production of misfolded, inactive proteins or even inclusion bodies. In those cases, a fusion system (hybrid protein) should be considered to increase protein expression, prevent proteolytic degradation, improve solubility and support purification.

As described in the Examples above, use of the $P_{mmsA}$ expression system to drive gene expression resulted in different expression levels between the homologous mmsA gene, and the heterologous kgsA genes. The poor performance of the $P_{mmsA}$ expression system in controlling kgsA could come from the differences in properties of the kgsA and mmsA genes (secondary structure, translational initiation ability, codon bias, solubility). We modified the kgsA gene to reduce these differences.

Codon optimization of a whole gene is a common way to increase translation. However, this is an expensive and time-consuming process. As a result, this study focused on optimization of only the first ten codons of a heterologous gene to enhance translation initiation. We generated a codon usage table for the highly expressed native mmsA gene using the GenScript bioinformatics tool, which showed the codon frequency level of each amino acid in MmsA. We used this information to modify the first ten codons of KgsA (a heteßrologous protein), according to three options: (i) using codons showing a high frequency level in mmsA, (ii) using codons showing a medium frequency level, and (iii) using codons showing the same frequency level as first ten codons of MmsA, and removing rare codons of KgsA (0% of frequency) (Table 3).

We found that a codon optimization according to option 3 (Opt-3) could increase KgsA activity by 30% in either absence or presence of 3-HP. We found that by keeping the frequency of all of the first 10 codons the same as that of the mmsA gene (Opt-3), the translation of kgsA was improved. By contrast, enhancing the frequency of some codons, such as 1st, 4th, 7th, and 9th in Opt-1 and Opt-2 (Table 3), the expression was not increased, but even slightly reduced.

what effect fusing part of the MmsA protein on KgsA would have on KgsA activity, the length of MmsA was varied by 5, 10, 15 and 20 amino acids, corresponding to the Hyb-5, Hyb-10, Hyb-15 and Hyb-20 strains, respectively. The results showed that KgsA activity increased as the length of MmsA fused to KgsA increased, although this effect leveled off when once 15 amino acids of MmsA was used (Hyb-15) (FIG. 17A). The Hyb-15 fusion protein had ~3-fold increase in production in the presence of 3-HP, compared to control KgsA (without a MmsA fusion. Further extending the length to 20 amino acids of MmsA (Hyb-20) did not improve the expression when the system was fully induced; however, the basal level of protein production in the Hyb-20 strain was enhanced. This result was confirmed by the band intensity of KgsA on SDS-PAGE (FIG. 17B).

Aside from being involved in translation initiation, the 5' end of a target gene plays an important role in controlling the level of transcript via regulation of mRNA concentration. The stability of the kgsA transcript without and with an N-terminal fusion of the first 20aa of MmsA (mmsA(20) kgsA) was measured (FIG. 17C). The expression was examined with controls. The half-lives of kgsA and mmsA(20) kgsA were 2.7 and 5.4 minutes, respectively, indicating that the mmsA hybrid-fused kgsA mRNA was more stable compared to wild-type kgsA mRNA. The half-life of mmsA transcript was found to be around 6 minutes, so the improvement in mmsA(20)kgsA stability may result from the protection of the mmsA 5' end coding portion (20 amino acids) fused to the kgsA gene. Interestingly, among the genes we tested, the most stable transcript appeared to belong to mmsR, with a half-life of 9.5 min (FIG. 17D) s.

Example 15. Coenzyme B12 Production

Coenzyme $B_{12}$ is an essential cofactor for many enzymes including glycerol dehydratase, methionine synthase or

TABLE 3

Frequency of first 10 codons of wild-type and optimized kgsA basing on mmsA codon usage in *P. denitrificans.*

| | | | | Modification | | | | | | | |
|---|---|---|---|---|---|---|---|---|---|---|---|
| | | kgsA-wt | % | Op1-1[a] | % | Opt-2[b] | % | Opt-3[c] | % | mmsA | % |
| 1 | Ala | GCU | 2.1 | GCC | 73.7 | GCU | 31.9 | GCG | 4.0 | 1st aa | 4.0 |
| 2 | Asn | AAC | 33.2 | AAC | 45.8 | AAC | 45.8 | AAC | 45.8 | 2nd aa | 45.8 |
| 3 | Val | GUG | 53.9 | GUG | 47.8 | GUG | 47.8 | GUG | 47.8 | 3rd aa | 47.8 |
| 4 | Thr | ACU | 21.0 | ACC | 69.7 | ACU | 69.7 | ACC | 2.0 | 4th aa | 2.0 |
| 5 | Tyr | UAU | 0.0 | UAC | 12.0 | UAC | 12.0 | UAC | 12.0 | 5th aa | 12.0 |
| 6 | Thr | ACG | 0.0 | ACC | 69.7 | ACC | 69.7 | ACC | 69.7 | 6th aa | 69.7 |
| 7 | Asp | GAU | 41.5 | GAC | 29.9 | GAU | 29.9 | GAC | 8.0 | 7th aa | 8.0 |
| 8 | Thr | ACG | 0.0 | ACC | 69.7 | ACC | 69.7 | ACC | 69.7 | 8th aa | 69.7 |
| 9 | Gln | CAA | 4.1 | CAG | 31.9 | CAA | 31.9 | CAG | 4.0 | 9th aa | 4.0 |
| 10 | Leu | CUG | 39.4 | CUG | 47.8 | CUG | 21.9 | CUC | 47.8 | 10th aa | 47.8 |

[a]Using codon showing high frequency level.
[b]Using codon showing medium frequency level.
[c]Using codon showing frequency level as same as first 10 codons of mmsA and removing rare codons.

Figure 21A:
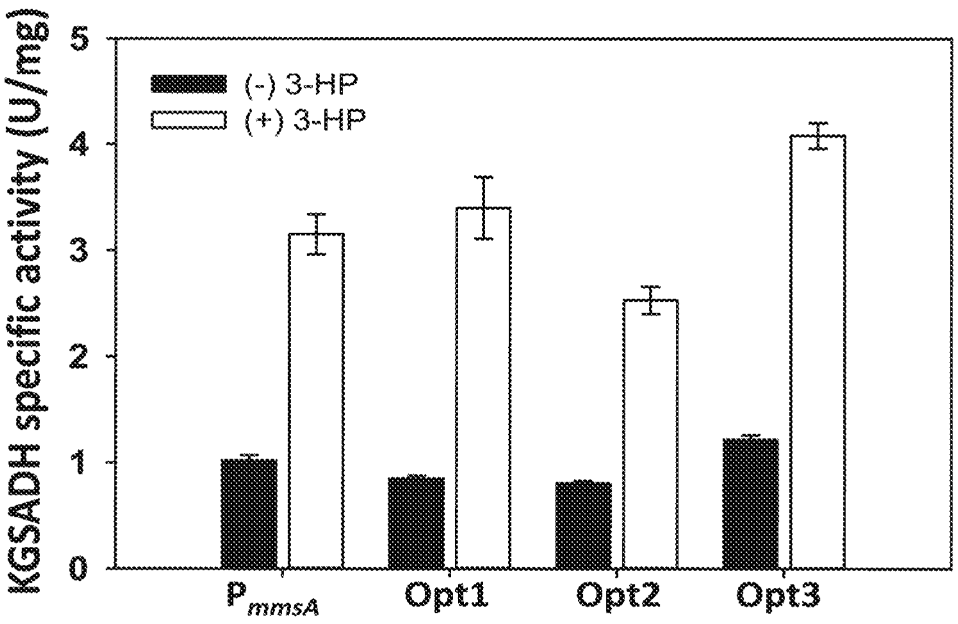
FIGS. 21A-B are a graph and image showing enzyme activity (FIG. 21A) and SDS-PAGE (FIG. 21B) analyses for KgsA expression level of strains which were optimized first 10 codons of KgsA. Three different constructs in terms of codon frequency level (high, medium and low) were developed and designated as Opt-1, Opt-2 and Opt-3, respectively.
Figure 21B:
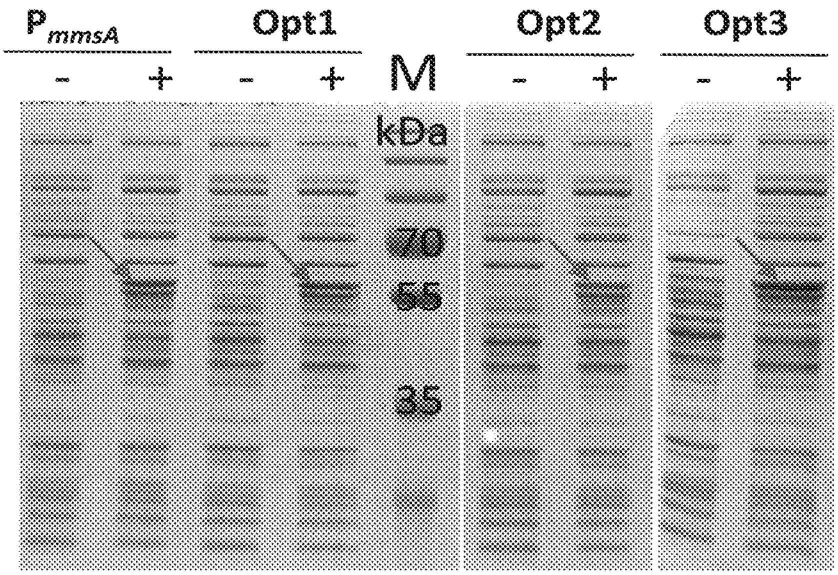
Figure 22:
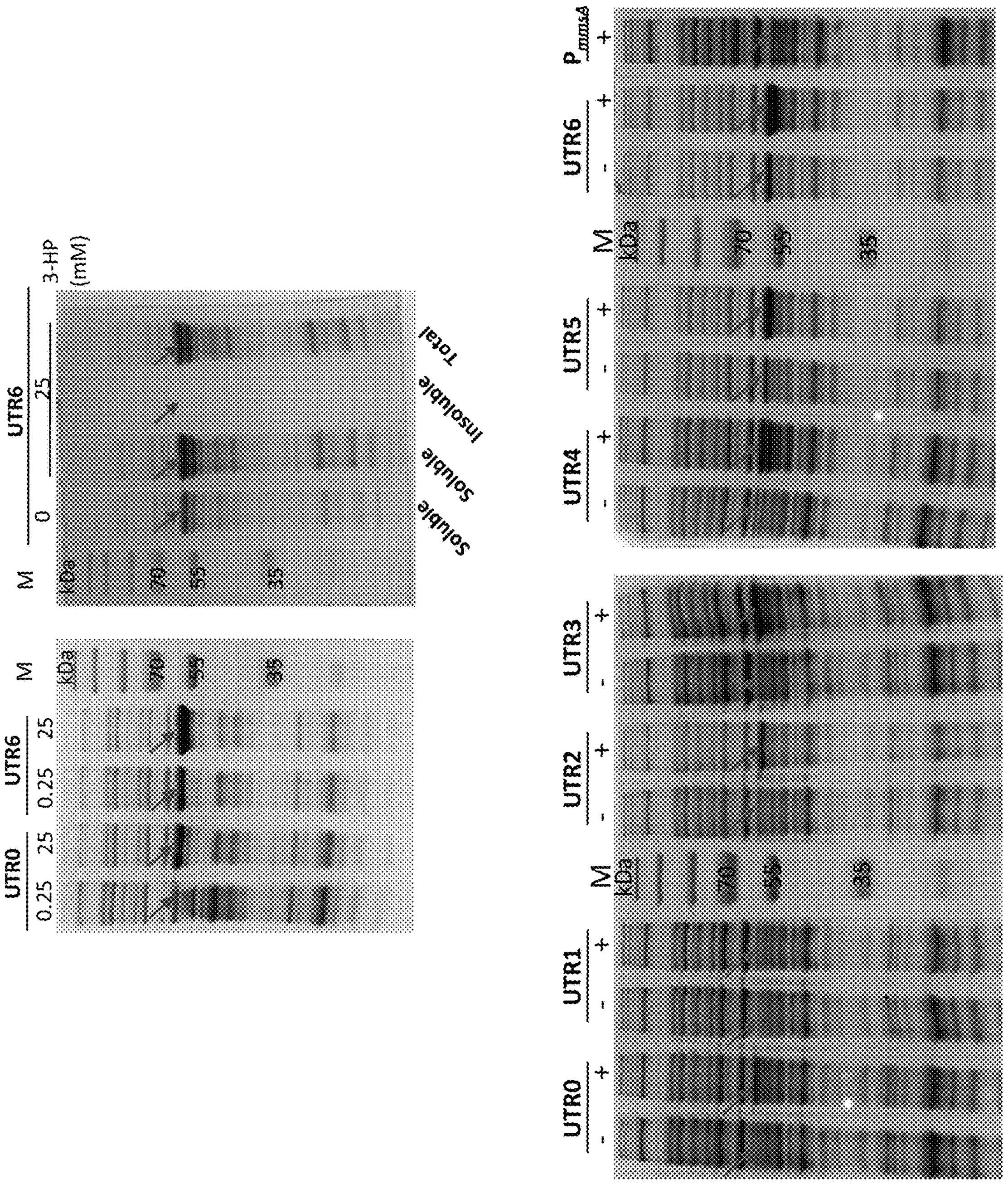
FIG. 22 is a set of images of SDS-PAGE showing the effect of UTR design on the expression of KgsA. UTR's with various strengths predicted by UTR designer in silico was tested.

The results were confirmed by protein production on SDS-PAGE (FIG. 21B).

Fusion proteins are often used in heterologous gene expression to enhance protein production, reduce proteolytic degradation and improve folding and solubility. We fused the N-terminal end of MmsA, produced by the highly expressed mmsA gene in *P. denitrificans*, to the KgsA enzyme. We reasoned that translation initiation of a heterologous gene (kgsA) transcript could be made more efficient by adding part of the 5' coding region of mmsA downstream of the $P_{mmsA}$ promoter. Since we were concerned about the methylmalonyl CoA mutase. Glycerol dehydratase (or, alternatively, diol dehydratase) is involved in converting glycerol to 3-hydroxypropanealdehyde (3-HPA) and is an essential enzyme for the production of 3-HP (of a salt thereof) or 1,3-PDO from glycerol. 3-HPA can be further converted to other industrially important chemicals such as 1,3-PDO or 3-HP (or a salt thereof). To continuously produce these biochemicals from glycerol at a commercial scale, an uninterrupted supply of coenzyme $B_{12}$ is essential. As coenzyme $B_{12}$ is very expensive, we examined 3-HP production from glycerol using a natural coenzyme $B_{12}$ producer. There are several microorganisms reported to produce coenzyme $B_{12}$ naturally (including, e.g., *Enterobacters*, including *Klebsiella* species, *Streptococcus* species, including *S. pneumonia, Pseudomonas* species, including *P. denitrificans, Rhizhobium species, Sinorhizobium* species, including *S. meliloti*, and *Rhodobacter* species, including *R. capusulatus* and *R. sphaeroides*, etc.). When we tested some of these microorganisms as hosts to produce 3-HP from glycerol, the amount of coenzyme $B_{12}$ produced was not sufficient enough to synthesize 3-HP at high titers (each producing <30 g/L).

It was noticed that *P. denitrificans* could produce 3-HP (or a salt thereof) at ~20.8 g/L without external addition of this cofactor. However, when this strain was supplemented with saturated amount of coenzyme B12 it could produce ~100 g/L of 3-HP. These results indicated that the naturally produced coenzyme B12 by this microorganism was not sufficient enough to support the 3-HP production at high titer. After careful analysis and by removing the regulations (secondary structures in mRNA) involved in coenzyme B12 synthesis a marginal improvement in its production was noticed. The improvement in coenzyme B12 was confirmed by various assays as mentioned in previous sections. This recombinant strain when used as host to produce 3-HP from glycerol, showed more than two times improvement in 3-HP production from glycerol at 38.6 g/L.

Figure 50:
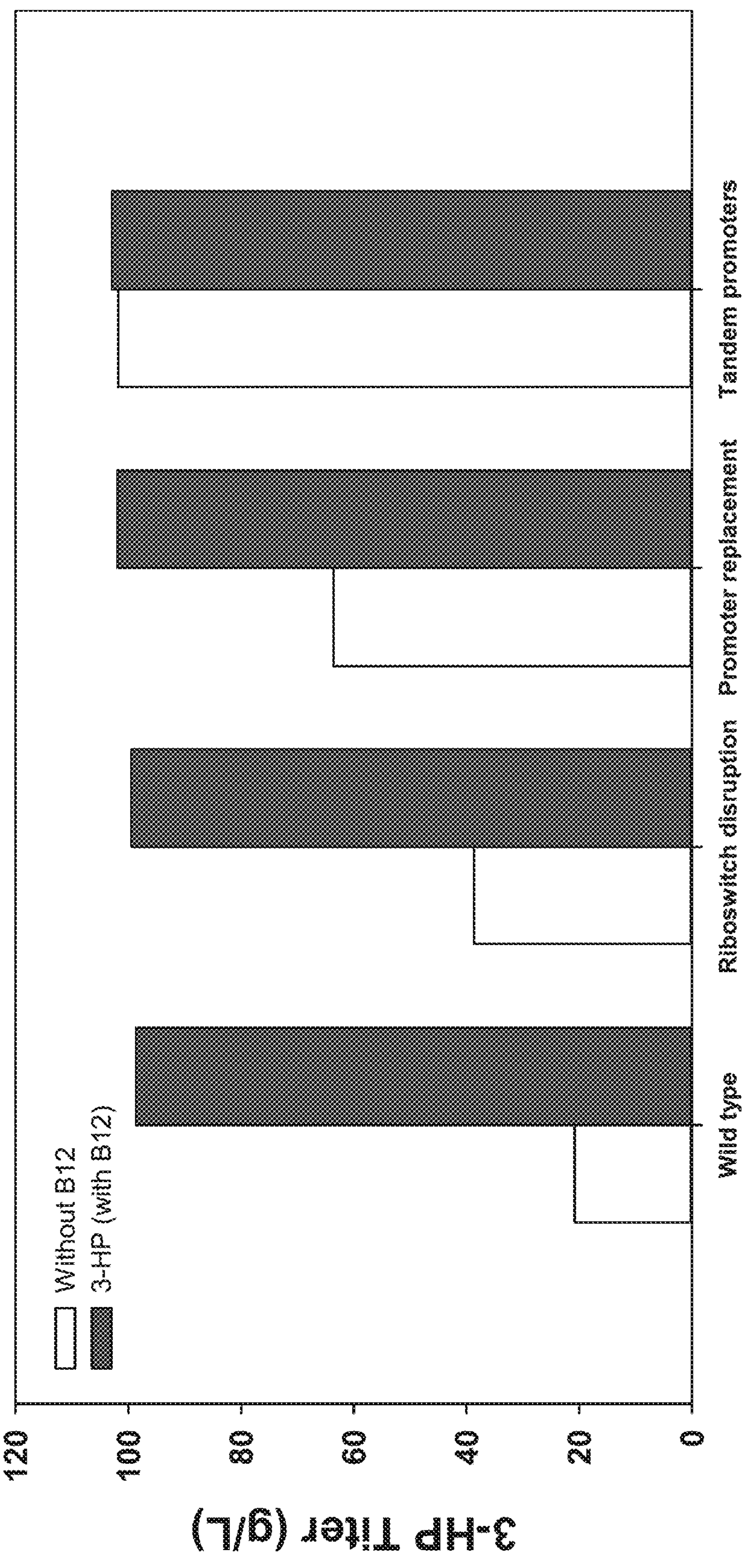
FIG. 50 is a graph showing the effect of improvement in coenzyme B12 production and thereby 3-HP production to commercial levels by sequentially disrupting B12 riboswitches, promoter replacement and finally by using tandem promoters.

In the next experiment, we examined this strain by supplementing small amount of coenzyme $B_{12}$ in the culture medium and the results are shown in FIG. 50. We notice that when the cultures are supplemented with small amount of coenzyme $B_{12}$ (10 mg/L) the 3-HP production improved substantially from 38.6 g/L to 100 g/L. This results indicate that the amount of coenzyme $B_{12}$ produced by the modified strain (IR1-RS1) was improved, but it was not sufficient enough to support the 3-HP production at high titer.

Further, to improve the coenzyme B12 production we need to enhance the activity of the enzyme involved in coenzyme B12 synthetic pathway. This can be done by enhancing the coenzyme B12 synthetic pathway by improving its enzyme activities. Enzyme activities can be improved by either enhancing its physical and kinetic properties or by improving its expression and increasing its amount. As this pathway is associated with many enzymes, initially we increased the enzyme amount and tried to enhance the coenzyme B12 synthesis. To enhance the amount of the enzyme in the cells the natural promotors were replaced with the synthetically engineered promotors described above.

In this study we attempted to improve coenzyme $B_{12}$ production by microorganisms to support the production of biochemicals from glycerol at a scale suitable for commercialization. To achieve this, we examined cobalamin gene clusters in natural microbial producers of coenzyme $B_{12}$, such as *P. denitrificans*, to understand the regulation of transcription and translation by various coenzyme $B_{12}$-riboswitches ($B_{12}$-riboswitches). Initially, we identified five secondary structures using software, which can be regulated by coenzyme $B_{12}$ (see FIG. 23). We determined that four of these structures are riboswitches. In vitro characterization showed that among them only three of the riboswitches, upstream of genes cobG and cbtB were transcriptionally regulated (FIG. 23). These riboswitches were regulated by coenzyme $B_{12}$, such that the addition of cobalamin B12 (at concentrations as low as ~5 nM) led to a substantial reduction in transcription/translation (see FIG. 28).

In addition, we examined whether six uncharacterized genes located in cob gene clusters I and II (gst, xre, dahp, gntR, bgpM, cobA) are involved in coenzyme $B_{12}$ synthesis (see FIG. 23). We found that the bgpM gene product was essential for coenzyme $B_{12}$ biosynthesis. The cobA gene, encoding uroporphyrinogen methyltransferase, is involved in an important branching point in coenzyme $B_{12}$ biosynthesis pathway, and thus, we expected deletion of cobA to hamper coenzyme $B_{12}$ production. However, we found that a cobA deletion mutant could synthesize substantial amount of coenzyme $B_{12}$. When we analyzed the genome of *P. denitrificans*, we noticed the presence of several CobA isoenzymes which potentially could substitute for CobA activity.

In the first part of this study, we describe the methods adopted to identify the $B_{12}$-riboswitches, and their regulatory role in transcription/translation involved in coenzyme $B_{12}$ synthesis. We also examined methods for enhancing coenzyme $B_{12}$ production by modulating regulation by riboswitches. We also further improve coenzyme $B_{12}$ production by replacing natural promoters with the synthetic expression modules (Tandem promoter, UTR, regulatory protein, N-terminal region of highly expressing genes) described in the Examples above. These modified strains had enhanced coenzyme $B_{12}$ production, which helped to increase 3-HP (or salt thereof) production from glycerol without the external addition of coenzyme $B_{12}$.

The strain with modified promoters showed good coenzyme B12 production, the analysis showed this strain could produce 4 fold higher coenzyme B12 than the wild type strain and 2 times higher than the riboswitches modified strains. When this strain was transferred with the plasmids containing 3-HP synthetic pathway enzymes, it showed substantial improvement in 3-HP production without addition of coenzyme B12. This strain produced 3-HP above 90 g/L from glycerol, however, the growth was little slow compared to the wild type strain, and this could be due to the modification in the coenzyme B12 synthetic pathway. In this study we successfully developed a mutant strain which could produce coenzyme B12 at higher amount and could support 3-HP production at higher titer.

Figure 24:
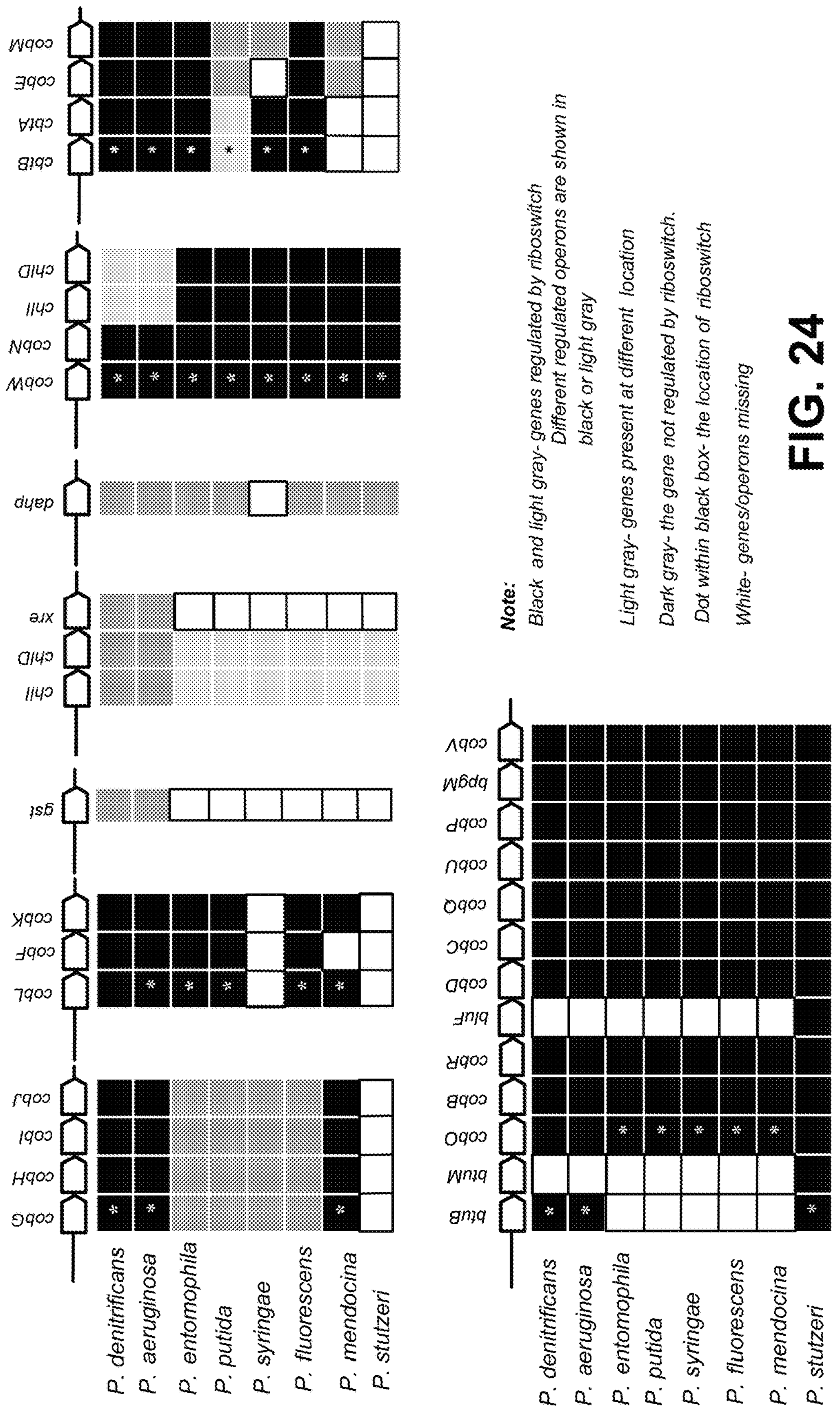
FIG. 24 is a schematic showing a comparative analysis of the organization of coenzyme B12 genes from various *Pseudomonas* species.

Example 16. In Silico Analysis and Comparison of B12 Genes Among Various *Pseudomonas* Species To understand the arrangement of genes and their regulation, we compared the coenzyme $B_{12}$ gene clusters that are present in various *Pseudomonas* strains. To date, as many as, thirty-one genes have been identified in the coenzyme $B_{12}$ biosynthetic gene clusters involved in the aerobic coenzyme $B_{12}$ biosynthetic pathway. Among them, the coenzyme $B_{12}$ biosynthetic pathway from *P. denitrificans* has been studied at the enzyme level Based on comparative analysis of the organization of coenzyme $B_{12}$ genes from various *Pseudomonas* species (FIG. 24), it was noticed that the genes in *P. denitrificans* ATCC 13867 and *P. aeruginosa* PAO1 strains were highly similar, with an average sequence identity of 73%. Interestingly, these strains harbor an additional four genes within the coenzyme B12 gene cluster that are uncharacterized: gst, xre, dahp and bgpM. Unlike other *Pseudomonas* strains, the genes encoding for magnesium chelatase (chlID) are located separately, along with xre genes, in these two strains. In addition, the genes and organization of genes in *P. entomophila, P. putida* and *P. fluorescens* are similar to *P. denitrificans*. Additionally, these strains lack the ton-dependent B 12 transporter (btuB), known to encode coenzyme $B_{12}$ transport system. Also the operon cobGHIJ in these microorganisms are not controlled by a $B_{12}$-dependent riboswitch structure (FIG. 24).

Nitrogen-fixing bacteria such as *Ensifer/Rhizobium* species are also reported to have high $B_{12}$ production capability. Interestingly, comparison of gene organization between *P. denitrificans* SC510 (and industrial $B_{12}$ producer), *P. denitrificans* ATCC 13867, and *Ensifer meliloti*, revealed that *P. denitrificans* SC510 and *Ensifer meliloti* are more closely linked and are distinct from the *P. denitrificans* ATCC 13867 strain. These differences could not be studied further due to the unavailability of a whole genome sequence for *P. denitrificans* SC510.

Figure 25A:
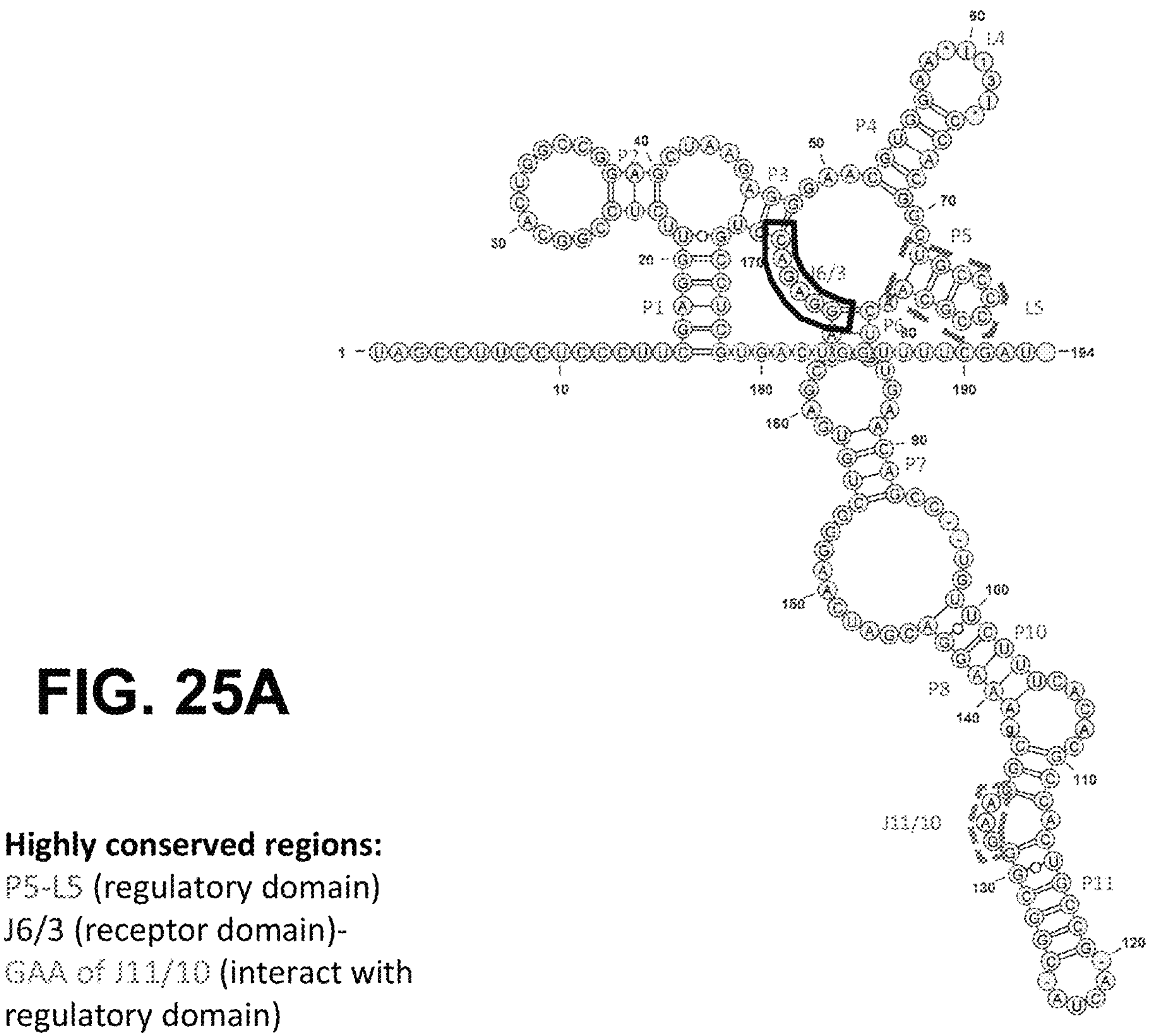
FIGS. 25A-D are schematics showing the structures of vitamin B12 riboswitches.
Figure 25B:
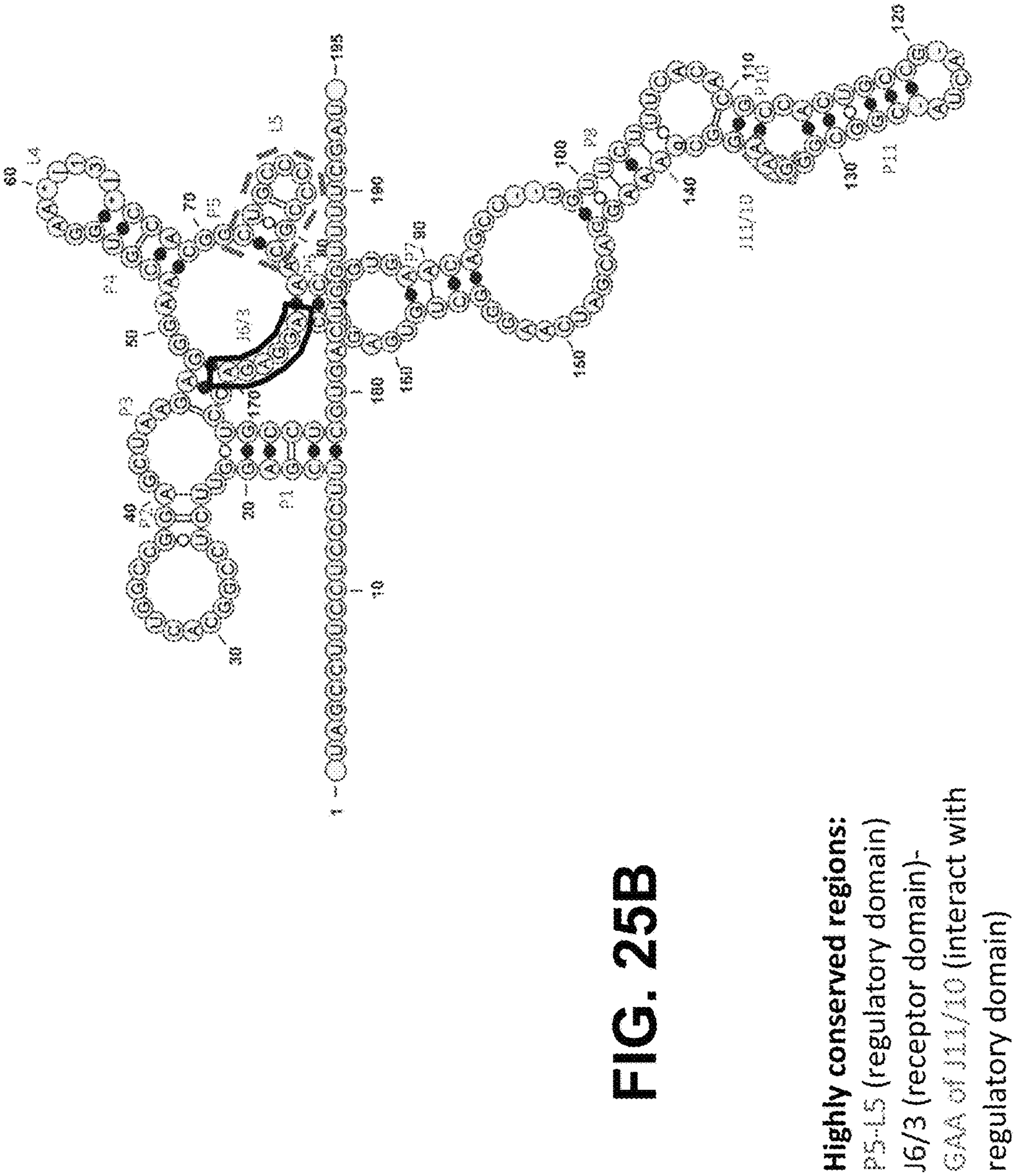
Figure 25C:
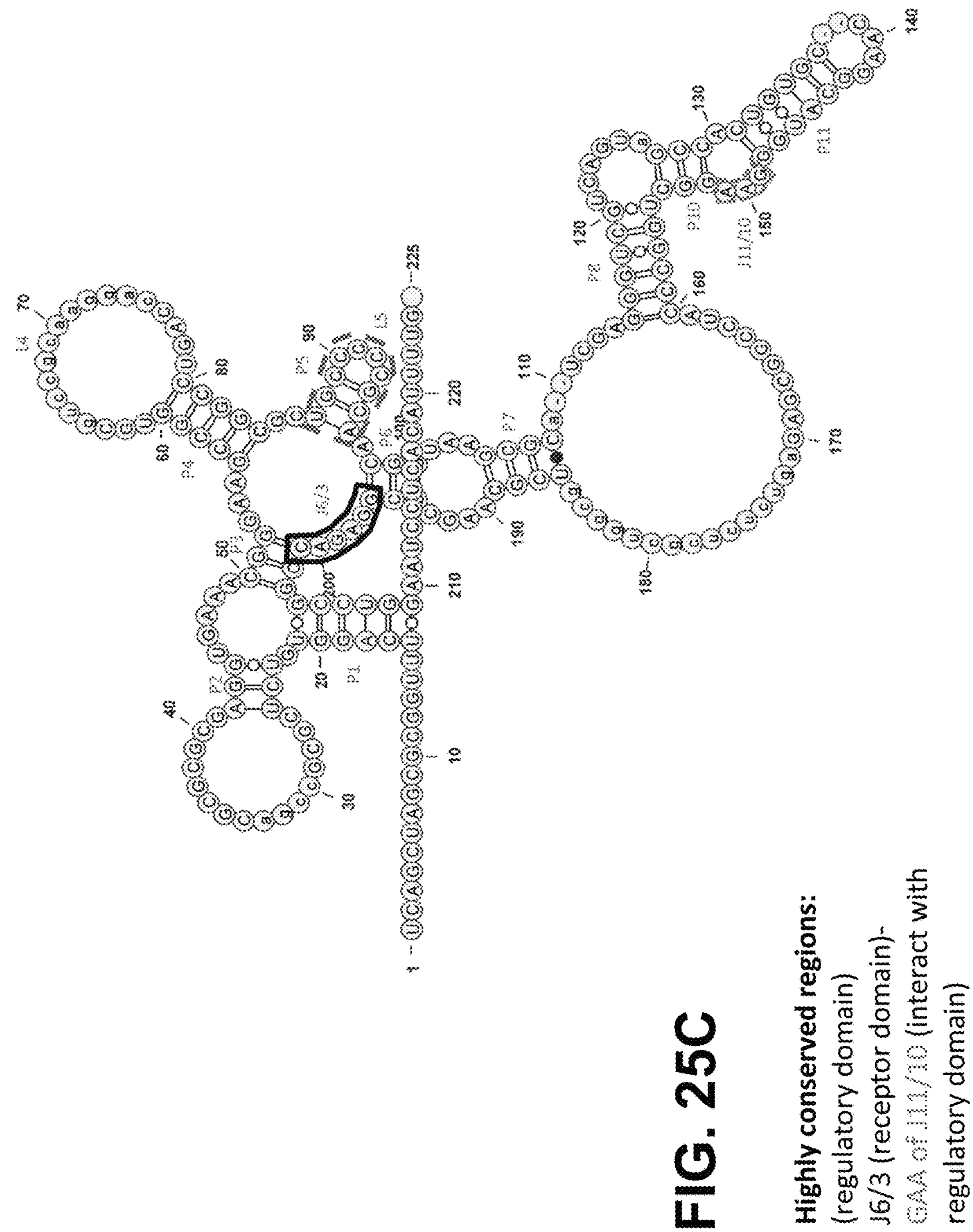
Figure 25D:
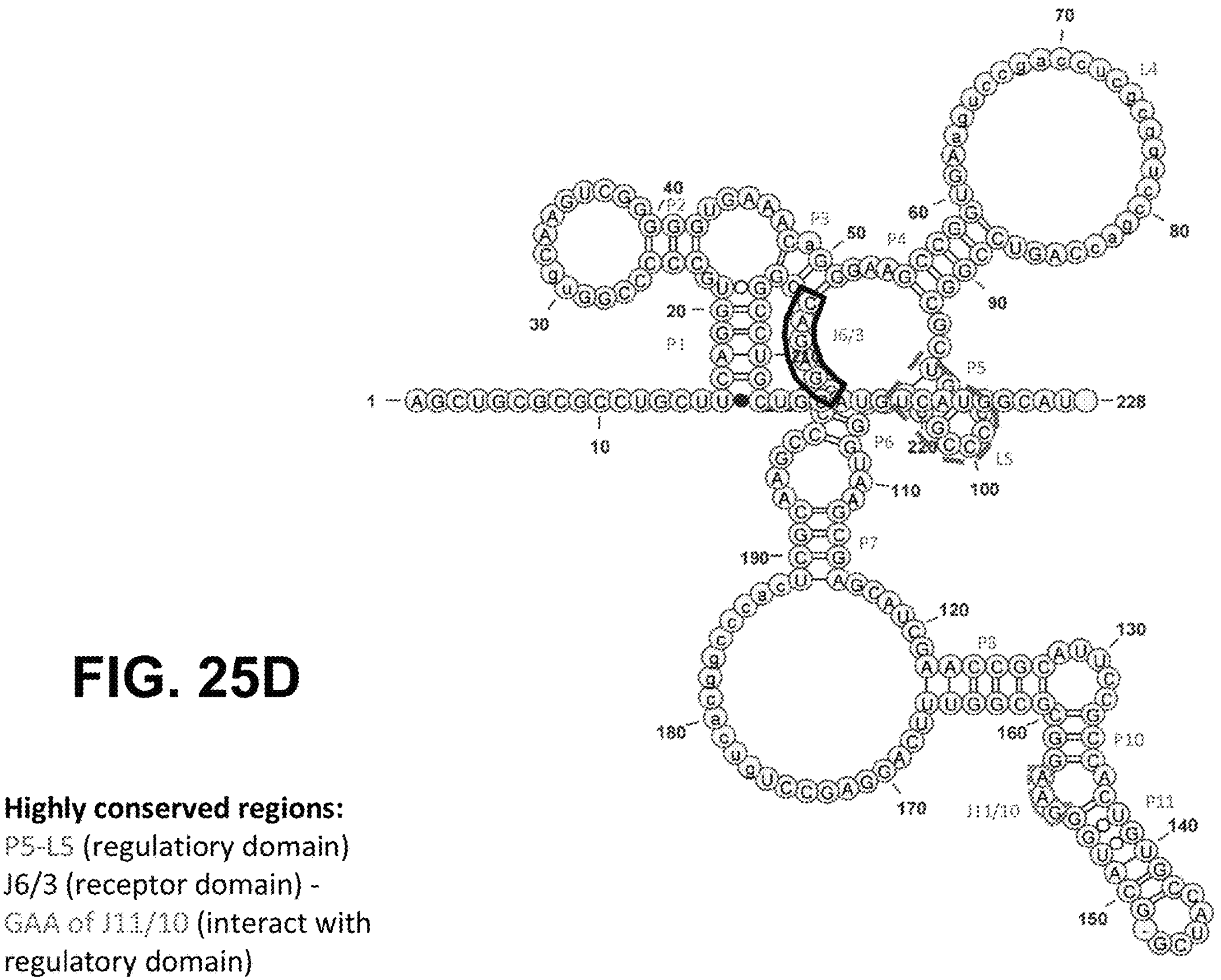

Apart from understanding the gene organization in *P. denitrificans*, we identified the presence of four potential $B_{12}$-riboswitches using the Rfam database/tools. One representative of these riboswitch-structures is shown in FIG. 25A, which is believed to control the expression of cobalamin biosynthesis. These $B_{12}$-riboswitches each have a cobalamin binding consensus domain (regulatory and receptor domains) similar to the one present in *Escherichia coli*, and to the *Salmonella enterica* btuB $B_{12}$-riboswitch. One riboswitch (RS1) is located between two divergently located cobGHIJ and cobLFK operons that encode enzymes responsible for the formation of hydrogenobyrinate from precorrin-2 intermediate (excepting the cobM gene) (FIG. 25A; see FIG. 23). As shown in FIG. 23, based on the importance of the genes at this locus, we assume tight control at intergenic region 1 (IR1) by RS1 in the diversion of flux between coenzyme $B_{12}$ and siroheme biosynthetic nodes. Two of the $B_{12}$-specific riboswitch structures (RS2 and RS3) located between the operons, cobWN and cbtBA-cobEM, seems to independently regulate the expression of both the operons. Finally, RS4 is located upstream of the cob operon (btuB-cobOBRDCQUP-bgpM-cobV), which contains 11 genes that encode enzymes responsible for the formation of Ado-Cbl from hydrogenobyrinate.

We studied the mechanisms by which these riboswitch structures control the expression of cob operon genes. Briefly, the interaction of conserved regions J6/3 and J11/10 of the riboswitches makes each riboswitch specific and able to bind to coenzyme $B_{12}$ at an adenosyl-moiety, while the interaction between loops L5 and L13 of the riboswitches changes the regulatory status of the switch (see FIGS. 25A-25D).

Figure 26:
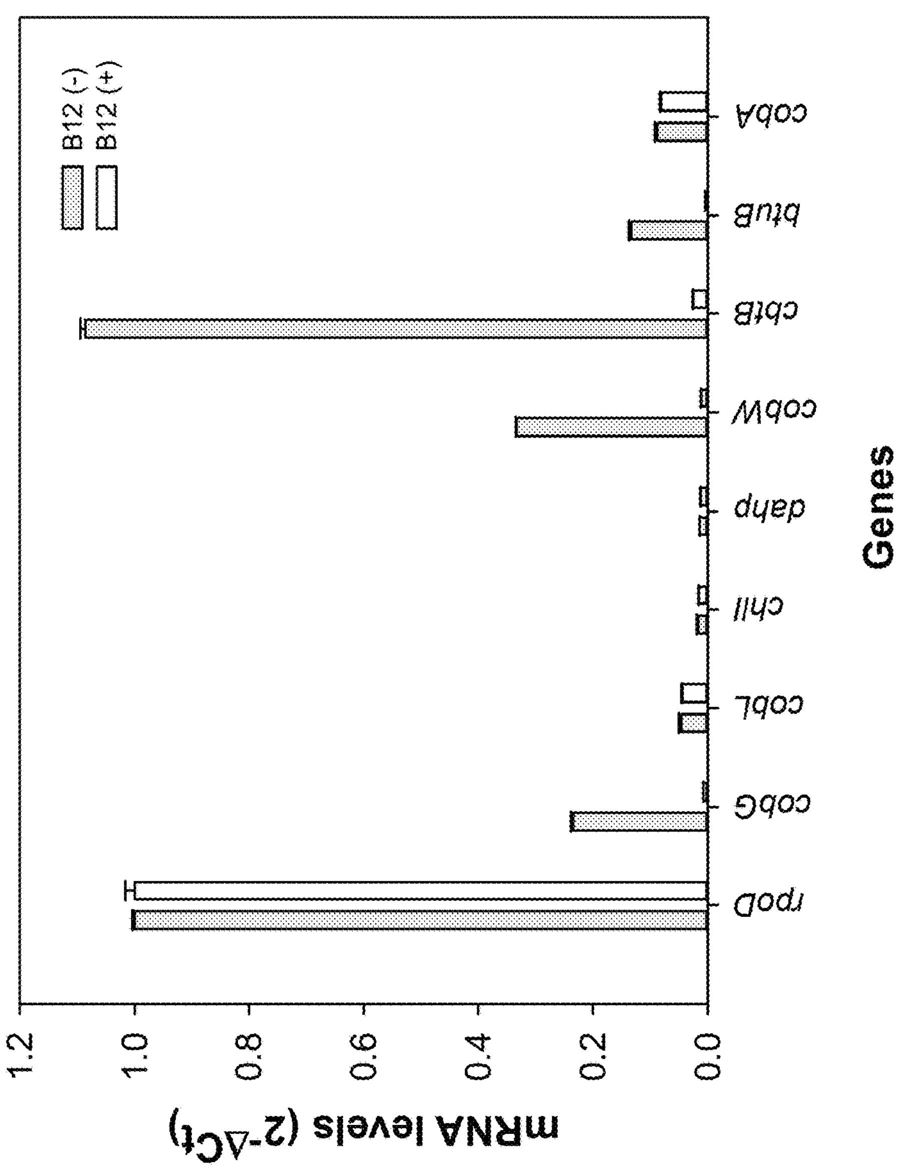
FIG. 26 is a graph showing the transcription of cob genes at chromosomal level in *Pseudomonas denitrificans*.

Example 17. Characterization of Coenzyme B12 Sensing Riboswitch Structures and their Promoter Systems The riboswitch structures modulate gene expression either at the level of transcription elongation or translation initiation. The location of the riboswitches within the intergenic regions determines the mode of regulation by these riboswitch structures. We noticed that most of the $B_{12}$ riboswitch structures in *P. denitrificans* overlaps promoter elements rather than the untranslated regions (UTR), suggesting that these riboswitches might be controlled at transcriptional levels. Therefore, we analyzed the mRNA levels of the selected genes (first gene in each operon) in the cob operons using real time PCR on *P. denitrificans* cultures harvested during the late exponential phases, grown in the presence or absence of coenzyme $B_{12}$. As expected, the mRNA levels of four genes (cobG, cobW, cbtB and btuB) in the cob operon were significantly repressed in the presence of coenzyme B12 (FIG. 26). The transcription of the operon, cbtBA-cobEM under the control of RS3 was highly repressed by 43.3-fold. We noticed that most of the genes in this operon does not encode for structural genes of the $B_{12}$ biosynthetic pathway (cobE, cbtBA functions as putative chaperone and cobalt transporter proteins, respectively). Its noteworthy that the transcription of structural gene encoding operons (cobGHIJ, cobWN and btuB-cobOBRDCQUP-bgpM-cobV) have transcription levels of at least 3.3-fold lower than that in operon cbtBA-cobEM, in the absence of $B_{12}$ (unrepressed form). From the in silico analysis of intergenic regions, it is unclear whether the RS1 controls the expression of either cobGHIJ/cobLFK operons or both. However, based on mRNA levels it seems that RS1 controls the expression of the cobGHIJ operon, but not the cobLFK operon. We observed a decreasing order of transcriptional repression by various $B_{12}$-RS in cob gene clusters: cbtB-RS3>cobG-RS1>cobW-RS2>btuB-RS4. No repression was noticed in the cobLFK, chlID-xre and dahp operons, these results correlates with the fact that they lack riboswitch structures upstream to these operons.

Figure 27:
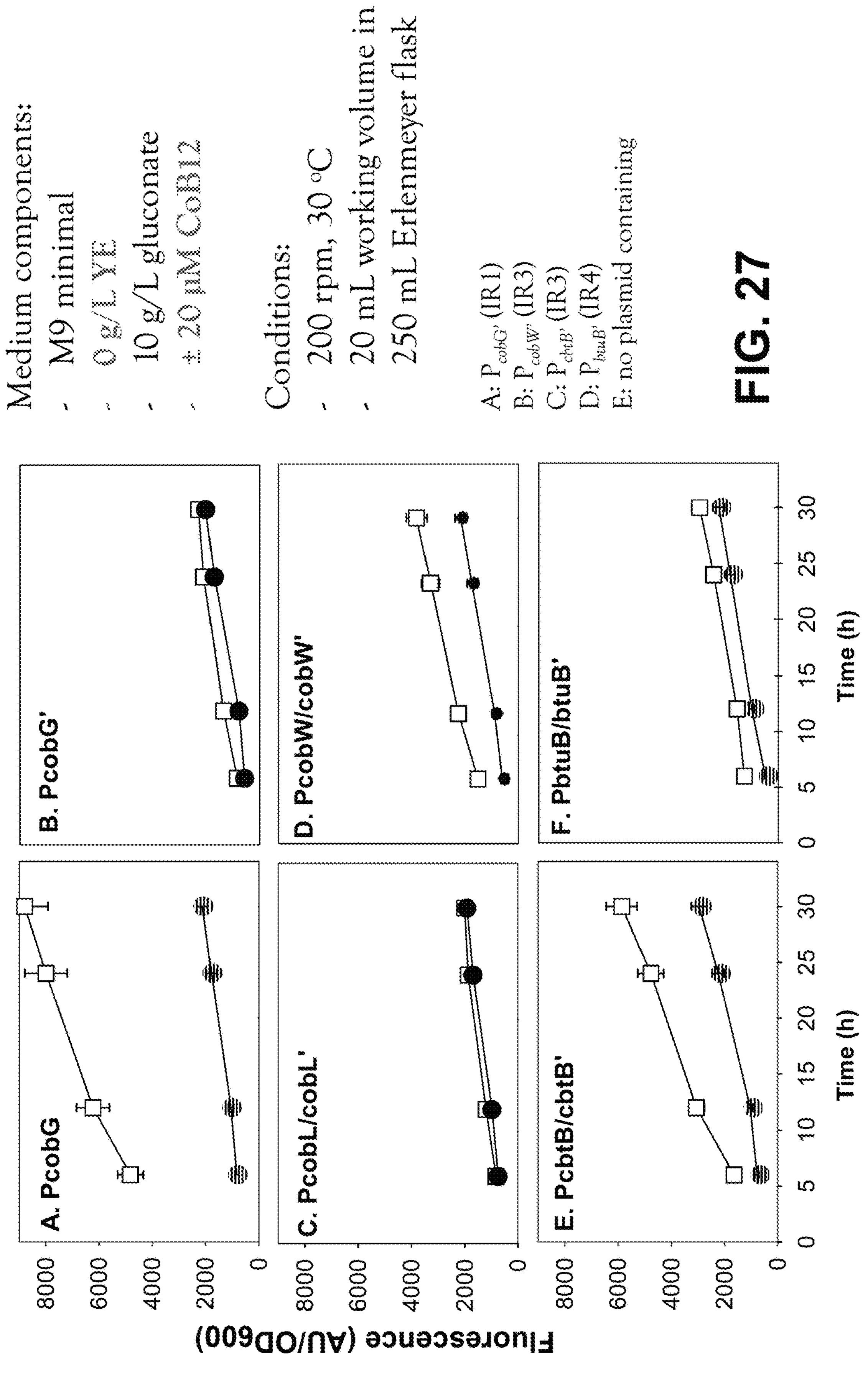
FIG. 27 is a set of graphs characterizing the in vivo characterization of vitamin B12 intergenic regions in *P. denitrificans*.

We suspect that these riboswitches might also be controlled at the initiation of translation, in addition to regulation at the transcriptional level. Furthermore, we sought to predict the regulatory strength of these riboswitches, by cloning the intergenic regions between promoter and enzyme coding regions (upstream) of the cob operons into plasmids. To these plasmids, we added Green Fluorescent Protein as a reporter protein (fluorescence marker) downstream of secondary structure locations selected from the cob operons. Two versions of these plasmid systems were constructed. One version where the first 35 bp of the respective native protein coding sequence was fused to the gene encoding GFP in the plasmid, and one version that did not have this fusion. The fused form of cobG (first 35 bp of cobG fused to the gfp) exhibited a 4.2-fold higher florescence, compared to its unfused gfp construct (FIG. 27, Table 6). However, we observed no significant difference in the florescence levels produced by other promoters systems (intergenic segments from other B12 operons) when the first 35 of cobG was fused to gfp, suggesting that they are not controlled at the translational initiation level. These results further suggest that PcobG-RS1, tightly controls the expression of genes both at the transcription and translation initiation levels. The stringent regulation at transcription and translation signifies the importance of controlled expression of genes in the cobGHIJ operon.

The estimation of the strength of native promoters is crucial when overexpressing any pathways involving several genes, such as the vitamin $B_{12}$ pathway, or pathways involving several membrane proteins. The overexpression of pathways with many genes can be deleterious to cell growth, and imbalanced expression of the pathway genes/operons might lead to the accumulation of toxic pathway intermediates. The analysis and quantification of native promoter strength can assist us in redesigning the operons with synthetic promoters without overexpressing the pathway enzymes during engineering. Table 5 shows the estimated promoter strengths (in relative florescence units) we observed for various native cob promoters in the operon. The promoter PebrB that controls the expression of cobalt transporter genes has the highest strength, and the PcobL promoter has the lowest strength of this group. The genes encoding for methyltransferase enzymes appeared to usually be by weak promoter systems.

TABLE 6

Characterization of cob regulon intergenic regions in *P. denitrificans*.

| Intergenic regions | Promoters | R/S control | Promoter strength ($AU/OD_{600}$) |
|---|---|---|---|
| IR1 | $P_{cobG}$ | ○ | 2200 |
| IR1 | $P_{cobL}$ | x | 1800 |
| IR3 | $P_{cobW}$ | ○ | 3,000 |
| IR3 | $P_{cbtB}$ | ○ | 5,000 |
| IR4 | $P_{btuB}$ | ○ | 2,800 |

Engineering Coenzyme B12 Production Pathway

Figure 57:
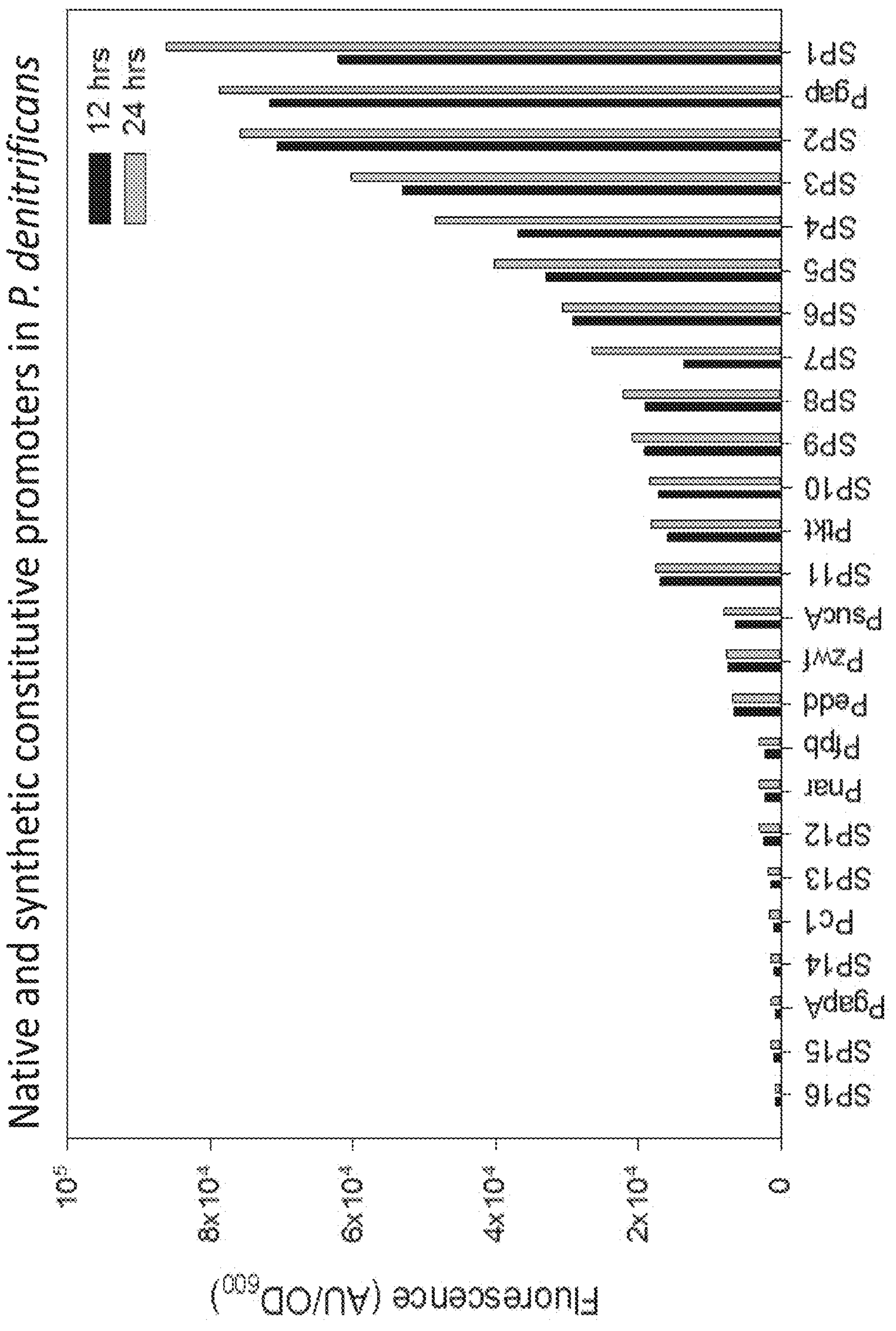
FIG. 57 is a graph showing the effect of native and synthetic constitutive promoters in *P. denitrificans.*

Rational engineering of B12 promoters requires quantification of promoter strengths along with their UTR structures (fused and unfused versions). Therefore, the native promoter strengths of cob operon, encoding coenzyme B12 synthetic pathway enzymes were meticulously quantified (FIG. 27, Table 6&10). Further, to increase the expression levels of these (cob) genes (by 3- and 5-folds relative to their native expression). The expression of cob operons were modified by replacing with suitable constitutive promoters (FIG. 57). The constitutive promoters were selected by screening and identifying their strengths of several native *Pseudomonas* promoters (Table 10). For instance, to develop Pedd-IR13-PsucA recombinant strain with three fold improved promoter strengths, PcobG and PcobL were replaced with constitutive promoters, Pedd and PsucA respectively (See Table 8, for more details).

TABLE 10

Strategy for B12 promoter replacement

| Promoter | Native strength | Recombinant strength 3-fold | Recombinant strength 5-fold |
|---|---|---|---|
| $P_{cobG}$ | 2200 | 6600 ($P_{edd}$) | 11000 ($P_{sp9}$) |
| $P_{cobL}$ | 1800 | 5400 ($P_{sucA}$) | 9000 ($P_{zwf}$) |
| $P_{cobW}$ | 3000 | 9000 ($P_{zwf}$) | 15000 ($P_{tkt}$) |
| $P_{cbtB}$ | 5000 | 15000 ($P_{sp9}$) | 25000 ($P_{sp2}$) |
| $P_{btuB}$ | 2800 | | 14000 ($P_{sp9}$) |

Example 18. Development of a Riboswitch-Based B12 Sensing System

Vitamin $B_{12}$ quantification methods typically included microbiological assays and high performance liquid chromatography (HPLC) with UV detection. The HPLC method can detect $B_{12}$ at high concentrations (above μM level), but the microbial assays can detect $B_{12}$ at very low concentrations (as low as the nM level). Microbiological assays were based on $B_{12}$ as a growth factor in certain mutant strains of *Salmonella typhimurium* $metE^-$ $cbiB^-$. Briefly, the growth of these microorganisms was proportional to the concentration of $B_{12}$. However, $B_{12}$ quantification based on cell growth is effected by several physiological factors such as culture medium and time of incubation. Therefore, coenzyme $B_{12}$ quantification based on cell growth is tedious and difficult to reproduce.

Figure 28:
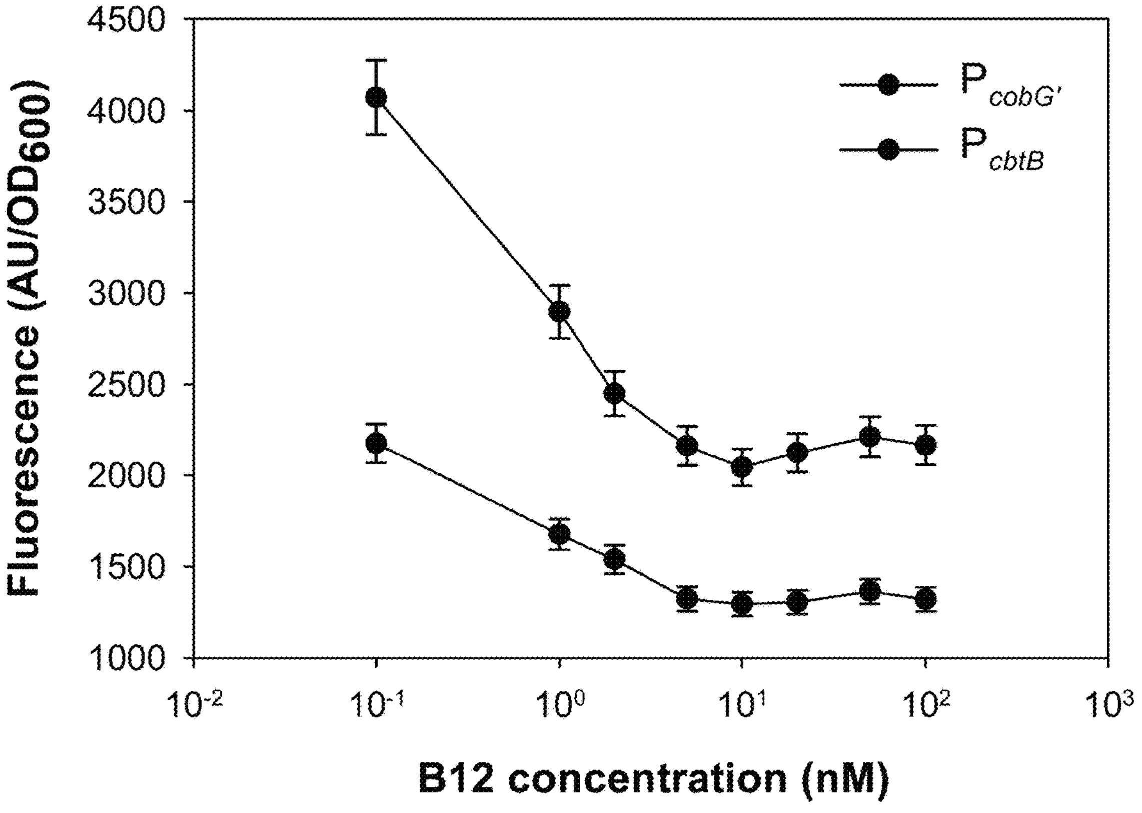
FIG. 28 is a graph showing a correlation between the B12 concentration and GFP fluorescence of a vitamin B12 ribosensor derived from the intergenic regions of the genes cobG and cbtB from *P. denitrificans*.

In this study, we found that among five putative $B_{12}$ riboswitch structures, two of them, found after promoters $P_{cobG}$' and $P_{cbtB}$, could exhibit differential expression of downstream genes in the presence and absence of coenzyme $B_{12}$. Further, the dynamic range of these riboswitches were evaluated by using various concentration of coenzyme $B_{12}$ (up to 100 nM) to verify their potential as novel $B_{12}$ sensors. A linear correlation of $B_{12}$ concentration to GFP florescence was noticed with a switch-off point at approximately 5 nM cobalamin $B_{12}$ (FIG. 28). The $B_{12}$ riboswitches $P_{cobG}$' and $P_{cbtB}$ exhibited ~2.1- and 1.7-fold differential expression in the presence and absence of $B_{12}$. In contrast to growth based $B_{12}$ detection, florescence based $B_{12}$ detection method is reproducible, convenient and less laborious.

Example 19. Coenzyme $B_{12}$ Quantitative Bioassay

*P. denitrificans* was grown at 0.1 initial $OD_{600}$ in M9 minimal medium containing NaCl 1 g/L, $NH_4Cl$ 1 g/L, $MgSO_4$ 2 mM, sodium gluconate 10 g/L supplemented with 5,6-dimethyl benzimidazole (DMB) 0.1 mM, betaine 1 g/L, and trace elements $H_3BO_3$ 0.232 g/L, $ZnSO_4·7H_2O$ 0.174 g/L, $Fe(NH_4)_2SO_4·6H_2O$ 0.116 g/L, $CoCl_2·6H_2O$ 0.025 g/L, $(NH_4)_6Mo_7O_{24}·4H_2O$ 0.022 g/L and $CuSO_4·5H_2O$ 0.008 g/L, $MnSO_4·4H_2O$ 0.008 g/L. Cell was harvested at exponential phase and broken by FastPrep-24™ 5G Homogenizer system (MP Biomedicals, Korea). The cell lysate was centrifuged at 13,000 rpm in 30 min and the supernatant was collected and sterilized through 0.2 μm membrane filter. The obtained lysate solution was used for bioassay. Coenzyme $B_{12}$ was quantified by using a mutant strain *Salmonella typhimurium* $metE^-$ $chiB^-$. Briefly, in *Salmonella typhimurium*, metE encodes $B_{12}$ independent methionine synthase and chiB encoding adenosylcobinamide-phosphate synthase, an essential enzyme for $B_{12}$ synthesis pathway. Mutation of these genes makes *S. typhimurium* becomes auxotroph to $B_{12}$ or methionine. Indicator strain *S. typhimurium* $metE^-$ $cbiB^-$ was pre-cultured in minimal medium containing NaCl, 0.5 g/L; $Na_2HPO_4$, 6 g/L; $KH_2PO_4$, 3 g/L; $NH_4Cl$ 1 g/L; glucose, 4 g/L; $MgSO_4$, 2 mM, $CaCl_2$ 0.1 mM with the supplementation of 50 mg/L methionine. The overnight broth was centrifuged and washed with water. The washed cells were inoculated with initial $OD_{600}$ of 0.01 in minimal medium. The cell lysate needed to measure $B_{12}$ was added to culture broth. The growth of indicator strain reflects the concentration of coenzyme $B_{12}$ in the sample. The concentration of coenzyme $B_{12}$ was varied to make the standard curve. The dynamic range of $B_{12}$ concentration was from 0 to 100 pM $B_{12}$. The concentration of $B_{12}$ was expressed as nM per 1 $OD_{600}$.

Example 20. Identification of bgpM as an Essential Gene for B12 Synthesis

Figure 29A:
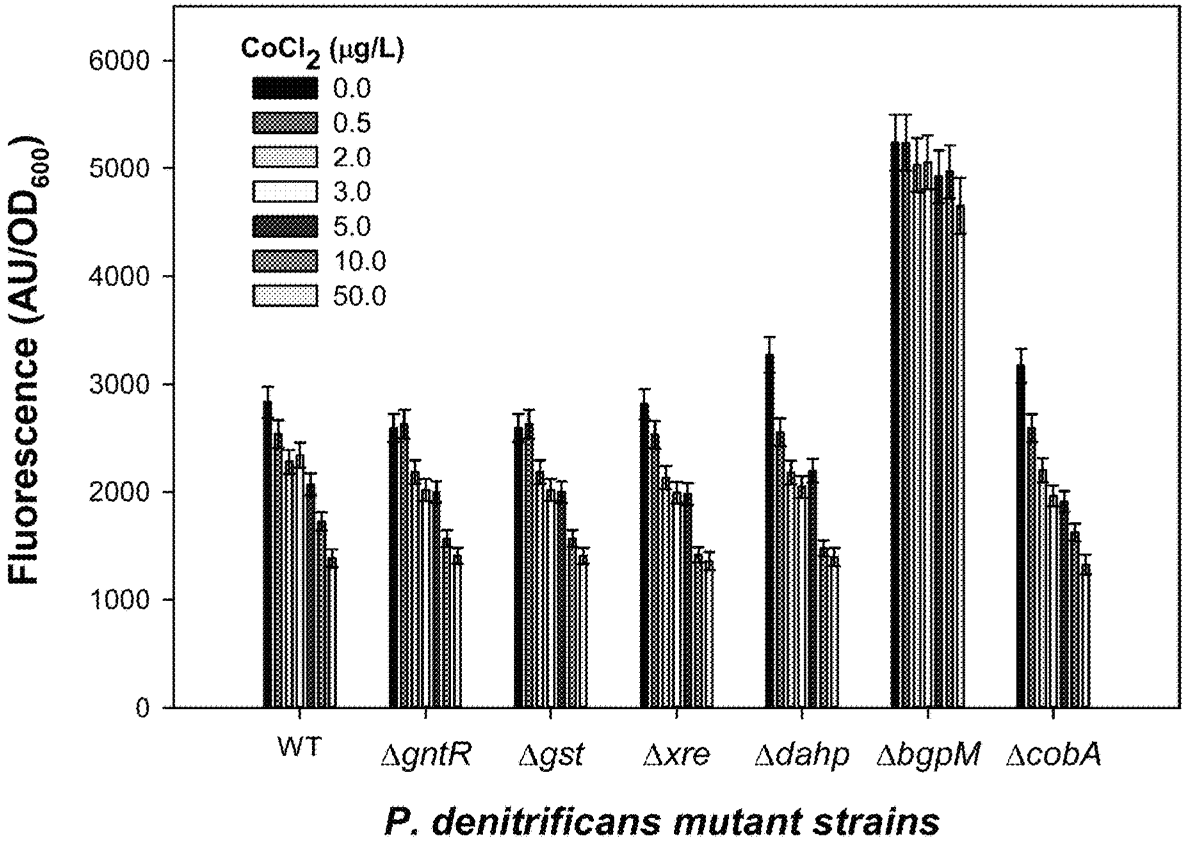
FIGS. 29A-B is a set of graphs showing (FIG. 29A) Gene essentiality profiling revealed that only gene encoding for bgpM is essential for coenzyme B 12 biosynthesis. The varied concentration of cobalt chloride was used to understand the essentiality of several uncharacterized or less understood genes within the cob gene cluster.
Figure 29B:
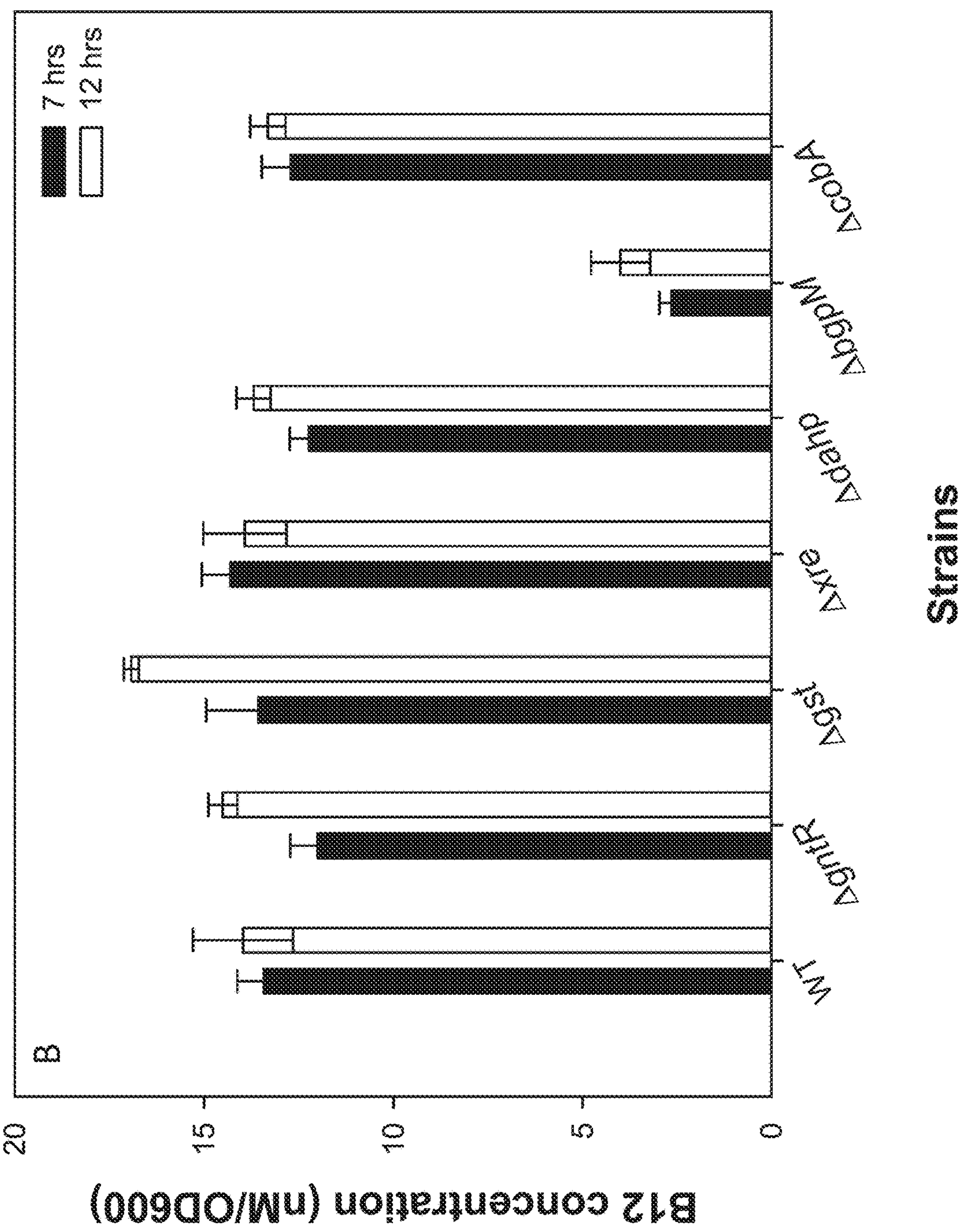

For complete insight on the essentiality of genes within the cob biosynthetic operon, the essentiality of several uncharacterized genes within the cob gene cluster, such as gnt, gst, xre, dahp and bgpM, for $B_{12}$ biosynthesis was studied. To elucidate whether these genes are necessary for $B_{12}$ biosynthesis, single knockout mutants of each of these genes were created. The $B_{12}$ biosynthetic capability of these mutant strains was investigated, using both the $B_{12}$-specific riboswitch sensor system described in the Example above, and the conventional *S. typhimurium* $metE^-$ $chiB^-$ based $B_{12}$-assay systems (see materials). As coenzyme $B_{12}$ biosynthesis involves cobalt in its metal center, its biosynthesis depends on the concentration of $CoCl_2$. When these mutant strains were cultivated with increased concentrations of $CoCl_2$ (up to 50 μg $L^{-1}$), the GFP-florescence decreased proportionally, except for the ΔbgpM mutant (FIG. 29A). These results indicate that each of these mutant strains could synthesize coenzyme $B_{12}$ similar to that of the wild type strain, except for ΔbgpM. The gene product of bgpM plays an essential role for the biosynthesis of coenzyme $B_{12}$ in *P. denitrificans*. However, its precise role in $B_{12}$ biosynthesis is yet to be elucidated. An essentiality analysis was also performed using *S. typhimurium* as an indicator strain. The intracellular concentration of coenzyme $B_{12}$ synthesized by these mutant strains was quantified (FIG. 29B). Similar to the results in *P. denitrificans*, only the ΔbgpM mutant could not synthesize (or could only synthesize trace amounts of) coenzyme $B_{12}$ (~7-fold lower $B_{12}$ than the wild type strain). Based on these results, the genes located at IR2 (see FIG. 23) are not essential for $B_{12}$ biosynthesis. Therefore, overexpression of these genes might not be effective in enhancing coenzyme $B_{12}$ production. Surprisingly, a cobA deletion mutant (encoding for uroporphyrinogen methyltransferase), an important branching point in $B_{12}$ biosynthesis pathway, could still synthesize coenzyme $B_{12}$ (FIG. 29B). Upon further analysis, we identified the presence of several CobA isoenzymes in the genome of *P. denitrificans* that might substitute for the role of CobA in *P. denitrificans*.

Example 21. Coenzyme B12 Production is Improved by the Deletion of Riboswitch Structures To improve $B_{12}$ production, the identified negative regulatory domains (P5-L5 regions) of all the riboswitch structures were deleted individually. The mRNA levels produced by these riboswitch-deleted mutants were quantified in the presence and absence of coenzyme $B_{12}$ (Table 7). In the presence of coenzyme $B_{12}$ at >5 nM, the cob operon transcription can be suppressed due to the riboswitches in *P. denitrificans* strain, while in the riboswitch mutant strains, the presence of coenzyme $B_{12}$ could result in higher amount of coenzyme $B_{12}$ production. Therefore, it would be easier to evaluate enhancement of the coenzyme $B_{12}$ biosynthetic genes due to mutation in riboswitches by measuring the amount of $B_{12}$ synthesized by these mutant strains. Interestingly, there was no significant difference in coenzyme $B_{12}$ production in the ΔRS1 (riboswitch 1 deleted) and ΔRS2/RS3 (riboswitches 2 and 3 deleted) mutants, compared to the wildtype strain. However, there was a significant difference in coenzyme $B_{12}$ in the ΔRS4 (riboswitch 4 deleted) mutant when compared to wildtype. The production of coenzyme $B_{12}$ was substantially repressed in the ΔRS4 strain. The above results show that the deletions in ΔRS1 and ΔRS2/RS3 did not influence coenzyme $B_{12}$ production, while the ΔRS4 deletion substantially decreased coenzyme $B_{12}$ production. One possibility is that the regions in riboswitches 1, 2, and 3 that were randomly selected for mutation were not sufficient to eliminate function, therefore we did not see any alteration in coenzyme $B_{12}$ production in the ΔRS1 and ΔRS2/RS3 mutant strains. On the other hand, the mutation in ΔRS4 likely affects protein expression, as the riboswitch was overlapping with the coding region. To overcome this limitation, instead of developing a deletion mutant, we modified riboswitch regions where the secondary structures in mRNA are mutationally neutralized, and at the same time the protein sequence is maintained by codon optimization.

TABLE 7

Transcription levels of $B_{12}$ synthetic genes in the presence and absence of 25 mg/L $CoCl_2$.

| Genes | WT | WT ($CoCl_2$) | ΔRS1 | ΔRS1 ($CoCl_2$) | ΔRS2,3 | ΔRS2,3 ($CoCl_2$) | ΔRS4 | ΔRS4 ($CoCl_2$) |
|---|---|---|---|---|---|---|---|---|
| rpoD | 1.00 | 1.00 | 1.00 | 1.00 | 1.00 | 1.00 | 1.00 | 1.00 |
| cobG | 0.26 | 0.05 | 0.28 | 0.05 | 0.30 | 0.05 | 0.28 | 0.18 |
| cobW | 0.28 | 0.07 | 0.32 | 0.08 | 0.35 | 0.09 | 0.28 | 0.26 |

TABLE 7-continued

Transcription levels of $B_{12}$ synthetic genes in the presence and absence of 25 mg/L $CoCl_2$.

| Genes | WT | WT ($CoCl_2$) | ΔRS1 | ΔRS1 ($CoCl_2$) | ΔRS2,3 | ΔRS2,3 ($CoCl_2$) | ΔRS4 | ΔRS4 ($CoCl_2$) |
|---|---|---|---|---|---|---|---|---|
| cbtB | 0.94 | 0.16 | 0.88 | 0.19 | 0.82 | 0.22 | 0.92 | 0.63 |
| btuB | 0.17 | 0.04 | 0.17 | 0.04 | 0.17 | 0.04 | 0.13 | 0.13 |

We designed the sequences using software, and the nucleic acids were chemically synthesized and replaced in the genome to avoid secondary structure formation in the cob mRNA, which encodes enzymes of the coenzyme $B_{12}$ synthetic pathway. We developed seven recombinant strains by changing each riboswitch, or a combination of riboswitches. Interestingly we noticed that when riboswitch 1 was deleted (ΔRS1 strain), a there was marginal decrease in cell growth and coenzyme $B_{12}$ production was noticed. This could possibly be due to the accumulation of some toxic intermediate. However, deletion of riboswitches 2 and 3 (ΔRS2/RS3) or riboswitch 4 (ΔRS4) did not improve coenzyme $B_{12}$ production. This could be due to a limitation in the upper pathway carbon flux. However, when riboswitch 1 was deleted either with riboswitches 2 and 3 (ΔRS1 ΔRS2/RS3) or with riboswitch 4 (ΔRS1 ΔRS4), there was marginal improvement in coenzyme $B_{12}$ production. Moreover, a mutant strain lacking all the riboswitches showed comparably higher coenzyme $B_{12}$ production (Table 8).

This study showed that coenzyme $B_{12}$ production by *P. denitrificans* can be improved by removing the secondary structures from the cob mRNA. When the mutant strain with improved coenzyme $B_{12}$ production was used as host to produce 3-HP (or a salt thereof) from glycerol, it produced <38.6 g/L of 3-HP (Table 8). This mutant strain produced marginally higher 3-HP titers than the wild type strain, which produced <30 g/L. The improvement in 3-HP production from glycerol by the mutant strain compared to the wildtype strain can be attributed to an improved coenzyme $B_{12}$ pathway. When this mutant strain was externally supplemented with 10 mg/L of coenzyme $B_{12}$ in the culture medium, the strain could produce 3-HP production from glycerol at ~100 g/L (FIG. 50). These experiments clearly indicated the mutant strain had increased coenzyme $B_{12}$ production, however, this strain could be modified further to more significantly increase production of higher titers of 3-HP.

To further improve coenzyme $B_{12}$ production, the native promoters of the cob operons in the riboswitch mutant strain were replaced with the synthetic expression modules (Tandem promoter, UTR, regulatory protein, N-terminal region of highly expressing genes) described in the Example above. An analysis of cob gene clusters showed the presence of five promoters controlling the expression of genes in B12 biosynthetic pathway, several recombinant strains were developed by replacing native promoters individually or in combination as shown in Table 8. The choice of promoters chosen for promoter replacement was tabulated 10. The replacement of each promoter showed a marginal improvement in coenzyme $B_{12}$ production, however, when all of the promoters were replaced with the synthetic gene expressing module, a substantial improvement in coenzyme $B_{12}$ was noticed. When this strain (PhpdH-Pedd-IR15-PsucA-PhpdH: PhpdH-Ptkt-IR45-Psp2-PhpdH) was used as a host to produce 3-HP from glycerol in a bioreactor, the strain was able to produce ~100 g/L of 3-HP, which is similar to the amount of 3-HP that can be produced when wild-type *P. denitrificans* is externally supplemented with coenzyme $B_{12}$ (up to 50 mg/L) in a bioreactor to produce industrial quantities of 3-HP (see FIG. 50). Thus, we successfully developed a recombinant *P. denitrificans* strain which could synthesis higher amount of coenzyme $B_{12}$, which in turn supports the commercial scale production of 3-HP from crude glycerol without the need for external supplementation of coenzyme $B_{12}$. The production cost for 3-HP from glycerol was substantially decreased, as nearly 38% of 3-HP production cost is attributed to the costs of externally supplying coenzyme $B_{12}$ to the culture medium.

TABLE 8

Summary on the development and evaluation of various coenzyme B12 overproducing *P. denitrificans* strains.

| *Pseudomonas* recombinant strains | B12 operons modified | B12 production ($nM/OD_{600}$) 9 h | 18 h | 3-HP production (g/L) |
|---|---|---|---|---|
| *P. denitrificans* | | 4.1 | 5.3 | 20.8 |
| I. Riboswitch disruption | | | | |
| IR1-RS1 | 1, 2 | 7.2 | 8.1 | 38.6 |
| IR4-RS2 | 3 | 6.6 | 7.9 | 35.4 |
| IR4-RS3 | 4 | 6.1 | 8.3 | 36.9 |
| IR5-RS4 | 5 | 1.6 | 3.9 | 16.2 |
| II. Promoter replacement by constitutive or inducible | | | | |
| Pedd-IR13-PsucA | 1, 2 | 16.5 | 21.0 | 63.6 |
| Psp9-IR15-Pzwf | 1, 2 | 8.8 | 17.5 | 54.7 |
| Pzwf-IR43-Psp9 | 3, 4 | 12.0 | 13.2 | 52.9 |
| Ptkt-IR45-Psp2 | 3, 4 | 12.6 | 11.0 | 53.1 |
| IR55-Psp9 | 5 | 2.0 | 4.8 | 12.6 |
| Pedd-IR13-PsucA: Pzwf-IR43-Psp9 | 1, 2, 3, 4 | 7.0 | 19.6 | 51.6 |
| Pedd-IR13-PsucA: Ptkt-IR45-Psp2 | 1, 2, 3, 4 | 9.3 | 17.5 | 54.2 |
| Pedd-IR13-PsucA: IR55-Psp9 | 1, 2, 5 | ND | 1.3 | 4.9 |
| Psp9-IR15-Pzwf: Pzwf-IR43-Psp9 | 1, 2, 3, 4 | 6.7 | 15.6 | 48.7 |
| Psp9-IR15-Pzwf: Ptkt-IR45-Psp2 | 1, 2, 3, 4 | 13.5 | 19.8 | 61.2 |
| Psp9-IR15-Pzwf: IR55-Psp9 | 1, 2, 5 | 1.8 | 4.0 | 11.2 |
| Pzwf-IR43-Psp9: IR55-Psp9 | 3, 4, 5 | 1.6 | 2.2 | 10.9 |
| Ptkt-IR45-Psp2: IR55-Psp9 | 3, 4, 5 | 1.1 | 1.9 | 9.2 |
| III. Tandem promoters | | | | |
| PhpdH-Pedd-IR13-PsucA-PhpdH | 1, 2 | 32.5 | 59.1 | 91.7 |
| PhpdH-Pedd-IR15-PsucA-PhpdH: PhpdH-Ptkt-IR45-Psp2-PhpdH | 1, 2, 3, 4 | 37.9 | 68.4 | 101.8 |

Example 22. Development of an Aldehyde-Dehydrogenase Expression Cassette

Figure 30A:
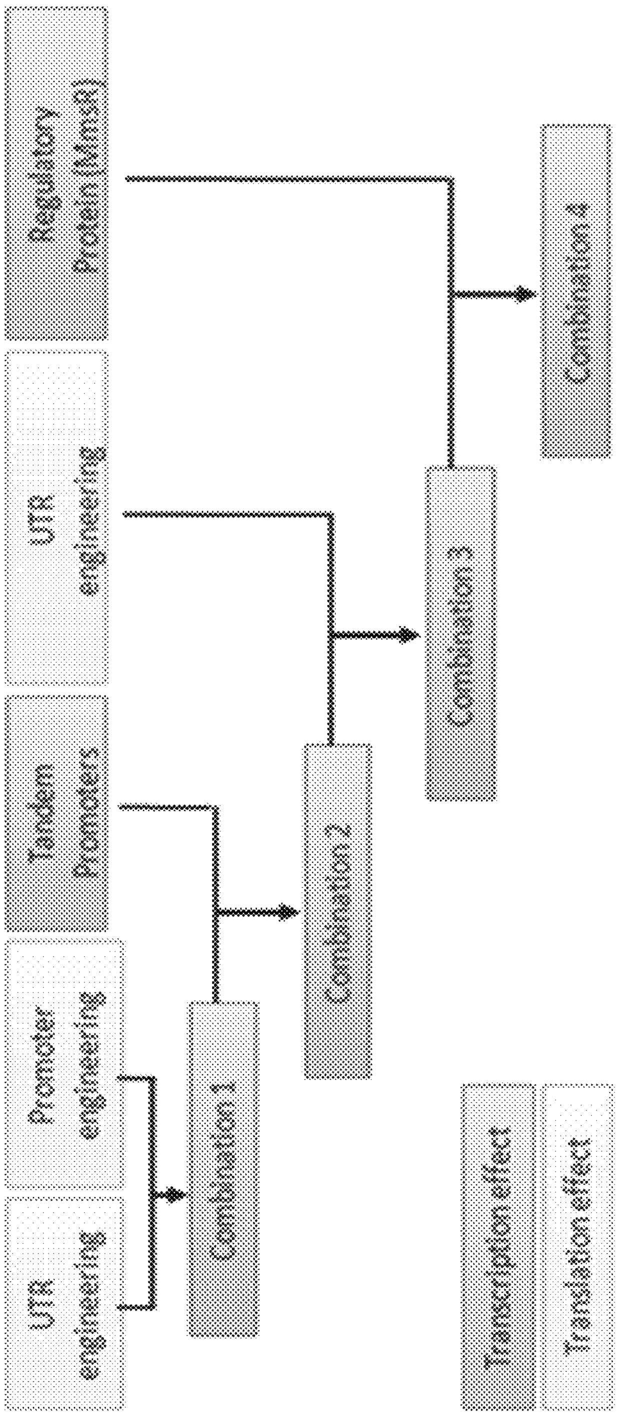
FIGS. 30A-B are a set of schematics showing development of dhaB-gdrAB expression cassette.
Figure 30B:
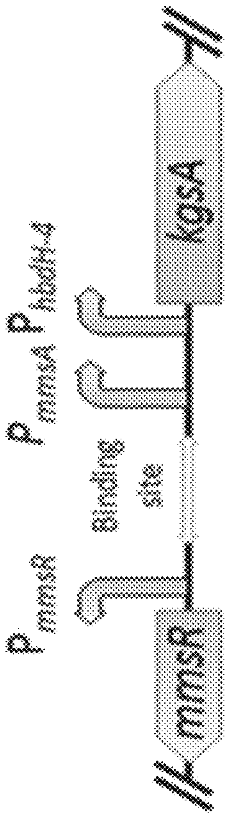

Aldehyde dehydrogenase (ALDH) catalyzes the conversion of 3-HPA to 3-HP (second reaction in 3-HP synthetic pathway). In order to minimize the accumulation of 3-HPA in the cell, which is toxic, the expression of ALDH (e.g., by the kgsA gene) should be maintained at a higher level than that glycerol dehydratase (DhaB). Furthermore, to integrate ALDH into the chromosome, its expression was increased to an even higher level (to track the observed gene expression from plasmids). To achieve this, the expression module/cassette containing the inducible tandem promoter system described in the Examples above was employed as the base promoter to drive a gene that expresses ALDH (e.g., kgsA), and further developed The strength of the ALDH expression cassette was varied/improved via various genetic alternations, as described in the Example above. To summarize, the expression module/cassette had the following features: (i) a tandem promoter, with one promoter inducible and the other promoter constitutive or inducible, of which the promoters may be native to the host microorganism or synthetic; (ii) a mutation (randomization) of the binding (operator) site of the activator protein in the promoter region (iii) a change in expression level of activator protein; (iv) a fusion of varying length, wherein a portion of the N-terminus of a highly expressing native protein, e.g., MmsA, is fused to ALDH, and codon optimization of the first 10 codons of ALDH (according to the codon usage of the host microorganism, e.g., *P. denitrificans*); and (v) 5'-untranslated region (UTR) engineering (see FIG. 30A for a schematic of genetic modifications to the expression system; see FIG. 30B for the expression system used to integrate ALDH expressing gene into the chromosome).

Example 23. Development of a DhaB-GdrAB Expression Cassette

Figure 31A:
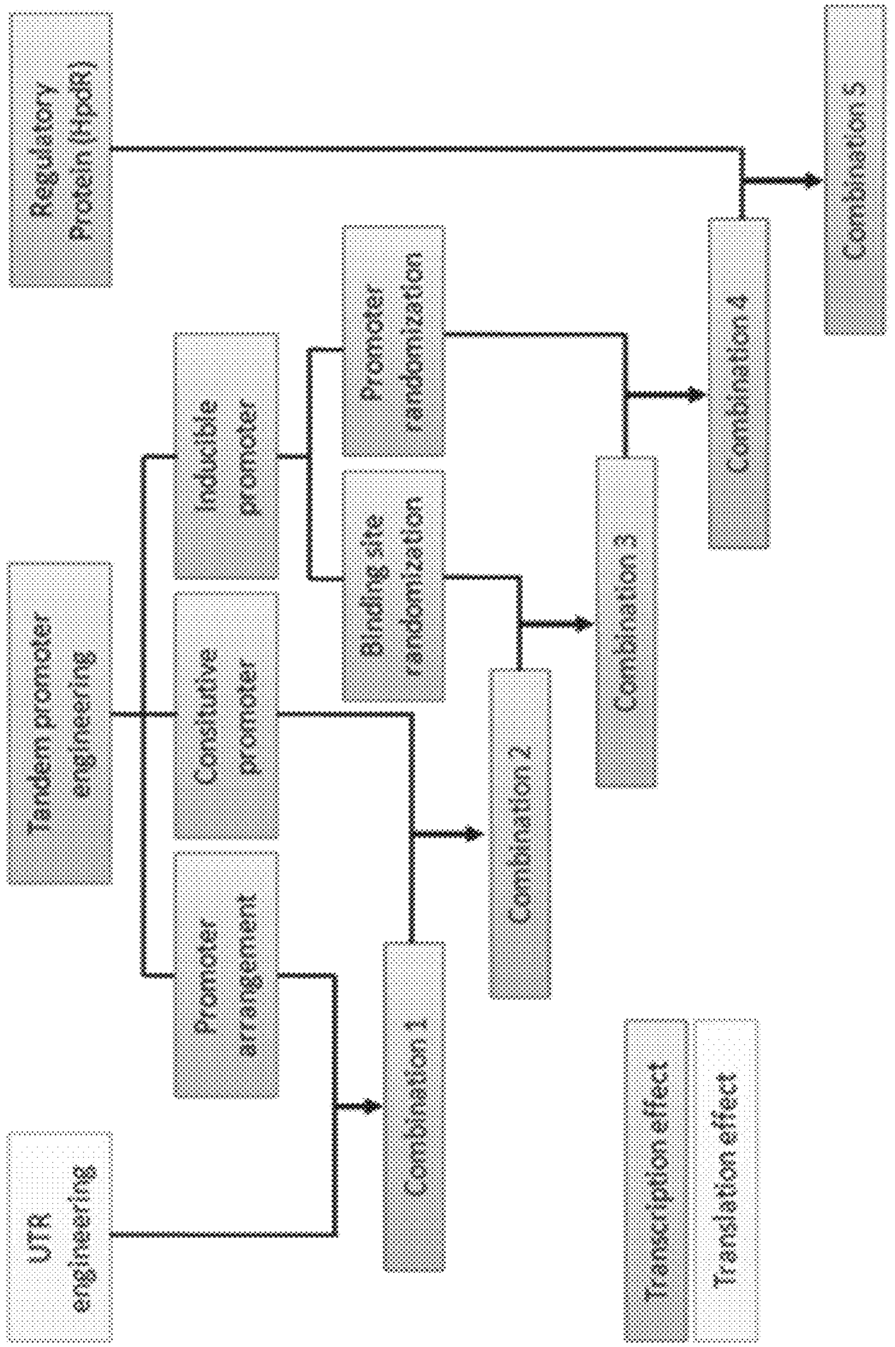
FIGS. 31A-B are schematics showing the combination of transcriptional and translational modifications that were used for the development of a DhaB-GdrAB expression system (FIG. 31A) and a schematic (FIG. 31B) of the DhaB-GdrAB (DhaB) expression system for integration in the chromosome.
Figure 31B:
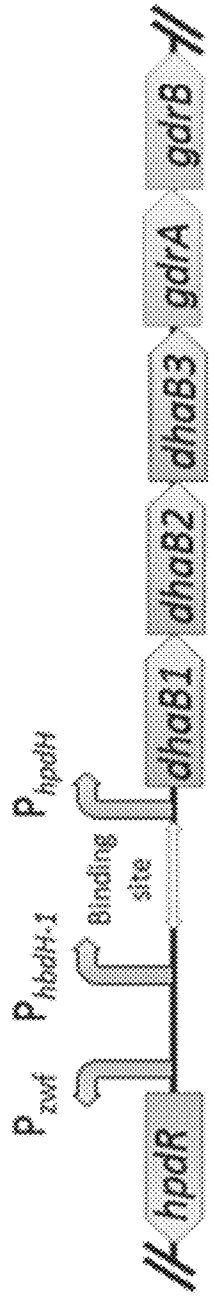

The dhaB and gdrAB genes were integrated into the chromosome of *P. denitrificans*, and their expression levels were improved by enhancing both transcription and translation efficiencies. To avoid 3-HPA accumulation, dhaB and gdrAB should be expressed at lower levels than ALDH. To achieve this, a 3-HP inducible promoter that is of medium strength, relative to the promoter used to produce ALDH, was used to drive the expression of the dhaB and gdrAB genes. The expression cassette was designed as follows: (i) UTR engineering; (ii) use of tandem promoters, with one promoter constitutive and the other promoter inducible; (iii) modification of the constitutive promoter; (iv) modification of the inducible promoter (−10 and −35 boxes) and the binding (operator) sites of the activator protein, HpdR; and (v) variation of the expression level of the activator protein (see FIG. 31A for a schematic of genetic modifications to the expression system; see FIG. 31B for the expression system used to integrate DhaB into the chromosome).

Thus, the aldehyde-dehydrogenase expression cassette described in Example 22, and the DhaB-gdrAB expression cassette described here, were used to produce 3-HP from glycerol by recombinant strains.

Example 24. Expression of ALDH and DhaB from Plasmids Using *Pseudomonas denitrificans*

*P. denitrificans* Δ3hpdhΔ3hibdhIVΔ3hibdhIpUCPK' was transformed with different combinations of plasmids for the expression of DhaB a KgsA. The plasmids carried different expression modules of different strengths. Thus a range of different strength promoters driving expression of DhaB and KgsA were tested, in order to find those expression modules for DhaB and KgsA that, together, would produce large amounts of 3-HP. In order to try to avoid 3-HPA accumulation, while still allowing significant 3-HP production and cell growth, lower strength expression modules were used for DhaB, GdrAB expression, while higher strength expression modules were used for KgsA expression.

Among all the strains produced, one strain designated as P1-1 exhibited substantial 3-HP production in a bioreactor experiment (see Table 9). However, in this strain, we determined that ALDH activity was relatively low and the toxic intermediate 3-HPA appeared during an early period of fermentation. Using P1-1 as a reference strain (with reference expression levels of DhaB, GdrAB, and KgsA), we next sought to reduce 3-HPA accumulation by increasing plasmid expression levels of ALDH. We developed a series of plasmids that expressed higher ALDH levels by employing the various gene expression cassettes described in the Examples above. These plasmids were introduced into *P. denitrificans* to generate the strains, P1-1x (x=a, b, c, d, . . . ). The ALDH activity in crude cell extract of the newly developed recombinant strains was increased to between 10 to 19 U/mg protein, relative to an ALDH activity of 2.5 U/mg protein in the P1-1 strain. The recombinant strains were evaluated for 3-HP production at bioreactor scale.

TABLE 9

Evaluation of *P. denitrificans* strains expressing KgsA and DhaB from plasmid

| Strain | DhaB activity[a] (U/mg) | KgsA activity[a] (U/mg) | Cell growth[b] | Productivity[b] (g/L/h) | Titer[b] (g/L) | Yield[b] (mol/mol) |
|---|---|---|---|---|---|---|
| P1-1 | 0.95 | 2.50 | 5.55 | 1.69 | 81.21 | 0.94 |
| P1-2 | 0.95 | 10.58 | 5.25 | 1.34 | 64.53 | 0.95 |
| P1-3 | 0.95 | 14.00 | 5.72 | 1.34 | 64.38 | 0.97 |
| P1-4 | 0.95 | 18.97 | 5.58 | 1.32 | 63.95 | 0.97 |
| P1-5 | 0.95 | 12.39 | 5.23 | 1.38 | 62.30 | 0.96 |

[a]Measured from flask experiments 4 h after induction with 25 mM 3-HP.
[b]From bioreactor experiments.

Example 25. Development of *P. denitrificans* with Chromosomal Integration of the ALDH Expression Module, and an Episomal DhaB Expression Module Development of the ALDH Integrant Strain:

The chromosomal location of integration is known to affect the expression level of integrated genes and should be selected carefully. Generally, a gene is more highly expressed when located closer to an origin of replication, due to a gene dosage effect. The kgsA gene was first integrated in place of the endogenous mmsA gene, which is located ~3,000 Kb away from the replication origin. The mmsA gene expression unit (i.e., intergenic region and mmsA) on the chromosome was replaced by a kgsA expression cassette (see FIG. 30; the expression cassette had tandem promoters (20 amino acids of mmsA fused to the N-terminus of kgsA (hybrid protein); codon optimization of the first 10 codons of kgsA; and an a modified UTR (UTR-6)) to create a first KgsA integrant strain (designated as P2-0). For P2-0, wild type kgsA was used.

Figure 32:
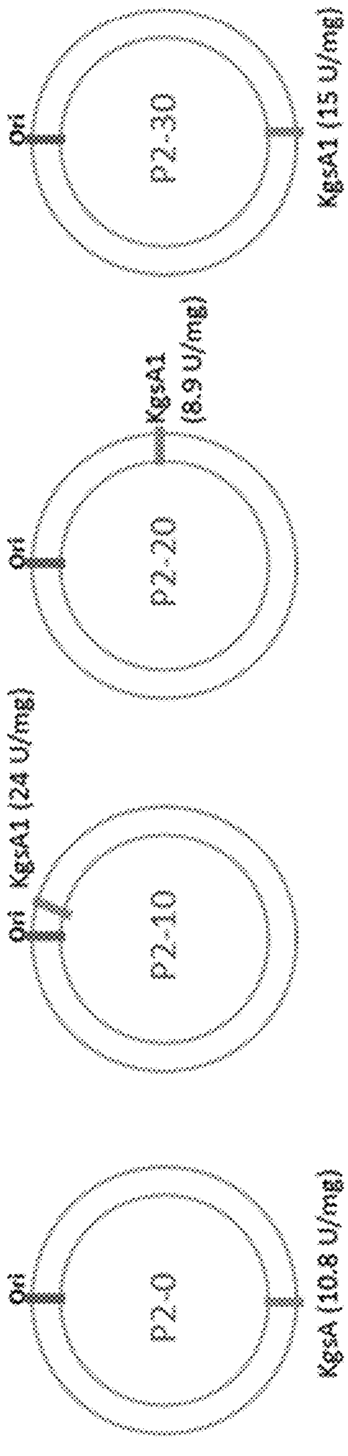
FIG. 32 is a set of cartoons showing the effect of genome location on the expression of KgsA (e.g., location of kgsA gene and activity of KgsA after chromosomal integration (P2-0, P2-10, P2-20, P2-30; the strains without the plasmid for DhaB). The numbers indicate the KgsA activity 4 hours after induction with 25 mM 3-HP.

More integrant strains (e.g., P2-0, P2-10, P2-20, and P2-30) were developed by changing the location of integration (see FIG. 32). For these strains, a fusion kgsA gene, was employed (e.g., 20 amino acids of mmsA fused to the N-terminus of a kgsA gene). Many strains with kgsA at different locations of the chromosome, for example ~500 Kb (P2-10), ~1500 Kb (P2-20), ~3000 Kb (P2-30) away from the replication origin, were studied. These strains did not have a plasmid expressing DhaB. The strains were induced with 25 mM of 3-HP for 4 hours, and KgsA activity was assayed. FIG. 32 shows that the P2-10, where mutant kgsA was located closest to the replication origin, produced the most KgsA1 activity (24 U/mg). The P2-30 strain, having a mutant kgsA inserted at the same chromosomal location as the P2-0 strain (wild type kgsA), produced more protein than the P2-0 strain (15 U/mg vs. 10.8 U/mg, respectively). The result shows that; (i) when tested after integration at the same chromosomal location, mutant KgsA1 activity was higher than that of KgsA, and (ii) ALDH activity significantly varied depending on the location of its chromosomal integration (FIG. 32).

Varying Expression of DhaB from Plasmids, and Chromosome-Integrated KgsA:

The ratio of DhaB and ALDH could be varied by modulating the expression of episomal DhaB from a plasmid and/or the expression of chromosome-integrated ALDH. Only the recombinant P2-0 and P2-10 strains were modified with plasmids containing DhaB expression cassettes (dhaB gdrAB in pUCPK backbone) (Table 11). The P2 strains depicted in Table 11 differ in the promoter systems used to express the DhaB expression cassette. Promoters used for P2-1 to P2-5 are as follows: Pc3, Pc3 with UTR design (i.e., modified UTR, as described herein), Pc3-Pc1 with UTR design, Pc1-Pc3 with UTR design, and Pc3-Pzwf with UTR design respectively. These promoter systems vary in their promoter strengths in ascending order.

TABLE 11

Evaluation of *P. denitrificans* strains with chromosomal ALDH and episomal DhaB

| Strain | DhaB activity[a] (U/mg) | ALDH activity[a] (U/mg) | Cell growth[b] | Productivity[b] (g/L/h) | Titer[b] (g/L) | Yield[b] (mol/mol) |
|---|---|---|---|---|---|---|
| P2-1 | 1 | 10.8 | 4.84 | 1.48 | 71.26 | 0.96 |
| P2-2 | 1.2 | 10.8 | 6.71 | 1.85 | 88.64 | 0.93 |
| P2-3 | 3.9 | 10.8 | 6.48 | 1.76 | 84.53 | 0.96 |
| P2-4 | 5.8 | 10.8 | 6.03 | 1.79 | 86.08 | 0.95 |
| P2-5 | 7.8 | 10.8 | 6.59 | 1.90 | 91.47 | 0.97 |

[a]Measured from flask experiments 4 h after induction with 25 mM 3-HP.
[b]From bioreactor experiments.

Figure 33:
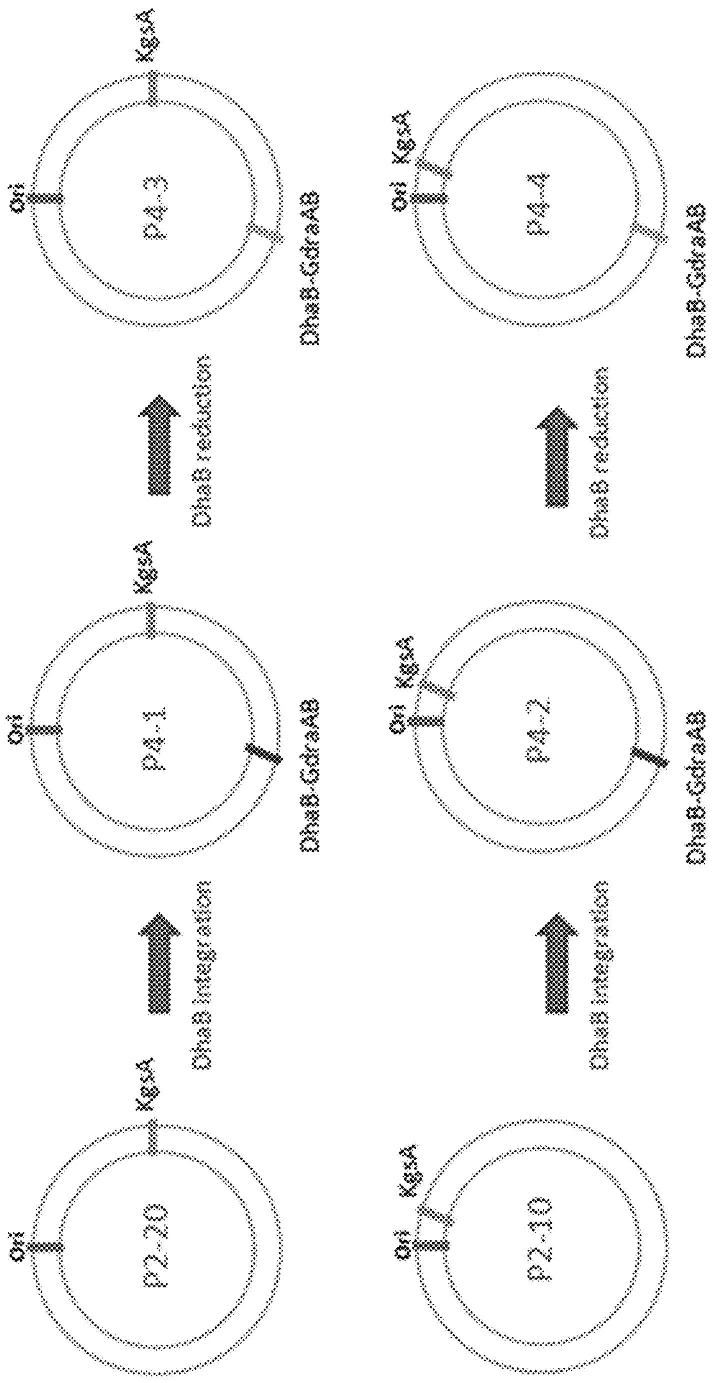
FIG. 33 is a set of cartoons showing the genomic integration of the DhaB expression cassette into the chromosome of P2-20 strain to create P4-1, or into P2-10 to create P4-2. The promoters of the DhaB-GdrAB expression cassettes in the P4-1 and P4-2 were subsequently weakened (DhaB reduction) to create strains P4-3 and P4-4.
Figure 34:
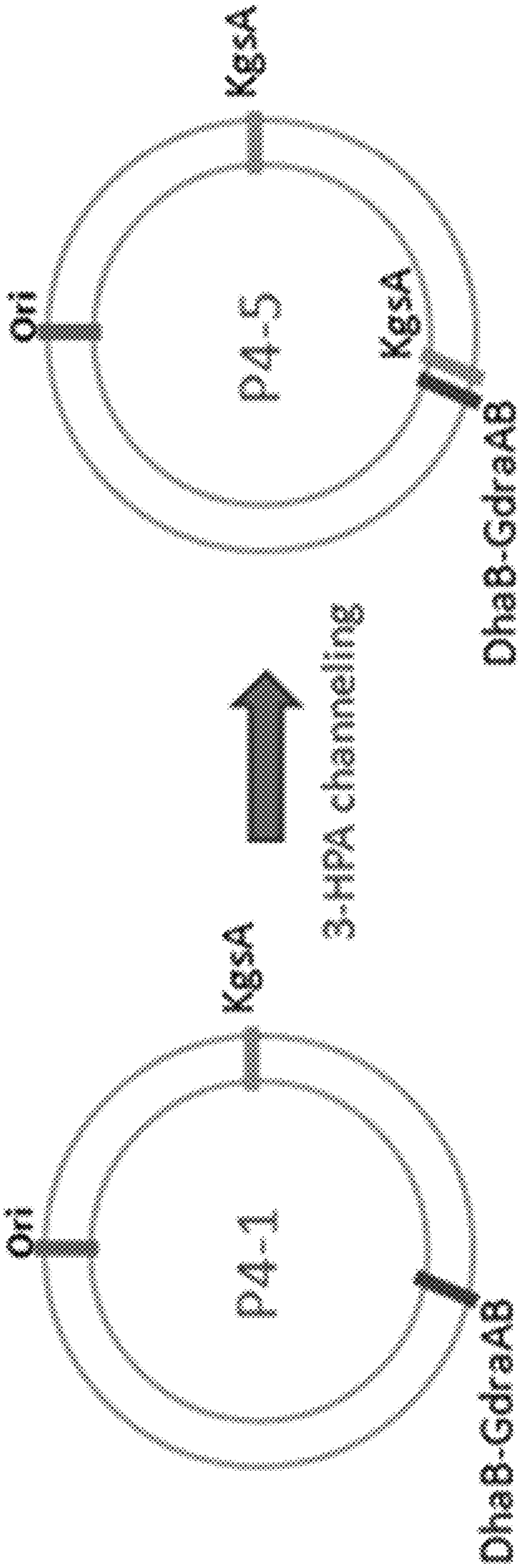
FIG. 34 is a cartoon showing the strain development for 3-HPA channeling (P4-5). P4-5 has one copy of KgsA located close to DhaB.

Example 26. Development of Recombinant *P. denitrificans* with Chromosomal Integration of ALDH and DhaB Optimization of the DhaB/ALDH Ratio:

Recombinant *Pseudomonas denitrificans* strains with both the DhaB-GdrAB and the KgsA expression cassettes integrated into the chromosome were developed. As described in the Examples above, ALDH activity varies depending on the chromosomal location of the kgsA gene insertion (FIG. 32), and we developed several integrants for ALDH showing different activities (P2-10, P2-20, P2-30). We integrated the DhaB-GdrAB expression cassette into the P2-10 and P2-20 recombinant strains described in Example 25. The location of the chromosomal integration site of the DhaB-GdrAB expression cassette was varied in relation to the KgsA expression cassette in the recombinant strains. For example, the P4-1 integrant strain was developed by integrating the DhaB-GdrAB expression cassette (see FIG. 31B) into the chromosome of the host P2-20 (see FIGS. 32 and 37). In the P4-1 strain, the DhaB-GdrAB cassette was integrated ~4,150 kb away from the replication origin. The P4-1 strain highly expressed DhaB and KgsA from the chromosome (Table 12). Additional strains were developed to optimize the ratio between DhaB and KgsA activity by varying the expression of KgsA, DhaB, or both KgsA and DhaB. We also took the P2-10 strain and integrated the DhaB-GdrAB cassette (the same cassette that was used for P4-1), thereby creating the P4-2 strain (FIG. 33).

Further, to reduce DhaB expression relative to KgsA expression, the promoter regions of the DhaB cassette in P4-1 and P4-2 were modified. We selected a weaker promoter for expressing DhaB cassette (see Example 10). This resulted in the two new integrant strains, P4-3 and P4-4, respectively (FIG. 33). Table 12 summarizes the DhaB and KgsA activity in each of these strains. In the strains P4-3 and P4-4, tandem promoter Pc3-$P_{zwf}$ was used with lower promoter strength than the Pc1-Pc3 tandem promoter used in P4-1 and P4-1 strains. Promoter strengths were weakened in the P4-5 and P4-6 strains for KgsA expression.

TABLE 12

Evaluation of recombinant *P. denitrificans* strains with chromosomal integration for both KgsA and DhaB

| Strain | DhaB activity[a] (U/mg) | KgsA activity[a] (U/mg) | Cell growth[b] | Productivity[b] (g/L/h) | Titer[b] (g/L) | Yield[b] (mol/mol) |
|---|---|---|---|---|---|---|
| P4-1 | 4.1 | 6.7 | 5.30 | 1.73 | 82.9 | 0.95 |
| P4-2 | 3.0 | 21.0 | 4.62 | 2.07 | 99.2 | 0.97 |
| P4-3 | 1.2 | 7.0 | 4.80 | 1.71 | 82.0 | 0.97 |
| P4-4 | 0.75 | 24.0 | 4.42 | 1.86 | 89.2 | 0.96 |
| P4-5 | 3.5 | 11.8 | 4.19 | 1.99 | 95.4 | 0.93 |
| P4-6 | 4.0 | 7.2 | 4.01 | 1.83 | 87.7 | 0.95 |

[a]Measured from flask cultures 4 h after induction with 3-HP.

[b]Measured from bioreactor experiments.

Example 27: Channeling of DhaB and KgsA

A clustered arrangement of genes encoding enzymes of one pathway is observed in bacteria to avoid accumulation of intermediates of specific pathway in the cell. It is important to notice that in prokaryotes such as bacteria, transcription and translation happens simultaneously. In most of the cases the product of first enzyme will be the substrate of second enzyme. If the genes are located close to each other the substrate for the second gene/enzyme will be localized near to it. This kind of mechanism can increase the efficiency of a pathway and avoid toxicity of intermediates, if any, by immediately consuming it by the second enzyme. This kind of clustering of genes close to each other is known as channeling effect. To improve 3-HP production and cell viability, we channeled 3-HPA through the DhaB and ALDH enzymes to reduce the exposure of other enzymes and cellular components to toxic 3-HPA. We sought to establish a system where 3-HPA is quickly catalyzed to 3-HP. To do this, we studied the effects of varying the locations of DhaB and kgsA (ALDH) relative to each other in the chromosome to promote channeling of 3-HPA. In one strain the dhaB, gdrAB genes, and kgsA were located next to each other. While in another strain, the location of kgsA was more than 2000 bp away from the DhaB and GdrAB encoding genes. As mentioned above, positioning of genes at various locations on the chromosomes influence expression and activity substantially. When the kgsA was placed at different locations (close to DhaB, GdrAB (strain P4-20), and 2000 bp away from DhaB, GdrAB (strain P4-10)) we notice a huge difference in enzyme activities. Both the strains (with (P4-20) and without (P4-10) channeling effect) showed similar KgsA and DhaB activity. The only difference among these two strains was the location of genes to study channeling effect (FIG. 51).

Channeling Effect of 3-HPA on Cellular Metabolism and 3-HP Production.

We examined two strains (with (P4-20) and without (P4-10) channeling effect) showed noticeable differences in 3-HP production. The P4-20 strain, in which the genes located close to each other promoted the channeling effect, showed a higher 3-HP production rate and improved 3-HP titer when compared to the P4-10 strain, in which the genes were located 2000 bp apart on the chromosome. Interesting a marginal difference in 1,3-PDO was also noticed in these strains. P4-10 showed marginally higher 1,3-PDO production when compared to P4-20. This could due to the induction of oxidoreductases by higher 3-HPA accumulation. While in the strain P4-20 where the genes are located next to each other the low 1,3-PDO and high 3-HP indicate that the 3-HPA produced by DhaB enzyme was immediately consumed by the closely located KgsA enzyme, without allowing 3-HPA accumulation.

Example 28. Bioproduction Conditions of 3-HP in Recombinant Organisms

3-Hydroxypropionic acid has been recognized as a potential industrial chemical which can be used as platform chemical to derive industrially important commodity chemicals. Being precursor for commodity (bulk) chemicals its production has to be inexpensive and economical. For biological production of 3-HP or a salt thereof, though several good recombinant strains were developed, however, most of these strains showed good performance when cultivated in analytical grade medium. Analytical grade medium is expensive and not applicable for commercialization of bulk chemicals. Therefore, an industrial medium using inexpensive media components should be formulated which assist the recombinant strains to produce 3-HP from glycerol at commercialization scale. Moreover, the performance of the recombinant strains are highly dependent on the physiological/bioprocess conditions. Therefore, along with industrial medium development the physiological/bioprocess conditions should be carefully optimized to achieve high titer of target product.

The medium used to cultivate microorganisms is combination of many inorganic and organic chemicals. To formulate a good media, it is important to understand the metabolism of the recombinant strains and the properties of the target product. To develop inexpensive medium, several low grade raw materials were used which contain significant amount of unwanted toxic materials. These toxic materials either affect the performance of the strain by reducing its growth and viability or interfere in the purification of the target product. Therefore, selection of correct combination of medium component suitable for the process is painstaking but significantly important. In this study we carefully selected and screened several components and analyzed each components meticulously to formulate industrial medium.

Apart from industrial medium formulation, the bioprocess conditions such as, temperature, pH, aeration, etc. should be studied and optimized in bioreactor conditions. Cellular metabolism and NAD+ regeneration, which are extremely critical to 3-HP production, it was analytically studied by varying physiological parameters under controlled conditions. The effect of pH, which plays a vital role in improving the acid tolerance of recombinant strains and enzyme efficiencies of 3-HP production pathway, was examined. Aeration and temperature and induction time optimization was studied carefully as each physiological parameter significantly influence 3-HP production. Good improvement in performance of recombinant strains to produce 3-HP from glycerol by bioprocess optimization was achieved.

pH

Apart from developing efficient recombinant strains the other serious challenge for the biological production of organic acids at commercially meaningful titers, is to deal with the toxic effects of these acids on the cell growth and cellular metabolisms of the microorganisms producing these acids. As most weak acids are known to have antimicrobial properties. Several mechanisms for the antimicrobial activities of organic acids have been suggested. One such mechanism includes intracellular pH perturbation or a decrease in intracellular pH by protons which cause acid toxicity.

During continuous production of organic acids, which accumulate in the culture broth due to which the concentration of its undissociated form increases according to Henderson-Hasselbalch equation. This undissociated form of acid can easily pass through the plasma membrane and dissociate to proton and to respective anion upon entry into the cytoplasm. The released protons lower the cytoplasmic pH while the anions, on the other hand are reported to affect the specific metabolism and results in impaired growth. Several studies on acid toxicity have been shown to decrease the cytoplasm pH of microorganisms producing organic acid production.

For commercialization, the important factor that affects the microbial 3-HP synthesis at high titer is its toxicity (organic acid toxicity). 3-HP being an isomer of lactic acid is reported to be approximately 4.4-times more toxic than lactic acid due to the weaker acidity or 0.64 higher pKa value. The two acids presented no appreciable difference when the growth inhibition was correlated with the undissociated or protonated free acid concentration calculated by the Henderson-Hasselbalch equation. Chun et al. suggested that the growth inhibition by small weak acids is mainly caused by the proton effect (rather than the anion effect), i.e., an increase in the intracellular proton concentration. In this study, an appropriate increase in the medium pH was suggested to alleviate the acid toxicity by reducing the free acid concentration in the culture medium.

The recombinant strain used in this study is a neutrophile which has optimum growth at 6.8 to 7 pH, however this strain was evolution adapted to grow at 7.5 pH. The target product of our interest is acid (3-HP) or a salt thereof, these recombinant microorganisms produce the target product in cytoplasm and secrete them to the culture media. Uninterrupted production and secretion of acids by microorganisms result in substantially decreasing the pH of culture medium which was explained in detail in earlier sections. For continuous production of 3-HP or a salt thereof and to sustain cell viability the medium should be maintained at neutral pH. Therefore, to maintain pH, neutralizing base has been used in bacterial bioreactor studies. Generally strong base such as NaOH, KOH or even $NH_4OH$ are used to uphold the pH in bacterial bioreactor studies. Use of such strong bases results in accumulation of salts such as Na+ or K+ when NaOH or KOH are used, respectively. This accumulation of salts at high concentration has been reported as toxic to cell growth and its metabolism. On the other hand, ammonium hydroxide or ammonium bicarbonate were used to neutralize acid production, the advantage with ammonia containing neutralizing base is that $NH_3^+$ can be consumed as nitrogen source by microorganisms. While the bicarbonate is reported to have effect on central metabolism, which enhance the flux to TCA cycle and hence improve the cell growth and viablity. Hence using bicarbonate based neutralizing agent was used to develop commercially viable bioprocess for 3-HP production.

Figure 35:
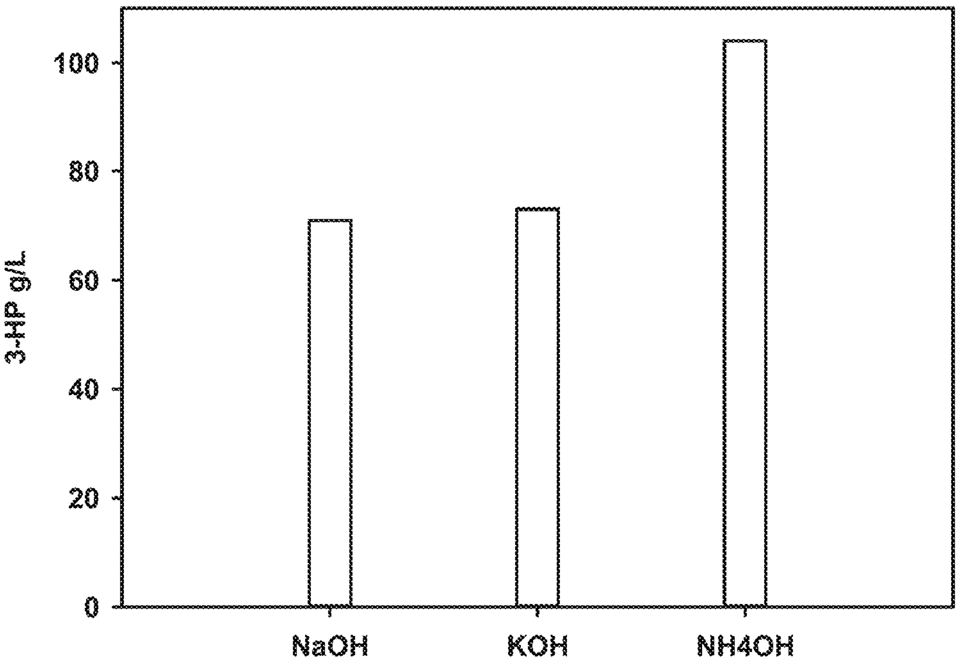
FIG. 35 is a graph showing the effect of various neutralizing bases on the production of 3-HP.
Figure 52:
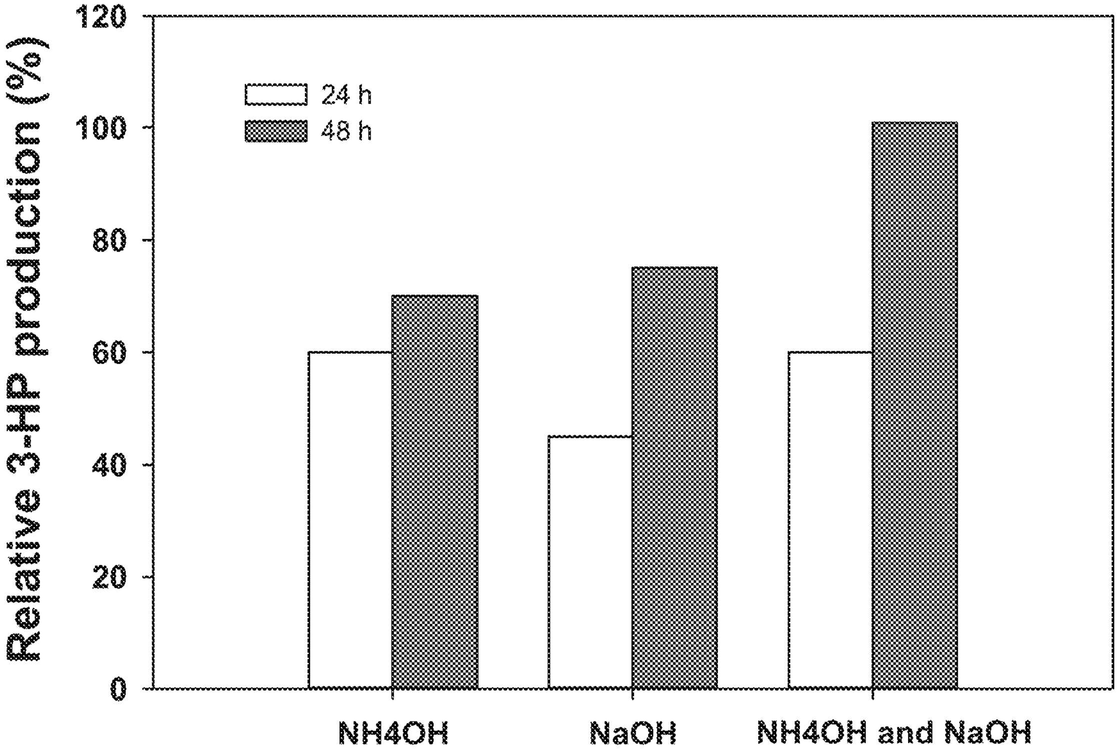
FIG. 52 is a graph showing the effect of various neutralizing agents such as NH4OH and NaOH on the production of 3-HP (%). In one of the condition, NH4OH was used as neutralizing agent until 24 h followed by NaOH up to 48 h of fermentation.

The bioreactor experiments to produce 3-HP or a salt thereof from glycerol by recombinant strains were performed using different bases NaOH, KOH, and $NH_4OH$ to study its effect on cell growth and 3-HP production (FIG. 35). The cultures with NaOH and KOH as neutralizing base showed almost identical results. The bioreactor studies with $NH_4OH$ showed similar final titer as that of other neutralizing bases used in these studies. However, careful analysis of the results obtained from $NH_4OH$ showed an improvement in growth as well as productivity in first 22 h bioreactor studies. Interestingly productivity decreased after 22 h with $NH_4OH$, which could be due to the toxicity of $NH_3$+ accumulation. The reason of $NH_4OH$ to show higher cell growth could be due to the assimilation of $NH_3$+ resulted from $NH_4OH$ utilization. On the other hand, the 3-HP productivity was comparatively higher and consistence with NaOH/KOH as neutralizing base after 22 h. The results motivated to cultivate the cultures initially with $NH_4OH$ for good growth and higher productivity at early stages and change the base to NaOH for continued and consistent productivity after 22 h. An experiment was performed with this strategy and the results are shown in FIG. 52. Combining two neutralizing base resulted in higher growth as well as higher 3-HP titer. This experiment resulted in producing >90 g/L in 48 h.

As aforementioned the important factor to avoid acid toxicity was by avoiding accumulation of undissociated form of acid. This can be done by two methods 1) by increasing the pH away from pKa value of organic acid, which was examined as mentioned previously, 2) by decreasing the concentration of acid accumulation. To avoid the accumulation of acid in the culture broth the most suitable option is to extract the acid from the broth as it is producing. This method is practically not feasible due to the economical uncomfortability. The other approach is to dilute the culture broth so that the concentration can be reduced which will result in decreasing the undissociated form of organic acid. According to Henderson-Hasselbalch equation the undissociated form of acid can be substantially decreased either by high pH or by decreasing the concentration of the acid in the culture medium. In the previous experiment we optimized the pH conditions, as very high pH is not suitable for cell growth. Here, in this study, we examined the second approach. To study these experiments, we focused on diluting the neutralizing base. Among the various neutralizing base examined in our experiments we notice that ammonium hydroxide gave us the best results.

Therefore, for experiments to reduce the 3-HP concentration and increase 3-HP amount, ammonium hydroxide was used as neutralizing base. The strategy was to dilute the 3-HP concentration in the medium by using diluted neutralizing base. In previous experiment 15% ammonium hydroxide which resulted in >100 g/L concentration and overall 280 g (amount) of 3-HP was produced. In the next set of experiments further diluted concentration of ammonium hydroxide at 10, 7 and 3.5% were used, which resulted in 72, 61 and 54 g/L of 3-HP titer, respectively. However, the total amount produced was comparable at 295, 304, 326 g, respectively. These results show that decreasing the acid concentration in the culture broth can enhance the acid production by increasing the total amount of acid produced by the recombinant cells. On the hand when ammonium hydroxide was used to neutralize acid production, the advantage with ammonia containing neutralizing base is that $NH_3^+$ can be consumed as nitrogen source by microorganisms.

Figure 36:
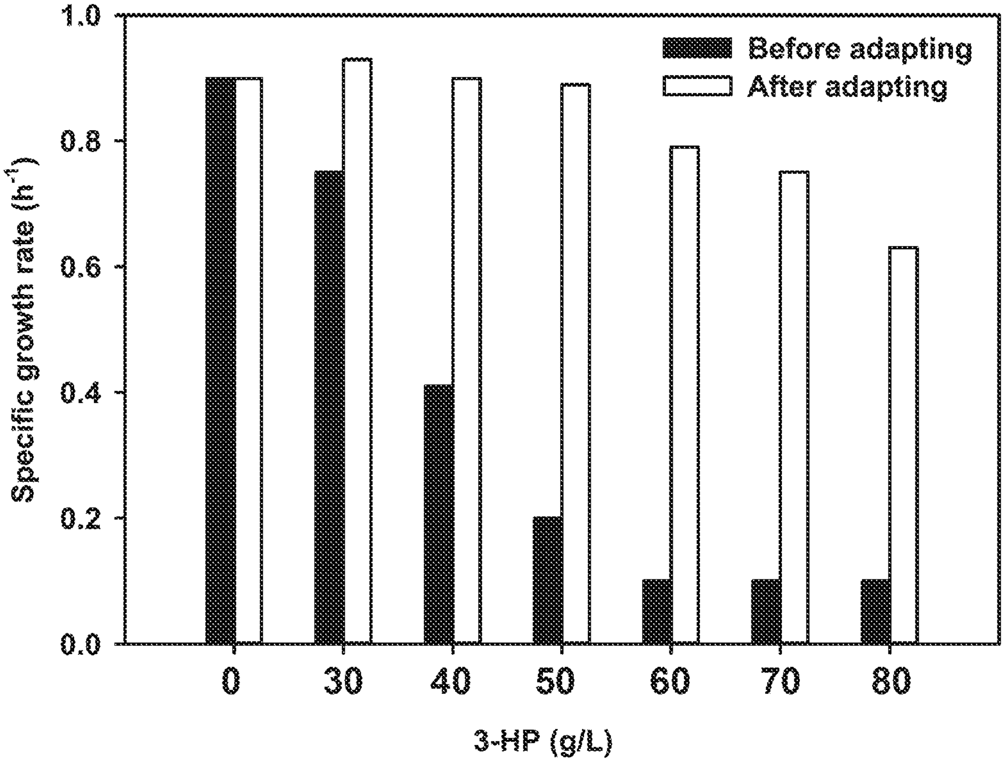
FIG. 36 is a graph showing the modification of recombinant strains in medium supplemented with various 3-HP concentrations.

In one study, we develop recombinant strains by adaptive mutations to grow at higher acidic concentrations. 3-HP producing recombinant strains were grown in organic acid production medium by supplementing organic acid (in this case 3-HP) at certain concentration. It was noticed that when the recombinant strain were grown in culture medium supplemented with 30 g/L of 3-HP, the cultures showed retarder growth when compared to the cultures without supplementing any organic acid. However, recombinant strains showed no significant difference in cell growth or specific growth rate in the medium supplemented with less than 30 g/L. Therefore, 30 g/L 3-HP was considered as toxic concentration for recombinant strains. For adaptive evolution, the recombinant strains were repeatedly cultured in medium supplemented with 30 g/L until the specific growth rate increased and matched to the cultures in the medium without supplementing 3-HP. Once the specific growth rate was comparable between the cultures, the adapted strains were transferred into the fresh medium supplemented with higher concentration of 3-HP (>30 g/L). This adaptive evolution procedure was repeated several times until proper specific growth rate was achieved. Interestingly it was noticed that these recombinant strains took longer time (number of repeated cultures) to adapt and reach higher specific growth rate as the concentration of 3-HP (>50 g/L) was increasing in the culture medium. These recombinant cells were adapted up to 80 g/L of 3-HP (FIG. 36).

Figure 37:
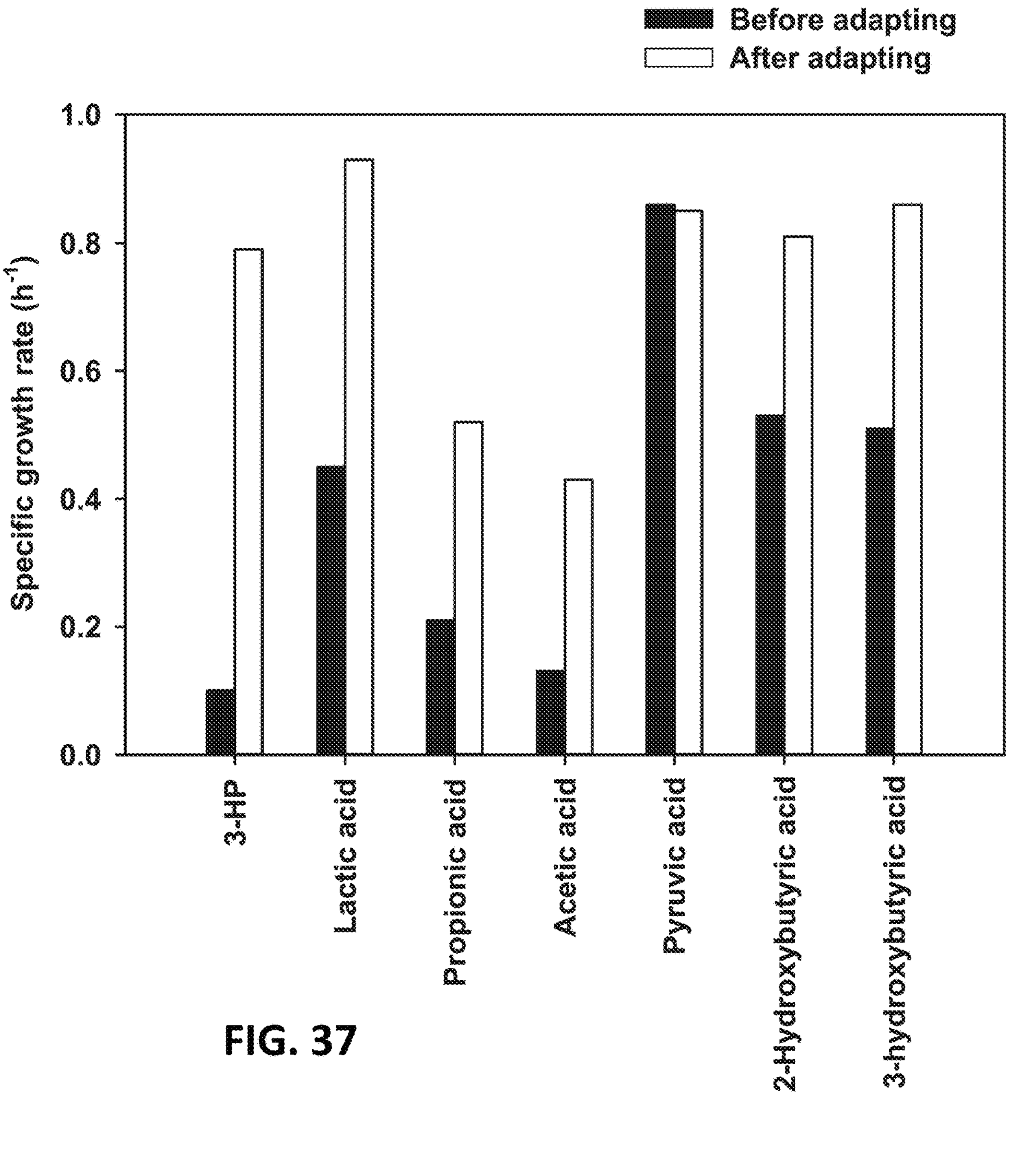
FIG. 37 is a graph showing the growth of 3-HP modified recombinant strains (80 g/L) in a medium supplemented with various organic acids at 50 g/L concentrations.

The recombinant strains developed for 3-HP or a salt thereof production were adapted to grow in industrial medium supplemented with 80 g/L 3-HP. However, it was important for us to understand the tolerant mechanism activated in these adopted strains. Whether the mechanisms are very specific to 3-HP tolerant or it is against several organic acids tolerant. To confirm this, the adapted strains were grown in industrial medium by supplementing 50 g/L concentrations of other organic acids, such as lactic acid, acetic acid, propionic acid, pyruvic acid 2-hydroxybutyric acid and 3-hydroxybutyric acid. The results are shown in (FIG. 37). Interestingly, it was noticed that the adapted strains showed certain level of tolerance to the other organic acids examined in this study. These results confirm that the acid toxicity was rather due to the protons generated when compared to the cations. Identification of specific mechanism by studying omics for these organic acid tolerance in the adapted microorganism are under progress.

Figure 38:
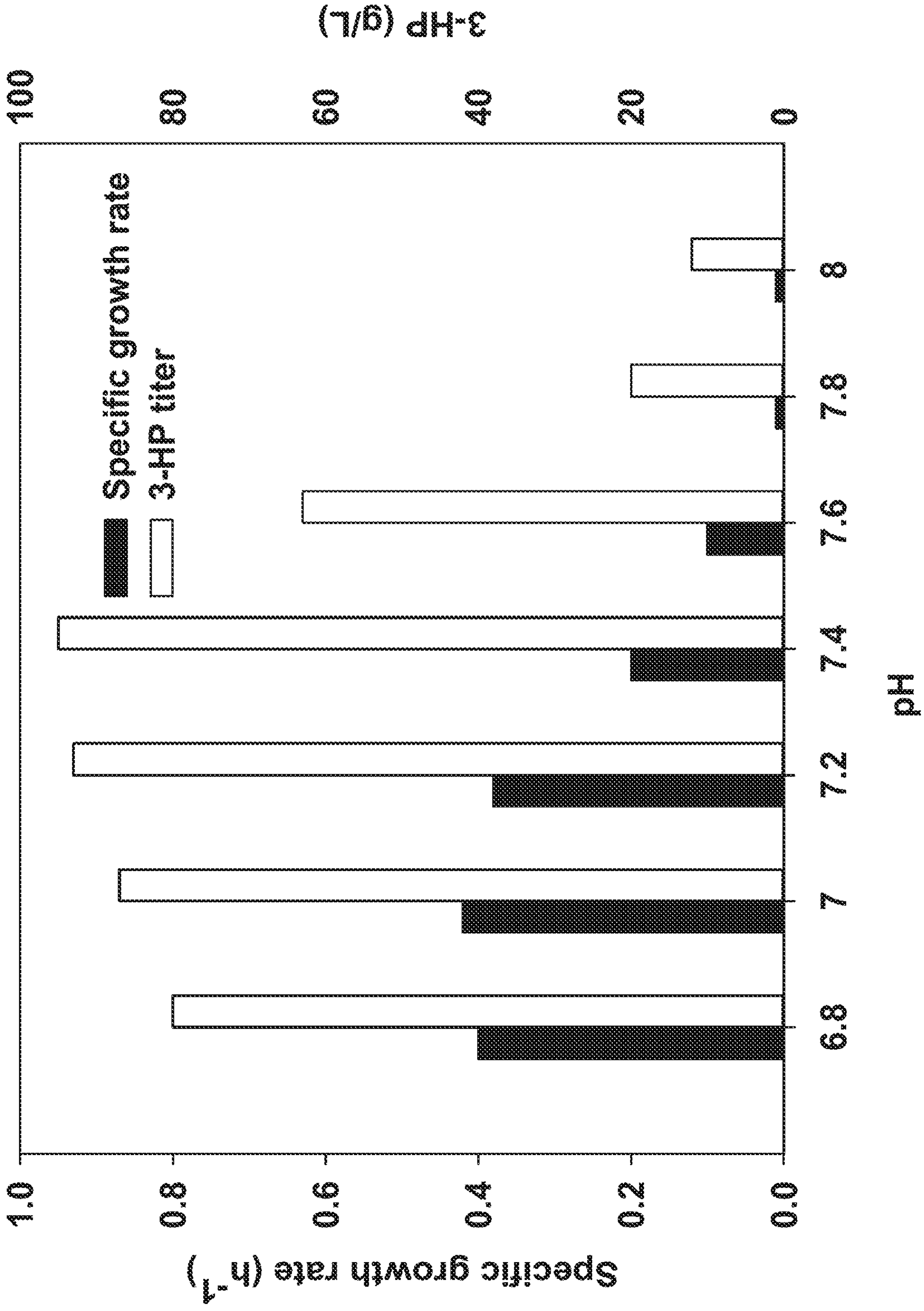
FIG. 38 is a graph showing the cultivation of 3-HP modified recombinant strains (80 g/L) in media at different pHs.
Figure 39:
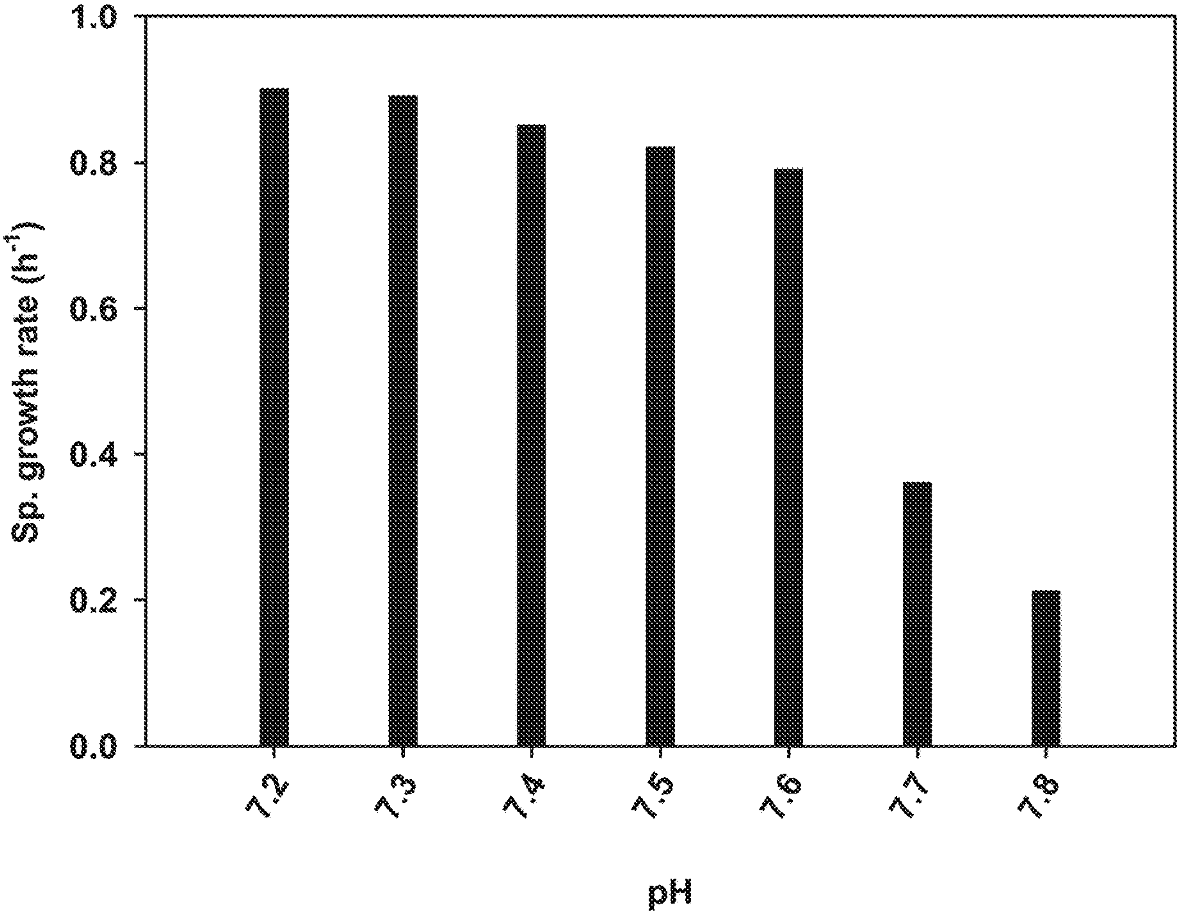
FIG. 39 is a graph showing the modification of 3-HP (80 g/L) tolerant recombinant strains to improve specific growth rates at higher pH.

As aforementioned, in several studies it has been reported that acid toxicity is due to the increased concentration of undissociated form of acids. The concentration of undissociated form increases with the accumulation of higher concentration of acids according to Henderson-Hasselbalch equation (HH equation). However, according to Henderson-Hasselbalch equation the undissociated form of acid decreases substantially when the pH is increased away from pKa values. The effect of higher pH on acid tolerance and its production by recombinant strains were examined. The recombinant strains isolated from adaptive evolution experiment were grown in culture medium with different pH ranging from 6.8 to 8.0 pH with intervals of 0.2 pH as shown in FIG. 38. The results shows a sequential improvement in 3-HP titer and specific production rate with increase in pH. However it was noticed that the cell growth was substantially affected with increase in pH. The recombinant strains showed decline in cell growth above 7.4 pH. Therefore, the recombinant strains isolated from acid adaptive experiment (adapted for 80 g/L of 3-HP) were further adapted in the cultures maintained at higher pH values. Optimum pH for these recombinant strains is 7, therefore, these strains were repeatedly grown in medium with higher pH until the specific growth was comparable to the cultures grown at 7 pH. With this procedure the acid tolerant strains were adopted to grown at 7.6 pH with same specific growth rate to the cultures grown at 7 pH. Interestingly the specific growth rate of recombinant cell did not improve when we tried to adapt the cells above 7.6 pH even after several attempts of adaptive evolution studies (FIG. 38 and FIG. 39).

Figure 40:
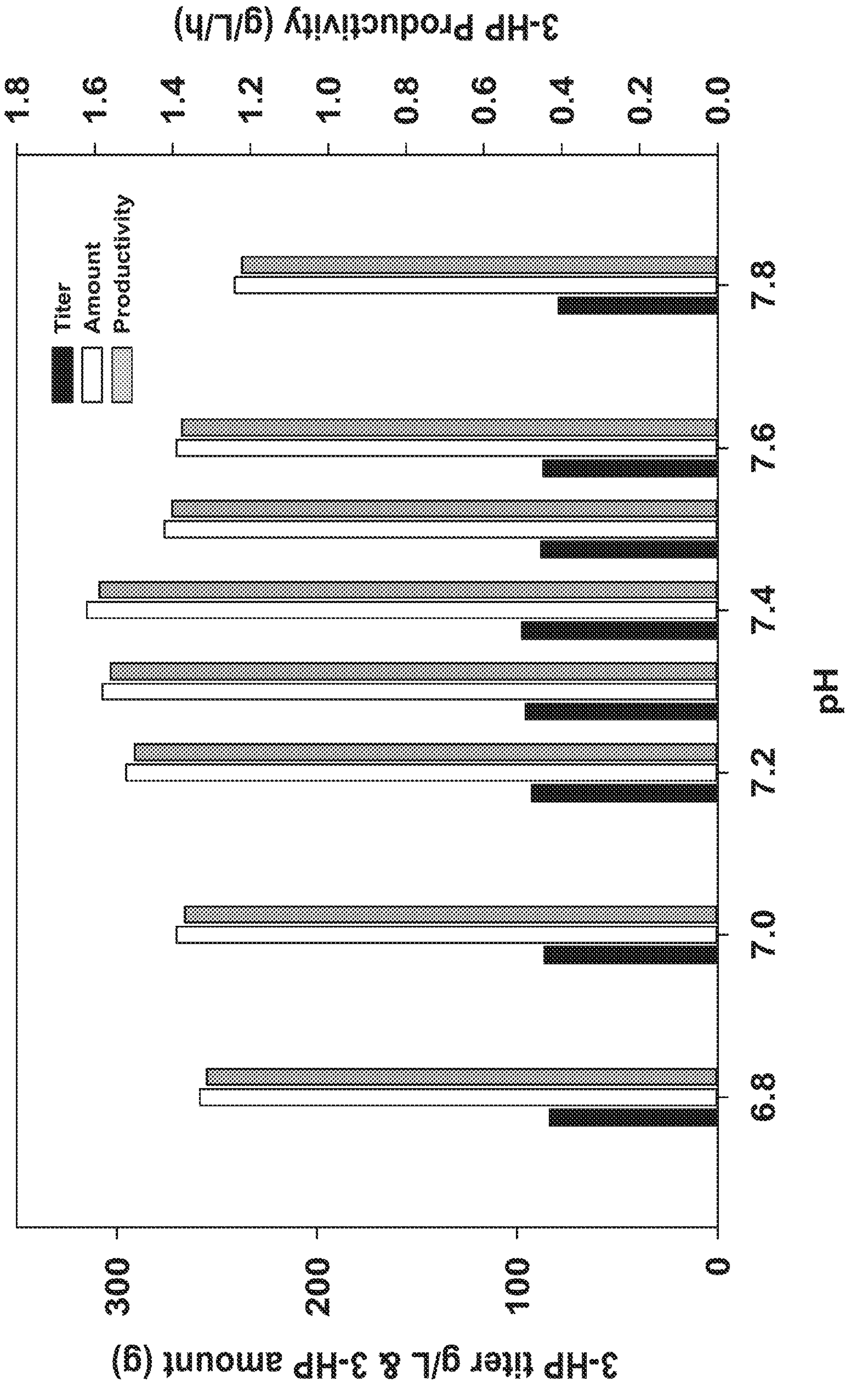
FIG. 40 is a graph showing the cultivation of pH 7.6 adapted 3-HP (80 g/L) tolerant recombinant strains at different pHs.

In the next study, the 7.6 pH adapted recombinant strains were subjected to bioreactor studies with the objective to produce higher 3-HP titer and amount. The adapted strains were examined at 7 to 8 pH for growth and 3-HP production. It was noticed that the adapted strains showed better performance when compared to non-adapted strains. Interestingly, at 7.4-7.5 the adapted recombinant showed comparable growth to the non-adapted cells and showed substantially improved growth, 3-HP titer, yield on glycerol and productivity from crude glycerol. The results are shown in FIG. 40 Identification of the optimal pH for higher target product production is important in regard to bioprocess optimization. Optimum pH is important to attain the highest activity of enzymes. In this case, the recombinant strain harboring 3-HP synthetic pathway was constructed by importing enzymes from various different microorganisms and its enzyme characterizations show that each enzyme has different optimum physiological properties. Therefore, it is important to identify the optimum pH for the strain to produce highest 3-HP titer from crude glycerol. Several experiments were designed to identify the optimum pH for the recombinant microorganisms harboring heterologous 3-HP synthetic pathway to produce 3-HP at high titers.

The results obtained by growing recombinant strains for 3-HP production at various pH ranging from 6.8 to 7.8 are shown in FIG. 38 The bioreactor with 6.8 showed good growth, but low 3-HP production; however, when the pH was increased an improvement in 3-HP production was noticed. These recombinant cell showed highest production when the pH was maintained at 7.4 to 7.5. Further increase in pH showed substantial decrease in 3-HP production. On the other hand, increase in pH reduced cell growth. The cell growth was substantial affected at 7.8 pH resulting in lower 3-HP production. An optimal pH was selected (pH 7.4) for further studies without compromising much on cell growth and 3-HP production. A highest 3-HP production was noticed at 7.4 pH Effect of Bicarbonate on 3-HP Production from Glycerol In one of our experiments with ammonium hydroxide as neutralizing base we notice accumulation of substantial amount of pyruvate indicating that the carbon flow from pyruvate to acetyl-CoA and TCA has been blocked in the 3-HP producing recombinant strains. Accumulation of pyruvate resulted in significant amount of acetic acid production. It has been well reported that the enzymes involved in catalyzing pyruvate to acetyl-CoA is allosterically suppressed by increased NADH concentration in the cytoplasm. We examined the cytoplasm of recombinant strains which are developed to produce 3-HP from glycerol for NAD/NADH. We notice that the 3-HP producing strains showed significant accumulation of NADH during its production. We hypothesize that the high NADH concentration in cytoplasm of recombinant strains during 3-HP production allosterically suppress the enzymes (PDHc) which are involved in converting pyruvate to acetyl-CoA, and results in pyruvate and acetate production (via Pox B enzyme). The low NAD/NADH ratio will results in low activity of aldehyde dehydrogenase which is involved in conversion of 3-HPA to 3-HP, this should result in accumulation of 3-HPA, a toxic aldehyde which are reported to damage host DNA and proteins. Interestingly, our experimental results did not show accumulation of 3-HPA. However, 3-HP production was completely hindered during low $NAD^+$/NADH ratio. These results indicate that along with second reaction of 3-HP production pathway, the first enzyme activity was also decreased substantially due to low NAD/NADH ratio.

Figure 53:
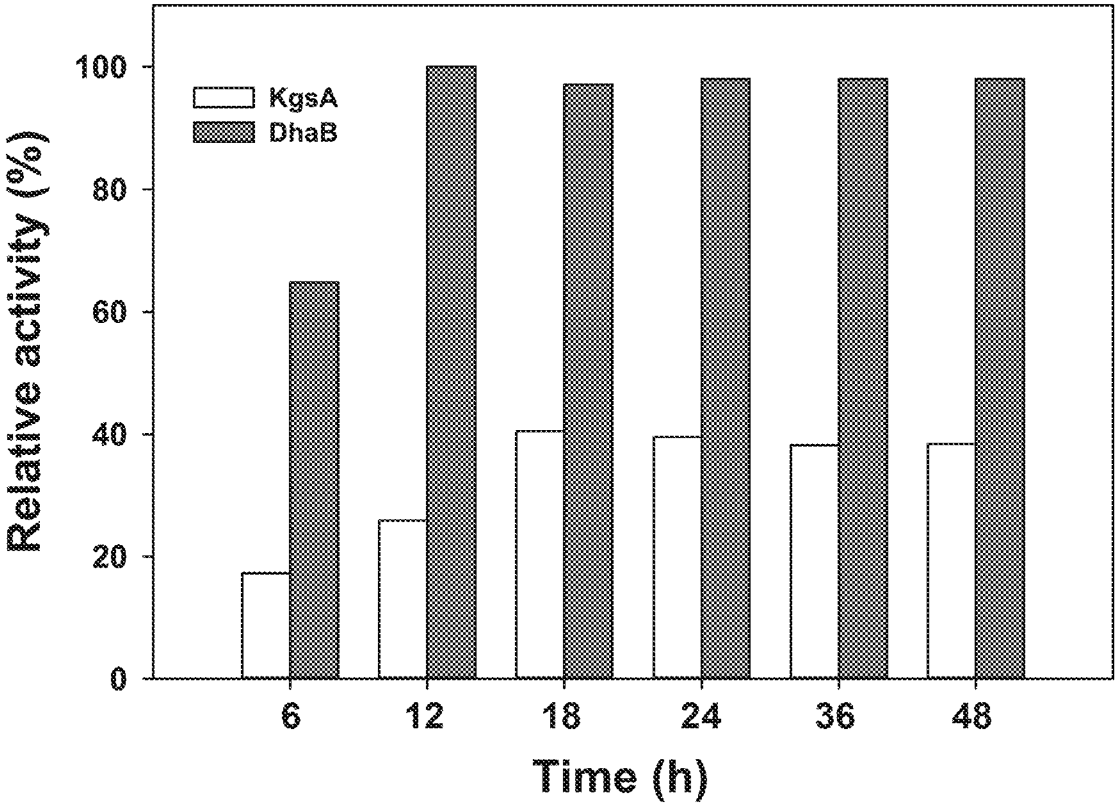
FIG. 53 is a glycerol dehydratase (DhaB) and KgsA in-vitro enzyme activities at different stages of bioreactor.
Figure 54:
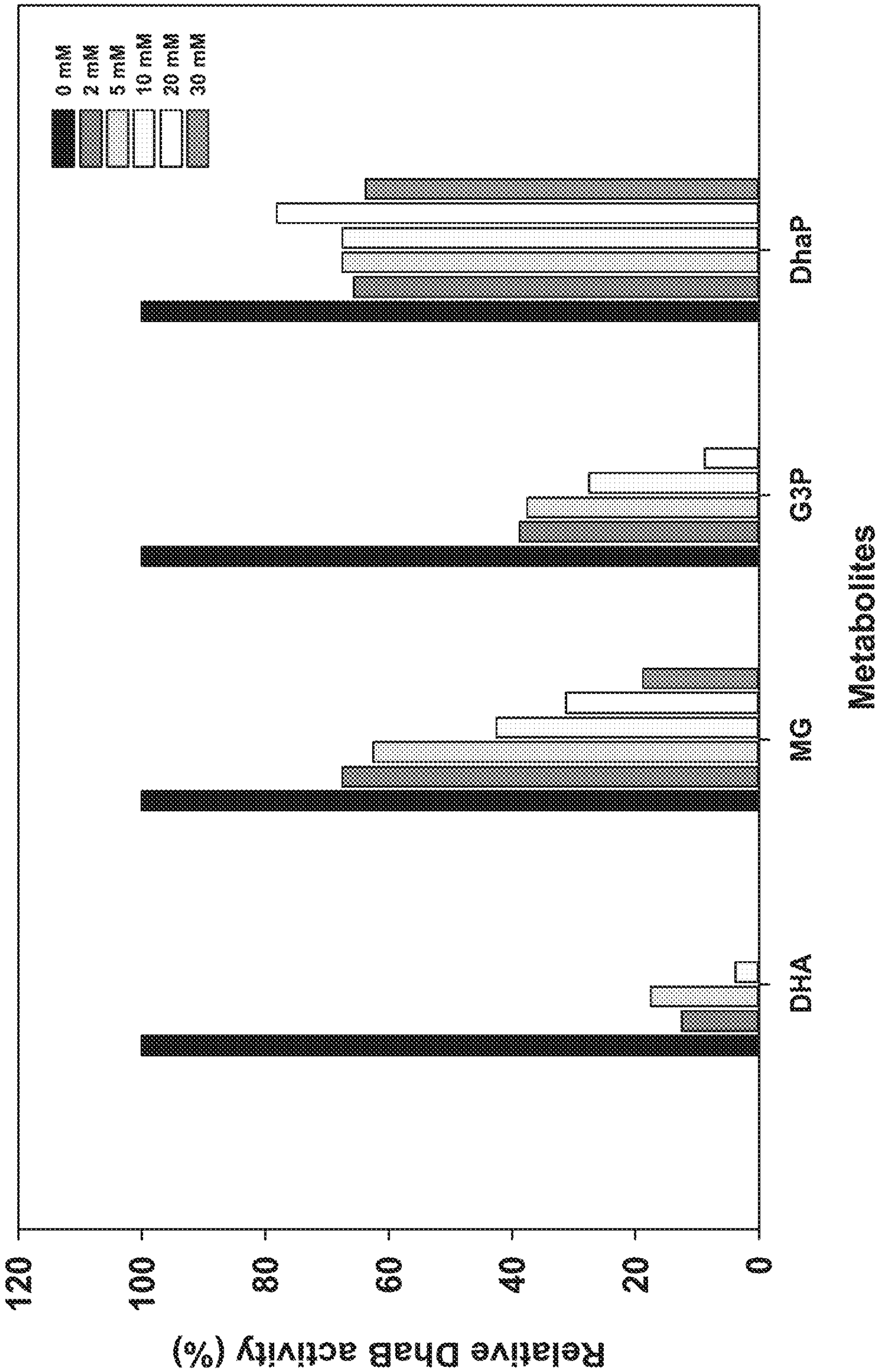
FIG. 54 is a graph showing the effect of various toxic intermediates on glycerol dehydratase (DhaB) in-vitro enzyme activities.

We analyzed the first enzyme, glycerol dehydratase expression level and in-vitro activity at different stages of bioreactor study (FIG. 53). We examined the expression level of glycerol dehydratase enzyme on SDS PAGE and confirmed that there is no significant change in enzyme expression throughout the bioreactor and its in-vitro activity. These analysis showed that the enzyme expression was not affected, however, we hypothesized that the physiological conditions/environment in the cytoplasm perhaps not favorable to glycerol dehydratase activity. Careful analysis revealed that there is an allosteric suppression of glycerol dehydratase enzyme by few of the glycolytic pathway intermediates. An in-vitro glycerol dehydratase enzyme activity was measured in presence of various concentrations of several glycolytic pathway intermediates in the reaction mixture (FIG. 54). In these results it was noticed that the presence of few glycolytic pathway intermediates in the enzyme activity reaction mixture decreased the enzyme activities substantially even at significantly low concentrations. As shown in FIG. 54 intermediates such as dihydroxyacetone phosphate and glycerol dehyde 3-phosphate had significant allosteric suppression on glycerol dehydratase enzyme activity. These results indicate for continuous production of 3-HP from glycerol glycolytic pathway intermediates accumulation should be avoided as it can allosterically suppress glycerol dehydratase. The best way to do this is to enhance the carbon flux towards TCA cycle.

Figure 47:
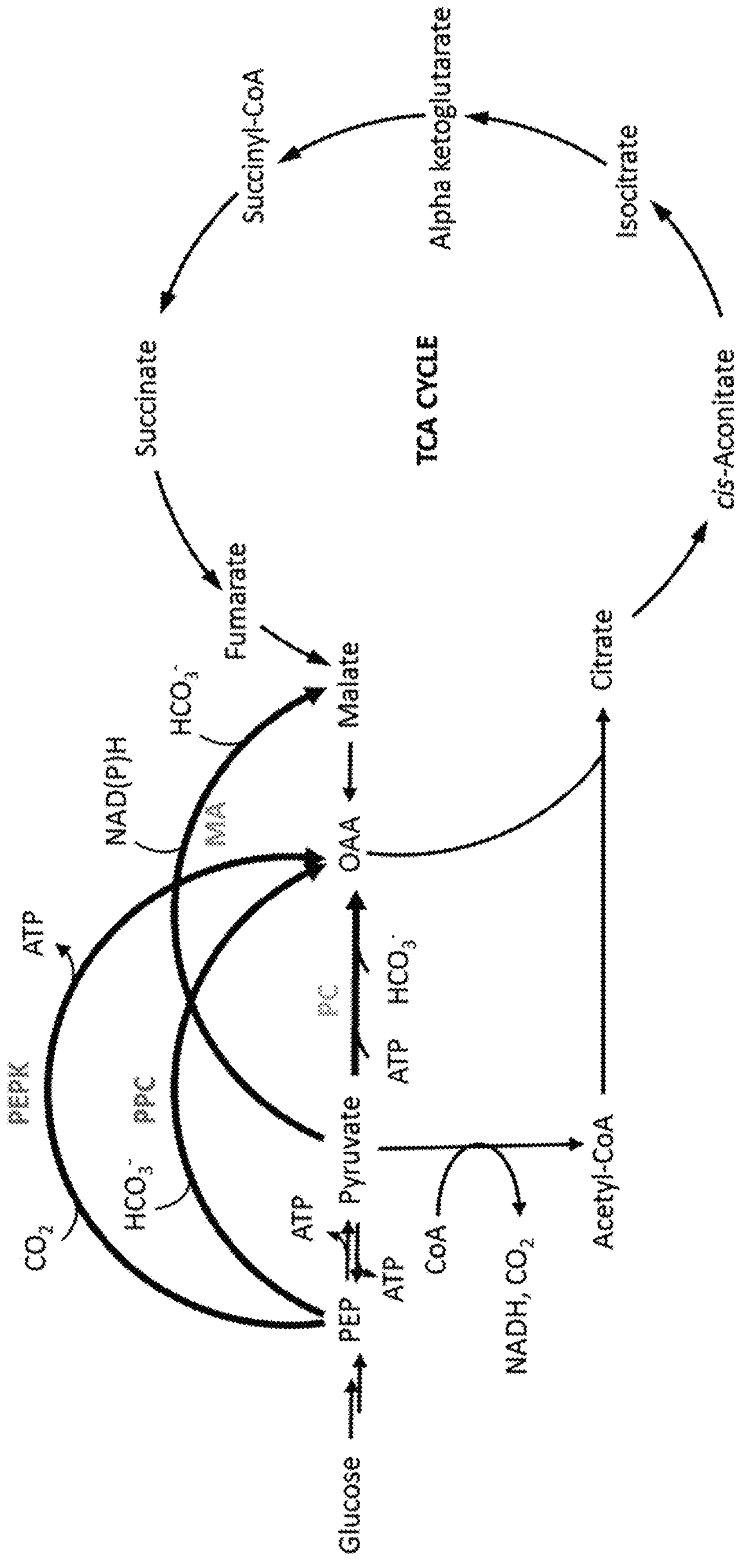
FIG. 47 is a schematic illustrating the anapleurotic reactions in central carbon metabolism. PPC, PEPcarboxylase; PEPK, PEP carboxykinase, ME, malic enzyme; and PC, pyruvate carboxylase.

Previously, it was successfully shown that the development of mutant PDHc enzyme which can maintain higher activity even at low NAD/NADH ratio can improve carbon flux towards TCA cycle. However, in this study we take different approach, as development of these mutant enzymes are painstaking. In this we use carbonate in the medium and enhance the carbon flux to oxaloacetic acid by activating anaplerotic pathway enzymes as shown in FIG. 47. Here, we plan to use carbonate in ammonium form or sodium form. Four different carbonates were used such as ammonium carbonate, sodium carbonate, ammonium bicarbonate and sodium bicarbonate. The objective of these studies were to produce organic acid in this case 3-HP at high titer, therefore we used these bases for two important purposes as a neutralizing base during acid production and also to enhance the anaplerotic pathway of central metabolism.

Figure 48:
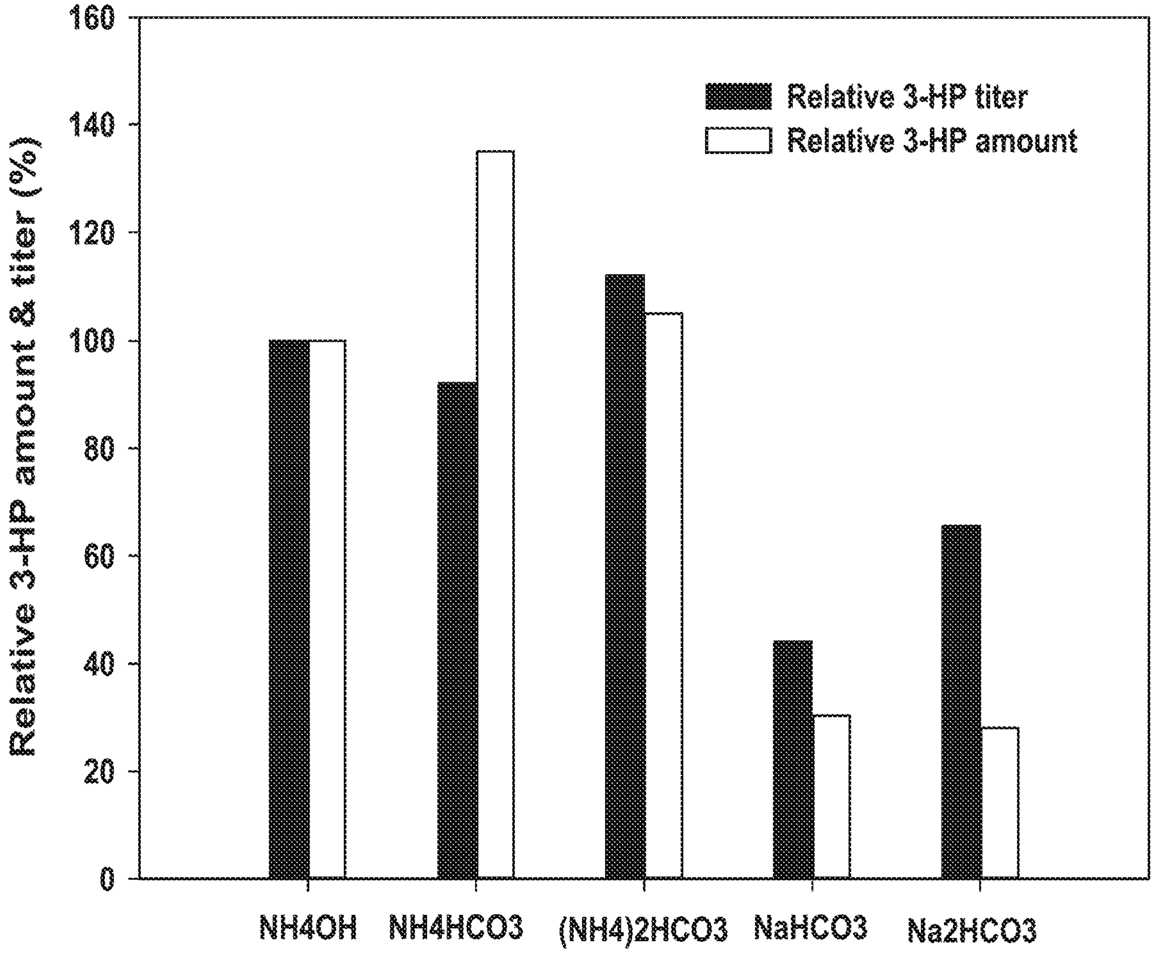
FIG. 48 is a graph illustrating the effect of various neutralizing agents on the production of 3-HP (%).
Figure 49:
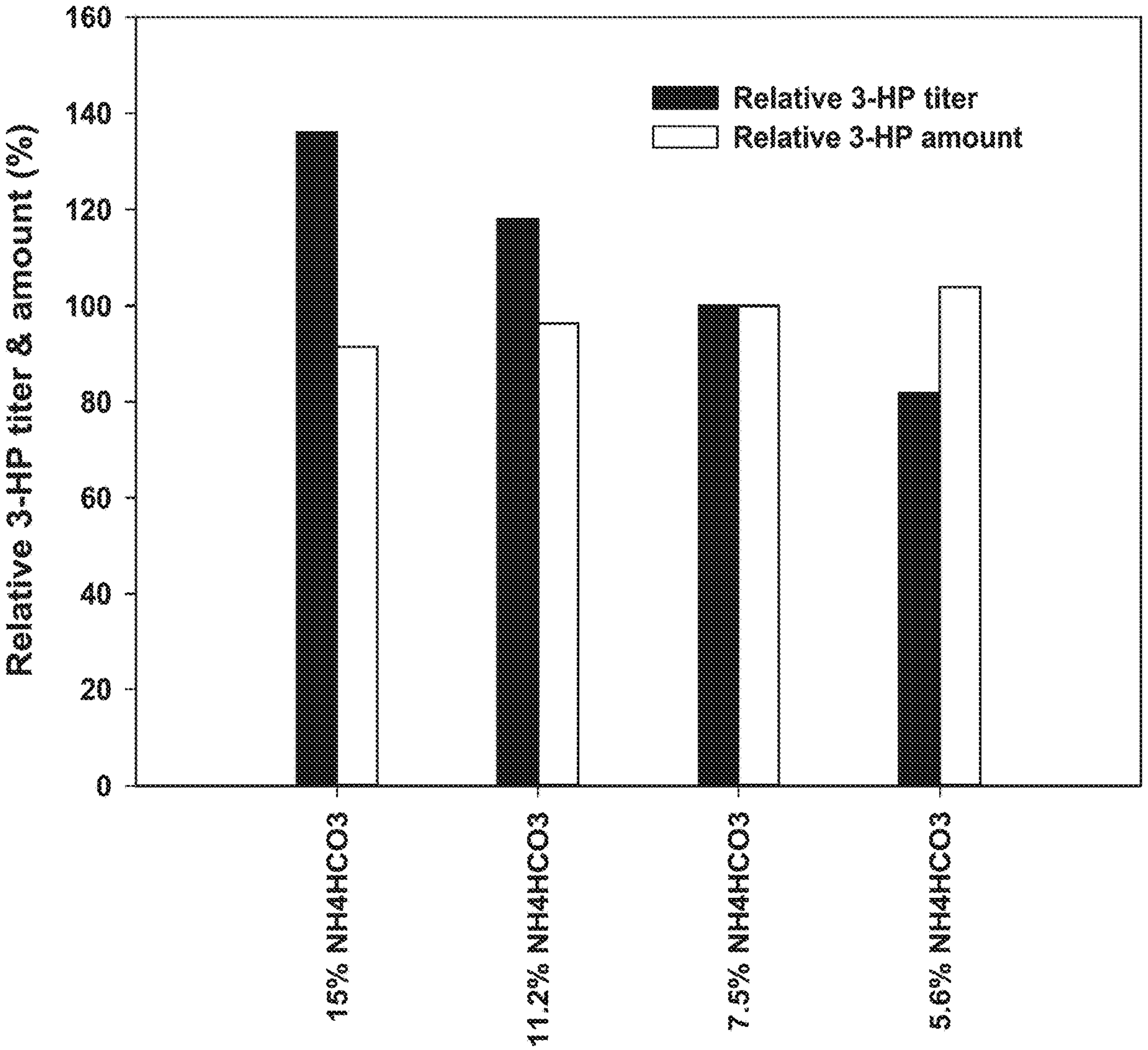
FIG. 49 is a graph illustrating the effect of various concentrations of $NH4HCO_3$ on 3-HP titer and amount (%).

The results obtained in this experiments are shown in FIG. 48 and FIG. 49. Initially, only one concentration of all the bicarbonates were studies based on solubility of these carbonate salts. Interestingly, as we hypothesized, we saw no pyruvate accumulation or acetic acid production by 3-HP producing recombinant strains. We also noticed that substantial improvement in the 3-HP amount produced by the recombinant strains. When compared the results with carbonate to previously optimized conditions with ammonium hydroxide a substantial improvement in 3-HP amount was evident. Use of carbonate resulted in more than 100 g increase in 3-HP amount in 5 L bioreactors. However, increase in 3-HP amount resulted in consuming more base, addition of excess amount of ammonium and carbonate resulted in higher concentrations of these elements in the broth. Higher concentration of ammonium and/or bicarbonate/carbonate resulted in cell lysis and cell death at later stages of bioreactor studies. To overcome this limitation, we examined several dilutions of these neutralizing bases. Dilution of neutralizing base resulted in decreasing the concentration by increasing the total volume of the culture broth. This dilution factor had two significant advantages, one it could avoid cell lysis by decreasing the concentration of ammonium and carbonate/bicarbonate, on the other hand, volume increase also decreased the concentration of organic acid accumulation in the culture broth, which results in its low undissociated form and avoided acid toxicity as described in earlier sections.

To further optimize the bioprocess, two different bases such as either ammonium bicarbonate and ammonium hydroxide or ammonium bicarbonate and sodium bicarbonate mixed in appropriate ratio and its effect on 3-HP production and cell viability were examined in bioreactor conditions. This was done to avoid the accumulation of ammonium ions and bicarbonate in large concentrations, and also to identify the ion responsible for cell lysis. If ammonium ion is toxic and resulted in cell lysis ammonium accumulation can be avoided by combining with sodium form of bicarbonate. If bicarbonate is toxic it can be avoided in combination with hydroxide form. Similar studies were also conducted by mixing sodium bicarbonate and sodium hydroxide in proper ration. Similarly, sodium bicarbonate and ammonium bicarbonate at suitable concentrations. Initially several combinations with different concentrations were analyzed and an appropriate mixture of concentration of neutralizing base was identified which would improve the titer of target organic acid product and also avoid cell lysis during bioprocess. After examining several different combinations of neutralizing base and its dilutions resulted in improving 3-HP amount to from 300 g to 450 g, which was nearly >150 g in 5 L bioreactor. These combinations increased 3-HP amount and avoided cell lysis problem associated with ammonium/sodium bicarbonate/carbonate forms of neutralizing base (FIG. 52). The results obtained in 5 L laboratory scale was scaled up to 50 L scale and the results were reproducible. This process optimization resulted in substantially decreasing the production cost of 3-HP from glycerol.

Aeration

Figure 41:
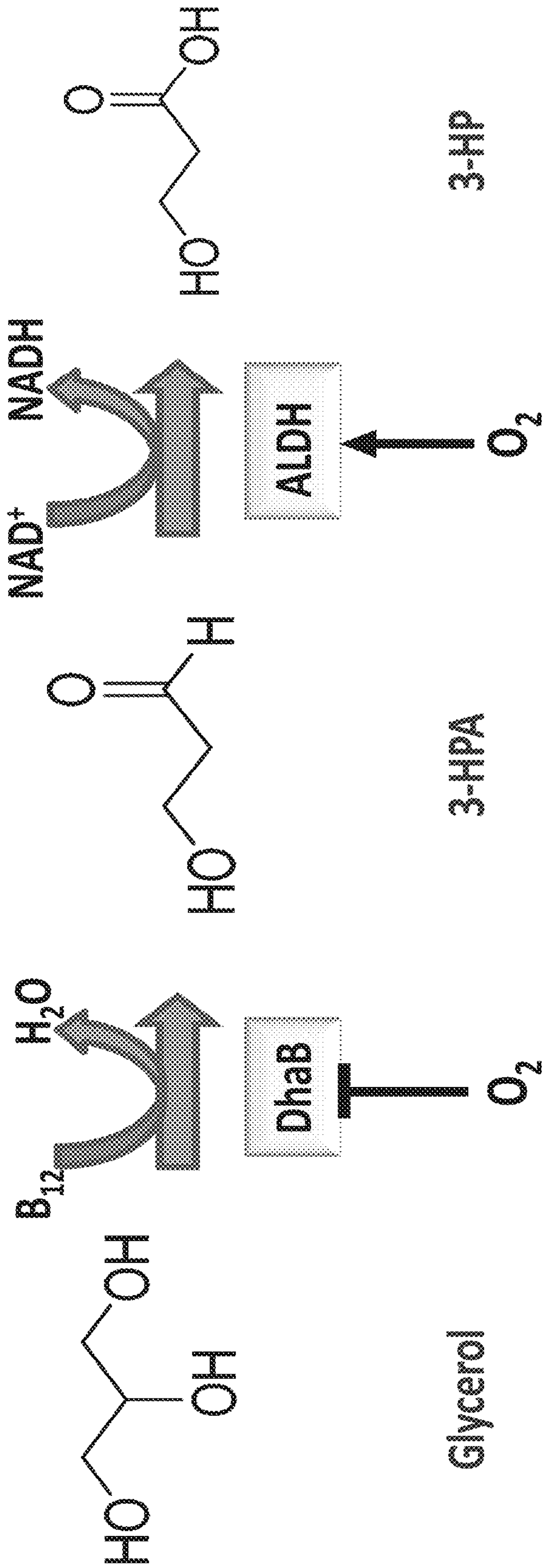
FIG. 41 is a schematic of the 3-HP synthetic pathway from glycerol adapted in recombinant strains. The first enzyme is sensitive to oxygen while the second reaction is enhanced in the presence of oxygen.

Aeration is one of the important physiological parameters for cell growth and its metabolism. Oxygen being the best electron acceptors, microorganisms has evolved to use oxygen to maintain the redox status of the cell, also it is utilized to produce ATP via electron transport chain. 3-HP (or a salt thereof) production from glycerol has been studied extensively by using oxygen sensitive glycerol dehydratase enzyme (DhaB). This enzyme catalyzes glycerol to 3-hydroxypropanealdehyde (3-HPA) during glycerol metabolism and 1,3-propanediol (1,3-PDO) production under anaerobic/microaerobic conditions and it is naturally found in several *Enterobacter*. In our study we have used a similar oxygen sensitive enzyme from *Klebsiella pneumoniae*. It has been well documented that the activity of DhaB substantially decreases in the presence of higher amounts of oxygen. On the other hand, as aforementioned several microorganisms have been evolved to use oxygen as the final electron acceptor and assist in redox balance of the cell, as it is at most important for cell growth. The recombinant strains developed for 3-HP production are also known to use oxygen efficiently to regenerate $NAD^+$ and maintain redox balance. 3-HP production pathway from glycerol in the recombinant cells involves an aldehyde dehydrogenase which oxidizes 3-HPA to 3-HP by transferring electrons to $NAD^+$ and produce NADH. These NADH should be regenerated to $NAD^+$ for uninterrupted production of 3-HP from glycerol. As you notice the two enzymes involved in 3-HP synthetic pathway from glycerol, one is oxygen sensitive while the second enzyme needs oxygen for its continuous activity (FIG. 41). Therefore optimization of aeration is highly important for 3-HP production from glycerol and should be studied meticulously. There must be sufficient oxygen dissolved in the media to regenerate NAD+ via electron transport chain, however not so much as to affect the activity of the glycerol/diol dehydratase. Aeration in bioreactor can be controlled by agitation and air flow which determines the mass transfer; therefore in this study we study the aeration by carefully controlling airflow and agitation rpm.

Figure 42:
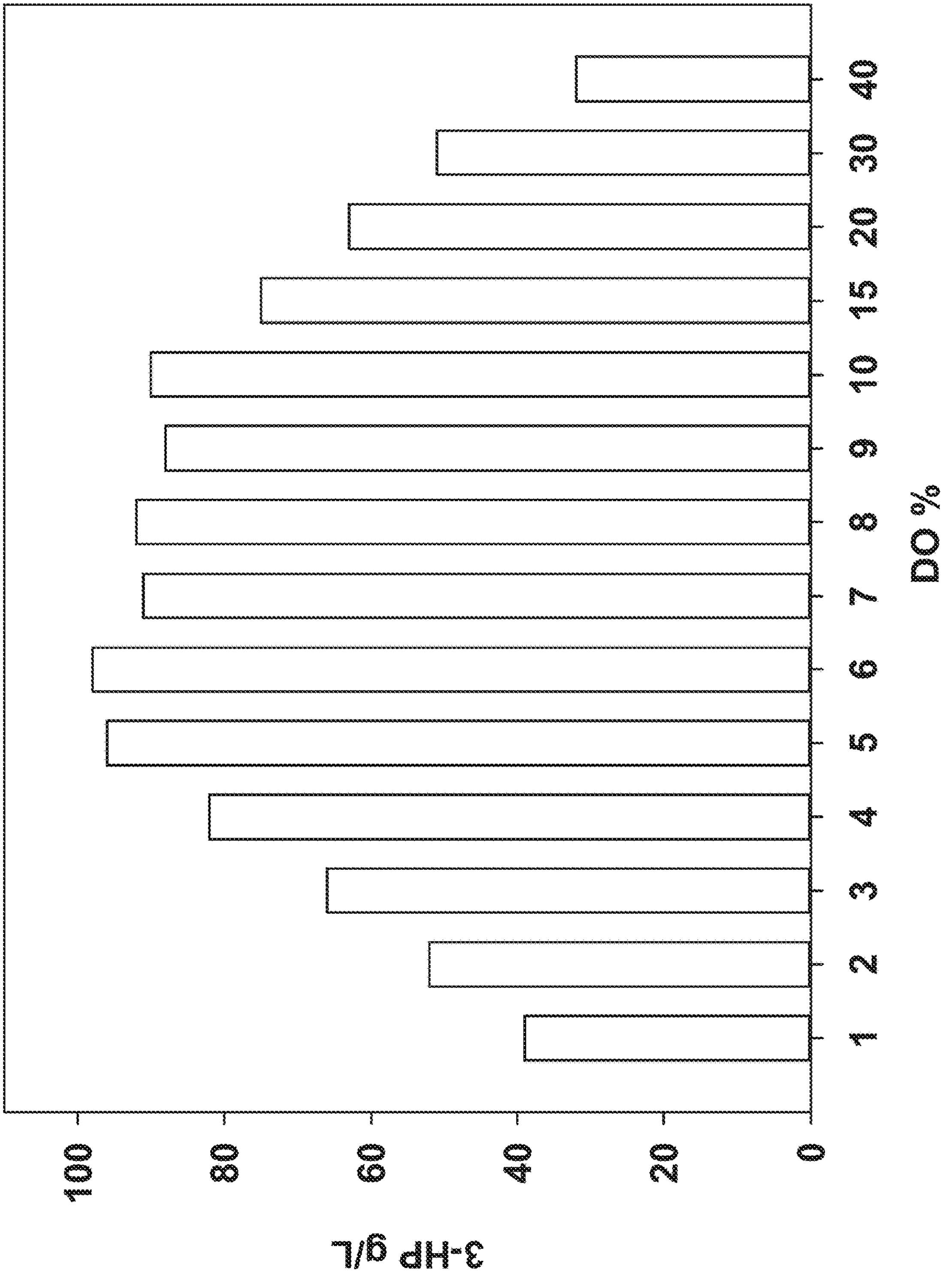
FIG. 42 is a graph showing the effect of different dissolved oxygen concentrations on 3-HP production.

Recombinant strains were cultivated under various agitation speed and air flow (results not shown). Initially the air flow was fixed at either 0.5 or 1 vvm and the agitation speed was varied from 400 to 800 with increment with every 50 rpm. The results showed that lower aeration condition showed low 3-HP production, this could be due to improper regeneration of $NAD^+$ which results in decreasing the ALDH catalytic activity and accumulates 3-HPA, a toxic aldehyde to cell growth. However, accumulation of 3-HPA (3-HP pathway intermediate) could not be measured accurately with HPLC due to improper peak. Therefore the strategy was changed to maintain dissolved oxygen (DO) rather than agitation and air flow variation. Initially DO was maintained at 40%, however, 3-HP production was not very encouraging at this percentage. Therefore, various DO levels were examined from 1% to 40%. The results are shown in FIG. 42. When DO was maintained at 1% the recombinant strains produced nearly 40 g/L 3-HP in 48 h. Cell growth was not satisfactory. Significant amount of 3-HPA accumulation was noticed. Marginal improvement in aeration (dissolved oxygen %) by increasing the agitation speed to 450 rpm showed improved 3-HP production from glycerol. Further incremental increase in rpm showed higher 3-HP productions. The highest production was noticed when DO was maintained at 5 to 6%, however, the 3-HP production was maintained up to 10% DO without any significant changes in the titer. On the other hand, further increase in DO above 10% showed decrease in 3-HP production, indicating that ~5-10% DO as an optimal for higher 3-HP production under these bioreactor conditions. Higher DO>10% showed marginally low 3-HP productions compared with the DO at 10%, this could be due to the decrease in the DhaB activity, which is oxygen sensitive at higher concentration. The highest production was noticed at 600 rpm, while further improvement in rpm above 600 rpm showed decrease in 3-HP production, indicating that 700 rpm as an optimal rpm for higher 3-HP production under these bioreactor conditions. Higher rpm at 800 showed marginally low 3-HP productions compared with the 700 rpm and 1 vvm, this could be due to the decrease in the DhaB activity, which is oxygen sensitive at higher concentration.

Temperature

Temperature is other important physiological parameter for optimal cell growth and cellular metabolism and it substantially influences production of target product by recombinant microorganisms. Identify the optimum temperature for higher target product production is extremely important in bioprocess optimization. On the other hand, temperature is important physiological parameters which determine the optimum catalytic activity of enzymes. In this case, the recombinant strain harboring 3-HP synthetic pathway was constructed by importing enzymes from various different microorganisms and its enzyme characterizations show that each enzyme has different optimum physiological properties. Therefore it is important to identify the optimum temperature for the strain to produce highest 3-HP titer. In this regard several experiments were designed to identify the optimum temperature for the recombinant microorganisms harboring heterologous 3-HP synthetic pathway to produce 3-HP at high titers.

Figure 43:
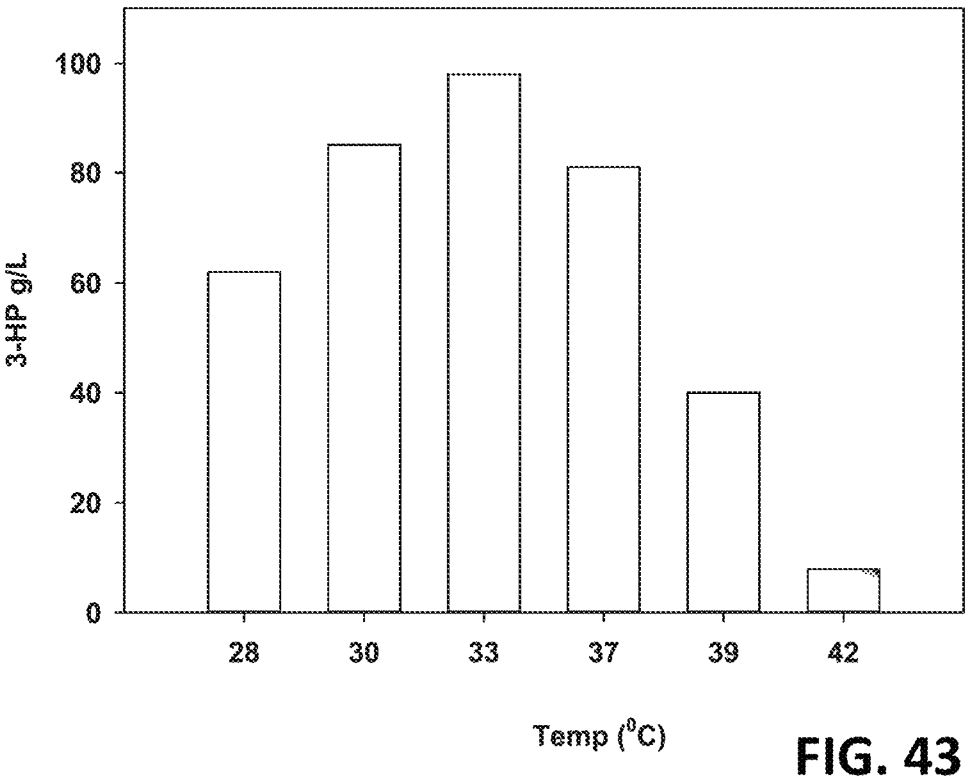
FIG. 43 is a graph showing the effect of different temperatures on 3-HP production.

The results obtained by growing recombinant strains for 3-HP production at various temperatures ranging from 28 to 40 deg C. are shown in FIG. 43. The bioreactor at 28 deg C. showed slow growth, slow cellular metabolism and low 3-HP production; however, when the temperature was elevated an improvement in cell growth and 3-HP production was noticed. These recombinant cell showed highest production when the temperature was maintained at 33 deg C. Further increase in temperature showed slow cell growth and substantial decrease in 3-HP production. Substantial decrease in cell growth and 3-HP production was noticed with the cultures with 40 deg C. The characterization of enzyme involved in 3-HP synthetic pathway show that optimum temperature for its activity around 37 to 45 deg C., however, and optimum cell growth for the parent strain as 30 deg C. However, 33 deg C. was found to more suitable for cell growth as well for highest 3-HP production. Therefore 33 deg C. temperatures was considered for further experiments.

Time of Induction

On the other hand, literature studies show that the ability of recombinant strains to produce target product and the protein depends on the phase/time of induction of specific enzymes. For instance, few products reach high titer when the enzymes of the pathway are induced at early log phase while few show higher production when induced at late stages of growth (late log or stationary phase). In this regard we analyzed the 3-HP producing ability of recombinant strains to high titer by inducing the synthetic pathway for 3-HP production at different stages of cell growth. The effect of different induction time on 3-HP production was examined by supplementing glycerol (source for 3-HP) at different cell OD points, such as 3, 5, 6, 7, 9, 11 and 15 OD). These results showed that induction at mid log phase results in highest 3-HP production by recombinant strains.

Figure 44:
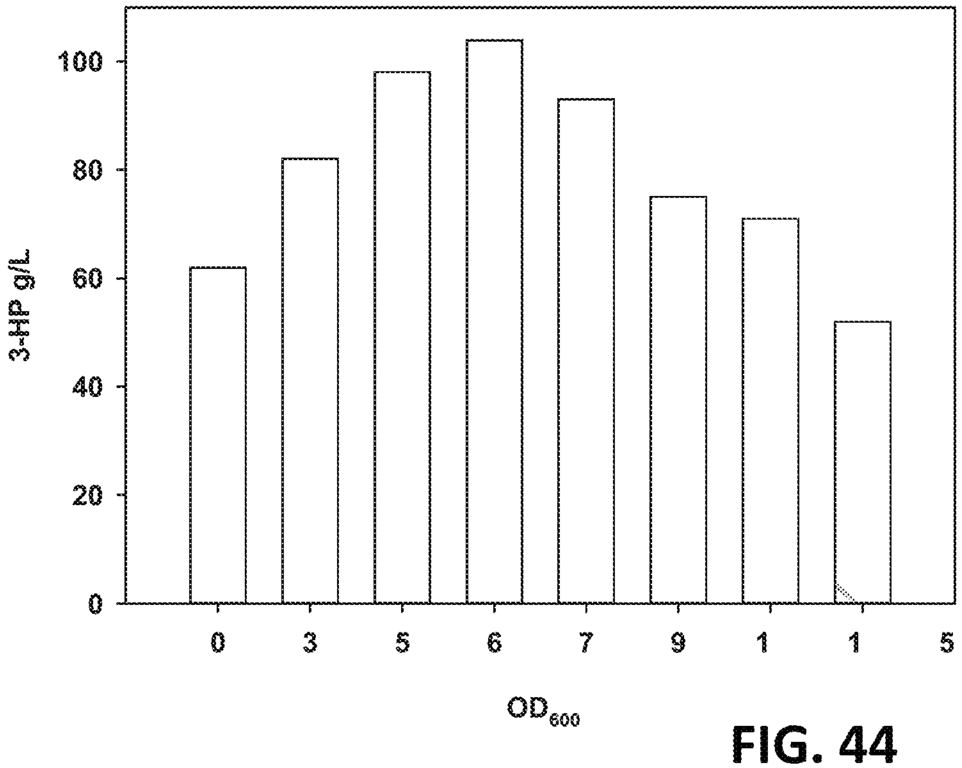
FIG. 44 is a graph showing the effect of different induction $OD_{600}$ on 3-HP production.
Figure 45:
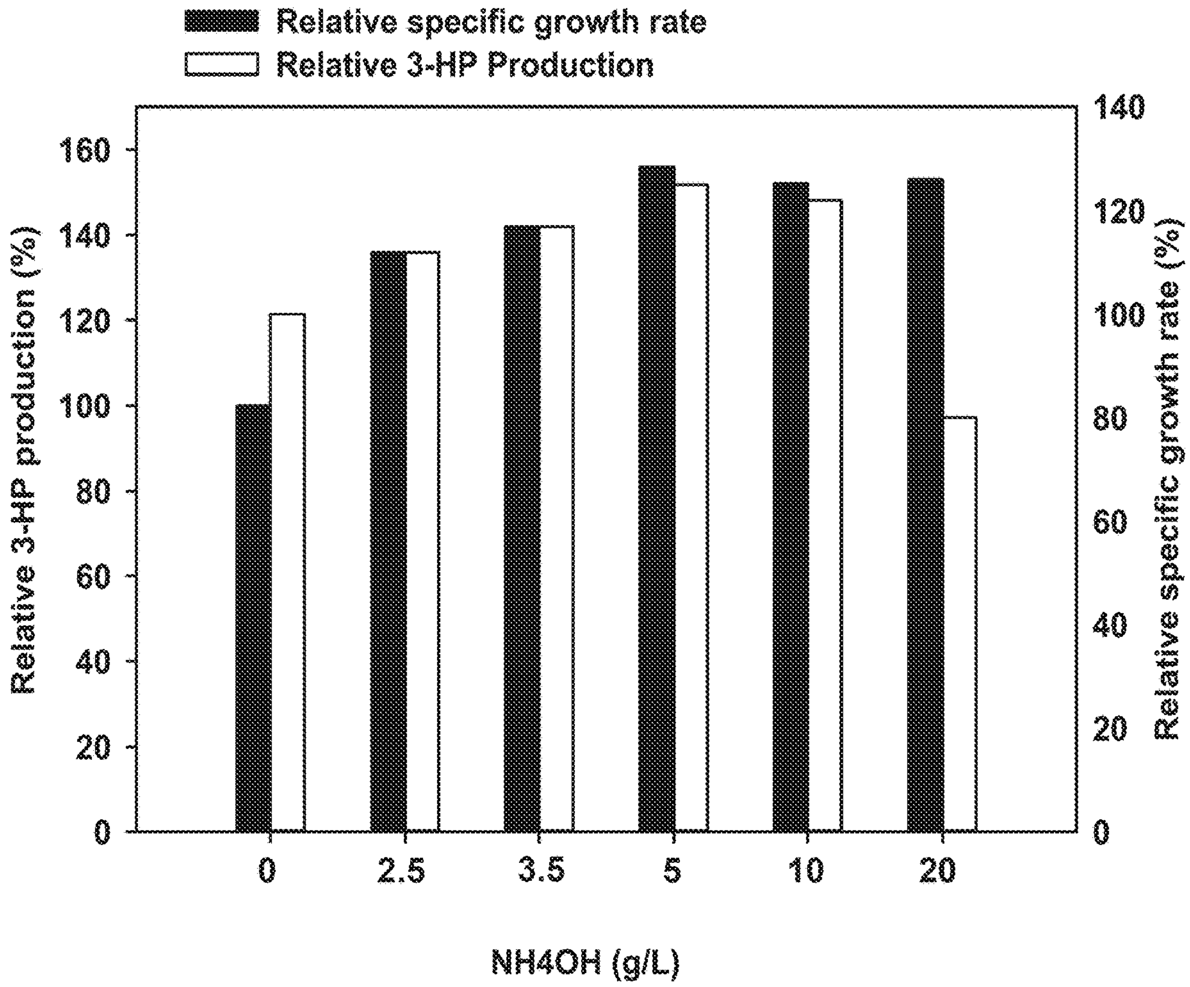
FIG. 45 is a graph showing the effect of various concentrations of $NH_4OH$ on 3-HP production and specific growth rate.
Figure 46:
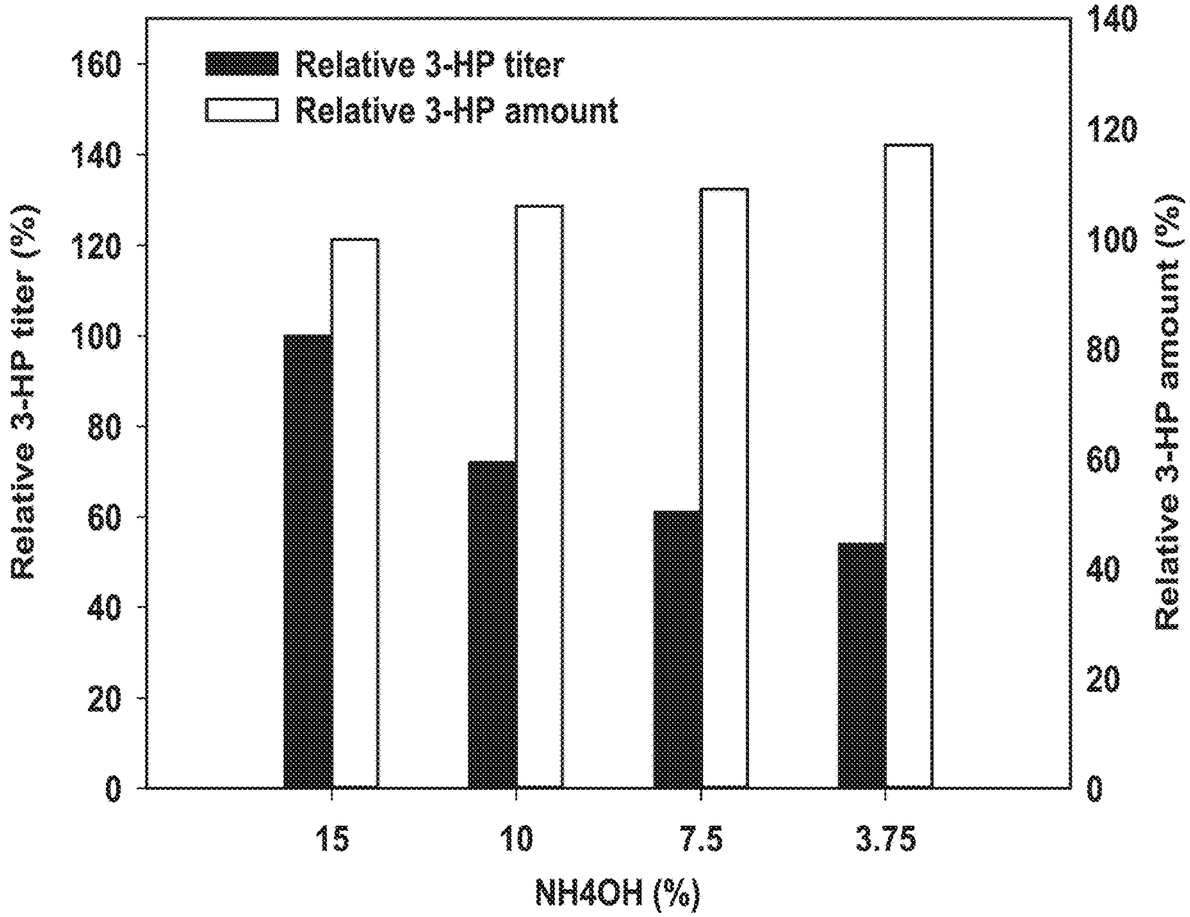
FIG. 46 is a graph showing the effect of $NH_4OH$ (%) on the relative 3-HP titer (%) and amount (%).

Induction of target product at different stages of cell growth can show a substantial difference in its production. Therefore, in this study the induction time for 3-HP production was varied from 3 to 15 OD. The results obtained from these experiments are shown in FIG. 44. These results showed that the cultures induced between 3 to 9 OD showed good production from the early stages of bioreactor studies. However, the cultures induced after 9 OD showed low 3-HP production. Among all these conditions the cultures induced at ~6 OD showed highest 3-HP production at 102 g/L in 48 h. Interestingly all the cultures induced between 3 to 9 OD produced ~100 g/L in 36 h with productivity at 2.5 g/L/h, after which the production decreased substantially. Metabolite analysis also showed accumulation of carbon source after 36 h indicating cells decreased gluconate consumption which would have also resulted in improper regeneration of NAD+ and hence the low 3-HP after 36 h.

Development of Industrial Medium for 3-HP Production by Recombinant Strains.

NBS bioreactor with 5 L working volume was used to examine the effect of carbon source on cell growth and 3-HP production by recombinant strains. Based on shake flask experiments, gluconate, glutamate (Monosodium glutamate, MSG) and citric acid which showed good cell growth and 3-HP production were subjected to bioreactor studies. Initially three different industrial grades MSG was examined in bioreactor and the results are shown in FIG. 2. There was no significant difference in cell growth, glycerol consumption and 3-HP production irrespective of different industrial grade MSG. In the beginning the cells were allowed to grown to a certain optical density (OD), there after they were induced to produce 3-HP by supplementing media with crude glycerol. Addition of glycerol or 3-HP production did not stop cell growth, however after the OD reached around 5 g cdw/L at 15 h the cell growth decreased substantially irrespective of different MSG as carbon source. Among several MSG, the one with small mesh size showed improved 3-HP production, while the other MSG with higher mesh size produced comparatively low 3-HP from crude glycerol.

Example 29. Identification of Suitable Carbon Source for High Titer 3-Hydroxypropionic Acid Production This study was intended to identify a suitable carbon source which can assist the recombinant strain to grow and produce the target acid products to high titer. Carbon source is one the major media component which play a vital role in cellular metabolism, cell growth and also 3-HP production. In this study, we examined carbon sources which can support recombinant strains to grow to higher cell densities and also produce 3-HP at high titer. In this regard we analyzed four different carbons sources as follows; glucose, glutamate, gluconate and citric acid. All these carbon sources were carefully selected based on metabolic pathway of recombinant strains and also based on the availability and cost.

Figure 1B:
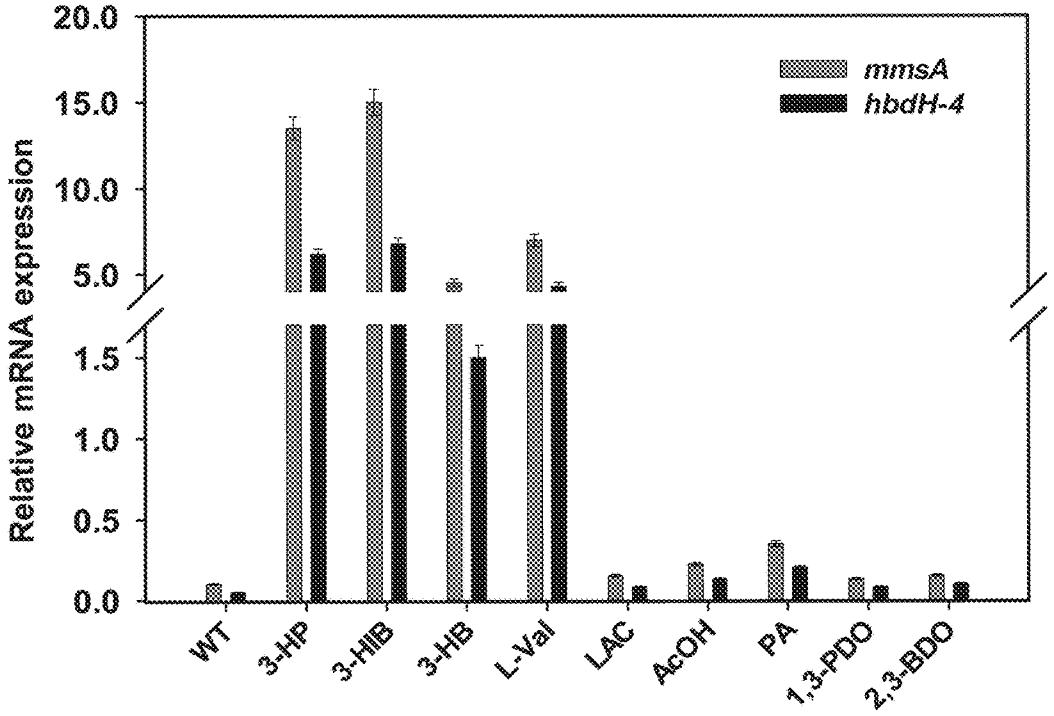

Recombinant strain was cultivated in shake flask containing industrial medium supplemented with various carbon sources as aforementioned. Experiments were carried out in duplicates to check the reproducibility. The results obtained are shown in FIG. 1. Among the several carbon sources used gluconate and glucose showed highest and lowest growth rate compared to other carbon sources used in this study, respectively. On the other hand, the other two carbon sources, glutamate and citric acid, which can enter TCA cycle directly showed comparable growth pattern. However the growth rate was marginally less when compared to gluconate. Similarly, 3-HP production from glycerol showed different production rate with diverse carbon sources. The production was highest with gluconate, and low with glucose. Among all the four carbon sources examined gluconate showed better growth and 3-HP production, however the growth and 3-HP production decreased substantially after 12 h in flask experiments, which could be due to substantial drop in pH or due to depletion of carbon source, which was not measured in this study. Therefore, this condition was examined in bioreactor under controlled conditions to study the potential of gluconate on 3-HP production from crude glycerol by recombinant strains. On the other hand, glutamate and citric acid also showed potential to produce comparable amount of 3-HP as of gluconate, therefore, in a separate study glutamate and citric acid were also examined as carbon source for 3-HP production under biorcactor conditions.

Example 29. Characterization of Gluconate as Suitable Carbon Source for High Titer 3-Hydroxypropionic Acid Production In the next set of experiments gluconate was examined as carbon source. One bioreactor was used to study the effect of gluconate on cell growth and 3-HP production, while in the other bioreactor gluconate was used for cell growth and MSG for 3-HP production, by changing the carbon source at 12 h of bioreactor studies. MSG was used for production conditions as it is well known substrate for one of the acid tolerance mechanisms in bacteria. On the other hand, glutamate metabolism results in fewer NADH generations, which indirectly assist in 3-HP production from glycerol (FIG. 3). Similarly, more bioreactor experiments were performed with citric acid as carbon source, one bioreactor citric acid for cell growth and 3-HP production, while the other bioreactor citric acid for cell growth and MSG for 3-HP production were used in combination. When citric acid was used as carbon source during initial cell growth a substantial variation in pH was noticed and it was difficult to control the pH during bioreactor studies However, addition of glycerol at 6 h of bioreactor studies resulted in substantial accumulation of toxic 3-hydroxypropanealdehyde (3-HPA), which resulted in cell death and no 3-HP production was noticed.

Use of gluconate resulted in good cell growth with the biomass reaching at 6 cdw 1-1. When the cells were induced for 3-HP production by adding glycerol, suddenly cell growth decreased substantially (FIG. 2*a*), and dropped to ~4.5 cdw 1-1 at later stages of bioreactor. Decrease in cell growth resulted in low 3-HP production. In 36 h with gluconate as carbon source for cell growth and 3-HP production showed reasonable good 3-HP production which was promising for commercialization. After 36 h production decreased and in next 12 h. At 48 h bioreactor was terminated and this study showed titer, yield and productivity at 83 g $l^{-1}$, >0.95 $molmol^{-1}$ and 1.72 g $l^{-1}$ $h^{-1}$, respectively. On the other hand, the bioreactor studies in which the carbon source was changed from gluconate to glutamate after 12 bioreactor hours showed substantial decrease in 3-HP production indicating the change in carbon source was not suitable under these conditions. This study resulted in only 65 g/L 3-HP from crude glycerol in 48 h (FIG. 2*b*).

These studies showed that gluconate as one of the good carbon source for cell growth as well as for 3-HP production. Therefore, several wide range of industrial grade gluconate from different sources were examined under optimized conditions and the one which showed good 3-HP production without affecting the cell growth to great extent was used for further studies.

Example 30. Identification of Suitable Nitrogen Source

Nitrogen source is the other important component in media used to cultivate microorganism along with carbon source. Nitrogen containing media components along with carbon source should be selected very carefully as they play vital role in cellular metabolism and 3-HP production. In this study, we identified and examined suitable nitrogen sources which can support recombinant strain grow to higher cell densities and also produce 3-HP at high titer. In this regard we analyzed several different types of corn steep liquor and yeast extract as nitrogen source. This analysis revealed that among several nitrogen sources yeast extract from China (SJB) showed better performance of recombinant strain by producing higher 3-HP titer and productivity from crude glycerol. NBS bioreactor with 3 L initial working volume was used to examine the effect of nitrogen source on cell growth and 3-HP production by recombinant strains. Various yeast extracts from different sources (industrial grade) were used in different bioreactor studies. Previously, it was confirmed that gluconate as reasonable carbon source to achieve good 3-HP titer and cell growth, therefore gluconate was used as carbon source to examine the effect of various types of nitrogen source on 3-HP production from glycerol.

Bioreactor studies show that there was a significant difference with cell growth and 3-HP production by recombinant strains with various nitrogen sources. Corn steep liquor (CSL), both powder and paste from showed very low 3-HP production. When CSL was used as nitrogen source cell growth measurement was difficult as undissolved particles in CSL interfered with OD measurements. The results are shown in FIG. 4*a*. On the other hand, there was no significant difference in time course profile of 3-HP production with yeast extract as nitrogen source. However, bioreactor baker's yeast extract showed marginally good 3-HP production at the early stages of bioreactor studies and also it assisted to slightly improve the cell growth.

After identifying the suitable nitrogen source its concentration was varied to identify the effect of yeast extract concentration on cell growth and 3-HP production from glycerol. It was notice that when yeast extract was used >1 g/L in the culture medium the recombinant cells produce good amount of 3-HP from crude glycerol. Similarly when corn steep liquor was used at >1 g/L concentration in combination of gluconate or glutamate as carbon source it also resulted in 3-HP production similar to yeast extract condition.

Example 31. Use of Water-Immiscible Solvent for Extracting 3-HP from Decellularized Broth General Protocol A To a specified amount of broth containing sodium salt of 3-HP at a specified titer, prepared as described in previous examples, was added a specified acid at room temperature until a specified pH was reached. The resultant reaction mixture was continuously extracted with a specified amount of a specified water-immiscible solvent at a specified temperature for a specified amount of time. In certain examples, the extraction was repeated with at least one additional portion of the same solvent at the same conditions. In such examples, the extraction time is indicated in the "Temperature, Extraction time" column of Table 13 in the following manner: time of the initial extraction/time of extraction with an additional portion of the solvent. Purity of obtained 3-HP was determined by $^1H$ NMR.

$^1H$ NMR of 3-HP: A triplet is observed at about 3.75 ppm for the $CH_2$ group next to OH, and a triplet at about 2.39 ppm is observed at about for $CH_2$ group next to COOH. No long range coupling is observed in 1H NMR.

$^1H$ NMR (400 MHZ, $D_2O$) δ 3.75 (t, J=6.6 Hz, 2H), 2.39 (t, J=6.6 Hz, 2H)

Table 13 describes acids, pH of the aqueous phase, water-immiscible solvents and their amounts, temperature, extraction time, and yield and purity of 3-HP that was obtained by following the general extraction protocol A.

TABLE 13

| Entry No. | Acid | Solvent, amount | Amount of broth, titer | Temperature, Extraction time | pH | yield | purity |
|---|---|---|---|---|---|---|---|
| 1A-1 | $H_2SO_4$ | iso-BuOH, 800 mL | 800 mL, 60 g/L | 107° C., 18/18 hours | 3.3 | 53% | n/a |
| 1A-2 | Oxalic acid | iso-BuOH, 6.2 L | 4.8 L, 81 g/L | 107° C., 18/18 hours | 4.3 | 83% | 77% |
| 1A-3 | Oxalic acid | iso-BuOH, 6.2 L | 4.8 L, 65 g/L | 107° C., 18/18 hours | 4.4 | 88.3% | 88% |
| 1A-4 | Oxalic acid | iso-BuOH, 6.2 L | 4.8 L, 74.7 g/L | 107° C., 18/18 hours | 4.5 | 99% | 69% |
| 1A-5 | HCl | iso-BuOH, 800 mL | 800 mL, 73 g/L | 107° C., 18/18/18 hours | 3.3 | 32% | 76% |
| 1A-6 | Acetic acid | iso-BuOH, 800 mL | 800 mL, 61 g/L | 107° C., 18/18/18 hours | 4.2 | n/a | n/a |
| 1A-7 | Oxalic acid | Ethyl acetate, 6.7 L | 4.3 L, 65 g/L | 78° C., 48 hours | 4.4 | 50.4% | 71% |

General Protocol B

To a broth 4.8 L containing sodium salt of 3-HP 65 g/L prepared as described in previous examples, was added a specified acid at room temperature until a specified pH was reached. The resultant reaction mixture was continuously extracted with isobutanol 6.2 L at a specified temperature for a specified amount of time. Purity of obtained 3-HP was determined by 1H NMR.

Table 14 describes acids, pH of the aqueous phase, water-immiscible solvents, temperature, extraction time, and yield of 3-HP that was obtained by following the general extraction protocol B.

TABLE 14

| Entry No. | Acid | Extraction time | Temperature | pH | yield | purity |
|---|---|---|---|---|---|---|
| 1B-1 | HCl | 3 days | 100~115° C. | 0.8 | decomposed | n/a |
| 1B-2 | HCl | 3 days | 100~115° C. | 1.0 | decomposed | n/a |
| 1B-3 | HCl | 3 days | 100~115° C. | 4.0 | 54% | n/a |
| 1B-4 | $H_2SO_4$ | 3 days | 100~115° C. | 1.0 | decomposed | n/a |
| 1B-5 | $H_2SO_4$ | 3 days | 100~115° C. | 2.0 | 43% | 32% |
| 1B-6 | $H_2SO_4$ | 3 days | 100~115° C. | 3.3 | 53% | n/a |
| 1B-7 | $H_2SO_4$ | 3 days | 100~115° C. | 3.0 | 70% | 40% |
| 1B-8 | Oxalic acid | 3 days | 100~115° C. | 2.4 | n/a | n/a |
| 1B-9 | Oxalic acid | 120 h | 100~115° C. | 3.5 | 89% | 84% |
| 1B-10 | Oxalic acid | 120 h | 100~115° C. | 4.3 | 83% | 77% |
| 1B-11 | Oxalic acid | 120 h | 100~115° C. | 4.4 | 100% | 72% |
| 1B-12 | Oxalic acid | 96 h | 100~115° C. | 4.4 | 91% | 85% |
| 1B-13 | Oxalic acid | 74 h | 100~115° C. | 4.4 | 78% | 80% |

Example 32. Use of a Water-Miscible Solvent and Water-Immiscible Solvent for Extracting 3-HP from Decellularized Broth General Protocol C Typical systems for extracting 3-HP from fermentation broth using a mixture of water-miscible solvent and water-immiscible solvent are shown in FIG. 58 and FIG. 59. To a specified amount of broth containing sodium salt of 3-HP prepared as described in previous examples, was added oxalic acid until pH 4.4 of the broth was reached at room temperature. Decrease in pH in the broth was monitored using a pH meter. Specified amount of ethyl acetate (water-immiscible solvent) was added to the solvent flask, followed by addition of a specified amount (as v/v % of the amount of broth in the system) of a specified water-miscible solvent to the solvent flask. The solvent flask was heated using a heating mantle to a boiling point of water-miscible solvent until all of the water-miscible solvent was evaporated and transferred to the flask containing the broth. The solvent flask was subsequently heated to the boiling point of ethyl acetate for about 48 hours, during which time 3-HP was continuously extracted from the broth by ethyl acetate. The resultant solution of 3-HP in ethyl acetate was concentrated in vacuo to give desired crude 3-HP as a yellow oil. Purity of obtained 3-HP was determined by 1H NMR.

Various conditions for extracting 3-HP from fermentation broth such as amount of broth and titer, water-miscible (w-m) solvents and their amounts, yield and purity of 3-HP that were obtained by following the general extraction protocol C, are shown in Table 15.

TABLE 15

| Entry No. | Amount of broth, titer | Combined amount of ethyl acetate | Water-miscible (w-m) solvent | Amount of w-m solvent | yield | purity |
|---|---|---|---|---|---|---|
| 2A-1 | 4.1 L, 82 g/L | 5.9 L | MeOH | 10 v/v % | 73% | 74% |
| 2A-2 | 4.3 L, 81.4 g/L | 5.3 L | MeOH | 20 v/v % | 78% | 70% |
| 2A-3 | 4.1 L, 87 g/L | 5.4 L | MeOH | 25 v/v % | 93% | 79% |
| 2A-4 | 4.5 L, 66 g/L | 5.0 L | MeOH | 25 v/v % | 100% | 90-95% |
| 2A-5 | 4.3 L, 89 g/L | 5.2 L | MeOH | 30 v/v % | 91% | 85% |
| 2A-6 | 4.3 L, 69 g/L | 5.1 L | MeOH | 35 v/v % | 99% | 80% |
| 2A-7 | 4.3 L, 69 g/L | 5.1 L | MeOH | 40 v/v % | 99% | 76% |
| 2A-8 | 5 L, 62 g/L | 4.5 L | EtOH | 25 v/v % | 94.5% | 88% |
| 2A-9 | 5 L, 63 g/L | 4.5 L | i-PrOH | 25 v/v % | 99% | 93% |

Figure 61:
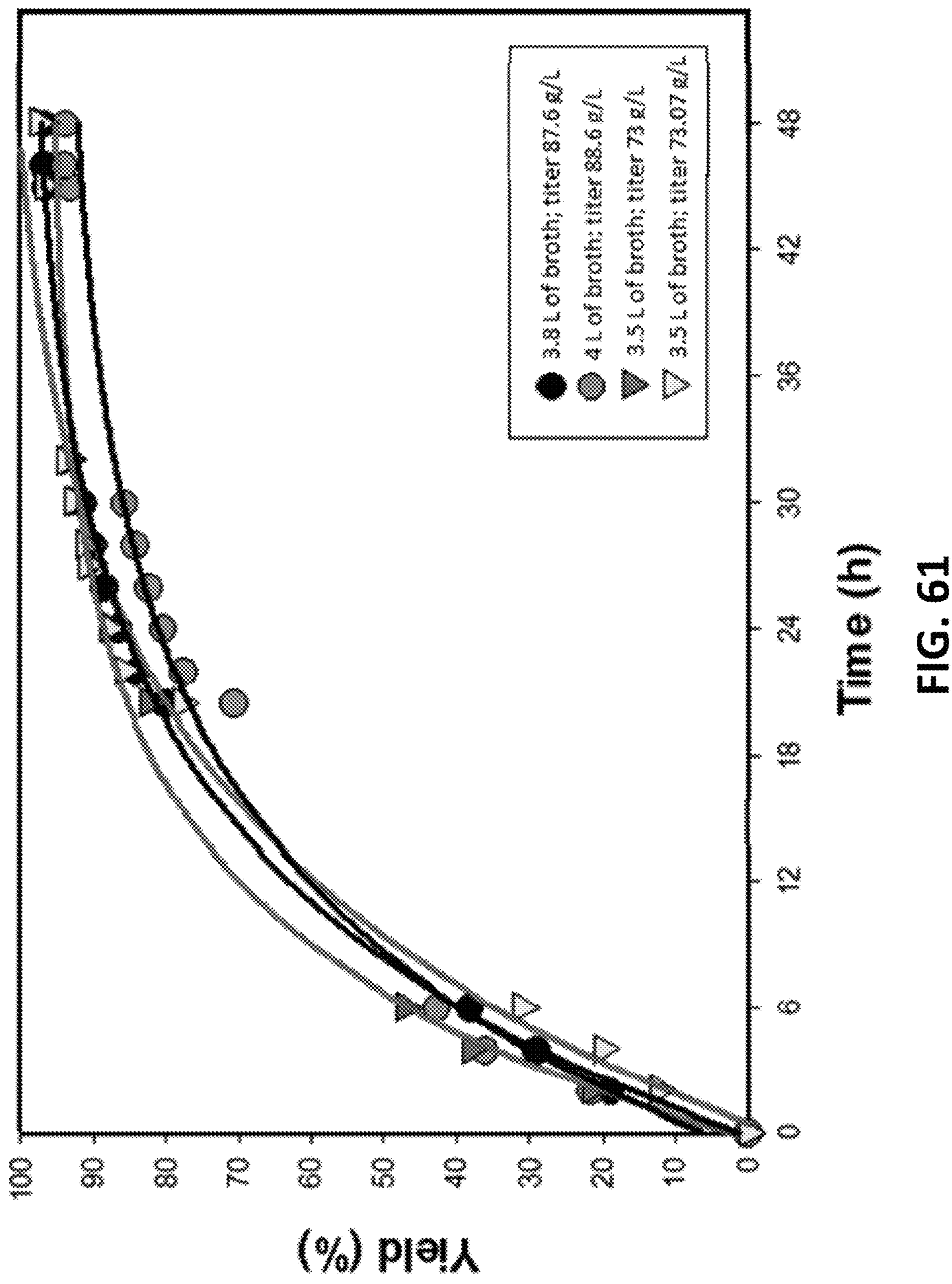
FIG. 61 is an exemplary line plot illustrating the increase in concentration of 3-HP in the solvent vessel during extraction of 3-HP from a decellularized fermentation using ethyl acetate.

FIG. 61 shows increase in concentration of 3-HP in ethyl acetate in the solvent flask throughout the extraction of decellularized broth using ethyl acetate and methanol as water-miscible solvent (amount of methanol is 25 v/v % of the amount of broth used for extraction) at 78° C. for 48 hours. Data depicted in FIG. 61 is summarized in Table 16.

TABLE 16

| Entry No. | Amount of broth | Titer of 3-HP in broth | Yield of 3-HP |
|---|---|---|---|
| 2B-1 | 3.8 L | 87.6 g/L | 97.2% |
| 2B-2 | 4 L | 88.6 L | 94.5% |

TABLE 16-continued

| Entry No. | Amount of broth | Titer of 3-HP in broth | Yield of 3-HP |
|---|---|---|---|
| 2B-3 | 3.5 L | 73 g/L | 97.2% |
| 2B-4 | 3.5 L | 73.07 g/L | 97.7% |

Example 33. Purification of Crude 3-HP

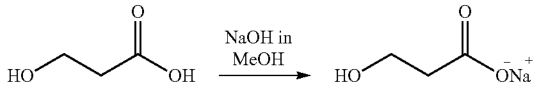

Step 1—Formation of 3-HP Sodium Salt

To a solution of crude 3-HP (prepared as described in previous examples) in IPA was added NaOH (2N solution in MeOH) until pH=7.0 at room temperature. After stirring the reaction mixture for 2 hours at room temperature, the reaction mixture was filtered and washed with IPA. The crude 3-HP sodium salt was dissolved in EtOH (ratio: 3-HP sodium salt:EtOH=1:4 or 1:6 or 1:8) and filtered to give pure desired product 3-HP sodium salt as a white solid in 63% yield at 99% purity as determined by 1H NMR.

Step 2-Formation of Pure 3-HP from 3-HP Sodium Salt

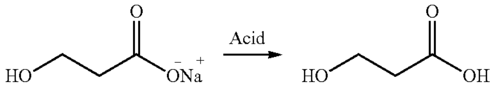

To a solution of 3-HP sodium salt was added an acid (acetic acid, con HCl, $H_2SO_4$, or oxalic acid) in MeOH at room temperature. After stirring for 2 hours at room temperature, the reaction mixture was filtered and washed with MeOH. The filtrate was concentrated in vacuo to give the desired pure 3-HP as a yellow oil in quantitative yield.

Example 34. Reactive Distillation of Crude 3-HP in the Presence of a Catalyst

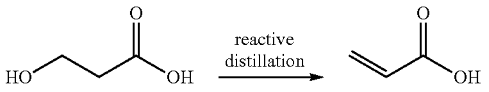

General Protocol D

A typical system for reactive distillation of acrylic acid is shown in FIG. 60. Specified amount of crude 3-HP as prepared in previous examples was placed in the reaction flask, followed by a specified amount of a catalyst (wt. % based on the amount of crude 3-HP in reaction mixture). Once the system was assembled, the vacuum was turned on and set to 74 mbar (throughout the reactive distillation process, the pressure was maintained at 70-100 mbar). When the pressure was set, the reaction mixture was heated to 80° C. using a heating mantle. The dehydration reaction started when the temperature of the reaction mixture reached 50° C. The mixture of acrylic acid and water (reaction products) evaporated and was collected in the still head and in the collection flask. The temperature of the reaction mixture was gradually increased from in 20° C. increments until the specified temperature was reached, and the process was continued for a specified amount of time until no more liquid collection was observed. Purity of the resultant acrylic acid was determined by $^1$H NMR.

$^1$H NMR (400 MHZ, $CDCl_3$) δ 6.51 (d, J=17.2 Hz, 1H), 6.14 (dd, J=17.3, 10.4 Hz, 1H), 5.96 (d, J=10.4 Hz, 1H).

$^1$H NMR (400 MHZ, DMSO) δ 6.24 (dd, J=17.3, 1.9 Hz, 1H), 6.07 (dd, J=17.3, 10.2 Hz, 1H), 5.86 (dd, J=10.2, 1.9 Hz, 1H).

Various conditions for making acrylic acid from crude 3-HP, such as amount of crude 3-HP, catalysts and their amounts, reaction temperature, reaction time, yield and purity of 3-HP that were obtained by following the general reaction protocol D, are shown in Table 17.

TABLE 17

| Entry No. | Catalyst | Amount of 3-HP | Amount of catalyst | Re-action temp. | Re-action time | Yield | Purity |
|---|---|---|---|---|---|---|---|
| 4A-1 | Oxalic acid, dihydrate | 849 g | 5 wt. % | 145° C. | 8 h | 79% | 63% |
| 4A-2 | Oxalic acid, dihydrate | 998 g | 5 wt. % | 180° C. | 8 h | 100% | 50% |
| 4A-3 | Oxalic acid, dihydrate | 550 g | 2 wt. % | 180° C. | 8 h | 89% | 80% |
| 4A-4 | Oxalic acid, dihydrate | 528 g | 1 wt. % | 180° C. | 8 h | 93% | 85% |
| 4A-5 | Oxalic acid, dihydrate | 225 g | 1 wt. % | 110° C. | 8 h | 66% | 86% |
| 4A-6 | Oxalic acid, dihydrate | 250 g | 4 wt. % | 180° C. | 8 h | 94% | 69% |
| 4A-7 | Oxalic acid, dihydrate | 266 g | 3 wt. % | 180 | 8 h | 91% | 80% |
| 4A-8 | Oxalic acid, dihydrate Silica gel | 251 g | 1 wt. % 5 wt. % | 180° C. | 8 h | 66% | 68% |
| 4A-9 | Oxalic acid Sea sand | 250 g | 1 wt. % 5 wt. % | 180° C. | 8 hours | 75% | 67% |
| 4A-10 | 4A molecular sieves | 250 g | 3 wt. % | 180° C. | 8 h | 102% | 76% |
| 4A-11 | Oxalic acid NaCl | 250 g | 1 wt. % 5 wt. % | 180° C. | 8 h | 98% | 81% |
| 4A-12 | 4A molecular sieves NaCl | 250 g | 1 wt. % 5 wt. % | 180° C. | 4 h | 95% | 80% |
| 4A-13 | Oxalic acid 4A molecular sieves | 1313 g | 1 wt. % 5 wt. % | 180° C. | 8 h | 96% | 82% |
| 4A-14 | 4A molecular sieves | 3 kg | 3 wt. % | 180° C. | 6 h | 102% | 83% |

Example 35. Reactive Distillation of 3-HP Catalyzed by Polyphosphoric Acid (PPA)

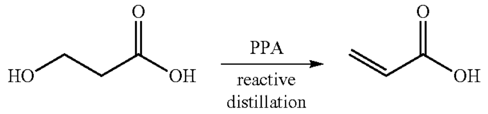

To a purified compound 3-HP (10.00 g, 0.11 mmol) was added PPA (1.00 g, 10 wt. %) at room temperature. The reaction mixture was heated at 180° C. for 5 hours, during which time the acrylic acid was formed and distilled from the reaction mixture to afford the desired product (4.90 g, 62%) as colorless oil in 62% yield at 76% purity as determined by 1H NMR.

Example 36. Reactive Distillation of 3-HP in the Presence of Phenothiazine

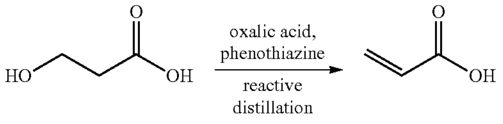

General Protocol E

To 3-HP was added a specified amount of phenothiazine (wt. % of the amount of 3-HP) and a specified amount of oxalic acid (wt. % of the amount of 3-HP) at room temperature. The reaction mixture was heated at 180° C. for 5 hours, during which time the acrylic acid was formed and distilled from the reaction mixture to afford the desired product as colorless oil.

Various conditions for making acrylic acid from crude 3-HP, such as amounts of phenothiazine and oxalic acid, and yield of 3-HP that were obtained by following the general reaction protocol E, are shown in Table 18.

TABLE 18

| Entry No. | Amount of phenothiazine | Amount of oxalic acid | Yield |
|---|---|---|---|
| 6A-1 | 0.5 wt. % | 5 wt. % | 66% |
| 6A-2 | 2 wt. % | 10 wt. % | 73% |
| 6A-3 | 2 wt. % | 5 wt. % | 62% |
| 6A-4 | 0.5 wt. % | 20 wt. % | 56% |
| 6A-5 | 4 wt. % | 20 wt. % | 67% |
| 6A-6 | 5 wt. % | 10 wt. % | 67% |
| 6A-7 | 2 wt. % | 10 wt. % | 60% |

Example 37. Reactive Distillation of 3-HP in the Presence of Hydroquinone

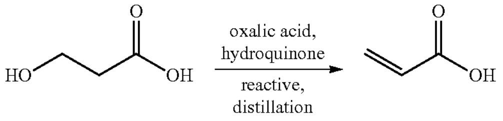

To a purified compound 3-HP (50 g) was added hydroquinone (2 wt. %), citric acid (10 wt. %) and oxalic acid (20 wt. %) at room temperature. The reaction mixture was heated at 180° C. for 5 hours, during which time the acrylic acid was formed and distilled from the reaction mixture to afford the desired product as colorless oil in 75% yield at 67% purity as determined by 1H NMR.

Example 38. Reactive Distillation of Purified 3-HP

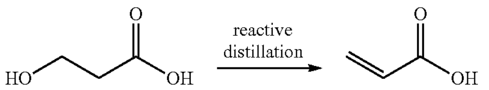

A purified compound 3-HP (1.36 kg) was heated at 180° C. for 8 hours, during which time the acrylic acid was formed and distilled to afford the desired product as a colorless oil in 56% yield at 75% purity as determined by 1H NMR.

Example 39. Reactive Distillation of 3-HP Treated with Activated Carbon and Oxalic Acid

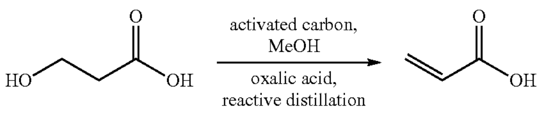

General Protocol F

The specified amount of crude compound 3-HP was dissolved in MeOH, followed by addition of activated carbon (1 wt. % of the amount of 3-HP) to the resultant solution. The solution was filtered through a pad of Celite, and the filtrate was concentrated in vacuo. To the resultant residue, specified amount of oxalic acid was added and at room temperature, and the reaction mixture was heated at a temperature progressively increasing from 135° C. to 180° C., over a period of time of 12 hours, during which time the acrylic acid was formed and distilled to afford the desired product as colorless oil. Purity was determined by $^{1}H$ NMR.

Various conditions for making acrylic acid from crude 3-HP, such as amounts of activated carbon and oxalic acid, and yield of 3-HP that were obtained by following the general reaction protocol F, are shown in Table 19.

TABLE 19

| Entry No. | Amount of 3-HP | Amount of oxalic acid | Yield | Purity |
|---|---|---|---|---|
| 9A-1 | 1473 g | 5 wt. % | 86% | 75% |
| 9A-2 | 976 g | 10 wt. % | 99% | 81% |
| 9A-3 | n/a | 20 wt. % | 93% | n/a |

Example 40. Purification of Crude Acrylic Acid by Distillation

A crude acrylic acid (650.8 g) was distilled at reduced pressure of 70-80 mbar and at a temperature of 80° C.-110° C. to afford the desired product as colorless oil (360.7 g. 55.4%).

Example 41. Purification of Crude Acrylic Acid by Purging with Gas

Crude acrylic acid (2457 g) was placed in the reaction flask equipped with the inlet tube for bubbling hot air through the reaction mixture at atmospheric pressure. The air was heated to about 60° C., and was vigorously bubbled through the crude acrylic acid. For about 12 hours The hot air carried the acrylic acid to the still head. Any vaporized acrylic acid was condensed to liquid state in the condenser. The reaction flask was also heated to 60° C. using a heating mantle. After the purification process, the collected acrylic acid product (1969 g, 80.1%) was pure by NMR, indicating the ratio of acrylic acid to water in the collected product of about 80:20 (pure acrylic acid product contains 20 wt. % water). $^{1}H$ NMR (400 MHZ, DMSO) δ 6.25 (dd, J=17.3, 1.8 Hz, 1H), 6.07 (dd, J=17.3, 10.3 Hz, 1H), 5.87 (dd, J=10.3, 1.8 Hz, 1H).

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A nucleic acid, comprising a first and a second promoter, wherein the first promoter is an inducible promoter and is inducible by a small molecule; the first and second promoters are operably linked to a first gene; and the first gene encodes a protein involved in the synthesis of 3-hydroxypropionic acid (3-HP), a salt of 3-HP, or coenzyme B12 wherein the nucleic acid comprises a sequence selected from the group consisting of SEQ ID NO:22-28 and 64 (UTR 0-6).

2. The nucleic acid of claim 1, wherein the first gene encodes a protein involved in the synthesis of 3-hydroxypropionic acid (3-HP) and is selected from the group consisting of a glycerol dehydratase, a glycerol dehydratase reactivase, and an aldehyde dehydrogenase, wherein:

the glycerol dehydratase is selected from the group consisting of dhaB1, dhaB2, dhaB3;

the glycerol dehydratase reactivase is selected from the group consisting of gdrA and gdrB; and the aldehyde dehydrogenase is selected from the group consisting of kgsA.

3. The nucleic acid of claim 1, wherein the first gene comprises a dhaB1 gene, a dhaB2 gene, a dhaB3 gene, a gdrA gene, and a gdrB gene, and the sequence comprises a sequence that is at least 95% identical to a SEQ ID selected from the group consisting of SEQ ID NO: 1, SEQ ID NO: 2, SEQ ID NO: 3, SEQ ID NO: 4, SEQ ID NO: 5, SEQ ID NO: 5 and SEQ ID NO: 6.

4. The nucleic acid of claim 1, wherein the small molecule acid or alcohol is selected from the group consisting of L-lactic acid (LAC), acetic acid (AcOH), propionic acid (PA), 3-hydroxypropionic acid (3-HP), 3-hydroxybutyrate (3-HB), 1,3-propanediol (1,3-PDO), 2,3-butanediol (2,3-BDO), L-valine (L-val), and 3-hydroxyisobutyrate (3-HIB).

5. The nucleic acid of claim 1, wherein the second promoter is derived from a $P_{mmsA}$ promoter, a $P_{hbdH\text{-}1}$ promoter, a $P_{hbdH\text{-}4}$ promoter, a $P_{hpdH}$ promoter, or a $P_{zwf}$ promoter, and the promoter comprises a sequence that it at least 95% identical to a SEQ ID selected from the group consisting of: SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 52-63; and SEQ ID NO: 65-72.

6. The nucleic acid of claim 1, wherein the nucleic acid further comprises a gene encoding a transcriptional regulator that regulates expression of the first gene, wherein the transcriptional regulator binds to the first or second promoter.

7. The nucleic acid of claim 6, wherein the transcriptional regulator is a LysR-type transcriptional regulator (LTTR), a MmsR regulator or a HpdR regulator.

8. The nucleic acid of claim 6, wherein the transcriptional regulator binds to the first promoter and has enhanced binding to the first promoter in the presence of the small molecule.

9. The nucleic acid of claim 6, wherein the transcriptional regulator is self-regulating.

10. The nucleic acid of claim 1, wherein the first gene is fused at its 5'-terminus to a sequence encoding up to 20 (5, 10, 15, or 20) amino acids that are derived from the 5'terminus of a second gene encoding a native *Pseudomonas denitrificans* protein, thereby creating a fusion gene, and the second promoter is derived from the native promoter for the second gene, and the fusion gene comprises a sequence encoding at least 5, 10, 15, or 20 amino acids in the N-terminus of a native protein.

11. The nucleic acid of claim 1, wherein the second promoter comprises the $P_{mmsA}$ promoter and the fusion gene comprises a sequence encoding five or more amino acids from the N-terminus of a native MmsA gene, and the fusion gene is operably linked to the 3' end of the $P_{mmsA}$ promoter, and wherein the nucleic acid comprises a sequence selected from the group consisting of SEQ ID NOs: 32-35.

12. The nucleic acid of claim 11, wherein the mRNA of the fusion gene has a higher stability and increases the gene translation when compared to the first gene alone.

* * * * *

SEQUENCE LISTING

```
Sequence total quantity: 92
SEQ ID NO: 1           moltype = DNA  length = 1668
FEATURE                Location/Qualifiers
source                 1..1668
                       mol_type = genomic DNA
                       organism = Klebsiella pneumoniae
SEQUENCE: 1
atgaaaagat caaaacgatt tgcagtactg gcccagcgcc ccgtcaatca ggacgggctg  60
attggcgagt ggcctgaaga ggggctgatc gccatggaca gcccctttga cccggtctct  120
tcagtaaaag tggacaacgg tctgatcgtc gagctggacg gcaaacgccg ggaccagttt  180
gacatgatcg accgatttat cgccgattac gcgatcaacg ttgagcgcac agagcaggca  240
atgcgcctgg aggcggtgga aatagcccgc atgctggtgg atattcacgt cagtcgggag  300
gagatcattg ccatcactac cgccatcacg ccggccaaag cggtcgaggt gatggcgcag  360
atgaacgtgg tggagatgat gatggcgctg cagaagatgc gtgcccgccg gaccccctcc  420
aaccagtgcc acgtcaccaa tctcaaagat aatccggtgc agattgctgc tgacgccgcc  480
gaggccggga tccgcggctt ctcagaacag gagaccacgg tcggtatcgc gcgctatgcg  540
ccgtttaacg ccctggcgct gttggtcggt tcgcagtgcg gccgccccgg cgttttgacg  600
cagtgctcgg tggaagaggc caccgagctg gagctgggca tgcgtggctt aaccagctac  660
gccgagacgg tgtcggtcta cggcaccgaa gcggtattta ccgacggcga tgatactccg  720
tggtcaaagg cgttcctcgc ctcggcctac gcctcccgcg ggttgaaaat gcgctacacc  780
tccggcaccg gatccgaagc gctgatgggc tattcggaga gcaagtcgat gctctacctc  840
gaatcgcgct gcatcttcat taccaaaggc gccggggttc aggggctgca aaacggcgcg  900
gtgagctgta tcggcatgac cggcgctgtg ccgtcgggca ttcgggcggt gctggcggaa  960
aacctgatcg cctctatgct cgacctcgaa gtggcgtccg ccaacgacca gactttctcc  1020
cactcggata ttcgccgcac cgcgcgcacc ctgatgcaga tgctgccggg caccgacttt  1080
attttctccg gctacagcgc ggtgccgaac tacgacaaca tgttcgccgg ctcgaacttc  1140
gatgcggaag attttgatga ttacaacatc ctgcagcgtg acctgatggt tgacggcggc  1200
ctgcgtccgg tgaccgaggc ggaaaccatt gccattcgcc agaaagcggc gcgggcgatc  1260
caggcggttt tccgcgagct ggggctgccg ccaatcgccg acgaggaggt ggaggccgcc  1320
acctacgcgc acggtagcaa cgagatgccg ccgcgtaacg tggtggagga tctgagtgcg  1380
gtggaagaga tgatgaagcg caacatcacc ggcctcgata ttgtcggcgc gctgagccgc  1440
```

```
agcggctttg aggatatcgc cagcaatatt ctcaatatgc tgcgccagcg ggtcaccggc  1500
gattacctgc agacctcggc cattctcgat cggcagttcg aggtggtgag tgcggtcaac  1560
gacatcaatg actatcaggg gccgggcacc ggctatcgca tctctgccga acgctgggcg  1620
gagatcaaaa atattccggg cgtggttcag cccgacacca ttgaataa              1668

SEQ ID NO: 2           moltype = DNA  length = 585
FEATURE                Location/Qualifiers
source                 1..585
                       mol_type = other DNA
                       organism = synthetic construct
SEQUENCE: 2
atgcaacaga caacccaaat tcagccctct tttaccctga aaacccgcga gggcggggta  60
gcttctgccg atgaacgcgc cgatgaagtg gtgatcggcg tcggccctgc cttcgataaa  120
caccagcatc acactctgat cgatatgccc catggcgcga tcctcaaaga gctgattgcc  180
ggggtggaag aagaggggct tcacgcccgg gtggtgcgca ttctgcgcac gtccgacgtc  240
tcctttatgg cctgggatgc ggccaacctg agcggctcgg ggatcggcat cggtatccag  300
tcgaagggga ccacggtcat ccatcagcgc gatctgctgc cgctcagcaa cctggagctg  360
ttctcccagg cgccgctgct gacgctggaa acctaccggc agattggcaa aaacgccgcg  420
cgctatgcgc gcaaagagtc accttcgccg gtgccggtgg tgaacgatca gatggtgcgg  480
ccgaaattta tggccaaagc cgcgctattt catatcaaag agaccaaaca tgtggtgcag  540
gacgccgagc ccgtcaccct gcacgtcgac ttagttaggg agtaa                585

SEQ ID NO: 3           moltype = DNA  length = 426
FEATURE                Location/Qualifiers
source                 1..426
                       mol_type = genomic DNA
                       organism = Klebsiella pneumoniae
SEQUENCE: 3
atgagcgaga aaaccatgcg cgtgcaggat tatccgttag ccacccgctg cccggagcat  60
atcctgacgc ctaccggcaa accattgacc gatattaccc tcgagaaggt gctctctggc  120
gaggtgggcc cgcaggatgt gcggatctcc tgccagaccc ttgagtacca ggcgcagatt  180
gccgagcaga tgcagcgcca tgcggtggcg cgcaatttcc gccgcgcggc ggagcttatc  240
gccattcctg acgagcgcat tctggctatc tataacgcgc tgcgcccgtt ccgctcctcg  300
caggcggagc tgctggcgat cgccgacgag ctggagcaca cctggcatgc gacagtgaat  360
gccgcctttg tccgggagtc ggcggaagtg tatcagcagc ggcataagct gcgtaaagga  420
agctaa                                                            426

SEQ ID NO: 4           moltype = DNA  length = 1824
FEATURE                Location/Qualifiers
source                 1..1824
                       mol_type = genomic DNA
                       organism = Klebsiella pneumoniae
SEQUENCE: 4
atgccgttaa tagccgggat tgatatcggc aacgccacca ccgaggtggc gctggcgtcc  60
gacgacccgc aggcgagggc gtttgttgcc agcgggatcg tcgcgacgac gggcatgaaa  120
gggacgcggg acaatatcgc cgggaccctc gccgcgctgg agcaggccct ggcgaaaaca  180
ccgtggtcga tgagcgatgt ctctcgcatc tatcttaacg aagccgcgcc ggtgattggc  240
gatgtggcga tggagaccat caccgagacc attatcaccg aatcgaccat gatcggtcat  300
aacccgcaga cgccgggcgg ggtgggcgtt ggcgtgggga cgactatcgc cctcgggcgg  360
ctggcgacgc tgccggcggc gcagtatgcc gaggggtgga tcgtactgat tgacgacgcc  420
gtcgatttcc ttgacgccgt gtggtggctc aatgaggcgc tcgaccgggg gatcaacgtg  480
gtggcggcga tcctcaaaaa ggacgacggc gtgctggtga acaaccgcct gcgtaaaacc  540
ctgccggtgg tagatgaagt gacgctgctg gagcaggtcc ccgagggggt aatggcggcg  600
gtggaagtgg ccgcgccggg ccaggtggtg cggatcctgt cgaatcccta cgggatcgcc  660
accttcttcg ggctaagccc ggaagagacc caggccatcg tccccatcgc ccgcgccctg  720
attggcaacc gttcagcggt ggtgctcaag accccgcagg gggatgtgca gtcgcgggtg  780
atcccggcgg gcaacctcta cattagcggc gaaaagcgcc gcggagaggc cgatgtcgcc  840
gagggcgcgg aagccatcat gcaggcgatg agcgcctgcg ctccggtacg cgacatccgc  900
ggcgaaccgg gcactcacgc cggcggcatg cttgagcggg tgcgcaaggt aatggcgtcc  960
ctgaccgacc atgagatgag cgcgatatac atccaggatc tgctggcggt ggatacgttt  1020
attccgcgca aggtgcaggg cgggatggcc ggcgagtgcg ccatggaaaa tgccgtcggg  1080
atggcggcga tggtgaaagc ggatcgtctg caaatgcagg ttatcgcccg cgaactgagc  1140
gcccgactgc agaccgaggt ggtggtgggc ggcgtggagg ccaacatggc catcgccggg  1200
gcgttaacca ctcccggctg tgcggcgccg ctggcgatcc tcgacctcgg cgccggctcg  1260
acggatgcgg cgatcgtcaa cgcggagggg cagataacgg cggtccatct cgccggggcg  1320
gggaatatgg tcagcctgtt gattaaaacc gagctgggcc tcgaggatct ttcgctggcg  1380
gaagcgataa aaaaataccc gctggccaaa gtggaaagcc tgttcagtat tcgtcacgag  1440
aatggcgcgg tggagttctt tcgggaagcc ctcagcccgg cggtgttcgc caaagtggtg  1500
tacatcaagg agggcgaact ggtgccgatc gataacgcca gcccgctgga aaaaattcgt  1560
ctcgtgcgcc ggcaggcgaa agagaaagtg tttgtcacca actgcctgcg cgcgctgcgc  1620
caggtctcac ccggcggttc cattcgcgat atcgcctttg tggtgctggt gggcggctca  1680
tcgctggact ttgagatccc gcagcttatc acggaagcct tgtcgcacta tggcgtggtc  1740
gccgggcagg gcaatattcg gggaacagaa gggccgcgca atgcggtcgc caccgggctg  1800
ctactggccg gtcaggcgaa ttaa                                        1824

SEQ ID NO: 5           moltype = DNA  length = 354
FEATURE                Location/Qualifiers
source                 1..354
                       mol_type = genomic DNA
```

-continued

```
                         organism = Klebsiella pneumoniae
SEQUENCE: 5
atgtcgcttt caccgccagg cgtacgcctg ttttacgatc cgcgcgggca ccatgccggc  60
gccatcaatg agctgtgctg ggggctggag gagcaggggg tcccctgcca gaccataacc  120
tatgacggag gcggtgacgc cgctgcgctg ggcgccctgg cggccagaag ctcgcccctg  180
cgggtgggta ttgggctcag cgcgtccggc gagatagccc tcactcatgc ccagctgccg  240
gcggacgcgc cgctggctac cggacacgtc accgatagcg acgatcatct gcgtacgctc  300
ggcgccaacg ccgggcagct ggttaaagtc ctgccgttaa gtgagagaaa ctga        354

SEQ ID NO: 6             moltype = DNA  length = 1461
FEATURE                  Location/Qualifiers
source                   1..1461
                         mol_type = other DNA
                         organism = synthetic construct
SEQUENCE: 6
atgagaggat cgggatccgc taacgtgact tatacggata cgcaactgct gatcgacggt  60
gagtgggtcg acgccgcgag cggcaagacg atcgacgtcg tgaacccggc gaccggcaag  120
ccgatcggca gggtggccca tgcgggcatc gccgatctcg accgtgcgct cgccgccgcg  180
caaagcggct tcgaggcatg gcgcaaggtg cccgcgcacg agcgcgcggc gacgatgcgc  240
aaggcggccg cgctggtgcg tgaacgcgcc gacgcgatcg cgcagctgat gacgcaggag  300
cagggcaagc cgctcaccga agcgcgcgtc gaagtgctgt cgtccgcgga catcatcgaa  360
tggttcgcgg acgaaggccg ccgcgtgtac ggccggatcg tgccgccgcg caacctcggc  420
gcacagcaga cggtcgtgaa ggagccggtc ggcccggtcg ccgcgttcac gccgtggaat  480
ttcccggtca accaggtcgt gcgcaagctg agcgccgcgc tggcaaccgg ctgttcgttc  540
ctcgtgaaag cgccggaaga aacccccgcg tcgccggccg cgctgctgcg cgccttcgtc  600
gacgcaggcg tgccggccgg cgtgatcggc ctcgtgtacg gcgatccggc cgaaatctcg  660
tcgtacctga tcccgcaccc ggtgatccgc aaggtcacgt tcacgggttc gacgccggtc  720
ggcaagcagc tcgcctcgct ggcgggcctg cacatgaagc gcgcgacgat ggagctgggc  780
gggcacgcac cggtgatcgt ggccgaagac gccgacgttg cgctcgcggt ggcagcggcc  840
ggcggcgcga agttccgcaa cgcggggcag gtctgcatct cgccgacgcg cttcctcgtg  900
cacaacagca tccgcgacga attcacgcgc gcgctggtca agcatgccga agggctgaag  960
gtcggcaacg gcctcgagga aggcacgacg ctcggcgcgc tcgcgaaccc gcgccggctg  1020
accgcgatgg cgtcggtcat cgacaacgcg cgcaaggtcg gtgcgagcat cgaaaccggc  1080
ggcgagcgga tcggctcgga aggcaacttc ttcgcgccga ccgtgatcgc gaacgtgccg  1140
ctcgatgcgg acgtgttcaa caacgagccg ttcggcccgg tcgcggcgat tcgcggtttc  1200
gacaagctcg aagaggcgat cgcggaagcg aaccgtttgc cgttcggtct tgccggctac  1260
gcgttcacgc gttcgttcgc gaacgtgcac ctgctcacgc agcgcctcga agtcgggatg  1320
ctgtggatca accagccgcc gactacatgg ccggaaatgc cgttcggcgg cgtgaaggac  1380
tcgggctacg gttcggaagg cggcccggaa gcgctcgagc cgtacctcgt cacgaagtcg  1440
gtgacggtaa tggccgtctg a                                            1461

SEQ ID NO: 7             moltype = DNA  length = 113
FEATURE                  Location/Qualifiers
source                   1..113
                         mol_type = genomic DNA
                         organism = Pseudomonas denitrificans
SEQUENCE: 7
ggcgaccaac aacggcgcga ggtggcaaaa atatcttgtt taattactac atatttgtct  60
taatgccggc gtgtaaggct aactatcgtt caaaatttag ttggtaacaa caa         113

SEQ ID NO: 8             moltype = DNA  length = 113
FEATURE                  Location/Qualifiers
source                   1..113
                         mol_type = other DNA
                         organism = synthetic construct
SEQUENCE: 8
ggcgaccaac aacggcgcga ggtggcaaaa acggtttgac acagtaatta aaaagacgta  60
taattgcgtt gtgtaaggct aactatcgtt caaaatttag ttggtaacaa caa         113

SEQ ID NO: 9             moltype = DNA  length = 113
FEATURE                  Location/Qualifiers
source                   1..113
                         mol_type = other DNA
                         organism = synthetic construct
SEQUENCE: 9
ggcgaccaac aacggcgcga ggtggcaaaa gtatattgac attccatgcg aaggtcgtta  60
taatacagta gtgtaaggct aactatcgtt caaaatttag ttggtaacaa caa         113

SEQ ID NO: 10            moltype = DNA  length = 100
FEATURE                  Location/Qualifiers
source                   1..100
                         mol_type = other DNA
                         organism = synthetic construct
SEQUENCE: 10
ggcgcgaggt ggcaaaataa tcttgacaac tggagagaat tgtggtataa tgggagcgtg  60
taaggctaac tatcgttcaa aatttagttg gtaacaacaa                        100

SEQ ID NO: 11            moltype = DNA  length = 106
FEATURE                  Location/Qualifiers
```

source 1..106
mol_type = genomic DNA
organism = Pseudomonas denitrificans
SEQUENCE: 11
gcccccgcct acccgcccca gccaccccgg actcagcaag gatgctggcc cgggcctggg 60
cggagacgtc tttcgcgccc gaccatcaga acaagaggac aacccc 106

SEQ ID NO: 12 moltype = DNA length = 150
FEATURE Location/Qualifiers
source 1..150
mol_type = genomic DNA
organism = Pseudomonas putida
SEQUENCE: 12
tgtgggagcg ggcgtgcccg cgaagaggcc agcacagact taccactgtg ctaaaacgca 60
cagcggctgc gcgaaatctc gtgtttcctc cacgaaatta ctcactaaga tggatcggga 120
caagaataat aatcaggccc gaggttgcac 150

SEQ ID NO: 13 moltype = DNA length = 200
FEATURE Location/Qualifiers
source 1..200
mol_type = genomic DNA
organism = Pseudomonas putida
SEQUENCE: 13
tgcgtaatgc cccaccgttc tgccaggcaa cgcgaaacct gtaggagcgg ccttgtgtcg 60
cgatgggctg cgcagcagcc ccggcatttt ttgcatcgat gcggagatct ggggctgctg 120
cgcagcccat cgcgacacaa ggccgctcct acaggttcct ggcccgcatg ggtaaagttc 180
gaaccagtca ggagtcattg 200

SEQ ID NO: 14 moltype = DNA length = 115
FEATURE Location/Qualifiers
source 1..115
mol_type = genomic DNA
organism = Pseudomonas denitrificans
SEQUENCE: 14
cctcgaatgt gcaaaaacgc agaccatact tgcacatcac cgcattgagt acatcaaaaa 60
tgcactgtta ggatcgatcc agacaacaaa aaagccacag gctgggagaa tcccg 115

SEQ ID NO: 15 moltype = DNA length = 48
FEATURE Location/Qualifiers
source 1..48
mol_type = other DNA
organism = synthetic construct
SEQUENCE: 15
ttaggatcga tccagacaac aaaaaagcca caggctggga gaatcccg 48

SEQ ID NO: 16 moltype = DNA length = 34
FEATURE Location/Qualifiers
source 1..34
mol_type = genomic DNA
organism = Pseudomonas denitrificans
SEQUENCE: 16
aatgtgcaaa aacgcagacc atacttgcac atca 34

SEQ ID NO: 17 moltype = DNA length = 33
FEATURE Location/Qualifiers
source 1..33
mol_type = genomic DNA
organism = Pseudomonas denitrificans
SEQUENCE: 17
caaaaatgca ctgttaggat cgatccagac aac 33

SEQ ID NO: 18 moltype = DNA length = 118
FEATURE Location/Qualifiers
source 1..118
mol_type = genomic DNA
organism = Pseudomonas denitrificans
SEQUENCE: 18
gcacctcgaa tgtgcaaaaa cgcagaccat acttgcacat caccgcattg agtacatcaa 60
aaatgcactg ttaggatcga tccagacaac aaaaaagcca caggctggga gaatcccg 118

SEQ ID NO: 19 moltype = DNA length = 171
FEATURE Location/Qualifiers
source 1..171
mol_type = other DNA
organism = synthetic construct
SEQUENCE: 19
tccgatttat gcgcctctag aggatccccg ggtactaaca tgtcagcctc agcgcacctc 60
gaatgtgcaa aaacgcagac catacttgca catcaccgca ttgagtacat caatccttgc 120
ttgttaggat cgatccagac aacaaaaaag ccacaggctg ggagaatccc g 171

```
SEQ ID NO: 20          moltype = DNA  length = 171
FEATURE                Location/Qualifiers
source                 1..171
                       mol_type = other DNA
                       organism = synthetic construct
SEQUENCE: 20
tccgatttat gcgcctctag aggatccccg ggtactaaca tgtcagcctc agcgcacctc  60
gaatgtgcaa aaacgcagac catacttgca catcaccgca ttgagtacat caaaaatgca  120
ctgttaggat cgcgcccagg cacaaaaaag ccacaggctg ggagaatccc g           171

SEQ ID NO: 21          moltype = DNA  length = 171
FEATURE                Location/Qualifiers
source                 1..171
                       mol_type = other DNA
                       organism = synthetic construct
SEQUENCE: 21
tccgatttat gcgcctctag aggatccccg ggtactaaca tgtcagcctc agcgcacctc  60
gaatgtgcaa aaacgcagac catacttgca catcaccgca ttgagtacat caatccttgc  120
ttgttaggat cgcgcccagg cacaaaaaag ccacaggctg ggagaatccc g           171

SEQ ID NO: 22          moltype = DNA  length = 60
FEATURE                Location/Qualifiers
source                 1..60
                       mol_type = other DNA
                       organism = synthetic construct
SEQUENCE: 22
cgacggcaag cccgtcgagt ccaccatggc taacgtgact tacaccgata cccaactgct  60

SEQ ID NO: 23          moltype = DNA  length = 60
FEATURE                Location/Qualifiers
source                 1..60
                       mol_type = other DNA
                       organism = synthetic construct
SEQUENCE: 23
cgacggcaag ccaactgaac ccaccatggc taacgtgact tacaccgata cccaactgct  60

SEQ ID NO: 24          moltype = DNA  length = 60
FEATURE                Location/Qualifiers
source                 1..60
                       mol_type = other DNA
                       organism = synthetic construct
SEQUENCE: 24
cgacggcaag ccctaactgg acaccatggc taacgtgact tacaccgata cccaactgct  60

SEQ ID NO: 25          moltype = DNA  length = 60
FEATURE                Location/Qualifiers
source                 1..60
                       mol_type = other DNA
                       organism = synthetic construct
SEQUENCE: 25
cgacggcaag ccctaacagg acaccatggc taacgtgact tacaccgata cccaactgct  60

SEQ ID NO: 26          moltype = DNA  length = 60
FEATURE                Location/Qualifiers
source                 1..60
                       mol_type = other DNA
                       organism = synthetic construct
SEQUENCE: 26
cgacggcaag cccaagctgg acaccatggc taacgtgact tacaccgata cccaactgct  60

SEQ ID NO: 27          moltype = DNA  length = 60
FEATURE                Location/Qualifiers
source                 1..60
                       mol_type = other DNA
                       organism = synthetic construct
SEQUENCE: 27
cgacggcaag ccctagcagg acaccatggc taacgtgact tacaccgata cccaactgct  60

SEQ ID NO: 28          moltype = DNA  length = 60
FEATURE                Location/Qualifiers
source                 1..60
                       mol_type = other DNA
                       organism = synthetic construct
SEQUENCE: 28
cgacggcaag cccaagcagg acaccatggc taacgtgact tacaccgata cccaactgct  60

SEQ ID NO: 29          moltype = DNA  length = 45
FEATURE                Location/Qualifiers
```

```
source                  1..45
                        mol_type = other DNA
                        organism = synthetic construct
SEQUENCE: 29
atggccaacg tgacctacac cgacacccag ctgctgatcg acggc                  45

SEQ ID NO: 30           moltype = DNA  length = 45
FEATURE                 Location/Qualifiers
source                  1..45
                        mol_type = other DNA
                        organism = synthetic construct
SEQUENCE: 30
atggctaacg tgacttacac cgatacccaa ctgctgatcg acggc                  45

SEQ ID NO: 31           moltype = DNA  length = 45
FEATURE                 Location/Qualifiers
source                  1..45
                        mol_type = other DNA
                        organism = synthetic construct
SEQUENCE: 31
atggcgaacg tgacctacac cgacacccag ctcctgatcg acggc                  45

SEQ ID NO: 32           moltype = DNA  length = 130
FEATURE                 Location/Qualifiers
source                  1..130
                        mol_type = other DNA
                        organism = synthetic construct
SEQUENCE: 32
cctcgaatgt gcaaaaacgc agaccatact tgcacatcac cgcattgagt acatcaaaaa  60
tgcactgtta ggatcgatcc agacaacaaa aaagccacag gctgggagaa tcccgatgac  120
cgcaactgcc                                                         130

SEQ ID NO: 33           moltype = DNA  length = 145
FEATURE                 Location/Qualifiers
source                  1..145
                        mol_type = other DNA
                        organism = synthetic construct
SEQUENCE: 33
cctcgaatgt gcaaaaacgc agaccatact tgcacatcac cgcattgagt acatcaaaaa  60
tgcactgtta ggatcgatcc agacaacaaa aaagccacag gctgggagaa tcccgatgac  120
cgcaactgcc ccgaccgtca aactg                                        145

SEQ ID NO: 34           moltype = DNA  length = 160
FEATURE                 Location/Qualifiers
source                  1..160
                        mol_type = other DNA
                        organism = synthetic construct
SEQUENCE: 34
cctcgaatgt gcaaaaacgc agaccatact tgcacatcac cgcattgagt acatcaaaaa  60
tgcactgtta ggatcgatcc agacaacaaa aaagccacag gctgggagaa tcccgatgac  120
cgcaactgcc ccgaccgtca aactgttcct cgacggcaag                        160

SEQ ID NO: 35           moltype = DNA  length = 175
FEATURE                 Location/Qualifiers
source                  1..175
                        mol_type = other DNA
                        organism = synthetic construct
SEQUENCE: 35
cctcgaatgt gcaaaaacgc agaccatact tgcacatcac cgcattgagt acatcaaaaa  60
tgcactgtta ggatcgatcc agacaacaaa aaagccacag gctgggagaa tcccgatgac  120
cgcaactgcc ccgaccgtca aactgttcct cgacggcaag cccgtcgagt ccacc       175

SEQ ID NO: 36           moltype = DNA  length = 300
FEATURE                 Location/Qualifiers
source                  1..300
                        mol_type = genomic DNA
                        organism = Pseudomonas denitrificans
SEQUENCE: 36
ggcagcattc tcctacagac tatcagttgt tgtttttaca acataatctt cgaatacaaa  60
gcatttactt ttcttcgaag cggaaattta atgtttttta ccacaacata agaaaagaga  120
cgaccttcat gactatacgc ctggcgatca acgggttcgg ccgcatcggt cggaatatcc  180
tccgtgcact ctactccggc ccctaccgcc agcacctgca ggtagtggcg atcaacgacc  240
tgggcgatgc ggcgatcaac gcccacctgt tgcagtacga cagcgtgcac ggacgcttcc  300

SEQ ID NO: 37           moltype = DNA  length = 300
FEATURE                 Location/Qualifiers
source                  1..300
                        mol_type = genomic DNA
                        organism = Pseudomonas denitrificans
```

```
SEQUENCE: 37
ccaaggcaat cggtcacatc cgtaacatgc tgctgcagag cggcacttga tccgagggcc  60
tcgcgcccaa agatcattgc aagagcgaca cctgtaccgc cggaacattg tccggcggta  120
cagtccctag gacccaagcc cacaaagcgg gggtcctgtt ttgaaaacgt atatatgacc  180
agcaggggca tccgggctgg tacccggact atctgcgggg atcggtggct tgaagtcgct  240
gtgtatgact tcgcgccaga gattccacag gtggagtccc cttaccgagg gtgaccaagc  300

SEQ ID NO: 38          moltype = DNA  length = 615
FEATURE                Location/Qualifiers
source                 1..615
                       mol_type = other DNA
                       organism = synthetic construct
SEQUENCE: 38
gacggcagca ttctcctaca gactatcagt tgttgttttt acaacataat cttcgaatac  60
aaagcattta cttttcttcg aagcggaaat ttaatgtttt ttaccacaac ataagaaaag  120
agacgacctt catgactata cgcctggcga tcaacgggtt cggccgcatc ggtcggaata  180
tcctccgtgc actctactcc ggcccctacc gccagcacct gcaggtagtg gcgatcaacg  240
acctgggcga tgcggcgatc aacgcccacc tgttgcagta cgacagcgtg cacggacgct  300
tccgtagagt tgccaaggca atcggtcaca tccgtaacat gctgctgcag agcggcactt  360
gatccgaggg cctcgcgccc aaagatcatt gcaagagcga cacctgtacc gccggaacat  420
tgtccggcgg tacagtccct aggacccaag cccacaaagc ggggtcctg ttttgaaaac  480
gtatatatga ccagcagggg catccgggct ggtacccgga ctatctgcgg ggatcggtgg  540
cttgaagtcg ctgtgtatga cttcgcgcca gagattccac aggtggagtc cccttaccga  600
gggtgaccaa gcatg                                                  615

SEQ ID NO: 39          moltype = DNA  length = 83
FEATURE                Location/Qualifiers
source                 1..83
                       mol_type = other DNA
                       organism = synthetic construct
SEQUENCE: 39
ttgttgttac caactaaatt ttgaacgata gttagcctta caccgggata ttataacaga  60
caaacacgca gttgtcaacc ccc                                         83

SEQ ID NO: 40          moltype = DNA  length = 300
FEATURE                Location/Qualifiers
source                 1..300
                       mol_type = genomic DNA
                       organism = Pseudomonas denitrificans
SEQUENCE: 40
gatgctgaag cgcgtggcct gctgcgggtc gtgcaggatc acttcggcga ccttgcgctc  60
ggccttgttc agctgttcca gacggctctg gatctgctcc agcaggtttt tcatccgtgc  120
tccttgggca atcgacggtt ggccgggtag gggcggccag cggcgctatc ctaacgtcag  180
gccggcaggc gaccaacaac ggcgcgaggt ggcaaaaata tcttgtttaa ttactacata  240
tttgtcttaa tgccggcgtg taaggctaac tatcgttcaa aatttagttg gtaacaacaa  300

SEQ ID NO: 41          moltype = DNA  length = 403
FEATURE                Location/Qualifiers
source                 1..403
                       mol_type = other DNA
                       organism = synthetic construct
SEQUENCE: 41
catttgttgt taccaactaa attttgaacg atagttagcc ttacaccggg atattataac  60
agacaaacac gcagttgtca acccccatg cgcagctaga gatgctgaag cgcgtggcct  120
gctgcgggtc gtgcaggatc acttcggcga ccttgcgctc ggccttgttc agctgttcca  180
gacggctctg gatctgctcc agcaggtttt tcatccgtgc tccttgggca atcgacggtt  240
ggccgggtag gggcggccag cggcgctatc ctaacgtcag gccggcaggc gaccaacaac  300
ggcgcgaggt ggcaaaaata tcttgtttaa ttactacata tttgtcttaa tgccggcgtg  360
taaggctaac tatcgttcaa aatttagttg gtaacaacaa atg                   403

SEQ ID NO: 42          moltype = DNA  length = 300
FEATURE                Location/Qualifiers
source                 1..300
                       mol_type = genomic DNA
                       organism = Pseudomonas denitrificans
SEQUENCE: 42
ttgttgttac caactaaatt ttgaacgata gttagcctta cacgccggca ttaagacaaa  60
tatgtagtaa ttaaacaaga tatttttgcc acctcgcgcc gttgttggtc gcctgccggc  120
ctgacgttag gatagcgccg ctggccgccc ctacccggcc aaccgtcgat tgcccaagga  180
gcacggatga aaaacctgct ggagcagatc cagagccgtc tggaacagct gaacaaggcc  240
gagcgcaagg tcgccgaagt gatcctgcac gacccgcagc aggccacgcg cttcagcatc  300

SEQ ID NO: 43          moltype = DNA  length = 83
FEATURE                Location/Qualifiers
source                 1..83
                       mol_type = other DNA
                       organism = synthetic construct
SEQUENCE: 43
gggggttgac aactgcgtgt ttgtctgtta taatatcccg gtgtaaggct aactatcgtt  60
```

```
caaaatttag ttggtaacaa caa                                          83

SEQ ID NO: 44          moltype = DNA  length = 403
FEATURE                Location/Qualifiers
source                 1..403
                       mol_type = other DNA
                       organism = synthetic construct
SEQUENCE: 44
catttgttgt taccaactaa attttgaacg atagttagcc ttacacgccg gcattaagac  60
aaatatgtag taattaaaca agatattttt gccacctcgc gccgttgttg gtcgcctgcc  120
ggcctgacgt taggatagcg ccgctggccg cccctacccg gccaaccgtc gattgcccaa  180
ggagcacgga tgaaaaacct gctggagcag atccagagcc gtctggaaca gctgaacaag  240
gccgagcgca aggtcgccga agtgatcctg cacgacccgc agcaggccac gcgcttcagc  300
atctctagct gcgcataggg ggttgacaac tgcgtgtttg tctgttataa tatcccggtg  360
taaggctaac tatcgttcaa aatttagttg gtaacaacaa atg                    403

SEQ ID NO: 45          moltype = DNA  length = 300
FEATURE                Location/Qualifiers
source                 1..300
                       mol_type = genomic DNA
                       organism = Pseudomonas denitrificans
SEQUENCE: 45
cgctgaatct cctgcggggg ctgcttcgaa acttcgaagg gaatgaaaaa aggccggtat  60
tttcgcccag ccgggccccg tggggcaatg acagatcggc agaagcctga tgcagagcat  120
ccgagcgggc cgggcaactg atcaaaaacc gctcatccgt caatatcaaa actttttgat  180
acagctattg ccccaccctg caagccacga ctagactgcg cgacctatga gcctgcgcct  240
gcccgaaatc cgccacgacg actgcgacca gctggccgcc ctgtgcaagg ccggcggcga  300

SEQ ID NO: 46          moltype = DNA  length = 83
FEATURE                Location/Qualifiers
source                 1..83
                       mol_type = other DNA
                       organism = synthetic construct
SEQUENCE: 46
acggtttgac acagtaatta aaaagacgta taattgcgtt gtgtaaggct aactatcgtt  60
caaaatttag ttggtaacaa caa                                          83

SEQ ID NO: 47          moltype = DNA  length = 403
FEATURE                Location/Qualifiers
source                 1..403
                       mol_type = other DNA
                       organism = synthetic construct
SEQUENCE: 47
catcgctgaa tctcctgcgg gggctgcttc gaaacttcga agggaatgaa aaaaggccgg  60
tattttcgcc cagccgggcc ccgtggggca atgacagatc ggcagaagcc tgatgcagag  120
catccgagcg ggccgggcaa ctgatcaaaa accgctcatc cgtcaatatc aaaacttttt  180
gatacagcta ttgccccacc ctgcaagcca cgactagact gcgcgaccta tgagcctgcg  240
cctgcccgaa atccgccacg acgactgcga ccagctggcc gccctgtgca aggccggcgg  300
cgatctagct gcgcataacg gtttgacaca gtaattaaaa agacgtataa ttgcgttgtg  360
taaggctaac tatcgttcaa aatttagttg gtaacaacaa atg                    403

SEQ ID NO: 48          moltype = DNA  length = 300
FEATURE                Location/Qualifiers
source                 1..300
                       mol_type = genomic DNA
                       organism = Pseudomonas denitrificans
SEQUENCE: 48
gatgctgaag cgcgtggcct gctgcgggtc gtgcaggatc acttcggcga ccttgcgctc  60
ggccttgttc agctgttcca gacggctctg gatctgctcc agcaggtttt tcatccgtgc  120
tccttgggca atcgacggtt ggccgggtag ggcggccag cggcgctatc ctaacgtcag  180
gccggcaggc gaccaacaac ggcgcgaggt ggcaaaaata tcttgtttaa ttactacata  240
tttgtcttaa tgccggcgtg taaggctaac tatcgttcaa aatttagttg gtaacaacaa  300

SEQ ID NO: 49          moltype = DNA  length = 303
FEATURE                Location/Qualifiers
source                 1..303
                       mol_type = genomic DNA
                       organism = Pseudomonas denitrificans
SEQUENCE: 49
gatgctgaag cgcgtggcct gctgcgggtc gtgcaggatc acttcggcga ccttgcgctc  60
ggccttgttc agctgttcca gacggctctg gatctgctcc agcaggtttt tcatccgtgc  120
tccttgggca atcgacggtt ggccgggtag ggcggccag cggcgctatc ctaacgtcag  180
gccggcaggc gaccaacaac ggcgcgaggt ggcaaaaata tcttgtttaa ttactacata  240
tttgtcttaa tgccggcgtg taaggctaac tatcgttcaa aatttagttg gtaacaacaa  300
atg                                                                303

SEQ ID NO: 50          moltype = DNA  length = 83
FEATURE                Location/Qualifiers
source                 1..83
```

```
                         mol_type = other DNA
                         organism = synthetic construct
SEQUENCE: 50
gggggttgac aactgcgtgt ttgtctgtta taatatcccg gtgtaaggct aactatcgtt  60
caaaatttag ttggtaacaa caa                                          83

SEQ ID NO: 51            moltype = DNA  length = 86
FEATURE                  Location/Qualifiers
source                   1..86
                         mol_type = other DNA
                         organism = synthetic construct
SEQUENCE: 51
gggggttgac aactgcgtgt ttgtctgtta taatatcccg gtgtaaggct aactatcgtt  60
caaaatttag ttggtaacaa caaatg                                       86

SEQ ID NO: 52            moltype = DNA  length = 40
FEATURE                  Location/Qualifiers
source                   1..40
                         mol_type = other DNA
                         organism = synthetic construct
SEQUENCE: 52
tccacttgac ataccctaac atcgggatta taatgtctgc                        40

SEQ ID NO: 53            moltype = DNA  length = 40
FEATURE                  Location/Qualifiers
source                   1..40
                         mol_type = other DNA
                         organism = synthetic construct
SEQUENCE: 53
gttggttgac atggcgctgt cgatcggata taatgtttgt                        40

SEQ ID NO: 54            moltype = DNA  length = 40
FEATURE                  Location/Qualifiers
source                   1..40
                         mol_type = other DNA
                         organism = synthetic construct
SEQUENCE: 54
gcgtcttgac atcttactag attgtgcgta taatagtcgc                        40

SEQ ID NO: 55            moltype = DNA  length = 40
FEATURE                  Location/Qualifiers
source                   1..40
                         mol_type = other DNA
                         organism = synthetic construct
SEQUENCE: 55
ggcgtttgac atgtggatgt aatcctgtta taattttta                         40

SEQ ID NO: 56            moltype = DNA  length = 40
FEATURE                  Location/Qualifiers
source                   1..40
                         mol_type = other DNA
                         organism = synthetic construct
SEQUENCE: 56
gatccttgac agcgaggtat gagtgaggta taatgtaacc                        40

SEQ ID NO: 57            moltype = DNA  length = 40
FEATURE                  Location/Qualifiers
source                   1..40
                         mol_type = other DNA
                         organism = synthetic construct
SEQUENCE: 57
tgcgtttgac aatttgttac gttagtgcta taatctagtt                        40

SEQ ID NO: 58            moltype = DNA  length = 40
FEATURE                  Location/Qualifiers
source                   1..40
                         mol_type = other DNA
                         organism = synthetic construct
SEQUENCE: 58
tacccttgac ataacggcat tctggtggta taatcatgcc                        40

SEQ ID NO: 59            moltype = DNA  length = 40
FEATURE                  Location/Qualifiers
source                   1..40
                         mol_type = other DNA
                         organism = synthetic construct
SEQUENCE: 59
gggggttgac aactgcgtgt ttgtctgtta taatatcccg                        40
```

```
SEQ ID NO: 60          moltype = DNA  length = 37
FEATURE                Location/Qualifiers
source                 1..37
                       mol_type = other DNA
                       organism = synthetic construct
SEQUENCE: 60
gagaattgac agatgactta tttcgttgaa ttcctgc                           37

SEQ ID NO: 61          moltype = DNA  length = 40
FEATURE                Location/Qualifiers
source                 1..40
                       mol_type = other DNA
                       organism = synthetic construct
SEQUENCE: 61
acggtttgac acagtaatta aaaagacgta taattgcgtt                        40

SEQ ID NO: 62          moltype = DNA  length = 40
FEATURE                Location/Qualifiers
source                 1..40
                       mol_type = other DNA
                       organism = synthetic construct
SEQUENCE: 62
gtatattgac attccatgcg aaggtcgtta taatacagta                        40

SEQ ID NO: 63          moltype = DNA  length = 40
FEATURE                Location/Qualifiers
source                 1..40
                       mol_type = other DNA
                       organism = synthetic construct
SEQUENCE: 63
taatcttgac aactggagag aattgtggta taatgggagc                        40

SEQ ID NO: 64          moltype = DNA  length = 60
FEATURE                Location/Qualifiers
source                 1..60
                       mol_type = genomic DNA
                       organism = Pseudomonas denitrificans
SEQUENCE: 64
cgacggcaag cccgtcgagt ccaccatggc taacgtgact tacaccgata cccaactgct  60

SEQ ID NO: 65          moltype = DNA  length = 221
FEATURE                Location/Qualifiers
source                 1..221
                       mol_type = other DNA
                       organism = synthetic construct
SEQUENCE: 65
cctcgaatgt gcaaaaacgc agaccatact tgcacatcac cgcattgagt acatcaaaaa  60
tgcactgtta ggatcgatcc agacaacaaa aaagccacag gctgggagaa tcccggcccc  120
cgcctacccg ccccagccac cccggactca gcaaggatgc tggcccgggc ctgggcggag  180
acgtctttcg cgcccgacca tcagaacaag aggacaaccc c                      221

SEQ ID NO: 66          moltype = DNA  length = 5393
FEATURE                Location/Qualifiers
source                 1..5393
                       mol_type = other DNA
                       organism = synthetic construct
SEQUENCE: 66
caggtcgact ctagagctga tcctttttgg cagttcgttc cggcctcttc gcgggcacgc  60
ccgctcccac agggatcgcg ttaccttgtg ggagcgggcg tgcccgcgaa gaggccagca  120
cagacttacc actgtgctaa aacgcacagc ggctgcgcga aatctcgtgt ttcctccacg  180
aaattactca ctaagatgga tcgggacaag aataataatc aggggagagg ttgcacatga  240
aaagatcaaa acgatttgca gtactggccc agcgccccgt caatcaggac gggctgattg  300
gcgagtggcc tgaagagggg ctgatcgcca tggacagccc ctttgacccg gtctcttcag  360
taaaagtgga caacggtctg atcgtcgagc tggacggcaa acgccgggac cagtttgaca  420
tgatcgaccg atttatcgcc gattacgcga tcaacgttga gcgcacagag caggcaatgc  480
gcctggaggc ggtggaaata gcccgcatgc tggtggatat tcacgtcagt cgggaggaga  540
tcattgccat cactaccgcc atcacgccgg ccaaagcggt cgaggtgatg gcgcagatga  600
acgtggtgga gatgatgatg gcgctgcaga agatgcgtgc ccgccggacc ccctccaacc  660
agtgccacgt caccaatctc aaagataatc cggtgcagat tgctgctgac gccgccgagg  720
ccgggatccg cggcttctca gaacaggaga ccacggtcgg tatcgcgcgc tatgcgccgt  780
ttaacgccct ggcgctgttg gtcggttcgc agtgcggccg ccccggcgtt ttgacgcagt  840
gctcggtgga agaggccacc gagctggagc tgggcatgcg tggcttaacc agctacgccg  900
agacggtgtc ggtctacggc accgaagcgg tatttaccga cggcgatgat actccgtggt  960
caaaggcgtt cctcgcctcg gcctacgcct cccgcgggtt gaaaatgcgc tacacctccg  1020
gcaccggatc cgaagcgctg atgggctatt cggagagcaa gtcgatgctc tacctcgaat  1080
cgcgctgcat cttcattacc aaaggcgccg gggttcaggg gctgcaaaac ggcgcggtga  1140
gctgtatcgg catgaccggc gctgtgccgt cgggcattcg ggcggtgctg gcggaaaacc  1200
tgatcgcctc tatgctcgac ctcgaagtgg cgtccgccaa cgaccagact ttctcccact  1260
cggatattcg ccgcaccgcg cgcaccctga tgcagatgct gccgggcacc gactttattt  1320
```

-continued

```
tctccggcta cagcgcggtg ccgaactacg acaacatgtt cgccggctcg aacttcgatg  1380
cggaagattt tgatgattac aacatcctgc agcgtgacct gatggttgac ggcggcctgc  1440
gtccggtgac cgaggcggaa accattgcca ttcgccagaa agcggcgcgg gcgatccagg  1500
cggttttccg cgagctgggg ctgccgccaa tcgccgacga ggaggtggag gccgccacct  1560
acgcgcacgg tagcaacgag atgccgccgc gtaacgtggt ggaggatctg agtgcggtgg  1620
aagagatgat gaagcgcaac atcaccggcc tcgatattgt cggcgcgctg agccgcagcg  1680
gctttgagga tatcgccagc aatattctca atatgctgcg ccagcgggtc accggcgatt  1740
acctgcagac ctcggccatt ctcgatcggc agttcgaggt ggtgagtgcg gtcaacgaca  1800
tcaatgacta tcaggggccg ggcaccggct atcgcatctc tgccgaacgc tgggcggaga  1860
tcaaaaaatat tccgggcgtg gttcagcccg acaccattga ataaggcggt attcctatgc  1920
aacagacaac ccaaattcag ccctctttta ccctgaaaac ccgcgagggc ggggtagctt  1980
ctgccgatga acgcgccgat gaagtggtga tcggcgtcgg ccctgccttc gataaacacc  2040
agcatcacac tctgatcgat atgccccatg gcgcgatcct caaagagctg attgccgggg  2100
tggaagaaga ggggcttcac gcccgggtgg tgcgcattct gcgcacgtcc gacgtctcct  2160
ttatggcctg ggatgcggcc aacctgagcg gctcggggat cggcatcggt atccagtcga  2220
aggggaccac ggtcatccat cagcgcgatc tgctgccgct cagcaacctg gagctgttct  2280
cccaggcgcc gctgctgacg ctggaaacct accggcagat tggcaaaaac gccgcgcgct  2340
atgcgcgcaa agagtcacct tcgccggtgc cggtggtgaa cgatcagatg gtgcggccga  2400
aatttatggc caaagccgcg ctatttcata tcaaagagac caaacatgtg gtgcaggacg  2460
ccgagcccgt caccctgcac gtcgacttag ttagggagta aagatgagcg agaaaaccat  2520
gcgcgtgcag gattatccgt tagccacccg ctgcccggag catatcctga cgcctaccgg  2580
caaaccattg accgatatta ccctcgagaa ggtgctctct ggcgaggtgg gcccgcagga  2640
tgtgcggatc tcctgccaga cccttgagta ccaggcgcag attgccgagc agatgcagcg  2700
ccatgcggtg gcgcgcaatt tccgccgcgc ggcggagctt atcgccattc ctgacgagcg  2760
cattctggct atctataacg cgctgcgccc gttccgctcc tcgcaggcgg agctgctggc  2820
gatcgccgac gagctggagc acacctggca tgcgacagtg aatgccgcct ttgtccggga  2880
gtcggcggaa gtgtatcagc agcggcataa gctgcgtaaa ggaagctaag aggaggacag  2940
catgccgtta atagccggga ttgatatcgg caacgccacc accgaggtgg cgctggcgtc  3000
cgacgacccg caggcgaggg cgtttgttgc cagcgggatc gtcgcgacga cgggcatgaa  3060
agggacgcgg gacaatatcg ccgggaccct cgccgcgctg gagcaggccc tggcgaaaac  3120
accgtggtcg atgagcgatg tctctcgcat ctatcttaac gaagccgcgc cggtgattgg  3180
cgatgtggcg atggagacca tcaccgagac cattatcacc gaatcgacca tgatcggtca  3240
taacccgcag acgccgggcg gggtgggcgt tggcgtgggg acgactatcg ccctcgggcg  3300
gctggcgacg ctgccggcgg cgcagtatgc cgaggggtgg atcgtactga ttgacgacgc  3360
cgtcgatttc cttgacgccg tgtggtggct caatgaggcg ctcgaccggg ggatcaacgt  3420
ggtggcggcg atcctcaaaa aggacgacgg cgtgctggtg aacaaccgcc tgcgtaaaac  3480
cctgccggtg gtagatgaag tgacgctgct ggagcaggtc cccgaggggg taatggcggc  3540
ggtggaagtg gccgcgccgg gccaggtggt gcggatcctg tcgaatccct acgggatcgc  3600
caccttcttc gggctaagcc cggaagagac ccaggccatc gtccccatcg cccgcgccct  3660
gattggcaac cgttcagcgg tggtgctcaa gacccgcag ggggatgtgc agtcgcgggt  3720
gatcccggcg ggcaacctct acattagcgg cgaaaagcgc cgcggagagg ccgatgtcgc  3780
cgagggcgcg gaagccatca tgcaggcgat gagcgcctgc gctccggtac gcgacatccg  3840
cggcgaaccg ggcactcacg ccggcggcat gcttgagcgg gtgcgcaagg taatggcgtc  3900
cctgaccgac catgagatga gcgcgatata catccaggat ctgctggcgg tggatacgtt  3960
tattccgcgc aaggtgcagg gcgggatggc cggcgagtgc gccatggaaa atgccgtcgg  4020
gatggcggcg atggtgaaag cggatcgtct gcaaatgcag gttatcgccc gcgaactgag  4080
cgcccgactg cagaccgagg tggtggtggg cggcgtggag gccaacatgg ccatcgccgg  4140
ggcgttaacc actcccggct gtgcggcgcc gctggcgatc ctcgacctcg gcgccggctc  4200
gacggatgcg gcgatcgtca acgcggaggg gcagataacg gcggtccatc tcgccggggc  4260
ggggaatatg gtcagcctgt tgattaaaac cgagctgggc ctcgaggatc tttcgctggc  4320
ggaagcgata aaaaaatacc cgctggccaa agtggaaagc ctgttcagta ttcgtcacga  4380
gaatggcgcg gtggagttct ttcgggaagc cctcagcccg gcggtgttcg ccaaagtggt  4440
gtacatcaag gagggcgaac tggtgccgat cgataacgcc agcccgctgg aaaaaattcg  4500
tctcgtgcgc cggcaggcga aagagaaagt gtttgtcacc aactgcctgc gcgcgctgcg  4560
ccaggtctca cccggcggtt ccattcgcga tatcgccttt gtggtgctgg tgggcggctc  4620
atcgctggac tttgagatcc cgcagcttat cacggaagcc ttgtcgcact atggcgtggt  4680
cgccgggcag ggcaatattc ggggaacaga agggccgcgc aatgcggtcg ccaccgggct  4740
gctactggcc ggtcaggcga attaactctc aaggaggggt gtgttatgtc gctttcaccg  4800
ccaggcgtac gcctgtttta cgatccgcgc gggcaccatg ccggcgccat caatgagctg  4860
tgctgggggc tggaggagca gggggtcccc tgccagacca taacctatga cggaggcggt  4920
gacgccgctg cgctgggcgc cctggcggcc agaagctcgc cctgcgggt gggtattggg  4980
ctcagcgcgt ccggcgagat agccctcact catgcccagc tgccggcgga cgcgccgctg  5040
gctaccggac acgtcaccga tagcgacgat catctgcgta cgctcggcgc caacgccggg  5100
cagctggtta aagtcctgcc gttaagtgag agaaactgac ggtgatcccg tcctctcacg  5160
cttttgacgt gaaactccgc tcccggccgc cgaggtgtcg ggcggttcgc cagcaaggac  5220
tgggcgtccc cctcggtcct gcaaggagca acaccgaaac gctatcgcgc ggtgtgaaag  5280
ccgtggcagt agaggctgaa acaacaataa aagccccagc aggggcagga gagcccgcaa  5340
tgtctgatcc agcagtgacg agtgcgacac agagcaggac ctacgagcgg cag         5393

SEQ ID NO: 67          moltype = DNA  length = 1761
FEATURE                Location/Qualifiers
source                 1..1761
                       mol_type = other DNA
                       organism = synthetic construct
SEQUENCE: 67
caaggtgccc agcgccccct ccagcgaggt gatgcgccgc gacacagtgg tgtagtccac  60
gctcaggcgc ttggcggcgc tgctggcctt gcgcgtacgc gccacttcaa ggaagaactt  120
caggtcgtcc cagttgagcg cgctcaggga tgtaaggtct ttttgcatga tgatccggtt  180
tttttgtgcg ttcttgttgg atgtttgcac atctatactc gaaacaagcc tcaggacgcc  240
```

-continued

```
acctcgcgtt tgcacggcgc tggcgatctc gtcccgacaa taattcggag gggaacgcag  300
atgagaggat cgggatccgc taacgtgact tatacggata cgcaactgct gatcgacggt  360
gagtgggtcg acgccgcgag cggcaagacg atcgacgtcg tgaacccggc gaccggcaag  420
ccgatcggca gggtggccca tgcgggcatc gccgatctcg accgtgcgct cgccgccgcg  480
caaagcggct tcgaggcatg gcgcaaggtg cccgcgcacg agcgcgcggc gacgatgcgc  540
aaggcggccg cgctggtgcg tgaacgcgcc gacgcgatcg cgcagctgat gacgcaggag  600
cagggcaagc cgctcaccga agcgcgcgtc gaagtgctgt cgtccgcgga catcatcgaa  660
tggttcgcgg acgaaggccg ccgcgtgtac ggccggatcg tgccgccgcg caacctcggc  720
gcacagcaga cggtcgtgaa ggagccggtc ggcccggtcg ccgcgttcac gccgtggaat  780
ttcccggtca accaggtcgt gcgcaagctg agcgccgcgc tggcaaccgg ctgttcgttc  840
ctcgtgaaag cgccggaaga aacccccgcg tcgccggccg cgctgctgcg cgccttcgtc  900
gacgcaggcg tgccggccgg cgtgatcggc ctcgtgtacg gcgatccggc cgaaatctcg  960
tcgtacctga tcccgcaccc ggtgatccgc aaggtcacgt tcacgggttc gacgccggtc  1020
ggcaagcagc tcgcctcgct ggcgggcctg cacatgaagc gcgcgacgat ggagctgggc  1080
gggcacgcac cggtgatcgt ggccgaagac gccgacgttg cgctcgcggt ggcagcggcc  1140
ggcggcgcga agttccgcaa cgcggggcag gtctgcatct cgccgacgcg cttcctcgtg  1200
cacaacagca tccgcgacga attcacgcgc gcgctggtca agcatgccga agggctgaag  1260
gtcggcaacg gcctcgagga aggcacgacg ctcggcgcgc tcgcgaaccc gcgccggctg  1320
accgcgatgg cgtcggtcat cgacaacgcg cgcaaggtcg gtgcgagcat cgaaaccggc  1380
ggcgagcgga tcggctcgga aggcaacttc ttcgcgccga ccgtgatcgc gaacgtgccg  1440
ctcgatgcgg acgtgttcaa caacgagccg ttcggcccgg tcgcggcgat tcgcggtttc  1500
gacaagctcg aagaggcgat cgcggaagcg aaccgtttgc cgttcggtct tgccggctac  1560
gcgttcacgc gttcgttcgc gaacgtgcac ctgctcacgc agcgcctcga agtcgggatg  1620
ctgtggatca accagccgcc gactacatgg ccggaaatgc cgttcggcgg cgtgaaggac  1680
tcgggctacg gttcggaagg cggcccggaa gcgctcgagc cgtacctcgt cacgaagtcg  1740
gtgacggtaa tggccgtctg a                                            1761

SEQ ID NO: 68           moltype = DNA  length = 25
FEATURE                 Location/Qualifiers
source                  1..25
                        mol_type = other DNA
                        organism = synthetic construct
SEQUENCE: 68
taaaggaagc taagaggagg acagc                                        25

SEQ ID NO: 69           moltype = DNA  length = 25
FEATURE                 Location/Qualifiers
source                  1..25
                        mol_type = other DNA
                        organism = synthetic construct
SEQUENCE: 69
attaactctc aaggaggggt gtgtt                                        25

SEQ ID NO: 70           moltype = DNA  length = 210
FEATURE                 Location/Qualifiers
source                  1..210
                        mol_type = other DNA
                        organism = synthetic construct
SEQUENCE: 70
cgtggcgact ctcattgtta gaaaacgcac agcaggtgac tttaaacgtt cgtattttta  60
tcgcgaacga acgactaggc tccatcgtca tacccaaaag aacaagaacg acgagggact  120
ttccggcgtt tgacatgtgg atgtaatcct gttataattt tttagtgtaa ggctaactat  180
cgttcaaaat ttaggtggta acaacaaatg                                   210

SEQ ID NO: 71           moltype = DNA  length = 210
FEATURE                 Location/Qualifiers
source                  1..210
                        mol_type = other DNA
                        organism = synthetic construct
SEQUENCE: 71
ggcgtttgac atgtggatgt aatcctgtta taattttta gtgtaaggct aactatcgtt  60
caaaatttag gtggtaacaa caacgtggcg actctcattg ttagaaaacg cacagcaggt  120
gactttaaac gttcgtattt ttatcgcgaa cgaacgacta ggctccatcg tcatacccaa  180
aagaacaaga acgacgaggg actttccatg                                   210

SEQ ID NO: 72           moltype = DNA  length = 240
FEATURE                 Location/Qualifiers
source                  1..240
                        mol_type = other DNA
                        organism = synthetic construct
SEQUENCE: 72
cgtggcgact ctcattgtta gaaaacgcac agcaggtgac tttaaacgtt cgtattttta  60
tcgcgaacga acgactaggc tccatcgtca tacccaaaag aacaagaacg acgagggact  120
ttccggcgac caacaacggc gcgaggtggc aaaaatatct tgtttaatta ctacatattt  180
gtcttaatgc cggcgtgtaa ggctaactat cgttcaaaat ttagttggta acaacaaatg  240

SEQ ID NO: 73           moltype = DNA  length = 1148
FEATURE                 Location/Qualifiers
source                  1..1148
```

-continued

```
                         mol_type = other DNA
                         organism = synthetic construct
SEQUENCE: 73
ccagatgccg acgatggtca gccagggcgt catggggatt cctctgaagg gatgcgatga  60
tcgatccgac gggcaggctt gttccgccct cgggcaaagc aggcataata cccgcatcgt  120
cggtgctcgt aggacgcttc gctgtttgaa ggcgatgcat ccgagagccg aagagggaac  180
acggaaaaac cgtggctgcc cccgcaactg taagcagcga gtccgcgcac ttcgaccaca  240
gcgtctgttg tcgtcgatct ggccactggg caaccgggaa ggccgtgccg gatgaggacc  300
tgccagccag gagacctgcc gacgaaacca gtcgcgcgtg cagacatcga gcggggtgta  360
tcggtgtcgt gaagtcccct gtggggattc gcaggtcacc gcgacccagc cctggtgacc  420
tcaatgcaga gcaaaggcga agaactgttt accggcgtgg tgccgattct ggtggaactg  480
gatggcgatg tgaacggcca taaatttagc gtgcgtggcg aaggcgaagg cgatgcgacc  540
aacggcaaac tgaccctgaa atttatttgc accaccggta aactgccggt gccgtggccg  600
accctggtga ccaccctggg ttatggtgtg cagtgctttg cacgttatcc ggatcacatg  660
aaacgtcatg atttctttaa aagcgcgatg ccggaaggct atgtgcagga acgtaccatt  720
agctttaaag atgatggcac ctataaaacc cgtgcggaag tgaaatttga aggcgatacc  780
ctggtgaacc gtattgaact gaaaggcatt gattttaaag aagatggcaa cattctgggc  840
cataaactgg aatataactt taacagccat aaagtgtata ttaccgcgga taaacagaaa  900
aacggcatta aagcgaactt taaaattcgt cataacgtgg aagatggcag cgtgcagctg  960
gcggatcatt atcagcagaa cacccccgatt ggcgatggcc cggtgctgct gccggataac  1020
cattatctga gcacccagag cgtgctgctg aaagatccga acgaaaaacg tgatcacatg  1080
gtgctgctgg aatttgtgac cgcggcggca tggatgaact gtataaacac catcaccatc  1140
accattaa                                                           1148

SEQ ID NO: 74            moltype = DNA  length = 1218
FEATURE                  Location/Qualifiers
source                   1..1218
                         mol_type = other DNA
                         organism = synthetic construct
SEQUENCE: 74
ccagatgccg acgatggtca gccagggcgt catggggatt cctctgaagg gatgcgatga  60
tcgatccgac gggcaggctt gttccgccct cgggcaaagc aggcataata cccgcatcgt  120
cggtgctcgt aggacgcttc gctgtttgaa ggcgatgcat ccgagagccg aagagggaac  180
acggaaaaac cgtggctgcc cccgcaactg taagcagcga gtccgcgcac ttcgaccaca  240
gcgtctgttg tcgtcgatct ggccactggg caaccgggaa ggccgtgccg gatgaggacc  300
tgccagccag gagacctgcc gacgaaacca gtcgcgcgtg cagacatcga gcggggtgta  360
tcggtgtcgt gaagtcccct gtggggattc gcaggtcacc gcgacccagc cctggtgacc  420
tcaatgcaag actcctcagc tctgcccgtc cgtccgcatg cctgccctgg cctgctgcgc  480
atccagagca aaggcgaaga actgtttacc ggcgtggtgc cgattctggt ggaactggat  540
ggcgatgtga acggccataa atttagcgtg cgtggcgaag gcgaaggcga tgcgaccaac  600
ggcaaactga ccctgaaatt tatttgcacc accggtaaac tgccggtgcc gtggccgacc  660
ctggtgacca ccctgggtta tggtgtgcag tgctttgcac gttatccgga tcacatgaaa  720
cgtcatgatt tctttaaaag cgcgatgccg gaaggctatg tgcaggaacg taccattagc  780
tttaaagatg atggcaccta taaaacccgt gcggaagtga aatttgaagg cgataccctg  840
gtgaaccgta ttgaactgaa aggcattgat tttaaagaag atggcaacat tctgggccat  900
aaactggaat ataactttaa cagccataaa gtgtatatta ccgcggataa acagaaaaac  960
ggcattaaag cgaactttaa aattcgtcat aacgtggaag atggcagcgt gcagctggcg  1020
gatcattatc agcagaacac ccccgattggc gatggcccgg tgctgctgcc ggataaccat  1080
tatctgagca cccagagcgt gctgctgaaa gatccgaacg aaaaacgtga tcacatggtg  1140
ctgctggaat ttgtgaccgc ggcgggcatt acccacggca tggatgaact gtataaacac  1200
catcaccatc accattaa                                                1218

SEQ ID NO: 75            moltype = DNA  length = 423
FEATURE                  Location/Qualifiers
source                   1..423
                         mol_type = other DNA
                         organism = synthetic construct
SEQUENCE: 75
ccagatgccg acgatggtca gccagggcgt catggggatt cctctgaagg gatgcgatga  60
tcgatccgac gggcaggctt gttccgccct cgggcaaagc aggcataata cccgcatcgt  120
cggtgctcgt aggacgcttc gctgtttgaa ggcgatgcat ccgagagccg aagagggaac  180
acggaaaaac cgtggctgcc cccgcaactg taagcagcga gtccgcgcac ttcgaccaca  240
gcgtctgttg tcgtcgatct ggccactggg caaccgggaa ggccgtgccg gatgaggacc  300
tgccagccag gagacctgcc gacgaaacca gtcgcgcgtg cagacatcga gcggggtgta  360
tcggtgtcgt gaagtcccct gtggggattc gcaggtcacc gcgacccagc cctggtgacc  420
tca                                                                423

SEQ ID NO: 76            moltype = DNA  length = 825
FEATURE                  Location/Qualifiers
source                   1..825
                         mol_type = other DNA
                         organism = synthetic construct
SEQUENCE: 76
ggcggatgaa gggcgcgcgc gcgggttcgc cgcgcaacga aggtcgccac cggatcaccc  60
cgcccggttg tctgttgata acgaaccggt tccggatctc gcgagctaga gccaggcaag  120
gcggaggatc gtcggggacg cggagttgac tgtagtcaat gagcagtcca cgacgatccg  180
ccaacgcagc atggccgacg cgcagcagat cgaaaaccag tcacgaggca ggtctcctgg  240
ctcacagccc ttgatcgtcc tttcgccttc ccgccgtagt cggcagtggc gtgtgaaaga  300
acaggctgtt cacagttgcg gggcagccg tggcgcatcc gaagatttcc acgttccctc  360
```

```
ttagctccgg ccagtgccgg agaacctcga agggaggaag gctacgcagc gtggccgggg  420
cggtcaatcg ccggggatcg ggcgacgcgc agttgacgct gcgggactgc cgtggtcagc  480
tagcgcggtt tcaggtgtct cgcgccgacg cgcgcgaggt gaaacgggaa gccggtgcgt  540
ccgcaaggac cagtccggcg ctgccccccgc aacggtaagc gcatcgaggg tcgtcagtag  600
ccactgtgcc aaggcatggg aaggctggcc catccggcga gagtctctcg ctggcgtcgc  660
aagcccggag accggcctgg aatcctcaca ttttggcaaa cccgcggtgg gcgggcgcag  720
gccgtggcgc gaccgatccg gcgcgttcga atgcgttcaa cctctgcgtt ctcactcttt  780
tcagagggaa cgttcatgtc cagcagcatc ctgacgcaac aggcg                   825

SEQ ID NO: 77          moltype = AA  length = 555
FEATURE                Location/Qualifiers
source                 1..555
                       mol_type = protein
                       organism = Klebsiella pneumoniae
SEQUENCE: 77
MKRSKRFAVL AQRPVNQDGL IGEWPEEGLI AMDSPFDPVS SVKVDNGLIV ELDGKRRDQF  60
DMIDRFIADY AINVERTEQA MRLEAVEIAR MLVDIHVSRE EIIAITTAIT PAKAVEVMAQ  120
MNVVEMMMAL QKMRARRTPS NQCHVTNLKD NPVQIAADAA EAGIRGFSEQ ETTVGIARYA  180
PFNALALLVG SQCGRPGVLT QCSVEEATEL ELGMRGLTSY AETVSVYGTE AVFTDGDDTP  240
WSKAFLASAY ASRGLKMRYT SGTGSEALMG YSESKSMLYL ESRCIFITKG AGVQGLQNGA  300
VSCIGMTGAV PSGIRAVLAE NLIASMLDLE VASANDQTFS HSDIRRTART LMQMLPGTDF  360
IFSGYSAVPN YDNMFAGSNF DAEDFDDYNI LQRDLMVDGG LRPVTEAETI AIRQKAARAI  420
QAVFRELGLP PIADEEVEAA TYAHGSNEMP PRNVVEDLSA VEEMMKRNIT GLDIVGALSR  480
SGFEDIASNI LNMLRQRVTG DYLQTSAILD RQFEVVSAVN DINDYQGPGT GYRISAERWA  540
EIKNIPGVVQ PDTIE                                                    555

SEQ ID NO: 78          moltype = AA  length = 194
FEATURE                Location/Qualifiers
source                 1..194
                       mol_type = protein
                       organism = Klebsiella pneumoniae
SEQUENCE: 78
MQQTTQIQPS FTLKTREGGV ASADERADEV VIGVGPAFDK HQHHTLIDMP HGAILKELIA  60
GVEEEGLHAR VVRILRTSDV SFMAWDAANL SGSGIGIGIQ SKGTTVIHQR DLLPLSNLEL  120
FSQAPLLTLE TYRQIGKNAA RYARKESPSP VPVVNDQMVR PKFMAKAALF HIKETKHVVQ  180
DAEPVTLHVD LVRE                                                     194

SEQ ID NO: 79          moltype = AA  length = 141
FEATURE                Location/Qualifiers
source                 1..141
                       mol_type = protein
                       organism = Klebsiella pneumoniae
SEQUENCE: 79
MSEKTMRVQD YPLATRCPEH ILTPTGKPLT DITLEKVLSG EVGPQDVRIS CQTLEYQAQI  60
AEQMQRHAVA RNFRRAAELI AIPDERILAI YNALRPFRSS QAELLAIADE LEHTWHATVN  120
AAFVRESAEV YQQRHKLRKG S                                             141

SEQ ID NO: 80          moltype = AA  length = 607
FEATURE                Location/Qualifiers
source                 1..607
                       mol_type = protein
                       organism = Klebsiella pneumoniae
SEQUENCE: 80
MPLIAGIDIG NATTEVALAS DDPQARAFVA SGIVATTGMK GTRDNIAGTL AALEQALAKT  60
PWSMSDVSRI YLNEAAPVIG DVAMETITET IITESTMIGH NPQTPGGVGV GVGTTIALGR  120
LATLPAAQYA EGWIVLIDDA VDFLDAVWWL NEALDRGINV VAAILKKDDG VLVNNRLRKT  180
LPVVDEVTLL EQVPEGVMAA VEVAAPGQVV RILSNPYGIA TFFGLSPEET QAIVPIARAL  240
IGNRSAVVLK TPQGDVQSRV IPAGNLYISG EKRRGEADVA EGAEAIMQAM SACAPVRDIR  300
GEPGTHAGGM LERVRKVMAS LTDHEMSAIY IQDLLAVDTF IPRKVQGGMA GECAMENAVG  360
MAAMVKADRL QMQVIARELS ARLQTEVVVG GVEANMAIAG ALTTPGCAAP LAILDLGAGS  420
TDAAIVNAEG QITAVHLAGA GNMVSLLIKT ELGLEDLSLA EAIKKYPLAK VESLFSIRHE  480
NGAVEFFREA LSPAVFAKVV YIKEGELVPI DNASPLEKIR LVRRQAKEKV FVTNCLRALR  540
QVSPGGSIRD IAFVVLVGGS SLDFEIPQLI TEALSHYGVV AGQGNIRGTE GPRNAVATGL  600
LLAGQAN                                                             607

SEQ ID NO: 81          moltype = AA  length = 117
FEATURE                Location/Qualifiers
source                 1..117
                       mol_type = protein
                       organism = synthetic construct
SEQUENCE: 81
MSLSPPGVRL FYDPRGHHAG AINELCWGLE EQGVPCQTIT YDGGGDAAAL GALAARSSPL  60
RVGIGLSASG EIALTHAQLP ADAPLATGHV TDSDDHLRTL GANAGQLVKV LPLSERN      117

SEQ ID NO: 82          moltype = AA  length = 481
FEATURE                Location/Qualifiers
source                 1..481
                       mol_type = protein
                       organism = synthetic construct
```

SEQUENCE: 82
MANVTYTDTQ LLIDGEWVDA ASGKTIDVVN PATGKPIGRV AHAGIADLDR ALAAAQSGFE 60
AWRKVPAHER AATMRKAAAL VRERADAIAQ LMTQEQGKPL TEARVEVLSA ADIIEWFADE 120
GRRVYGRIVP PRNLGAQQTV VKEPVGPVAA FTPWNFPVNQ VVRKLSAALA TGCSFLVKAP 180
EETPASPAAL LRAFVDAGVP AGVIGLVYGD PAEISSYLIP HPVIRKVTFT GSTPVGKQLA 240
SLAGLHMKRA TMELGGHAPV IVAEDADVAL AVKAAGGAKF RNAGQVCISP TRFLVHNSIR 300
DEFTRALVKH AEGLKVGNGL EEGTTLGALA NPRRLTAMAS VIDNARKVGA SIETGGERIG 360
SEGNFFAPTV IANVPLDADV FNNEPFGPVA AIRGFDKLEE AIAEANRLPF GLAGYAFTRS 420
FANVHLLTQR LEVGMLWINQ PATPWPEMPF GGVKDSGYGS EGGPEALEPY LVTKSVTVMA 480
V 481

SEQ ID NO: 83 moltype = DNA length = 1665
FEATURE Location/Qualifiers
source 1..1665
mol_type = genomic DNA
organism = Klebsiella pneumoniae
SEQUENCE: 83
atgagatcga aaagatttga agcactggcg aaacgccctg tgaatcagga tggtttcgtt 60
aaggagtgga ttgaagaggg ctttatcgcg atggaaagcc ctaacgatcc caaaccttct 120
atccgcatcg tcaacggcgc ggtgaccgaa ctcgacgata aaccggttga gcagttcgac 180
ctgattgacc actttatcgc gcgctacggc attaatctcg cccgggccga agaagtgatg 240
gccatggatt cggttaagct cgccaacatg ctctgcgacc cgaacgttaa acgcagcgac 300
atcgtgccgc tcactaccgc gatgaccccg gcgaaaatcg tggaagtggt gtcgcatatg 360
aacgtggtcg agatgatgat ggcgatgcaa aaaatgcgcg cccgccgcac gccgtcccag 420
caggcgcatg tcactaatat caaagataat ccggtacaga ttgccgccga cgccgctgaa 480
ggcgcatggc gcggctttga cgagcaggag accaccgtcg ccgtggcgcg ctacgcgccg 540
ttcaacgcca tcgccctgct ggtcggttca caggttggcc gccccggcgt cctcacccag 600
tgttcgctgg aagaagccac cgagctgaaa ctgggcatgc tgggccacac ctgctatgcc 660
gaaaccattt cggtatacgg tacggaaccg gtgtttaccg atggcgatga caccccgtgg 720
tcgaaaggct tcctcgcctc ctcctacgcc tcgcgcggcc tgaaaatgcg ctttacctcc 780
ggttccggct cggaggtgca gatgggctat gccgaaggca aatcgatgct ttatctcgaa 840
gcgcgctgca tctacatcac caaagccgcc ggggtgcaag gcctgcagaa tggctccgtc 900
agctgtatcg gcgtgccgtc cgccgtgccg tccgggatcc gcgccgtact ggcggaaaac 960
ctgatctgct cagcgctgga tctggagtgc gcctccagca acgatcaaac ctttacccac 1020
tcggatatgc ggcgtaccgc gcgtctgctg atgcagttcc tgccaggtac cgactttatc 1080
tcctccggtt actcggcggt gccgaactac gacaacatgt tcgccggttc caacgaagat 1140
gccgaagact tcgatgacta caacgtgatc cagcgcgacc tgaaggtcga tggcggcctg 1200
cggccggtgc gtgaagagga cgtgatcgcc attcgcaaca aagccgcccg cgcgctgcag 1260
gcggtatttg ccggcatggg tttgccgcct attacggatg aagaagtaga agccgccacc 1320
tacgcccacg gttcaaaaga tatgcctgag cgcaatatcg tcgaggacat caagtttgct 1380
caggagatca tcaacaagaa ccgcaacggc ctggaggtgg tgaaagccct ggcgaaaggc 1440
ggcttccccg atgtcgccca ggacatgctc aatattcaga aagccaagct caccggcgac 1500
tacctgcata cctccgccat cattgttggc gagggccagg tgctctcggc cgtgaatgac 1560
gtgaacgatt atgccggtcc ggcaacaggc taccgcctgc aaggcgagcg ctgggaagag 1620
attaaaaata tcccgggcgc gctcgatccc aatgaacttg gctaa 1665

SEQ ID NO: 84 moltype = DNA length = 690
FEATURE Location/Qualifiers
source 1..690
mol_type = genomic DNA
organism = Klebsiella pneumoniae
SEQUENCE: 84
atggaaatta acgaaacgct gctgcgccag attatcgaag aggtgctgtc ggagatgaaa 60
tcaggcgcag ataagccggt ctcctttagc gcgcctgcgg cttctgtcgc ctctgccgcg 120
ccggtcgccg ttgcgcctgt gtccggcgac agcttcctga cggaaatcgg cgaagccaaa 180
cccggcacgc agcaggatga agtcattatt gccgtcggcc cagcgtttgg tctggcgcaa 240
accgccaata tcgtcggcat tccgcataaa aatattctgc gcgaagtgat cgccggcatt 300
gaggaagaag gcatcaaagc ccgggtgatc cgctgcttta agtcttctga cgtcgccttc 360
gtggcagtgg aaggcaaccg cctgagcggc tccggcatct cgatcggtat tcagtcgaaa 420
ggcaccaccg tcatccacca gcgcggcctg ccgccgcttt ccaatctgga actcttcccg 480
caggcgccgc tgctgacgct ggaaacctac cgtcagattg gcaaaaacgc cgcgcgctac 540
gccaaacgcg agtcgccgca gccggtgccg acgcttaacg atcagatggc tcgtcccaaa 600
taccaggcga agtcggccat tttgcacatt aaagagacca aatacgtggt gacgggcaaa 660
aacccgcagg aactgcgcgt ggcgctttaa 690

SEQ ID NO: 85 moltype = DNA length = 525
FEATURE Location/Qualifiers
source 1..525
mol_type = genomic DNA
organism = Klebsiella pneumoniae
SEQUENCE: 85
atgaataccg acgcaattga atccatggta cgcgacgtgc tgagccggat gaacagccta 60
caggacggga taacgcccgc gccagccgcg ccgacaaacg acaccgttcg ccagccaaaa 120
gttagcgact acccgttagc gacccgccat ccggagtggg tcaaaaccgc taccaataaa 180
acgctcgatg acctgacgct ggagaacgta ttaagcgatc gcgttacggc gcaggacatg 240
cgcatcactc cggaaacgct gcgtatgcag gcggcgatcg cccaggatgc cggacgcgat 300
cggctggcga tgaactttga gcgggccgca gagctcaccg cggttcccga cgaccgaatc 360
cttgagatct acaacgccct gcgcccatac cgttccaccc aggcggagct actggcgatc 420
gctgatgacc tcgagcatcg ctaccaggca cgactctgtg ccgcctttgt tcgggaagcg 480

```
gccgggctgt acatcgagcg taagaagctg aaaggcgacg attaa                525

SEQ ID NO: 86           moltype = DNA  length = 1833
FEATURE                 Location/Qualifiers
source                  1..1833
                        mol_type = genomic DNA
                        organism = Klebsiella pneumoniae
SEQUENCE: 86
atgcgctata tcgctggcat tgatattggc aactcctcga cagaagtcgc cctggcgacg  60
gtcgatgacg caggtgtgct gaacattcgc cacagcgcgt tggctgaaac cacgggtata  120
aaaggcacat tacgaaatgt gttcggtatc caggaggcgc taacgcaggc ggcaaaagcg  180
gccggcattc agctcagcga tatttcgctt attcgcatta acgaagccac gccggtcatt  240
ggcgatgtgg cgatggaaac catcacggaa accatcatca ccgagtccac catgatcggc  300
cataacccga agacacccgg cggcgtcgga ctgggggtcg gcatcaccat cacaccagag  360
gcgctgctgt cctgctccgc ggacactccc tatattctgg tggtctcctc ggcctttgac  420
tttgccgatg tcgccgcgat ggtcaatgcg gcaacggcag cgggctatca gataaccggc  480
attattttgc agcaggatga cggcgtgctg gtcaataacc ggctacagca accgctgccg  540
gtgatcgacg aagttcagca tatcgaccgg attccacttg gcatgctggc ggccgtcgag  600
gtcgctttac ccggtaagat catcgaaacg ctctccaacc cctacggtat tgcgaccgtt  660
ttcgatctca acgccgagga gaccaaaaat atcgtgccaa tggcgcgggc gctgattggc  720
aaccgctcgg ccgtggtggt gaaaaccccc tccggcgacg tcaaggcccg cgctattccg  780
gcaggtaatc tgctgctcat cgctcagggg cgcagcgtac aggttgatgt ggccgccggg  840
gcggaagcca tcatgaaagc ggttgacggc tgcggcaaac tggacaacgt cgcgggagaa  900
gcgggcacca atatcggcgg catgcttgag cacgtgcgcc agaccatggc ggagcttacc  960
aataagccag ctcaggagat ccgcattcag gatctgctgg ccgttgatac ggcggtgcca  1020
gtcagcgtga ccggcggtct tgcgggggag ttctcgctgg agcaggcggt gggtatcgcc  1080
tcgatggtca agtcggatcg cctgcagatg gccctcatcg cccgtgaaat tgagcacaaa  1140
ctgcagattg cggttcaggt gggcggcgcc gaagcggagg cggccattct tggggcgctc  1200
accactcccg gcaccacgcg cccgctggcg atcctcgatc tgggcgccgg gtcgaccgac  1260
gcctccatta tcaatgcgca gggagagatc agcgccactc acctggccgg cgccggcgat  1320
atggtcacga tgatcatcgc ccgcgagctg gggcttgagg accgctacct ggcggaagag  1380
atcaaaaaat atccgctggc aaaagtcgaa agcctgtttc atctgcgtca tgaagacggc  1440
agcgtccagt tttttccgtc ggccttacca ccggcggtat ttgcccgcgt ctgcgtggtg  1500
aaaccggatg aactggttcc cctgcccggc gatctgccgc tggagaaagt gcgcgccatt  1560
cgccgtagcg ccaaatcacg cgtctttgtc actaacgccc tgcgggcgtt acgccaggtg  1620
agccctaccg gcaacattcg cgacatcccg ttcgtggtgc tggtgggcgg ctcgtccctc  1680
gatttcgaga tcccccagct ggtcaccgac gcgctggcgc actaccggct ggttgccggg  1740
cgcggcaaca tccgcggctg tgaaggccca cgcaatgcgg tcgccagcgg attactcctt  1800
tcctggcaaa aaggaggcac acatggagag tag                             1833

SEQ ID NO: 87           moltype = DNA  length = 351
FEATURE                 Location/Qualifiers
source                  1..351
                        mol_type = genomic DNA
                        organism = Klebsiella pneumoniae
SEQUENCE: 87
atggagagta gcgtagtcgc ccccgccatc gtcattgccg tcactgacga atgcagcgaa  60
cagtggcgcg atgtcctgct gggcattgaa gaggaaggca ttccttttgt tctgcagccg  120
cagaccggcg gcgatcttat ccatcacgcc tggcaggcgg cgcagcgttc gccgctgcag  180
gtaggcatcg cctgcgaccg ggaacggctc atcgtgcact acaaaaattt acccgcatca  240
actccgctgt tttcgctgat gtatcaccag aacaggctgg cccggcgaaa cactggcaac  300
aatgcggctc gtctcgtcaa agggatccca tttcgggatc gccatgctta a         351

SEQ ID NO: 88           moltype = AA  length = 554
FEATURE                 Location/Qualifiers
source                  1..554
                        mol_type = protein
                        organism = Klebsiella pneumoniae
SEQUENCE: 88
MRSKRFEALA KRPVNQDGFV KEWIEEGFIA MESPNDPKPS IRIVNGAVTE LDDKPVEQFD  60
LIDHFIARYG INLARAEEVM AMDSVKLANM LCDPNVKRSD IVPLTTAMTP AKIVEVVSHM  120
NVVEMMMAMQ KMRARRTPSQ QAHVTNIKDN PVQIAADAAE GAWRGFDEQE TTVAVARYAP  180
FNAIALLVGS QVGRPGVLTQ CSLEEATELK LGMLGHTCYA ETISVYGTEP VFTDGDDTPW  240
SKGFLASSYA SRGLKMRFTS GSGSEVQMGY AEGKSMLYLE ARCIYITKAA GVQGLQNGSV  300
SCIGVPSAVP SGIRAVLAEN LICSALDLEC ASSNDQTFTH SDMRRTARLL MQFLPGTDFI  360
SSGYSAVPNY DNMFAGSNED AEDFDDYNVI QRDLKVDGGL RPVREEDVIA IRNKAARALQ  420
AVFAGMGLPP ITDEEVEAAT YAHGSKDMPE RNIVEDIKFA QEIINKNRNG LEVVKALAKG  480
GFPDVAQDML NIQKAKLTGD YLHTSAIIVG EGQVLSAVND VNDYAGPATG YRLQGERWEE  540
IKNIPGALDP NELG                                                  554

SEQ ID NO: 89           moltype = AA  length = 229
FEATURE                 Location/Qualifiers
source                  1..229
                        mol_type = protein
                        organism = Klebsiella pneumoniae
SEQUENCE: 89
MEINETLLRQ IIEEVLSEMK SGADKPVSFS APAASVASAA PVAVAPVSGD SFLTEIGEAK  60
PGTQQDEVII AVGPAFGLAQ TANIVGIPHK NILREVIAGI EEEGIKARVI RCFKSSDVAF  120
VAVEGNRLSG SGISIGIQSK GTTVIHQRGL PPLSNLELFP QAPLLTLETY RQIGKNAARY  180
```

-continued

```
AKRESPQPVP TLNDQMARPK YQAKSAILHI KETKYVVTGK NPQELRVAL           229

SEQ ID NO: 90           moltype = AA  length = 174
FEATURE                 Location/Qualifiers
source                  1..174
                        mol_type = protein
                        organism = Klebsiella pneumoniae
SEQUENCE: 90
MNTDAIESMV RDVLSRMNSL QDGITPAPAA PTNDTVRQPK VSDYPLATRH PEWVKTATNK  60
TLDDLTLENV LSDRVTAQDM RITPETLRMQ AAIAQDAGRD RLAMNFERAA ELTAVPDDRI  120
LEIYNALRPY RSTQAELLAI ADDLEHRYQA RLCAAFVREA AGLYIERKKL KGDD       174

SEQ ID NO: 91           moltype = AA  length = 610
FEATURE                 Location/Qualifiers
source                  1..610
                        mol_type = protein
                        organism = Klebsiella pneumoniae
SEQUENCE: 91
MRYIAGIDIG NSSTEVALAT VDDAGVLNIR HSALAETTGI KGTLRNVFGI QEALTQAAKA  60
AGIQLSDISL IRINEATPVI GDVAMETITE TIITESTMIG HNPKTPGGVG LGVGITITPE  120
ALLSCSADTP YILVVSSAFD FADVAAMVNA ATAAGYQITG IILQQDDGVL VNNRLQQPLP  180
VIDEVQHIDR IPLGMLAAVE VALPGKIIET LSNPYGIATV FDLNAEETKN IVPMARALIG  240
NRSAVVVKTP SGDVKARAIP AGNLLLIAQG RSVQVDVAAG AEAIMKAVDG CGKLDNVAGE  300
AGTNIGGMLE HVRQTMAELT NKPAQEIRIQ DLLAVDTAVP VSVTGGLAGE FSLEQAVGIA  360
SMVKSDRLQM ALIAREIEHK LQIAVQVGGA EAEAAILGAL TTPGTTRPLA ILDLGAGSTD  420
ASIINAQGEI SATHLAGAGD MVTMIIAREL GLEDRYLAEE IKKYPLAKVE SLFHLRHEDG  480
SVQFFPSALP PAVFARVCVV KPDELVPLPG DLPLEKVRAI RRSAKSRVFV TNALRALRQV  540
SPTGNIRDIP FVVLVGGSSL DFEIPQLVTD ALAHYRLVAG RGNIRGCEGP RNAVASGLLL  600
SWQKGGTHGE                                                        610

SEQ ID NO: 92           moltype = AA  length = 116
FEATURE                 Location/Qualifiers
source                  1..116
                        mol_type = protein
                        organism = Klebsiella pneumoniae
SEQUENCE: 92
MESSVVAPAI VIAVTDECSE QWRDVLLGIE EEGIPFVLQP QTGGDLIHHA WQAAQRSPLQ  60
VGIACDRERL IVHYKNLPAS TPLFSLMYHQ NRLARRNTGN NAARLVKGIP FRDRHA      116
```